US011691947B2

(12) United States Patent
Rishton et al.

(10) Patent No.: US 11,691,947 B2
(45) Date of Patent: *Jul. 4, 2023

(54) ISOINDOLINE COMPOSITIONS AND METHODS FOR TREATING NEURODEGENERATIVE DISEASE

(71) Applicant: COGNITION THERAPEUTICS, INC., Pittsburgh, PA (US)

(72) Inventors: Gilbert M. Rishton, Los Angeles, CA (US); Susan M. Catalano, Pittsburgh, PA (US); Gary C. Look, Santa Clara, CA (US)

(73) Assignee: Cognition Therapeutics, Inc., Pittsburgh, PA (US)

( * ) Notice: Subject to any disclaimer, the term of this patent is extended or adjusted under 35 U.S.C. 154(b) by 102 days.

This patent is subject to a terminal disclaimer.

(21) Appl. No.: 16/783,943

(22) Filed: Feb. 6, 2020

(65) Prior Publication Data

US 2021/0009517 A1 Jan. 14, 2021

Related U.S. Application Data

(63) Continuation of application No. 16/230,238, filed on Dec. 21, 2018, now Pat. No. 10,611,728, which is a continuation of application No. 15/700,923, filed on Sep. 11, 2017, now Pat. No. 10,207,991, which is a continuation of application No. 15/115,187, filed as application No. PCT/US2015/013754 on Jan. 30, 2015, now Pat. No. 9,796,672.

(60) Provisional application No. 61/934,528, filed on Jan. 31, 2014.

(51) Int. Cl.
| | |
|---|---|
| C07D 209/44 | (2006.01) |
| C07D 209/62 | (2006.01) |
| C07D 403/06 | (2006.01) |
| C07D 491/048 | (2006.01) |
| C07D 491/056 | (2006.01) |
| A61K 31/4035 | (2006.01) |
| A61K 31/404 | (2006.01) |
| A61K 31/407 | (2006.01) |
| A61K 31/496 | (2006.01) |
| A61P 25/00 | (2006.01) |

(52) U.S. Cl.
CPC ........ C07D 209/44 (2013.01); A61K 31/4035 (2013.01); A61P 25/00 (2018.01); C07D 209/62 (2013.01); C07D 403/06 (2013.01); C07D 491/048 (2013.01); C07D 491/056 (2013.01)

(58) Field of Classification Search
CPC .. C07D 209/44; C07D 209/62; C07D 403/06; C07D 491/048; C07D 491/056; A61K 31/4035; A61K 31/404; A61K 31/407; A61K 31/496; A61P 25/00
See application file for complete search history.

(56) References Cited

U.S. PATENT DOCUMENTS

| | | | |
|---|---|---|---|
| 4,321,386 A | 3/1982 | Lawson | |
| 4,582,849 A | 4/1986 | Marzolph et al. | |
| 4,697,024 A | 9/1987 | Donaldson et al. | |
| 4,958,029 A | 9/1990 | Nakagawa et al. | |
| 6,011,068 A | 1/2000 | Nemeth et al. | |
| 6,057,371 A | 5/2000 | Glennon | |
| 6,211,244 B1 | 4/2001 | Van Wagenen et al. | |
| 6,235,731 B1 | 5/2001 | Shibouta et al. | |
| 6,518,315 B1 | 2/2003 | Roufogalis et al. | |
| 6,991,814 B2 | 1/2006 | Ray et al. | |
| 7,723,377 B2 | 5/2010 | Rishton et al. | |
| 8,304,547 B2 | 11/2012 | Sugasawa et al. | |
| 8,765,816 B2 | 7/2014 | Rishton et al. | |
| 9,192,585 B2 | 11/2015 | Rishton et al. | |
| 9,365,491 B2 | 6/2016 | Rishton et al. | |
| 9,499,462 B2 | 11/2016 | Rishton et al. | |
| 9,796,672 B2 * | 10/2017 | Rishton ............... | C07D 403/06 |
| 9,815,770 B2 | 11/2017 | Rishton et al. | |
| 10,207,991 B2 * | 2/2019 | Rishton ............... | C07D 209/62 |
| 10,611,728 B2 * | 4/2020 | Rishton ............... | C07D 403/06 |
| 11,214,540 B2 | 1/2022 | Rishton et al. | |
| 2003/0148392 A1 | 8/2003 | Citron et al. | |
| 2004/0033277 A1 | 2/2004 | Ray et al. | |
| 2005/0059689 A1 | 3/2005 | Oksenberg et al. | |
| 2006/0153772 A1 | 7/2006 | Jacobsen | |
| 2007/0021413 A1 | 1/2007 | Herold et al. | |
| 2008/0101757 A1 | 5/2008 | Lin et al. | |
| 2008/0103107 A1 | 5/2008 | Ward et al. | |
| 2008/0131233 A1 | 6/2008 | Yao | |

(Continued)

FOREIGN PATENT DOCUMENTS

| | | |
|---|---|---|
| AU | 2008314922 A1 | 4/2009 |
| CA | 1018188 A | 9/1977 |

(Continued)

OTHER PUBLICATIONS

Extended European Search Report for European Patent Application No. 19154222.4 dated Mar. 19, 2019.

Fenili et al. "Properties of scyllo-inositol as a therapeutic treatment of AD-like pathology" J Mol Med. Jun. 2007 856:603-611.

Flood et al. "FAD mutant PS-1 gene-targeted mice: Increased Abeta42 and Abeta deposition without APP overproduction" Neurobiol Aging May-Jun. 2002 233:335-348.

Fujiwara et al "Acetylcholinesterase Inhibitory Activity of Volatile Oil from Peltophorum dasyrachis Kurz ex Bakar Yellow Batai and Bisabolane-Type Sesquiterpenoids" J. Agri. and Food Chem. Jan. 2010 585:2824-2829.

(Continued)

*Primary Examiner* — Sun Jae Yoo

(74) *Attorney, Agent, or Firm* — DLA Piper LLP (US)

(57) ABSTRACT

Isoindoline sigma-2 receptor antagonist compounds, pharmaceutical compositions comprising such compounds, and methods for inhibiting Abeta-associated synapse loss or synaptic dysfunction in neuronal cells, modulating an Abeta-associated membrane trafficking change in neuronal cells, and treating cognitive decline associated with Abeta pathology are provided.

20 Claims, No Drawings

(56) References Cited

U.S. PATENT DOCUMENTS

| | | |
|---|---|---|
| 2008/0153917 A1 | 6/2008 | Ellis et al. |
| 2008/0193573 A1 | 8/2008 | Gow et al. |
| 2008/0312333 A1 | 12/2008 | Mae et al. |
| 2009/0017038 A1 | 1/2009 | Colabufo et al. |
| 2009/0022667 A1 | 1/2009 | Peters et al. |
| 2009/0035295 A1 | 2/2009 | Hillen et al. |
| 2010/0028333 A1 | 2/2010 | Getty et al. |
| 2010/0029654 A1 | 2/2010 | Pasinetti |
| 2010/0093001 A1 | 4/2010 | Rousseau et al. |
| 2010/0297149 A1 | 11/2010 | Zhou et al. |
| 2011/0015209 A1 | 1/2011 | Shamloo et al. |
| 2011/0082154 A1 | 4/2011 | Oksenberg et al. |
| 2011/0092554 A1 | 4/2011 | Chesworth et al. |
| 2012/0283114 A1 | 11/2012 | Cohen et al. |
| 2013/0071330 A1 | 3/2013 | Catalano |
| 2014/0378460 A1 | 12/2014 | Catalano et al. |
| 2014/0378473 A1 | 12/2014 | Catalano et al. |
| 2015/0160228 A1 | 6/2015 | Catalano |
| 2017/0197977 A9 | 7/2017 | Catalano et al. |
| 2020/0299234 A1 | 9/2020 | Rishton et al. |
| 2020/0338045 A1* | 10/2020 | Catalano ............ A61K 31/4035 |

FOREIGN PATENT DOCUMENTS

| | | |
|---|---|---|
| CA | 1275934 C | 11/1990 |
| CA | 2073841 A1 | 1/1993 |
| CN | 101121670 A | 2/2008 |
| CN | 110283082 A | 9/2019 |
| DE | 4000610 A1 | 7/1991 |
| DE | 10320560 A1 | 1/2004 |
| EP | 0002222 A1 | 6/1979 |
| EP | 0443606 A2 | 8/1991 |
| EP | 0613007 A2 | 8/1994 |
| EP | 0881220 A1 | 12/1998 |
| EP | 1088550 A1 | 4/2001 |
| JP | S62283922 A | 12/1987 |
| JP | H01180822 A | 7/1989 |
| JP | H01305085 A | 12/1989 |
| JP | H02215789 A | 8/1990 |
| JP | H045266 A | 1/1992 |
| JP | H06321781 A | 11/1994 |
| JP | H09157144 A | 6/1997 |
| JP | 2003113117 A | 4/2003 |
| JP | 2004002517 A | 1/2004 |
| WO | 1982002551 A1 | 8/1982 |
| WO | 1991009594 A1 | 7/1991 |
| WO | 199511221 A1 | 4/1995 |
| WO | 1996012697 A2 | 5/1996 |
| WO | 1999025363 A1 | 5/1999 |
| WO | 1999029673 A1 | 6/1999 |
| WO | 2001030335 A2 | 5/2001 |
| WO | 2001091558 A1 | 12/2001 |
| WO | 2003016274 A2 | 2/2003 |
| WO | 2003051380 A2 | 6/2003 |
| WO | 2005087212 A1 | 9/2005 |
| WO | 2006020879 A1 | 2/2006 |
| WO | 2006138349 A1 | 12/2006 |
| WO | 2007077543 A2 | 7/2007 |
| WO | 2008042755 A2 | 4/2008 |
| WO | 2009059214 A1 | 5/2009 |
| WO | 2010062260 A1 | 6/2010 |
| WO | 2010088450 A2 | 8/2010 |
| WO | 2012027548 A1 | 3/2012 |
| WO | 2015020523 A1 | 2/2015 |
| WO | 2021163613 | 8/2021 |
| WO | 2022125925 A1 | 6/2022 |

OTHER PUBLICATIONS

Fukumoto et al. "Beta-Secretase Activity Increases with Aging in Human Monkey and Mouse Brain" Am. J. Path. Feb. 2004 1642:719-725.

Georganopoulou et al. "Nanoparticle-based detection in cerebral spinal fluid of a soluble pathogenic biomarker for Alzheimer's disease" PNAS Feb. 15, 2005 1027:2273-2276.

Golde "Alzheimer disease therapy: can the Amyloid cascade be haltered?" J Clin Invest. Jan. 2003 1111:11-18.

Gopalan et al. "Supercritical Carbon Dioxide Extraction of Tumeric Curcuma longa" J. Agric. Food Chem. 2000 48:2189-2192.

Greene et al. Protective Groups in Organic Synthesis 3rd Ed. Wiley & Sons New York 1999.

Griffith et al. "Elevated brain scyllo-inositol concentrations in patients with Alzheimer's disease" NMR Biomed Dec. 2007 208:709-716.

Grzanna et al. "Ginger—An herbal medicinal product with broad anti-inflammatory actions" J. Medicinal Foods 2005 82:125-132.

Görtz et al. "Neuronal network properties of human teratocarcinoma cell line-derived neurons" Brain Res Aug. 20, 2004 10181:18-25.

Hampel et al., Core candidate neurochemical and imaging biomarkers of Alzheimer's disease, Alzheimers Dement (Jan. 2008), 4(1):38-48.

Hansson et al. "Reduced Levels of Amyloid-beta-Binding Proteins in Cerebrospinal Fluid from Alzheimer's Disease Patients" J Alzheimers Dis 2009 162:389-397.

Hisashi et al. "Heptatoproctective Constituents from Zedoariae Rhizoma: Absolute Stereostructures of Three New Carabrane-type Sesquiterpenes Curcumenolactones A B and C" Bioorganic & Med. Chem. 2001 9:909-916.

Hisashi et al. "Medicinal Foodstuffs. XXVIII.1 Inhibitors of Nitric Oxide Production and New Sesquiterpenes Zedoarofuran 4-Epicurcumenol Neocurcumenol Gajutsulactones A and B y and Zedoarolides A and B from Zedoariae Rhizoma" Chem. Pharm. Bull. 2001 4912 13-15:1558-1566.

Ho et al. "Heterogeneity in red wine polyphenolic contents differentially influences Alzheimer's disease-type neuropathology and cognitive deterioration" J Alzheimers Dis. 2009 161:59-72.

Hong et al. "Candidate anti-Abeta fluorine compounds selected from analogs of Amyloid imaging agents" Neurobiol Aging. Oct. 2010 3110:1690-1699.

Hong et al. "Combining the rapid MTT formazan exocytosis assay and the MC65 protection assay led to the discovery of carbazole analogs as small molecule inhibitors of Abeta oligomer-induced cytotoxicity" Brain Res. Jan. 26, 2007 11301:223-234.

Hong et al. "Inhibition of Alzheimer's Amyloid toxicity with a trycyclic pyrone molecule in vitro and in vivo" J Neurochem. Feb. 2009 1084:1097-1108.

Hsieh et al. "AMPAR removal underlies Abeta-induced synaptic depression and Dendritic spine loss" Neuron. Dec. 7, 2006 525:831-843.

International Search Report and Written Opinion dated Apr. 30, 2015 for PCTUS2015013754.

International Search Report and Written Opinion dated Feb. 25, 2013 for PCTUS2012052572.

Lacor et al. "Synaptic targeting by Alzheimer's-related Amyloid beta oligomers" J Neurosci. Nov. 10, 2004 2445:10191-10200.

International Search Report and Written Opinion dated Jan. 18, 2013 for PCTUS2012052578.

International Search Report and Written Opinion dated Jun. 10, 2010 for PCTUS2010030130.

International Search Report and Written Opinion dated Jun. 3, 2008 for PCTUS200779850.

International Search Report and Written Opinion dated Jun. 30, 2012 for PCTUS2011026530.

International Search Report and Written Opinion dated May 31, 2012 for PCTUS2012023483.

International Search Report and Written Opinion dated Sep. 21, 2018 for PCT/US2018/032726.

International Search Report and Written Opinion dated Sep. 24, 2010 for PCTUS2010044136.

Ishikawa et al. "The role of sigma-1 receptors in the pathophysiology of neuropsychiatric diseases" J. Receptor Ligand and Channel Res. 2009 retrieved from http:researchgate.netprofileMasotomo_Ishikawapublication49606718 <http://researchgate.net/profile/Masotomo_Ishikawa/publication/49606718>_the_role_of_signa-1_receptors_in_the_pathophysiology_of_ Neuropsychatric_diseases.

(56) References Cited

OTHER PUBLICATIONS

Jacobsen et al. "GSI-953 is a Protein APP-Selective Gamma-Secretase Inhibitor for the Treatment of Alzheimer's Disease" Oral 03-06: Therapeutics and Therapeutic Strategies: Novel Targets 2008 1.
Japan Office Action for JP 2016-549224 dated Oct. 9, 2018.
Japan Search Report for JP 2016-549224 dated Sep. 7, 2018.
Jiang et al. "Metal-Organic Conjugated Microporous Polymers" Agnew. Chem. Int. Ed. 2011 50:1072-1075.
Jin et al. "Novel tricyclic pyrone compounds prevent intracellular APP C99-induced cell death" J Mol Neurosci Aug.-Oct. 2002 191-2:57-61.
Johansson et al. "Physiochemicai characterization of the Alzheimer's disease-related peptides Abeta1-42Arctic and Abeta1-42wt" FEBS J. Jun. 2006 27312:2618-2630.
Kaech et al. "Culturing hippocampal neurons" Nat Protoc 2006 15:2406-2415.
Kamal et al. "Total synthesis of R- and S-turmerone and 7S9R-bisacumol by an efficient chemoenzymatic approach" Tetrahedron: Asymmetry 2009 20:1267-1271.
Kamenetz et al. "APP processing and synaptic function" Neuron. Mar. 27, 2003 376:925-937.
Kholodov et al., Clinical pharmacokinetics, Moscow, Medicine, 1985, pp. 83-98, 134-138, 160, 378-380.
Kimura "Chemical Structural Requirement in Gingerol Derivatives for Potentiation of Prostaglandin F2 alpha-induced Contraction in Isolated Mesenteric Veins of Mice" J. Pharmacobio-Dyn. 1989 12:220-227.
Klyubin et al. "Amyloid beta Protein Dimer-Containing Human CSF Disrupts Synaptic Plasticity: Prevention by Systemic Passive Immunization" J Neurosci. Apr. 16, 2008 2816:4231-4237.
Koffie et al. "Oligomeric amyloid beta associates with postsynaptic densities and correlates with excitatory synapse loss near senile plaques" Proc Natl Acad Sci USA Mar. 10, 2009 10610:4012-4017.
Kornhuber et al. "Cerebrospinal fluid and serum concentrations of the N-methyl-D-aspartate NMDA receptor antagonist memantine in man" Neurosci Lett Aug. 4, 1995 1952:137-139.
Kotilinek et al. "Reversible memory loss in a mouse transgenic model of Alzheimer's disease" J Neurosci. Aug. 1, 2002 2215:6331-6335.
Krafft et al. "ADDLs and the signaling web that leads to Alzheimer's disease" Neuropharmacology 2010 59:230-242.
Lacor et al. "Abeta oligomer-induced aberrations in synapse composition shape and density provide a molecular basis for loss and connectivity in Alzheimer's disease" J Neurosci. Jan. 24, 2007 274:796-807.
Rishton "Reactive compounds and in vitro false positives in HTS" DDT Sep. 9, 1997 29:382-384.
Rishton et al. "Computational approaches to the prediction of blood-brain barrier permeability: a comparative analysis of central nervous system drugs versus secretase inhibitors for Alzheimer's disease" Curr Opin Drug Discov Devel. May 2006 93:303-313.
Rowan et al. "Mechanisms of the inhibitory effects of Amyloid beta-protein on synaptic plasticity" Exp Gerontol. Nov.-Dec. 2004 3911-12:1661-1667.
Rönicke et al. "Abeta mediated diminution of MTT reduction—an artifact of single cell culture?" PloS One Sep. 18, 2008 39:e3236.
Sampson et al. "Metal protein attenuating compounds for the treatment of Alzheimer's disease review" The Cochrane Collaboration published in The Cochrane Library 2009 Issue 1.
Scheff et al. "Hippocampal synaptic loss in early Alzheimer's disease and mild cognitive impairment" Neurobiol Aging Oct. 2006 2710:1372-1384.
Scheff et al. "Synaptic alternations in CA1 mild Alzheimer's disease and mild cognitive impairment" Neurology 2007 68:1501-1508.
Sejnowski et al. "The Book of Hebb: Minireview" Neuron Dec. 1999 24:773-776.
Sergeev, et al. "Concise course in the molecular pharmacology," Moscow, (1975), 10-11 (In Russian—English translation not available).
Shankar et al. "Amyloid-beta protein dimmers isolated directly from Alzheimer's brains impair synaptic plasticity and memory" Nat Med. Aug. 2008 148:837-842.
Shankar et al. "Natural oligomers of the Alzheimer Amyloid-beta protein induce reversible synapse loss by-modulating an NMDA-type glutamate receptor-dependent signaling pathway" J Neurosci. Mar. 14, 2007 2711:2866-2875.
Shin et al. "Zingerone as an Antioxidant against Peroxynitrite" J. of Agric. & Food Chem. 2005 53:7617-7622.
Shrestha et al. Amyloid beta peptide adversely affects spine number and motility in hippocampal neurons Mol Cell Neurosci Nov. 2006 333:274-282.
Snyder et al. "Regulation of NMDA receptor trafficking by Amyloid-beta" Nat Neurosci. Aug. 2005 38:1051-1058.
Song et al. "Memantine protects rat cortical cultured neurons against ?-amyloid-induced toxicity by attenuating tau phosphorylation" European J. Neuro. 2008 28:1989-2002.
Subbarayappa et al."An efficient method for the synthesis of 2, 3-dihydro-1 H-isoindoles." Indian Journal of Chemistry 2009 438:545-552.
Supplementary European Search Report by the European Patent Office dated Jun. 19, 2017 for European Patent Application No. 15743281.6.
Supplementary European Search Report from European Patent Office dated Sep. 21, 2015 for European Patent Application No. 12825341.6.
Surh et al. "Enzymic Reduction of [6]-Gingerol a Major Pungent Principle of Ginger in the Cell-Free Preparation of Rat Liver" Life Sci. 1994 5419:321-326.
Terry "Cell death or synaptic loss in Alzheimer's disease" J Neuropathol Exp Neurol. Dec. 2000 5912:1118-1119.
Ting et al. "Amyloid precursor protein overexpression depresses excitatory transmission through both presynaptic and postsynaptic mechanisms" Proc Natl Acad Sci USA Jan. 2, 2007 1041:353-358.
Tomiyama et al. "A New Amyloid beta Variant Favoring oligomerization in Aizheimer's-type dementia" Ann Neurol Mar. 2008 633:377-387.
Tong et al. "beta-amyloid Peptide at Sublethal Concentrations Downregulates Brain-Derived Neurotrophic Factor Functions in Cultured Cortical Neurons" J. Neurosci. Jul. 28, 2004 2430:6799-6809.
Townsend et al. "Orally available compound prevents deficits in memory caused by the Alzheimer Amyloid-beta oligomers" Ann Neurol Dec. 2006 606:668-676.
Turner et al. "Roles of amyloid precursor protein and its fragments in regulating neural activity plasticity and memeory" Prog. in Neurobiol. 2003 70:1-32.
Uehara et al. "New Bisabolane Sesquiterpenoids from the Rhizomes of Curuma Xanthorrhiza Zinziberaceae" Chem. and Pharma. Bulletin 1989 371:237-240.
Verdile et al. "The role of beta amyloid in Alzheimer's disease: still a cause of everything or the only one who got caught?" Pharmacol Res Oct. 2004 504:397-409.
Walsh et al. "Certain inhibitors of synthetic Amyloid beta-peptide Abeta fibrillogenesis block oligomerization of natural Abeta and thereby rescue long-term potentiation" J Neurosci. Mar. 9, 2005 2510:2455-2462.
Walsh et al. "Naturally secreted oligomers of Amyloid beta protein potently inhibit hippocampal long-term potentiation in vivo" Nature Apr. 4, 2002 4166880:535-539.
Wang et al. "A Versatile Catalyst for Reductive Amination by Transfer Hydogenation" Agnew. Chem. Int. Ed. 2010 49:7548-7552.
Wang et al. "Block of Long-Term Potentiation by Naturally Secreted and Synthetic Amyloid beta-Peptide in Hippocampal Slices is Mediated Via Activation of the Kinases c-Jun N-Terminai Kinase Cyclin-Dependent Kinase 5 and p38 Mitogen-Activated Protein Kinase as well as Metabotropic Glutamate Receptor Type 5" J. Neurosci. Mar. 31, 2004 2413:3370-3378.
Wang et al. "Grape-derived polyphenolics prevent Abeta oligomerization and attenuate cognitive deterioration in a mouse model of Alzheimer's disease" J Neurosci. Jun. 18, 2008 2825:6388-6392.

(56) References Cited

OTHER PUBLICATIONS

Wang et al. "Moderate consumption of Cabernet Sauvignon attenuates Abeta neuropathology in a mouse model of Alzheimer's disease" FASEB J. Nov. 2006 2013:2313-2320.
Wang et al. "Soluble oligomers of beta Amyloid 1-42 inhibit long-term potentiation but not long-term depression in rat dentate gyrus" Brain Res. Jan. 11, 2002 9242:133-140.
Weiyan et al. "Research Advances on Chemistry and Pharmacology of Zingiber officinale" Chinese J. of Ethnomedicine and Ethnopharmacology 2008 9.
West et al. "Hippocampal neurons in pre-clinical Alzheimer's disease" Neurobiol Aging Oct. 2004 259:1205-1212.
Whitlock et al. "Learning induces long-term potentiation in the hippocampus" Science Aug. 25, 2006 3135790:1093-1097.
Wolozin "Cholesterol and the Biology of Alzheimer's Disease" Neuron Jan. 8, 2004 41:7-10.
Yang et al. "New ELISAs with high specificity for soluble oligomers of amyloid ?-protein detect natural A? oligomers in human brain but not CSF" Alzheimers Dement. Mar. 2013 92:99-112.
Yao et al. "The Ginkgo biioba extract EGb 761 rescues the PC12 neuronal cells from beta-amyloid-induced cell death by inhibiting the formation of beta-amyloid-derived diffusible neurotoxic ligands" Brain Res. Jan. 19, 2001 8891-2:181-190.
Yu et al. "Per-6-Substituted beta—Cyclodextrin Libraries Inhibit Formation of beta-Amyloid-Peptide Abeta-Derived Soluble Oligomers" J Mol Neurosci Aug.-Oct. 2002 191-2:51-55.
Zhang et al. "A Simple Statistical Parameter for Use in Evaluation and Validation of High Throughput Screening Assays" J Biomol Screen 1999 42:67-73.
Zhang et al. "Chiral Benzyl Centers 1-6 through Asymmetric Catalysis. A Three-Step Synthesis of R-Alpha-Curcumene via Asymmetric Hydrovinylation" Organic Letters American Chemical Society Aug. 3, 2004 618:3159-3161.
Zhao et al. "Amyloid beta oligomers induce impairment of neuronal insulin receptors" FASEB J. 2008 22:246-260.
Zhao et al. "Identification of antihypertensive drugs which inhibit Amyloid-beta protein oligomerization" J Alzheimers Dis. 2009 161:49-57.
Zlokovic "New therapeutic targets in the neurovascular pathway in Alzheimer's disease" Neurotherapeutics Jul. 2008 53:409-414.
Aboul-Enein et al. "Synthesis of certain 1 7 7-trimethylbicyclo 2.2.1 heptane derivatives with anticonfulsant hypoglycemic and anti-inflammatory potential" 2006 CASREACT 147:10056 Accession No. 2006:599283.
Adams et al. "The Leaf Essential Oils and Taxonomy of *Juniperus oxycedrus* L. subsp. *oxycedrus* subsp. *badia* H. Gay Debeaux and subsp. *macrocarpa* Sibth & Sm. Ball." J. Essent. Oil Res. Mar.Apr. 1999 11:167-172.
Albright "Diverse Approaches to Alzheimer's Therapies Continue to Show Progress at ICAD" International Conference on Alzheimer's Disease 2008 Jul. 26-31, 2008 Chicago Illinois.
Arai et al., "Chemically conditioned extracts of ginger oil: leadlike 'alkaloidal' compounds derived from natural extracts via reductive amination" Gen. Biochem. Biotech. and Pharma.—Poster Wednesday Jan. 25, 2006 Laguna DoubleTree Hotel.
Balaji et al., "Toxicity Prediction of Compounds from Turmeric" Food and Chemical Toxicology 2010 vol. 48 2951-2959.
Banerjee et al. "Chemical Modification of Turmeric Oil to More Value Added Products" Indian Perfumer 1981 vol. 25 25-30.
Barghorn et al. "Globular amyloid beta-peptide 1-42 oligomer—a homogenous and stable neurophathological protein in Alzheimer's disease" J. Neurochem. Nov. 2005 953:834-847.
Batra et al. "Hydrogenolysis of 3-methyl-4-phenylmethyl-52H-isoxazolone derivatives: A reinvestigation" Indian J. Chem. Jan. 1992 31B:60-62.
Beckurts et al. Archiv der Pharmazie und Berichte der Deutschen Phamazeutischen Gessellschaft 1927 265:15-26.
Begum et al. "Curcumin Structure—Function Bioavailability and Efficacy in Models of Neuroinflammation and Alzheimer's Disease" J. Pharma. Experimental Thera. Feb. 4, 2008 3261:196-208.

Belikov et al. V.G., "Pharmaceutical Chemistry," Moscow, Vyshaya Shkola Publishing House, (1993), 43-46.
Blossom et al. "Beyond mild cognitive impairmentl vascular cognitive impairment, no dementia" Alzheimers Res Ther. 2009: 1(1): 16 pages.
Bornholdt et al. "Ring Opening of Pymisyl-Protected Aziridines with Organocuprates" Chem. A European J. 2010 16:12474-12480.
Brody et al. "Amyloid-beta Dynamics Correlate with Neurological Status in the Injured Human Brain" Science Aug. 29, 2008 3215893:1221-1224.
Bu "Apolipoprotein E and its receptors in Alzheimer's disease: pathways pathogenesis and therapy" Nat Rev Neurosci. May 2009 105:333-344.
Calabrese et al. "Rapid concurrent alternations in pre- and postsynaptic structure induced by naturally-secreted Amyloid-beta protein" Mol. Cell. Neurosci. Feb. 2, 2007 1-11.
Campbell Med. Hypotheses 2001 563:388-391.
Casagrande et al. "Systhesis of Some Isoindolines and 1234-Tetrahydroisoquinolines and Their Evaluation as ?-Adrenergic and Adrenergic Neuron Blocking Agents" Il Farmaco Edizion Scientifica 1972 276:445-470.
Catalano et al. "The role of Amyloid-beta derived diffusible ligands ADDLs in Alzheimer's disease" Curr Top Med Chem. 2006 66:597-608.
Chang et al. "AMPA receptor downscaling at the onset of Alzheimer's disease pathology in double knockin mice" PNAS Feb. 28, 2006 1039:3410-3415.
Chang et al. "Supercritical carbon dioxide extraction of turmeric oil from Curcuma longa Linn and purification of turmerones" Separation and Purification Technology 2006 47:119-125.
Chemical Abstracts Registry No. 1099652-84-2 *.
Chemical Abstracts Registry No. 1099652-96-6.
Chemical Abstracts Registry No. 1307058-18-9 *.
Chemical Abstracts Registry No. 1307880-18-7 *.
Chemical Abstracts Registry No. 416864-44-3.
Chemical Abstracts Registry No. 416870-18-3.
Chin et al. "Fyn kinase induces synaptic and cognitive impairments in a transgenic mouse model of Alzheimer's disease" J. Neurosci. Oct. 19, 2005 2542:9694-9703.
Cirrito et al. "Endocytosis is required for synaptic activity-dependent release of Amyloid-beta in vivo" Neuron. Apr. 10, 2008 581:42-51.
Citron "Strategies for Disease Modification in Alzheimer's Disease" Nat Rev Neurosci. Sep. 2004 59:677-685.
Citron et al. "Evidence that the 42- and 40-amino acid forms of amyloid beta protein are generated from the beta-amyloid precursor protein by different protease activities" Proc. Nat. Acad. Sci. USA Nov. 1996 93:13170-13175.
Cleary et al. "Natural oligomers of the Amyloid-beta protein specifically disrupt cognitive function" Nat Neurosci. Jan. 2005 81:79-84.
Craig et al. "How to build a central synapse: clues from cell culture" Trends Neurosci. Jan. 2006 291:8-20.
Crawford et al. "Methalation of limonene. Novel method for the synthesis of bisabolane sesquiterpenes" J. Amer. Chem. Soc. Jun. 14, 1972 9412:4298-4306.
Dahlgren et al. "Oligomeric and Fibrillar Species of Amyloid-beta Peptides Differentially Affect Neuronal Viability" J Biol Chem. Aug. 30, 2002 27735:32046-32053.
Database CA Chemical Abstracts Service Columbus Ohio Alexander et al. "Terpenoids. XVIII Facile Elaboration of +− ar-turmerone to +− nuciferal via +−ar-curcumene" retrieved from STN Database Accession No. 1971:541008; and Alexander et al. "Terpenoids. XVIII Facile Elaboration of+− ar-turmerone to +−nuciferal via +−ar-curcumene" Indian Journal of Chemistry 1971 98:776-9.
Database CA Chemical Abstracts Service Columbus Ohio Duchene et al. "improved Syntheses of .+−.-ar-turmerone via organotin reagents" retrieved from STN Database Accession No. 1986:479177; and Duchene et al. "Improved Syntheses of .+−.-ar-turmerone via organotin reagents" Synthetic Communications 1985 1510:873-882.
Database CA Chemical Abstracts Service Columbus Ohio Marterosyan et al. "Synthesis and reactions of .beta gamma -unsaturated amines.

(56) References Cited

OTHER PUBLICATIONS

X.Condensation of .beta, .gamma-unsaturated amines with aromatichydrocarbons in the presence of aluminum chloride" retrieved from STN Database Accession No. 1744, database accession No. 1972:153257 (abstract) And Marterosyan et al. "Synthesis and reactions of .beta, .gamma-unsaturated amines.X Condensation of .beta, .gamma-unsaturated amines with aromatichydrocarbons in the presence of aluminum chloride."
Database CA Chemical Abstracts Service Columbus Ohio MASE, Dec. 8, 1989 "Preparation of pyridylziatholidinecarboxamide derivatives asplatelet-activating factor (PAF) antagonists" retrieved from STN Database Accession No. 1749 (abstract).
Database CA Chemical Abstracts Service Columbus Ohio Park et al. "Allylic Fluorination" retrieved from STN Database Accession No. 1989:8424; and Park et al. "Allylic Fluorination" Archives of Pharmacal Research 1987 104 239-44.
Davigulus et al. 2010, NIH Consensus and State of the Science Statement, 27(4), 1-30 (abstract attached).
De Felice et al. "A Oligomers Induce Neuronal Oxidative Stress through an N-Methyl-D-aspartate Receptor-dependent Mechanism That is Blocked by the Alzheimer Drug Memantine" J. Biol. Chem. 2007 282:11590-11601.
De Felice et al. "Targeting the neurotoxic species in Alzheimer's disease: inhibitors of Abeta oligomerization" FASEB J. Sep. 2004 1812:1366-1372.
Dedov et al. "Gingerols: a novel class of vanilloid receptor VR1 agonists" Br. J. Pharm. Nov. 2002 1376:793-798.
Denniff "Syntheses of the ±-[n]-Gingerois Pungent Principles of Ginger and Related Compounds through Regioselective Aldol Condensations: Relative Pungency Assays" J. Chem. Soc. Perkin 1 1981 82-87.
Dodart et al. "Immunization reverses memory deficits without reducing brain Abeta burden in Alzheimer's disease model" Nat Neurosci May 2002 55:452-457.
Doody et al. "Effect of dimebon on cognition activities of daily living behavior and global function in patients with mild-to-moderate Alzheimer's disease: a randomized double-blind placebo-controlled study" Lancet Jul. 19, 2008 3729634:207-215.
European Search Report and Written Opinion for EP 15743281 dated May 11, 2017.
European Search Report and Written Opinion for EP 18802363 dated Nov. 26, 2020.
Extended European Search Report by the European Patent Office dated Apr. 15, 2015 for European Patent Application No. 12824979.4.
Lambert et al. "Monoclonal antibodies that target pathological assemblies of Abeta" J Neurochem Jan. 2007 1001:23-35.
Lambert et al. Diffusible nonfibrillar ligands derived from Abeta1-42 are potent central nervous system neurotoxins Proc Natl Acad Sci USA May 26, 1998 9511:6448-6453.
Lannfelt et al. "Safety efficacy and biomarker findings of PBT2 in targeting Abeta as a modifying therapy for Alzheimer's disease: a phase lia double-blind randomized placebo-controlled trial" Lancet Neurol Sep. 2008 79:779-786.
Laurén et al. "Cellular prion protein mediates impairment of synaptic plasticity by Amyloid-beta oligomers" Nature Feb. 26, 2009 4577233:1128-1132.
Leal P. et al. "Functional Properties of Spice Extracts Obtained via Supercritical Fluid Extraction" J. Agri. Food Chem. 2003 519:2520-2525 Derwent Abstract.
Lecanu et al. "Identification of naturally occurring spirostenois preventing beta-amyloid-induced neurotoxicity" Steroids Jan. 2004 691:1-16.
Lesné et al. "A specific amyloid-beta protein assembly in the brain impairs memory" Nature Mar. 16, 2006 4407082:352-357.
Lesuisse et al. "Long-term culture of mouse cortical neurons as a model for neuronal development aging and death" J. Neurobiol. 2002 51:9-23.
Levine "Alzheimer's beta-peptide oligomer formation at physiologic concentrations" Anal. Biochem. Dec. 1, 2004 3351:81-90.

Levine "Biotin-avidin interaction-based screening assay for Alzheimer's beta-peptide oligomer inhibitors" Analytical Biochemistry 2006 356:265-272.
Li et al. "Soluble oligomers of Amyloid beta protein facilitate hippocampal long-term depression by disrupting neuronal glutamate uptake" Neuron. Jun. 25, 2009 626:788-801.
Li et al. "Total asymmetric synthesis of 7S9R-+-bisacumol" Tetrahedrom: Asymmetry 2003 14:75-78.
Liu et al. "Amyloid ? peptide alters intracellular trafficking and cholesterol homeostasis" Proc. Natl. Acad. Sci 1998 95:13266-3271.
Liu et al. "Cytotoxic Amyloid Peptides Inhibit Cellular 3-45-Dimethylthlazol-2yl-25-Diphenyltetrazolium Bromide MTT Reduction by Enhancing MTT Formazan Exocytosis" J Neurochem. Dec. 1997 696:2285-2293.
Liu et al. "Detecting bioactive Amyloid beta peptide species in Alzheimer's disease" J Neurochem. Nov. 2004 91:648-656.
Liu et al. "Treating Alzheimer's Disease by Inactivating Bioactive Amyloid beta Peptide" Curr Alzheimer Res Apr. 2006 32:129-135.
Lleó et al. "Clinical pathological and biochemical spectrum of Alzheimer disease associated with PS-1 mutations" Am J Geriatr. Psychiatry Mar.-Apr. 2004 122:146-156.
Look et al. "Discovery of ADDL-Targeting Small Molecule Drugs for Alzheimer's disease" Curr Alzheimer Res. Dec. 2007 45:562-567.
Maezawa et al. "A novel tricyclic pyrone compound ameliorates cell death associated with intracellular Amyloid-beta oligomeric complexes" J Neurochem. Jul. 2006 981:57-67.
Maier et al. "Synthesis and SAR Studies of 3-Substituted 1'-Benzylspiro[[2] benzoxepine1 4'-piperidines]" Euro. J. Org. Chem. Feb. 2003 20034:714-720.
Majno "Apoptosis oncosis and necrosis: an overview of cell death" Am J Pathol. Jan. 1995 1461:3-15.
Mann et al. "Amyloid angiopathy and variability in Amyloid beta deposition is determined by mutation position in presenilin-1-linked Alzheimer's disease" Am J Pathol. Jun. 2001 1586:2165-2175.
Masaki et al., "A Facile Regio- and Sterio-Specific Allylic Oxidation of Gem-dimethyl Olefins Via Addition of Benzenesulphenyl Chloride. Synthesis of Allylic Oxygenated Terpenes" J. Chem. Soc. Perkin. Trans. I Jul. 4, 1984 4912;1289-1295.
Masuda et al. "Antioxidant properties of gingeroi related compounds from ginger" Biofactors 2004 211-4:293-296.
Matsubara et al. Soluble Abeta homeostasis in AD and DS: impairment of anti-amyloidogenic protection by lipoproteins Neurobiol Aging Aug. 2004 257:833-84.1.
Matsuda et al., "Hepatoprotective Constituents from Zedoariae Rhozoma: Absolute Stereostructures of Three New Carabrane-type Sesquiterpenes Curcumenolactones A B and C" Bioorganic & Medicinal Chem. 2001 9:909-916.
Matsuda et al. "Medicinal foodstuffs. XXVIII. Inhibitors of nitric oxide production and new sesquiterpenes zedoarofuran 4-epicurcumenol neocumenol gajutsulactones A and B and zedoarolides A and B from Sedoariae Rhizoma" Chem. Pharma. Bulletin Pharmaceutical Society of Japan Dec. 1, 2001 4912:1558-1566.
Maurice et al. "The pharmacology of sigma-1 receptors" Pharma. and Thera. Nov. 2009 1242:195-206.
Mayer et al. "Discovery of Begacestat a Notch-1-Sparing ?-Secretase Inhibitor for the Treatment of Alzheimer's Disease" J Med Chem Oct. 3, 2008 51:7348-7351.
Miklossy et al. "Two novel presenilin-1 mutations Y256S and Q222H are associated with early-onset Alzheimer's disease" Neurobiol. Aging Sep. 2003 245:655-662.
Mori et al. "Synthesis of a Mixture of +−Dehydrojuvabione and its Stereoisomer" Tetrahedron Letters 1967 48:4853-4856.
Morris "Episodic-like memory in animals: psychological criteria neural mechanisms and the value of episodic-like tasks to investigate animal models of neurodegenerative disease" Philos Trans R Soc Lond B Biol Sci. Sep. 29, 2001 3561413:1453-1465.
Morris "The Organization of Behavior" Wiley New York 1949 Brain Research Bulletin May 19, 1999 505-6:437-438.

(56) References Cited

OTHER PUBLICATIONS

Mucke et al. "High-level neuronal expression of Abeta1-42 in wild-type human Amyloid protein precursor transfenic mice: synaptotoxicity without plaque formation" J Neurochem. Jun. 1, 2000 2011:4050-4058.
Mukaiyama et al., "N-Alkylation of Phthalimide, Carboxamide, and Sulfonamides By Oxidation-Reduction Condensation Using Di-tert-butyl-1,4-benzoquinone and Alkyl Diphenylphosphinite," Chemistry Letters, vol. 34, No. 2, Apr. 25, 2004, pp. 142-143.
Mustafa et al. "Drug Development Report 9: Pharmacology of Ginger Zingiber Officinale" J. Drug. Dev. 1993 61:25-39.
Negron et al. "Study of the asymmetric induction of the 13-dipolar cycloaddition of chiral azomXethine ylides with unactivated double bonds" CASREACT 1992 117:26230 Accession No. 1992:426230.
Nielsen et al. "Binding and Uptake of Abeta1-42 by Primary Human Astrocytes In Vitro" GLIA 2009 57:978-988.
Nikolaev et al. "APP binds DR6 to trigger axon pruning and neuron death via distrinct caspases" Nature Feb. 19, 2009 4577232:981-989.
Nomura et al. "Mechanism of impairment of long-term potentiation by Amyloid beta is independent of NMDA receptors or voltage-dependent calcium channels in hippocampal CA1 pyramidal neurons" Neurosci Lett. Dec. 31, 2005 3911-2:1-6.
Ono et al. "Effects of grape seed-derived polyphenols on Amyloid beta-protein self-assembly and cytotoxicity" J Biol Chem. Nov. 12, 2008 28347:32176-32187.
Plant et al. "The Production of Amyloid ? Peptide is a Critical Requirement for the Viability of Central Neurons" The Journal of Neuroscience Jul. 2003 2313:5531-5535.
Poling et al. "Oligomers of the Amyloid-beta protein disrupt working memory: confirmation with two behavioral procedures" Behav Brain Res. Nov. 21, 2008 1932:230-234.
Price et al. "Neuron number in the entorhinal cortex and CA1 in preclinical Alzheimer disease" Arch Neurol. Sep. 2001 589:1395-1402.
Priller et al. "Mutant presenilin 1 alters synaptic transmission in cultured hippocampal neurons" J Biol Chem. Jan. 12, 2007 2822:1119-1127.
Puzzo et al. "Amyloid-beta Peptide Inhibits Activation of the Nitric OxidecGMPcAMP-Responsive Element-Binding Protein Pathway during Hippocampal Synaptic Plasticity" J Neurosci Jul. 20, 2005 2529:6887-6897.
Puzzo et al. Picomolar Amyloid-beta positively modulates synaptic plasticity and memory in hippocampus J Neurosci. Dec. 31, 2008 2853:14537-14545.
Rana, et al. "Syntheses of tricyclic pyrones and pyridinones and protection of Abeta-peptide induced MC65 neuronal cell death" Bioorg Med Chem Lett Feb. 1, 2009 193:670-674.
Remington's Pharmaceutical Sciences Mack Publishing Company Easton Pennsylvania 1985.
Rishton "Nonleadlikeness and leadlikeness in biochemical screening" Drug Discov Today Jan. 15, 2003 82:86-96.
European Search Report and Written Opinion for EP18872712.6 dated Jul. 22, 2021.
International Search Report and Written Opinion for PCT/US2021/018023 dated Jun. 25, 2021.
International Search Report and Written Opinion for PCT/US2021/062850 dated Feb. 28, 2022.
International Search Report and Written Opinion dated Jul. 26, 2022 for PCT/US2022/020687.
Izzo et al. "Preclinical and clinical biomarker studies of CT1812: A novel approach to Alzheimer's disease modification" Alzheimer's Dement. 2021; 17: 1365-1382.
PubChem SID 285282520, Aurora Fine Chemicals LLC, Jan. 15, 2016, p. 2, figure.
Response to Restriction Requirement filed Sep. 7, 2022 in U.S. Appl. No. 16/758,368.
Non-Final Office Action dated Nov. 22, 2022 in U.S. Appl. No. 16/758,368.

\* cited by examiner

ISOINDOLINE COMPOSITIONS AND METHODS FOR TREATING NEURODEGENERATIVE DISEASE

The present application is a Continuation of U.S. application Ser. No. 16/230,238, filed Dec. 21, 2018, now U.S. Pat. No. 10,611,728, which is a Continuation of U.S. application Ser. No. 15/700,923, filed Sep. 11, 2017, now U.S. Pat. No. 10,207,991, which is a continuation of U.S. application Ser. No. 15/115,187, filed Sep. 14, 2016, now U.S. Pat. No. 9,796,672, which is a U.S. national stage filing under 35 U.S.C. § 371 of International Application No. PCT/US2015/013754, filed Jan. 30, 2015, which claims priority to U.S. Provisional Application Ser. No. 61/934,528, filed Jan. 31, 2014, the disclosures of which are herein incorporated by reference in their entirety.

FIELD

Novel isoindoline compounds that bind to the sigma-2 receptor, pharmaceutical compositions comprising such compounds, and methods for inhibiting or restoring synapse loss in neuronal cells, modulating a membrane trafficking change in neuronal cells, and treating cognitive decline and neurodegenerative diseases and disorders are provided.

BACKGROUND

There are only five medications currently FDA-approved for the treatment of Alzheimer's Disease (AD). Four are cholinesterase inhibitors: tacrine (COGNEX®; Sciele), donepezil (ARICEPT®; Pfizer), rivastigmine (EXELON®; Novartis), and galantamine (RAZADYNE®; Ortho-Mc-Neil-Janssen). Donepezil, rivastigmine, and galantamine are successors to tacrine, a first generation compound rarely prescribed because of the potential for hepatotoxicity; they are roughly equally efficacious at providing symptomatic improvement of cognition and function at all stages of AD. The fifth approved medication is memantine (NAMENDA®; Forest), a low-affinity, use dependent N-methyl-D-aspartate glutamate receptor antagonist that offers similar benefits, but only in moderate to severe AD. The clinical effects of these compounds are small and impermanent, and currently available data are inconclusive to support their use as disease modifying agents. See, e.g., Kerchner et al, 2010, *Bapineuzumab*, Expert Opin Biol Ther., 10(7):1121-1130. Clearly, alternative approaches to treatment of AD are required.

Certain isoindoline compounds are provided that act as sigma-2 receptor functional antagonists and inhibit the deleterious effects of soluble A oligomers. In some embodiments, isoindoline sigma-2 receptor antagonist compounds and compositions are used to treat or prevent synaptic dysfunction in a subject.

SUMMARY

Novel isoindoline compounds that bind to the sigma-2 receptor, pharmaceutical compositions comprising such compounds, and methods for inhibiting or restoring synapse loss in neuronal cells, modulating a membrane trafficking change in neuronal cells, and treating cognitive decline and neurodegenerative diseases and disorders are provided.

In some embodiments, isoindoline compounds and pharmaceutically acceptable salts thereof according to Formula I and/or Formula II, or a pharmaceutically acceptable salt thereof, exhibit sigma-2 receptor antagonist activity, and also exhibit other aspects of a particular therapeutic phenotype, and thus inhibit deleterious effects of soluble amyloid-beta ("Abeta", "Aβ") peptides and oligomers and other soluble species thereof on neuronal cells, as defined below, and, consequently, can be used to treat conditions, including diseases and disorders, associated with Abeta oligomer-induced pathology, such as Alzheimer's disease.

Soluble Abeta oligomers behave like reversible pharmacological ligands that bind to specific receptors and interfere with signaling pathways critical for normal synaptic plasticity, ultimately resulting in spine and synapse loss. It has been discovered that isoindoline compounds according to Formula I, as provided herein, that bind to the sigma-2 receptor and that behave as functional neuronal antagonists exhibit pharmacological competition with Abeta oligomers. Isoindoline sigma-2 antagonist compounds as described herein thus can decrease or prevent Abeta oligomer effects such as Abeta induced cellular toxicity. Excluded are certain compounds of the prior art. Also provided are methods for inhibiting effects of Abeta oligomers or other soluble Abeta species on a neuronal cell and more generally amyloid beta pathologies comprising contacting the cell with a sigma-2 antagonist according to Formula I and/or Formula II, or a pharmaceutically acceptable salt thereof. In some embodiments, methods are provided for treating early stages of Alzheimer's disease comprising administering a therapeutically effective amount of a sigma-2 functional antagonist according to Formula I and/or Formula II, or a pharmaceutically acceptable salt thereof.

In one embodiment, an isolated compound, or a pharmaceutically acceptable salt thereof, is provided according to Formula I:

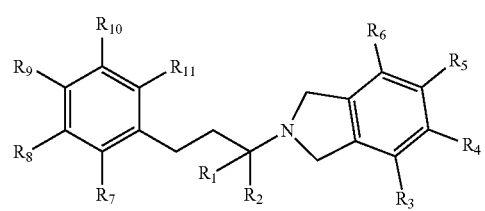

wherein:
$R_1$ and $R_2$ are each independently selected from H, $C_1$-$C_6$ alkyl, or $CH_2OR'$; where $R'$=H or $C_1$-$C_6$ alkyl;

$R_3$, $R_4$, $R_5$, and $R_6$ are each independently selected from H, $C_1$-$C_6$ alkyl, OH, $OCH_3$, $OCH(CH_3)_2$, $OCH_2CH(CH_3)_2$, $OC(CH_3)_3$, $O(C_1$-$C_6$ alkyl), $OCF_3$, $OCH_2CH_2OH$, $O(C_1$-$C_6$ alkyl)OH, $O(C_1$-$C_6$ haloalkyl), F, Cl, Br, I, $CF_3$, CN, $NO_2$, $NH_2$, $C_1$-$C_6$ haloalkyl, $C_1$-$C_6$ hydroxyalkyl, $C_{1-6}$ alkoxy $C_{1-6}$alkyl, aryl, heteroaryl, $C_{3-7}$ cycloalkyl, heterocycloalkyl, alkylaryl, heteroaryl, $CO_2R'$, $C(O)R'$, $NH(C_{1-4}$ alkyl), $N(C_{1-4}$ alkyl)$_2$, $NH(C_{3-7}$ cycloalkyl), $NHC(O)(C_{1-4}$ alkyl), $CONR'_2$, $NC(O)R'$, $NS(O)_nR'$, $S(O)_nNR'_2$, $S(O)_nR'$, $C(O)O(C_{1-4}$ alkyl), $OC(O)N(R')_2$, $C(O)$ $(C_{1-4}$ alkyl), and $C(O)NH(C_{1-4}$ alkyl); where n=0, 1, or 2; R' are each independently H, $CH_3$, $CH_2CH_3$, $C_3$-$C_6$ alkyl, $C_1$-$C_6$ haloalkyl; or optionally substituted aryl, alkylaryl, piperazin-1-yl, piperidin-1-yl, morpholinyl, heterocycloalkyl, heteroaryl, $C_{1-6}$ alkoxy, $NH(C_{1-4}$ alkyl), or $NH(C_{1-4}$ alkyl)$_2$, wherein optionally substituted group is selected from $C_1$-$C_6$ alkyl or $C_2$-$C_7$ acyl;

or $R_3$ and $R_4$, together with the C atom to which they are attached form a form a 4-, 5-, 6- 7- or 8-membered cycloalkyl, aryl, heteroaryl, or heterocycloalkyl that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^3$ and $R^4$, or $R^4$ and $R^5$, are each independently selected from a bond, C, N, S, and O; or $R_3$ and $R_4$ are linked together to form a —O—$C_{1-2}$ methylene-O— group;

or $R_4$ and $R_5$, together with the C atom to which they are attached form a form a 4-, 5-, 6- 7- or 8-membered cycloalkyl, aryl, heteroaryl, or heterocycloalkyl that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^3$ and $R^4$, or $R^4$ and $R^5$, are each independently selected from a bond, C, N, S, and O; or $R_4$ and $R_5$ are linked together to form a —O—$C_{1-2}$ methylene-O— group;

$R_7$, $R_8$, $R_9$, $R_{10}$, and $R_{11}$ are each independently selected from H, $C_1$-$C_6$ alkyl, OH, $OCH_3$, $OCH(CH_3)_2$, $OCH_2CH(CH_3)_2$, $OC(CH_3)_3$, $O(C_1$-$C_6$ alkyl), $OCF_3$, $OCH_2CH_2OH$, $O(C_1$-$C_6$ alkyl)OH, $O(C_1$-$C_6$ haloalkyl), $O(CO)R'$, F, Cl, Br, I, $CF_3$, CN, $NO_2$, $NH_2$, $C_1$-$C_6$ haloalkyl, $C_1$-$C_6$ hydroxyalkyl, $C_{1-6}$ alkoxy $C_{1-6}$alkyl, aryl, heteroaryl, $C_{3-7}$ cycloalkyl, heterocycloalkyl, alkylaryl, heteroaryl, $CO_2R'$, $C(O)R'$, $NH(C_{1-4}$ alkyl), $N(C_{1-4}$ alkyl)$_2$, $NH(C_{3-7}$ cycloalkyl), $NHC(O)(C_{1-4}$ alkyl), $CONR'_2$, $NC(O)R'$, $NS(O)_nR'$, $S(O)_nNR'_2$, $S(O)_nR'$, $C(O)O(C_{1-4}$ alkyl), $OC(O)N(R')_2$, $C(O)$ ($C_{1-4}$ alkyl), and $C(O)NH(C_{1-4}$ alkyl); where n=0, 1, or 2; R' are each independently H, $CH_3$, $CH_2CH_3$, $C_3$-$C_6$ alkyl, $C_1$-$C_6$ haloalkyl, aryl, alkylaryl, piperazin-1-yl, piperidin-1-yl, morpholinyl, heterocycloalkyl, heteroaryl, $C_{1-6}$ alkoxy, $NH(C_{1-4}$ alkyl), or $NH(C_{1-4}$ alkyl)$_2$;

or $R_7$ and $R_8$, together with the N or C atoms to which they are attached form a form a 4-, 5-, 6- 7- or 8-membered cycloalkyl, aryl, heterocycloalkyl or heteroaryl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^9$ and $R^{10}$ are each independently selected from a bond, C, N, S, and O; or $R_7$ and $R_8$ are linked together to form a —O—$C_{1-2}$ methylene-O— group;

or $R_8$ and $R_9$, together with the N or C atoms to which they are attached form a form a 4-, 5-, 6- 7- or 8-membered cycloalkyl, aryl, heterocycloalkyl or heteroaryl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^9$ and $R^{10}$ are each independently selected from a bond, C, N, S, and O; or $R_8$ and $R_9$ are linked together to form a —O—$C_{1-2}$ methylene-O— group, wherein each of the O, $C_{1-6}$ alkyl, $C_{1-6}$ haloalkyl, heteroaryl, aryl, heteroaryl, heterocycloalkyl, and cycloalkyl is optionally independently substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

with the proviso that the following compounds are excluded:

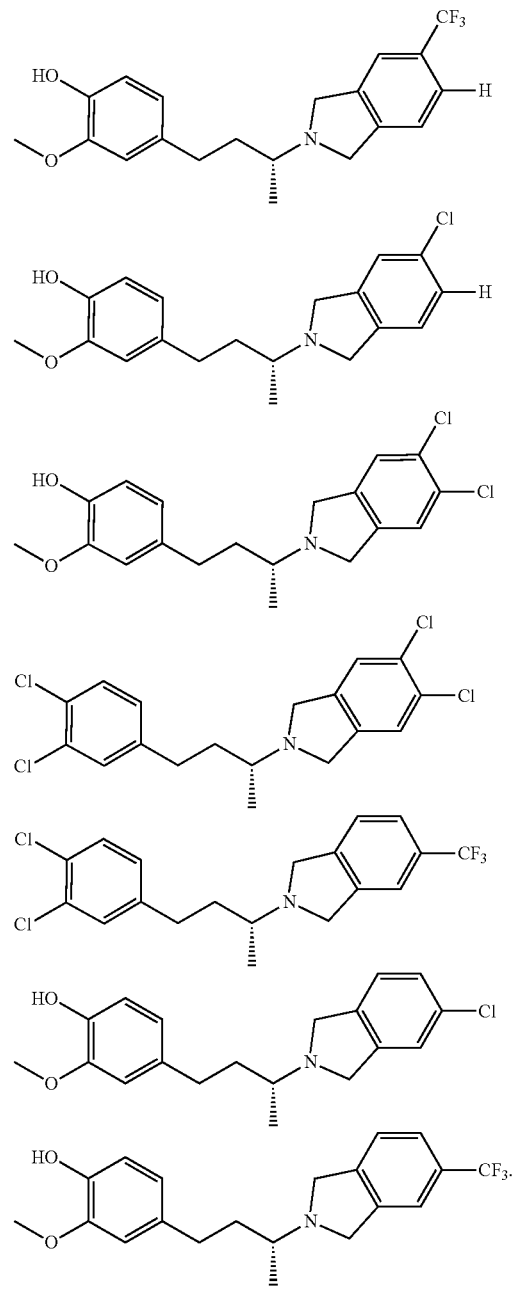

In another embodiment, a compound, or pharmaceutically acceptable salt thereof, is provided according to Formula I, wherein $R_1$ and $R_2$ are each independently selected from H or $CH_3$; $R_3$, $R_4$, $R_5$, and $R_6$ are each independently selected from H, $C_1$-$C_6$ alkyl, OH, $OCH_3$, $O(C_1$-$C_6$ alkyl), $O(C_1$-$C_6$ haloalkyl), F, Cl, $CF_3$, aryl, heteroaryl, $C_{3-7}$ cycloalkyl, $CO_2R'$, $C(O)R'$, $OC(O)N(R')_2$, $CONR'_2$, $NC(O)R'$, $NS(O)_nR'$, $S(O)_nNR'_2$, $S(O)R'$; where n=0, 1, or 2; R' are each independently H, $CH_3$, $CH_2CH_3$, $C_3$-$C_6$ alkyl, $C_1$-$C_6$ haloalkyl; or optionally substituted piperazin-1-yl, piperidin-1-yl, morpholinyl, heterocycloalkyl, or aryl, wherein optionally substituted group is selected from $C_1$-$C_6$ alkyl or $C_2$-$C_7$ acyl; or $R_3$ and $R_4$, together with the C atom to which they are attached, form a 5-, or 6-membered $C_{3-7}$cycloalkyl, or aryl; or $R_4$ and $R_5$, together with the C atom to which they are attached, form a $C_{3-7}$cycloalkyl, or a 5- or 6-membered aryl; or $R_3$ and $R_4$ are linked together to form a —O—$C_{1-2}$ methylene-O— group; or $R_4$ and $R_5$ are linked together to form a —O—$C_{1-2}$ methylene-O— group; and $R_7$, $R_8$, $R_9$, $R_{10}$, and $R_{11}$ are each independently selected from H, OH, $CH_3$, $CH_2CH_3$, F, Cl, $CF_3$, $OCF_3$, $C_1$-$C_6$ haloalkyl, $OCH_3$, $O(C_1$-$C_6$ alkyl), $OCH_2CH_2OH$, $O(C_1$-$C_6$ alkyl)OH, aryl, heteroaryl, $C_{3-7}$ cycloalkyl, alkylaryl, $CO_2R'$, $CONR'_2$, $S(O)_nNR'_2$, $S(O)_nR'$, $C(O)O(C_{1-4}$ alkyl), $OC(O)N(R')_2$, and $C(O)NH(C_4$ alkyl); where n=0, 1, or 2; R' are each independently H, $C_1$-$C_6$ alkyl, $C_1$-$C_6$ haloalkyl, aryl, alkylaryl, or $C_{1-6}$ alkoxy.

In a further embodiment, a compound, or pharmaceutically acceptable salt thereof, is provided according to Formula I, wherein $R_7$, $R_{10}$, $R_{11}$ are each H; $R_3$ and $R_4$ are each independently selected from H, F, Cl, $S(O)_nR'$, $C(O)R'$, wherein n=2, and R' is selected from $CH_3$, piperazin-1-yl, piperidin-1-yl, morpholinyl; $R_8$ is selected from OH, $OCH_3$, $OCH(CH_3)_2$, $OCH_2CH(CH_3)_2$, or $OC(CH_3)_3$; and $R_9$ is OH.

In another embodiment, a compound, or pharmaceutically acceptable salt thereof, is provided selected from the group consisting of:

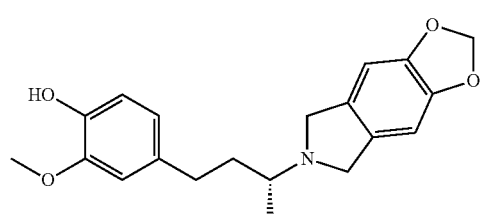

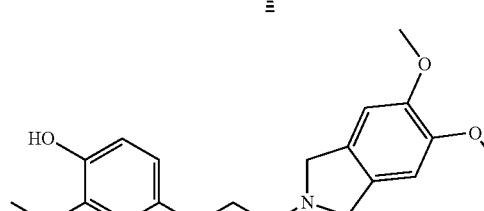

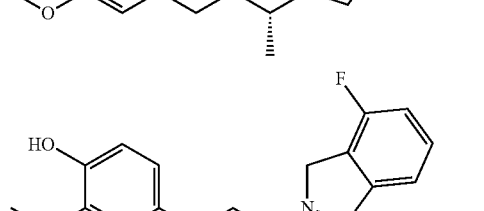

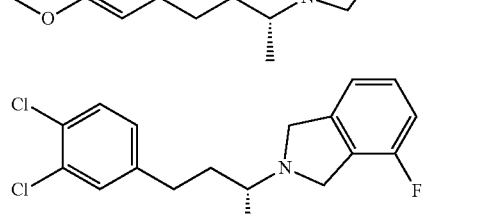

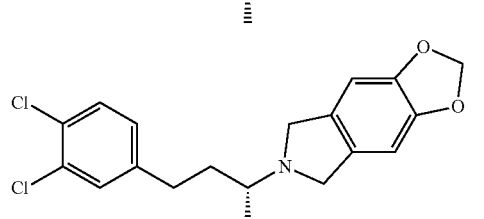

-continued

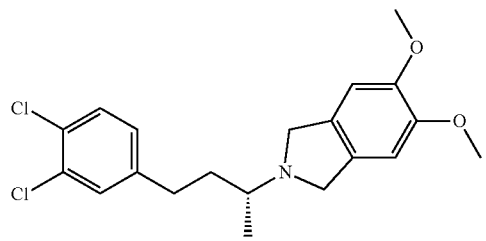

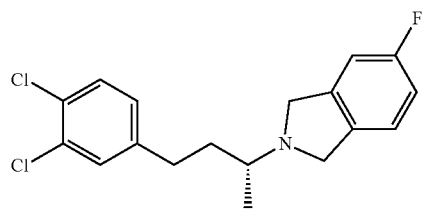

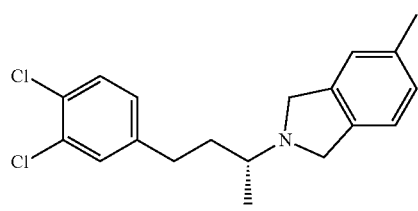

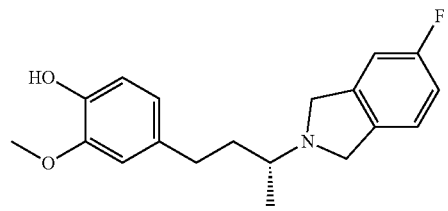

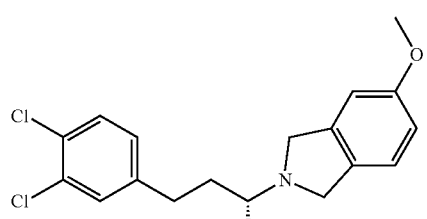

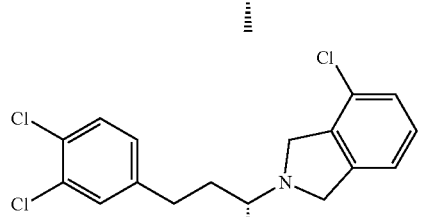

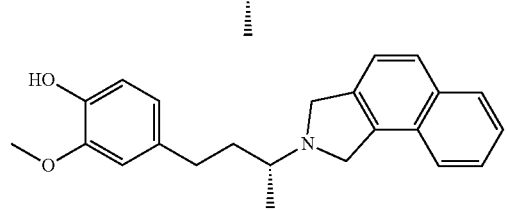

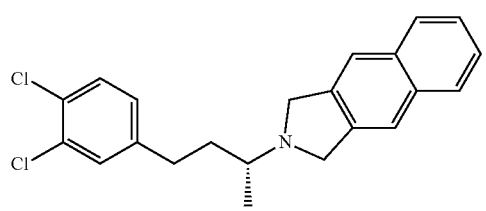

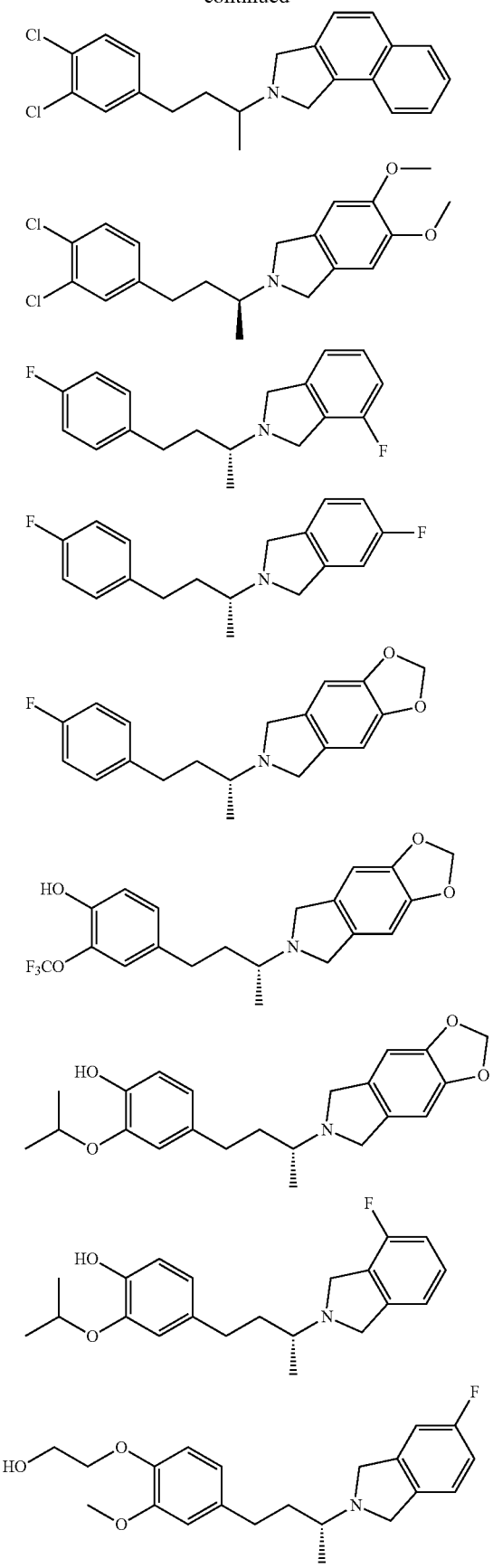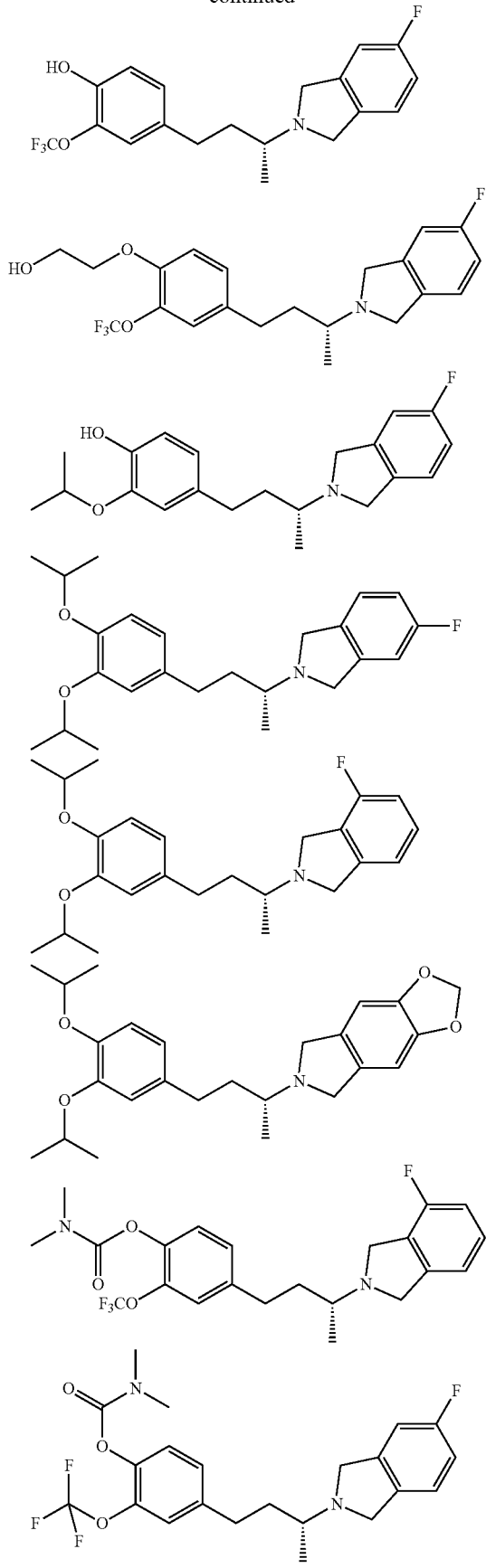

-continued

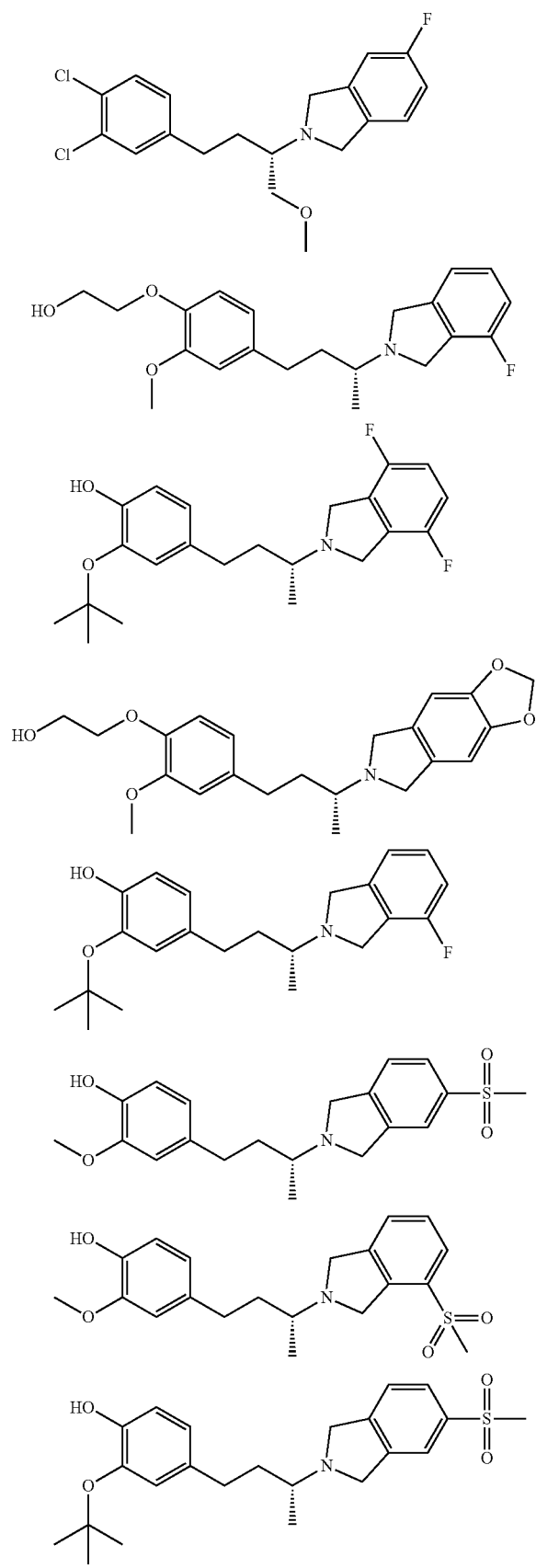

-continued

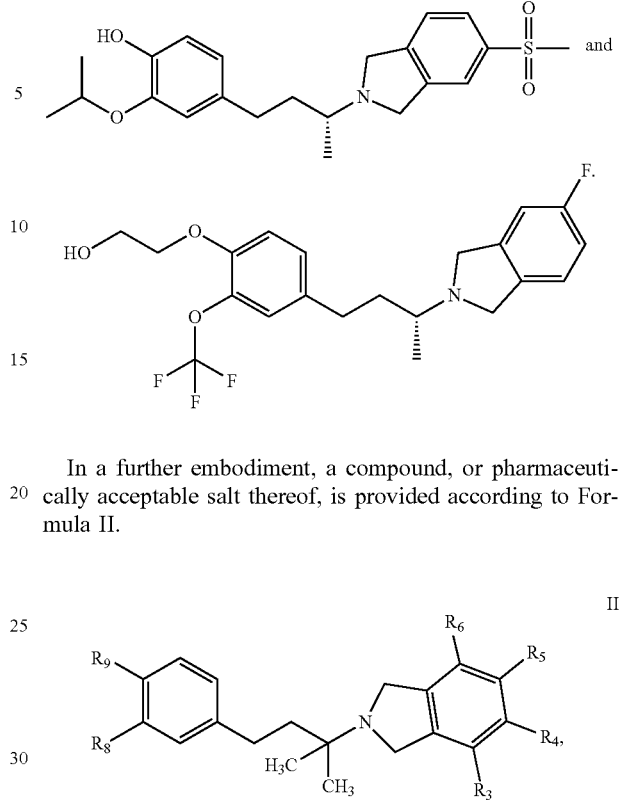

In a further embodiment, a compound, or pharmaceutically acceptable salt thereof, is provided according to Formula II.

wherein $R_3$, $R_4$, $R_5$, and $R_6$ are each independently selected from H, Cl, F, OH, $CH_3$, $C_{1-6}$ alkyl, $OCH_3$, $OCH(CH_3)_2$, $OCH_2CH(CH_3)_2$, $OC(CH_3)_3$, $OC_{1-6}$ alkyl, aryl, heteroaryl, heterocycloalkyl, $CO_2R'$, $CONR'_2$, $NC(O)R'$, $NS(O)_nR'$, $S(O)_nNR'_2$, $S(O)_nR'$, $C(O)R'$, $OC(O)N(R')_2$, or $C(O)NH(C_{1-4}$ alkyl), wherein n=0, 1, or 2; and R' are each independently H, $C_1$-$C_6$ alkyl, $C_1$-$C_6$ haloalkyl; or optionally substituted aryl, alkylaryl, piperazin-1-yl, piperidin-1-yl, morpholinyl, heterocycloalkyl, heteroaryl, $C_{1-6}$ alkoxy, NH($C_{1-4}$ alkyl), or NH($C_{1-4}$ alkyl)$_2$, wherein optionally substituted group is selected from $C_1$-$C_6$ alkyl or $C_2$-$C_7$ acyl; or $R_3$ and $R_4$, together with the C atom to which they are attached, form a 6-membered aryl; or $R_3$ and $R_4$ are linked together to form a —O—$C_{1-2}$ methylene-O— group; or $R_4$ and $R_5$, together with the C atom to which they are attached, form a 6-membered aryl; or $R_4$ and $R_5$ are linked together to form a —$C_{1-2}$ methylene-O— group; and $R_8$ and $R_9$ are each independently selected from H, Cl, F, OH, $CH_3$, $C_{1-6}$ alkyl, $OCH_3$, $OCH(CH_3)_2$, $OCH_2CH(CH_3)_2$, $OC(CH_3)_3$, $O(CO)R'$, $OC_{1-6}$ alkyl, aryl, heteroaryl, heterocycloalkyl, $CO_2R'$, $CONR'_2$, $NC(O)R'$, $NS(O)_nR'$, $S(O)_nNR'_2$, $S(O)_nR'$, $OC(O)N(R')_2$, or $C(O)NH(C_{1-4}$ alkyl); or $R_8$ and $R_9$, together with the N or C atoms to which they are attached form a form a 4-, 5-, 6- 7- or 8-membered cycloalkyl, aryl, heterocycloalkyl or heteroaryl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^9$ and $R^{10}$ are each independently selected from a bond, C, N, S, and O; or $R_8$ and $R_9$ are linked together to form a —O—$C_{1-2}$ methylene-O— group.

In a further embodiment, a compound, or pharmaceutically acceptable salt, is provided according to Formula II, wherein at least one of $R_3$, $R_4$, $R_5$ and $R_6$ is not H; and at least one of $R_8$ and $R_9$ is not H.

In another embodiment, a compound or pharmaceutically acceptable salt according to formula II is provided, wherein $R_7$, $R_{10}$, $R_{11}$ are each H; $R_3$ and $R_4$ are each independently selected from H, F, Cl, $S(O)_nR'$, $C(O)R'$, wherein n=2, and R' is selected from $CH_3$, or optionally substituted piperazin-1-yl, piperidin-1-yl, or morpholinyl, wherein optionally substituted group is selected from $C_1$-$C_6$ alkyl or $C_2$-$C_7$ acyl; $R_8$ is selected from OH, Cl, $OCH_3$, $OCH(CH_3)_2$, $OCH_2CH(CH_3)_2$, or $OC(CH_3)_3$; and $R_9$ is OH or Cl.

In a further embodiment, a compound, or pharmaceutically acceptable salt, is provided according to Formula II, wherein $R_3$ and $R_4$ are each independently selected from H, F, Cl, $S(O)_nR'$, $C(O)R'$, wherein n=2, and R' is selected from $CH_3$, piperazin-1-yl, piperidin-1-yl, or morpholinyl; $R_5$ and $R_6$ are each H; $R_8$ is selected from OH, $OCH_3$, $OCH(CH_3)_2$, $OCH_2CH(CH_3)_2$, or $OC(CH_3)_3$; and $R_9$ is OH.

In a further embodiment, a compound, or pharmaceutically acceptable salt thereof, is selected from the group consisting of

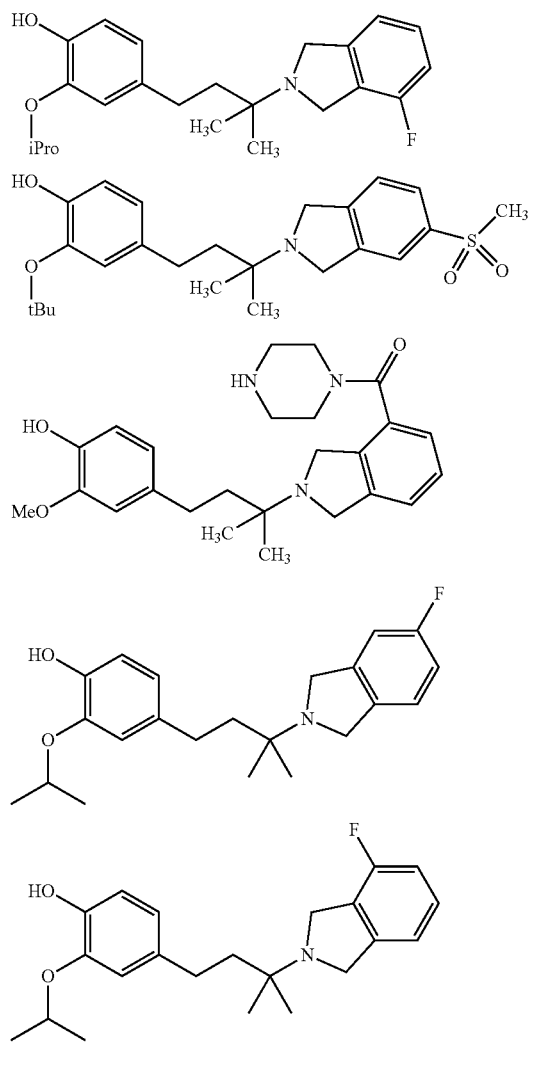

-continued

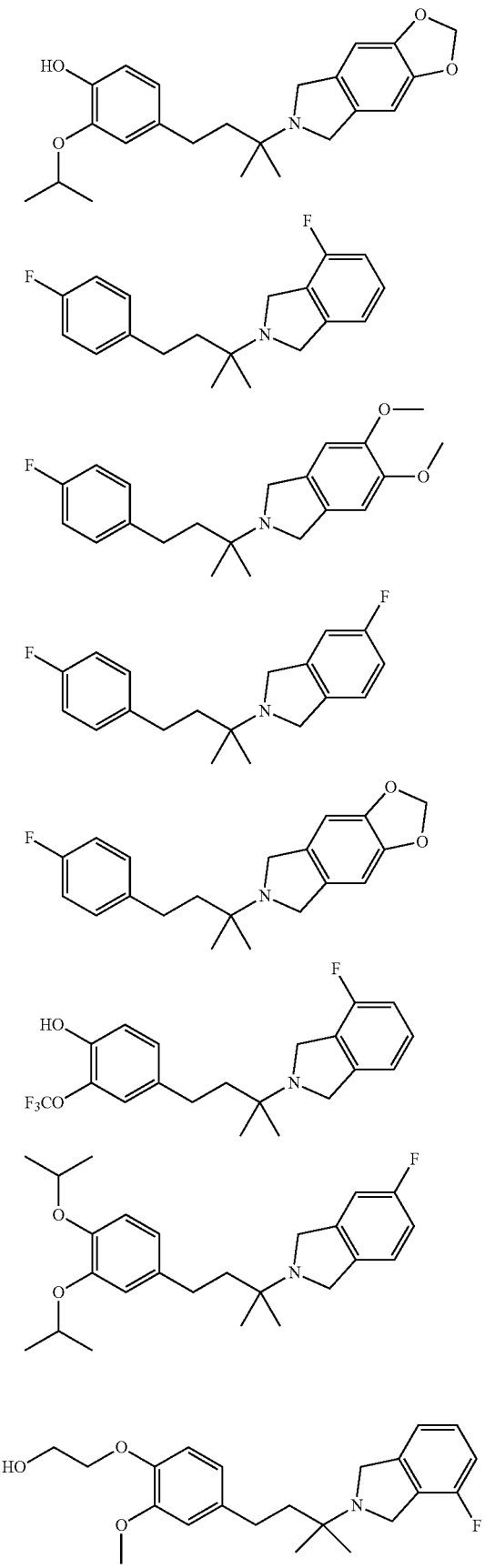

-continued
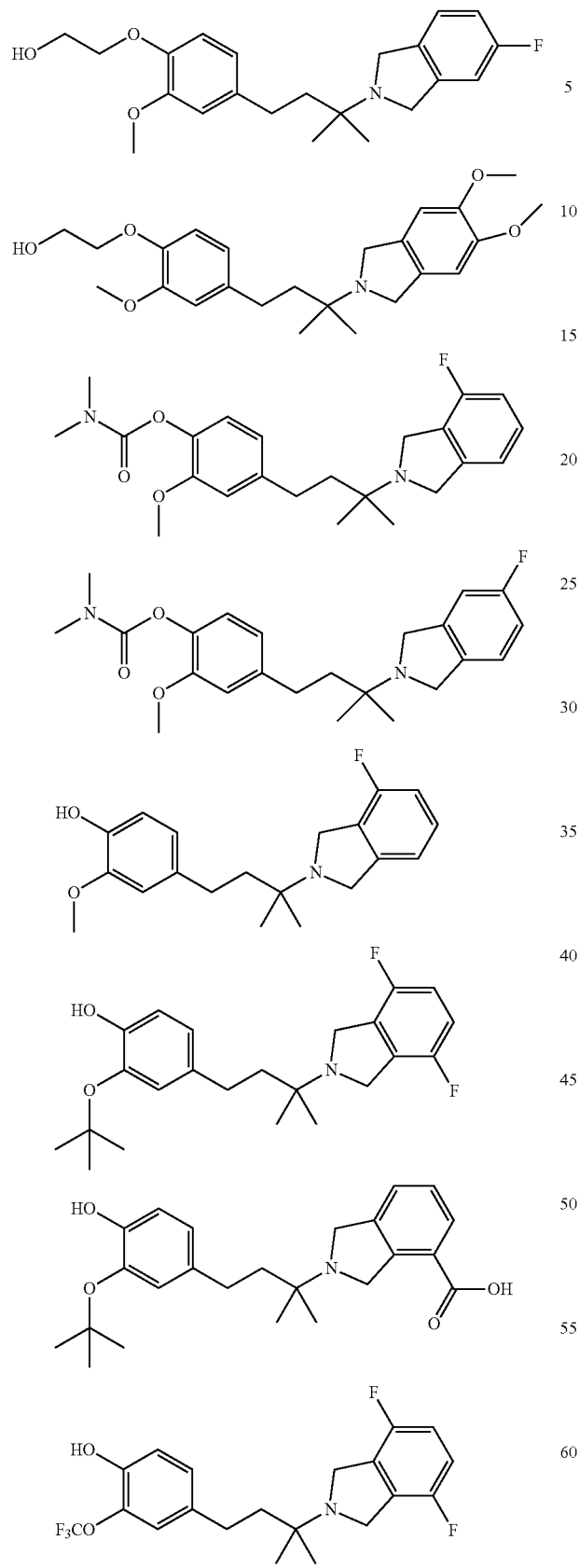
-continued
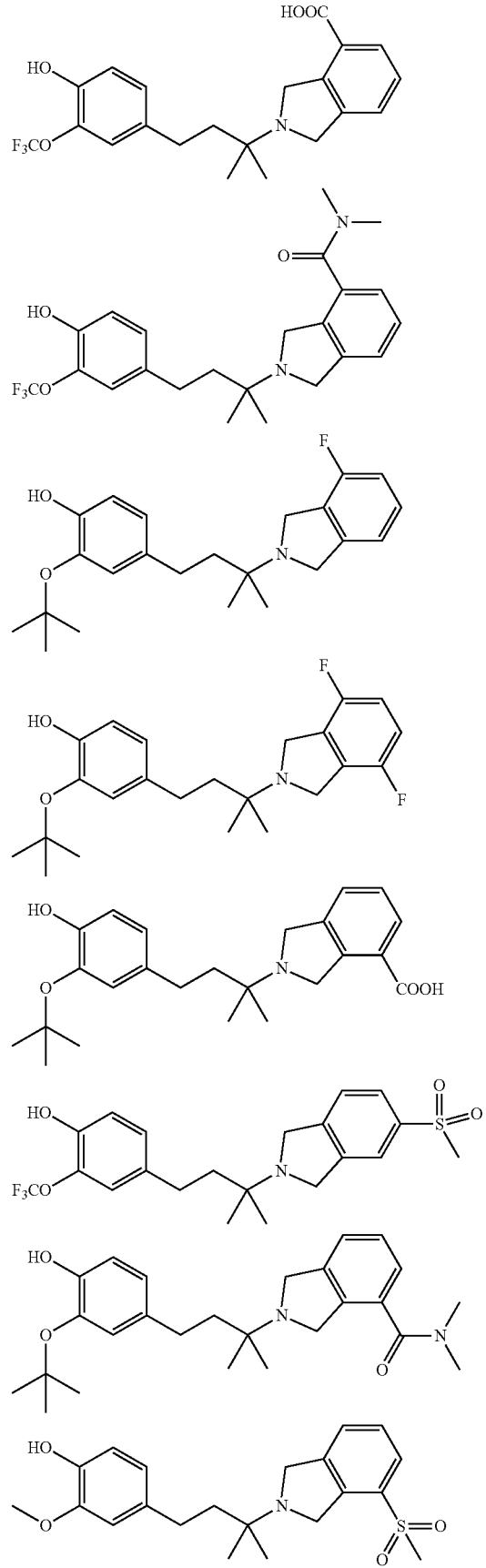

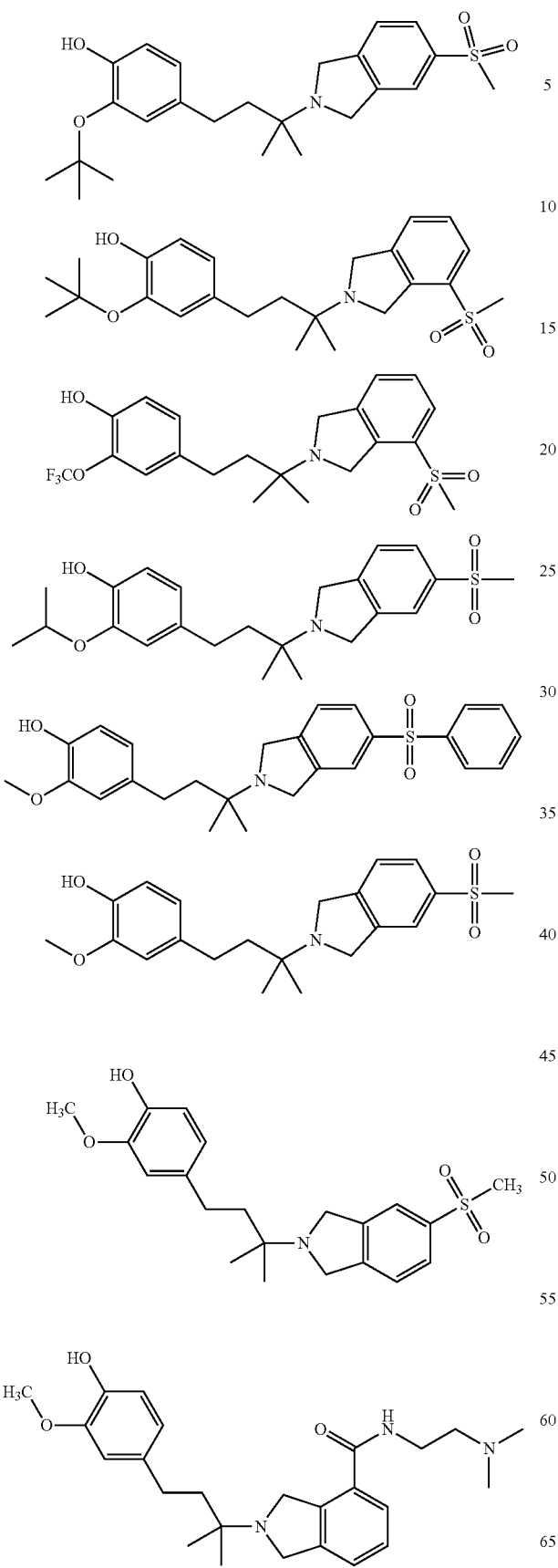
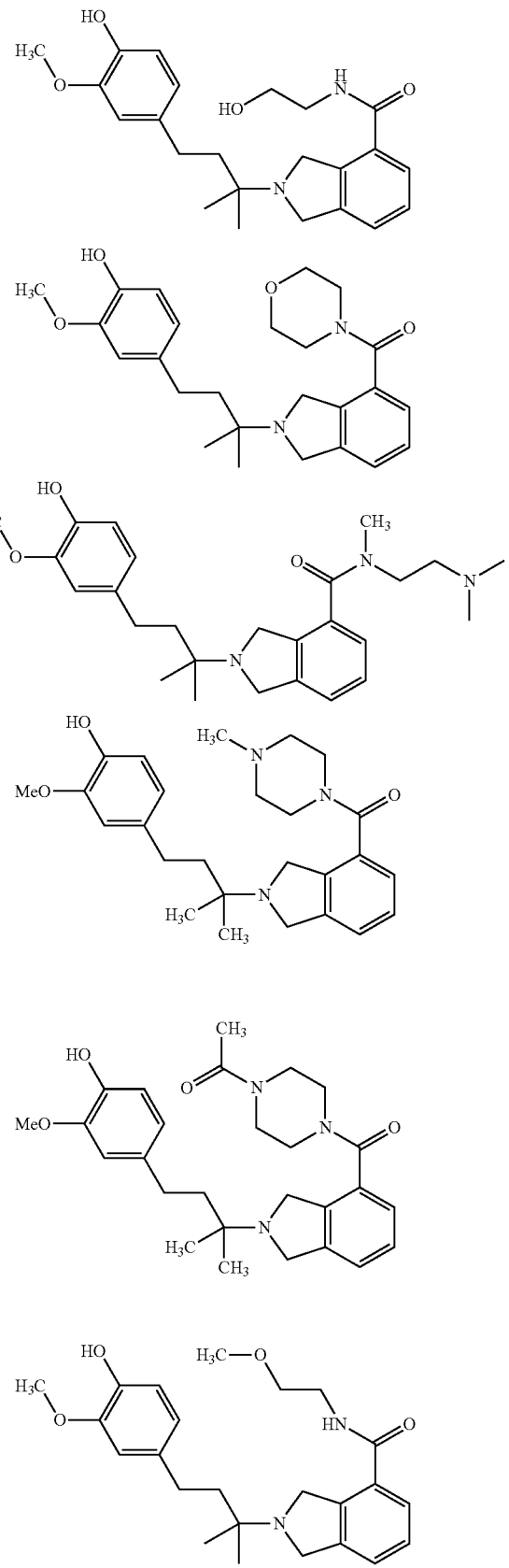

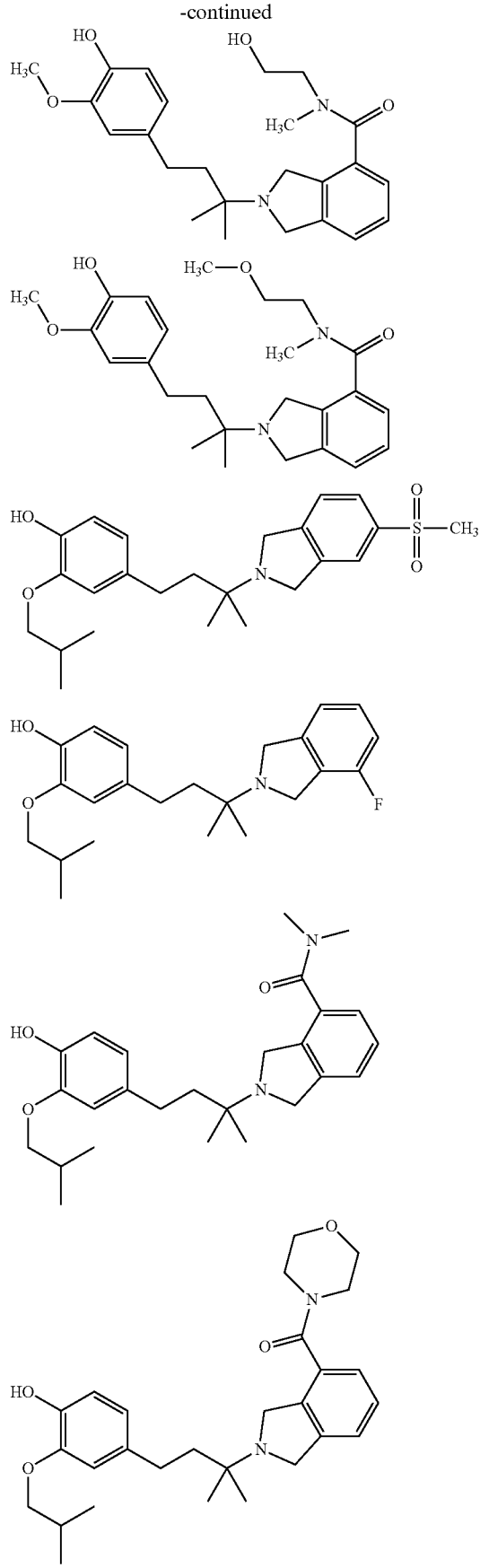
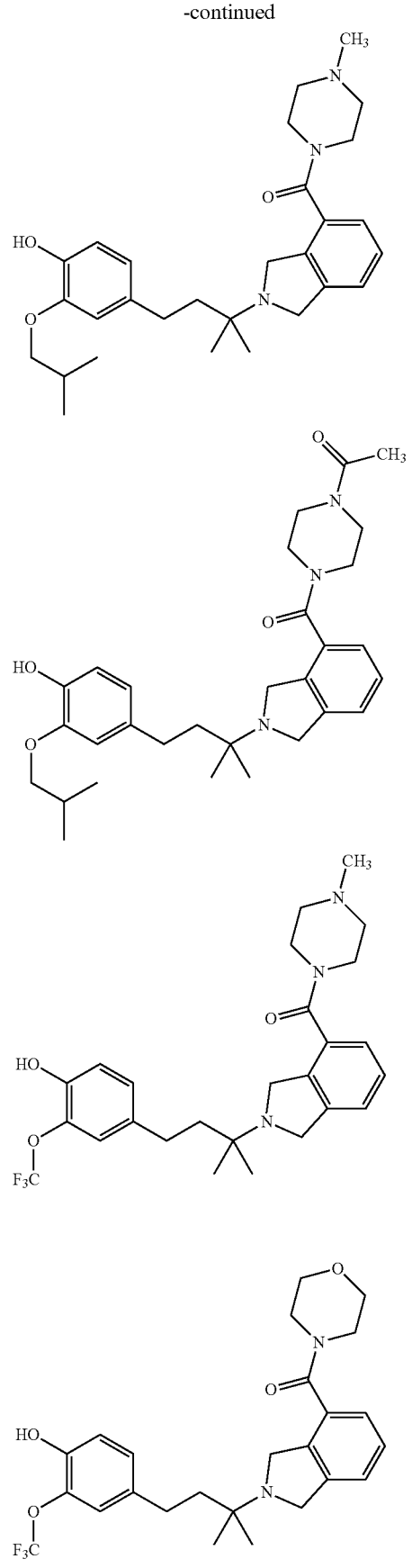

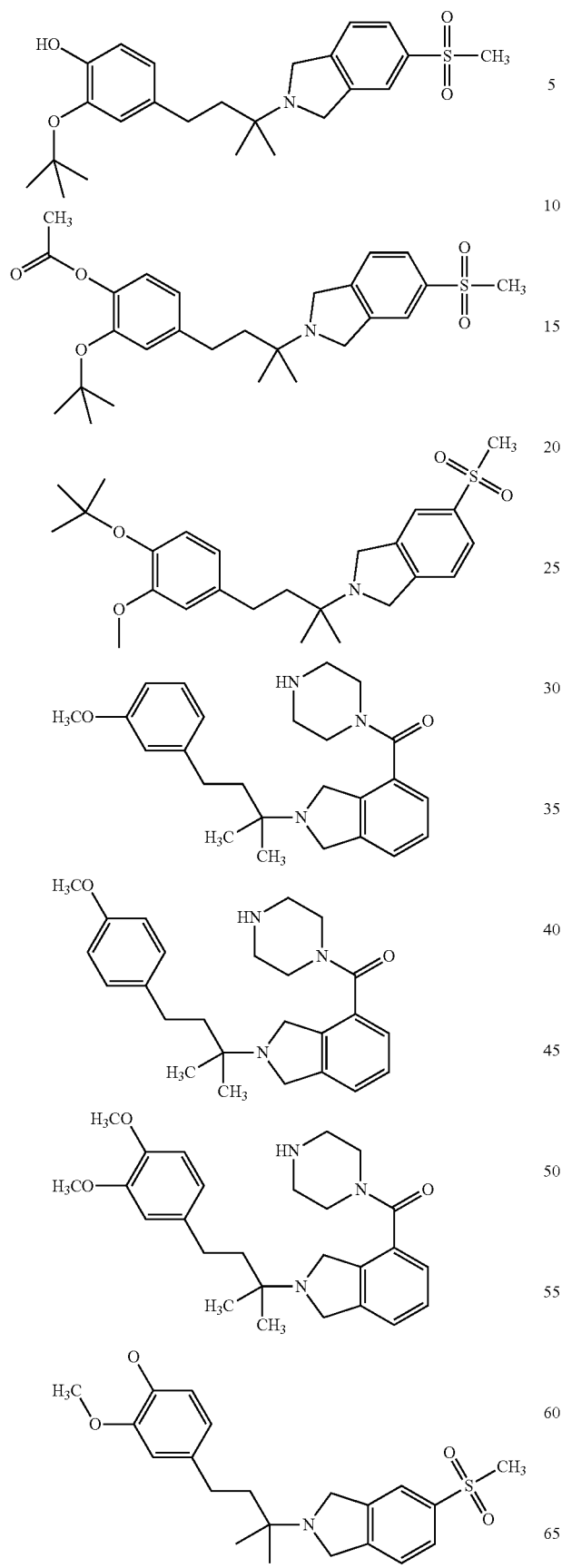

21
-continued
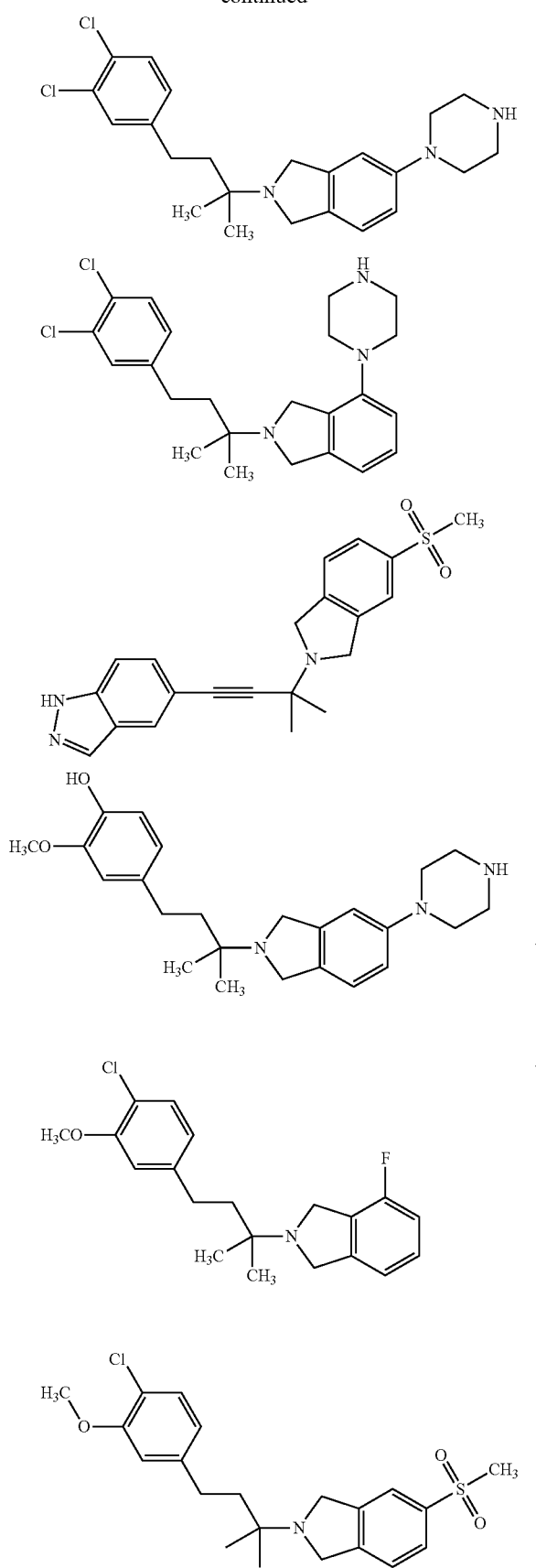
22
-continued
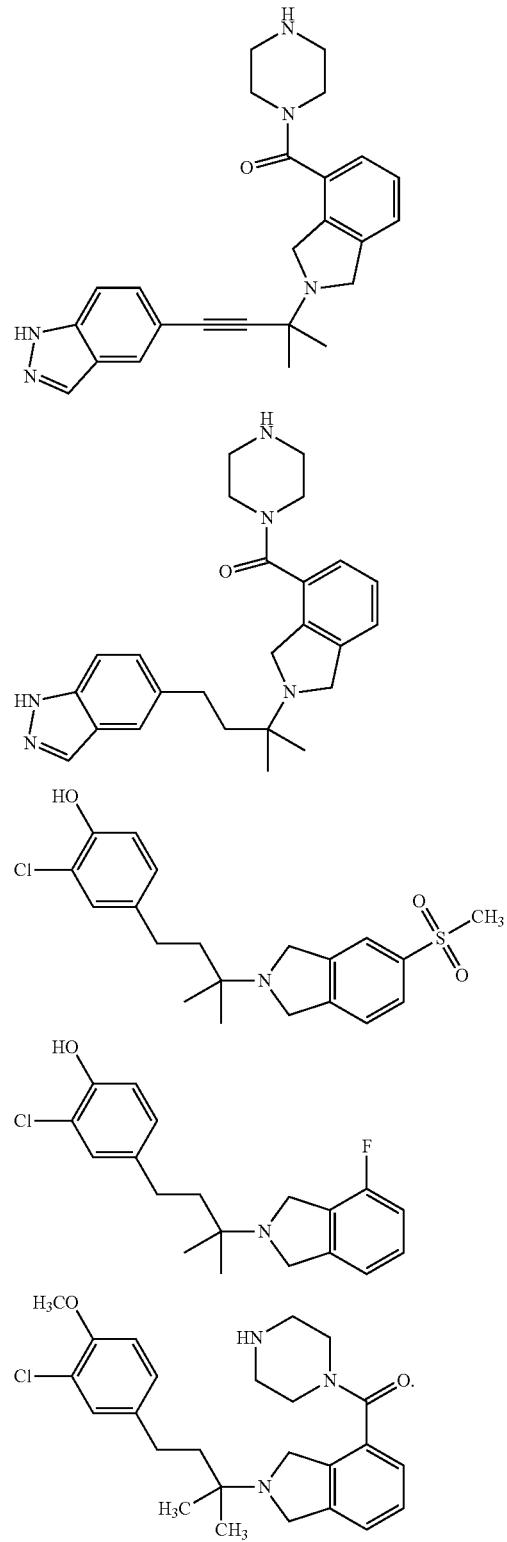
In a further embodiment, a compound, or pharmaceutically acceptable salt thereof, is provided selected from the group consisting of:

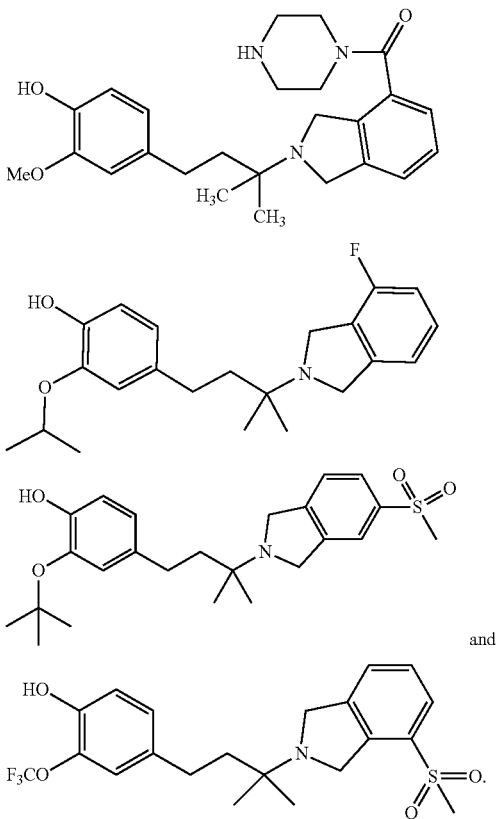

In a further embodiment, a compound, or pharmaceutically acceptable salt thereof, is provided selected from the group consisting of:

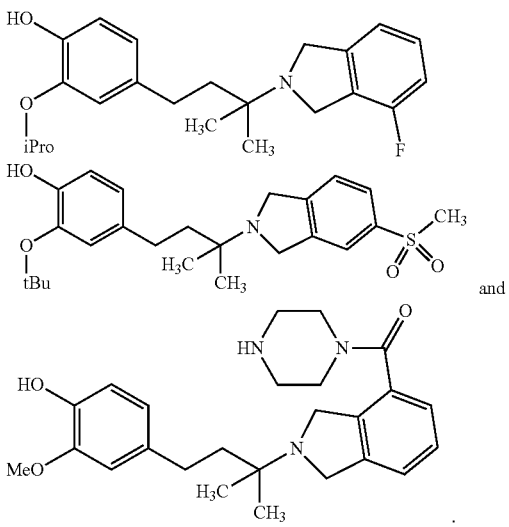

In another embodiment, a composition is provided for inhibiting an amyloid beta effect on a neuronal cell comprising a compound, or pharmaceutically acceptable salt thereof, according to Formula I:

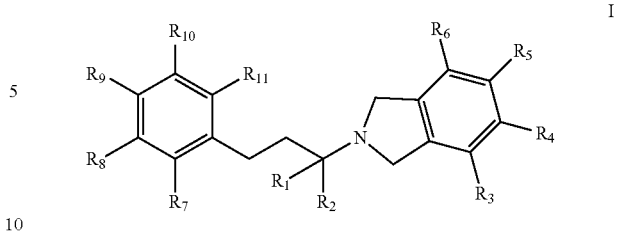

wherein:

$R^1$ and $R^2$ are each independently selected from H, $C_1$-$C_6$ alkyl, or $CH_2OR'$; where $R'$=H or $C_1$-$C_6$ alkyl;

$R_3$, $R_4$, $R_5$, and $R_6$ are each independently selected from H, $C_1$-$C_6$ alkyl, OH, $OCH_3$, $OCH(CH_3)_2$, $OCH_2CH(CH_3)_2$, $OC(CH_3)_3$, $O(C_1$-$C_6$ alkyl), $OCF_3$, $OCH_2CH_2OH$, $O(C_1$-$C_6$ alkyl)OH, $O(C_1$-$C_6$ haloalkyl), F, Cl, Br, I, $CF_3$, CN, $NO_2$, $NH_2$, $C_1$-$C_6$ haloalkyl, $C_1$-$C_6$ hydroxyalkyl, $C_{1-6}$ alkoxy $C_{1-6}$alkyl, aryl, heteroaryl, $C_{3-7}$ cycloalkyl, heterocycloalkyl, alkylaryl, heteroaryl, $CO_2R'$, $C(O)R'$, $NH(C_{1-4}$ alkyl), $N(C_{1-4}$ alkyl$)_2$, $NH(C_{3-7}$ cycloalkyl), $NHC(O)(C_{1-4}$ alkyl), $CONR'_2$, $NC(O)R'$, $NS(O)_nR'$, $S(O)_nNR'_2$, $S(O)_nR'$, $C(O)R'$, $C(O)O(C_{1-4}$ alkyl), $OC(O)N(R')_2$, $C(O)$ $(C_{1-4}$ alkyl), and $C(O)NH(C_{1-4}$ alkyl); where n=0, 1, or 2; R' are each independently H, $CH_3$, $CH_2CH_3$, $C_3$-$C_6$ alkyl, $C_1$-$C_6$ haloalkyl; or optionally substituted aryl, alkylaryl, piperazin-1-yl, piperidin-1-yl, morpholinyl, heterocycloalkyl, heteroaryl, $C_{1-6}$ alkoxy, $NH(C_{1-4}$ alkyl), or $NH(C_{1-4}$ alkyl$)_2$, wherein optionally substituted group is selected from $C_1$-$C_6$ alkyl or $C_2$-$C_7$ acyl;

or $R_3$ and $R_4$, together with the C atom to which they are attached form a form a 4-, 5-, 6- 7- or 8-membered cycloalkyl, aryl, heteroaryl, or heterocycloalkyl that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^3$ and $R^4$, or $R^4$ and $R^5$, are each independently selected from a bond, C, N, S, and O; or $R_3$ and $R_4$ are linked together to form a —O—$C_{1-2}$ methylene-O— group;

or $R_4$ and $R_5$, together with the C atom to which they are attached form a form a 4-, 5-, 6- 7- or 8-membered cycloalkyl, aryl, heteroaryl, or heterocycloalkyl that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^3$ and $R^4$, or $R^4$ and $R^5$, are each independently selected from a bond, C, N, S, and O; or $R_4$ and $R_5$ are linked together to form a —$C_{1-2}$ methylene-O— group;

$R_7$, $R_8$, $R_9$, $R_{10}$, and $R_{11}$ are each independently selected from H, $C_1$-$C_6$ alkyl, OH, $OCH_3$, $OCH(CH_3)_2$, $OCH_2CH(CH_3)_2$, $OC(CH_3)_3$, $O(C_1$-$C_6$ alkyl), $OCF_3$, $OCH_2CH_2OH$, $O(C_1$-$C_6$ alkyl)OH, $O(C_1$-$C_6$ haloalkyl), F, Cl, Br, I, $CF_3$, CN, $NO_2$, $NH_2$, $C_1$-$C_6$ haloalkyl, $C_1$-$C_6$ hydroxyalkyl, $C_{1-6}$ alkoxy $C_{1-6}$alkyl, aryl, heteroaryl, $C_{3-7}$ cycloalkyl, heterocycloalkyl, alkylaryl, heteroaryl, $CO_2R'$, $C(O)R'$, $NH(C_{1-4}$ alkyl), $N(C_{1-4}$ alkyl$)_2$, $NH(C_{3-7}$ cycloalkyl), $NHC(O)(C_{1-4}$ alkyl), $CONR'_2$, $NC(O)R'$, $NS(O)_nR'$, $S(O)_nNR'_2$, $S(O)_nR'$, $C(O)O(C_4$ alkyl), $OC(O)N(R')_2$, $C(O)$ $(C_{1-4}$ alkyl), and $C(O)NH(C_{1-4}$ alkyl); where n=0, 1, or 2; R' are each independently H, $CH_3$, $CH_2CH_3$, $C_3$-$C_6$ alkyl, $C_1$-$C_6$ haloalkyl, aryl, alkylaryl, piperazin-1-yl, piperidin-1-yl, morpholinyl, heterocycloalkyl, heteroaryl, $C_{1-6}$ alkoxy, $NH(C_{1-4}$ alkyl), or $NH(C_{1-4}$ alkyl$)_2$;

or $R_7$ and $R_8$, together with the N or C atoms to which they are attached form a 4-, 5-, 6- 7- or 8-membered cycloalkyl, aryl, heterocycloalkyl or heteroaryl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^9$ and $R^{10}$ are each independently selected from a bond, C, N, S, and O; or $R_7$ and $R_8$ are linked together to form a —O—$C_{1-2}$ methylene-O— group;

or $R_8$ and $R_9$, together with the N or C atoms to which they are attached form a form a 4-, 5-, 6- 7- or 8-membered cycloalkyl, aryl, heterocycloalkyl or heteroaryl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^9$ and $R^{10}$ are each independently selected from a bond, C, N, S, and O; or $R_8$ and $R_9$ are linked together to form a —O—$C_{1-2}$ methylene-O— group;

wherein each of the O, $C_{1-6}$ alkyl, $C_{1-6}$ haloalkyl, heteroaryl, aryl, heteroaryl, heterocycloalkyl, and cycloalkyl is optionally independently substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

with the proviso that the following compounds are excluded:

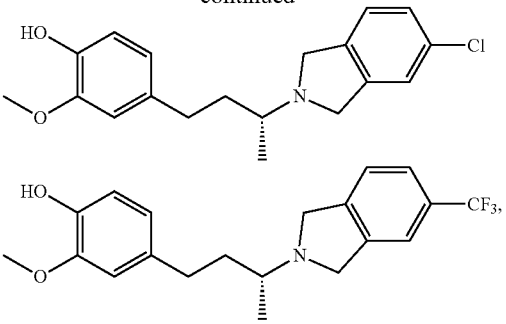

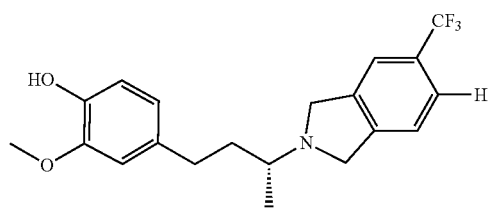

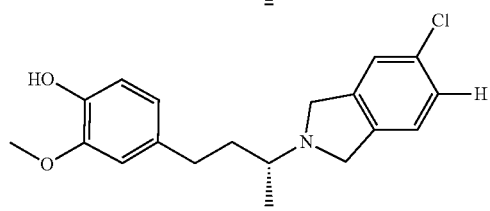

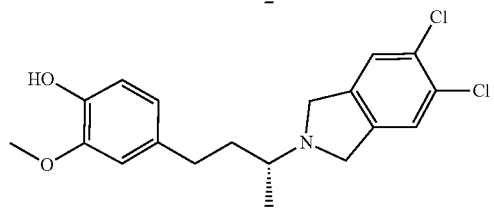

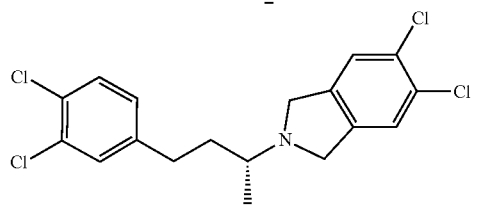

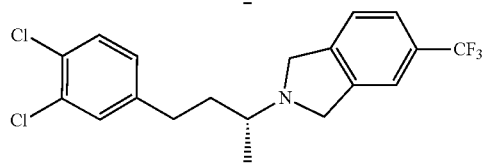

wherein the compound or salt thereof is present in the composition in an amount effective to inhibit amyloid beta oligomer binding in said cell; and a pharmaceutically acceptable carrier.

In another embodiment, a composition is provided for inhibiting an amyloid beta effect on a neuronal cell comprising a compound, or pharmaceutically acceptable salt thereof, according to Formula I:

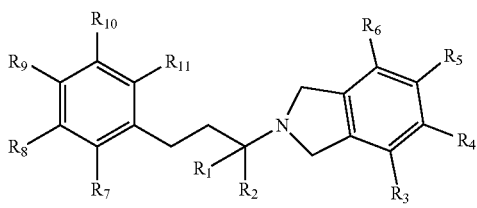

I wherein $R_1$, $R_2$, $R_3$, $R_4$, $R_5$, $R_6$, $R_7$, $R_8$, $R_9$, $R_{10}$, and $R_{11}$ are as defined herein, with the proviso that when $R_1$, $R_3$, $R_6$, $R_7$, $R_{10}$ and $R_{11}$ are each H; $R_2$ is $CH_3$; $R_8$ is $OCH_3$ or Cl; and $R_9$ is OH or Cl; then $R_4$ is not Cl or $CF_3$, and $R_5$ is not Cl or $CF_3$, and wherein the compound or salt thereof is present in the composition in an amount effective to inhibit amyloid beta oligomer binding in said cell; and a pharmaceutically acceptable carrier.

In another embodiment, a composition is provided comprising a compound, or pharmaceutically acceptable salt thereof, according to Formula I, wherein $R_1$ and $R_2$ are each independently selected from H or $CH_3$; $R_3$, $R_4$, $R_5$, and $R_6$ are each independently selected from H, $C_1$-$C_6$ alkyl, OH, $OCH_3$, $O(C_1$-$C_6$ alkyl), $O(C_1$-$C_6$ haloalkyl), F, Cl, $CF_3$, aryl, heteroaryl, $C_{3-7}$ cycloalkyl, $CO_2R'$, $C(O)R'$, $OC(O)N(R')_2$, $CONR'_2$, $NC(O)R'$, $NS(O)_nR'$, $S(O)_nNR'_2$, $S(O)_nR'$; where n=0, 1, or 2; R' are each independently H, $CH_3$, $CH_2CH_3$, $C_3$-$C_6$ alkyl, $C_1$-$C_6$ haloalkyl, piperazin-1-yl, piperidin-1-yl, morpholinyl, heterocycloalkyl, or aryl;

or $R_3$ and $R_4$, together with the C atom to which they are attached, form a 5-, or 6-membered $C_{3-7}$cycloalkyl, or aryl; or $R_4$ and $R_5$, together with the C atom to which they are attached, form a $C_{3-7}$cycloalkyl, or a 5- or 6-membered aryl;

or $R_3$ and $R_4$ are linked together to form a —O—$C_{1-2}$ methylene-O— group; or $R_4$ and $R_5$ are linked together to form a —O—$C_{1-2}$ methylene-O— group; and $R_7$, $R_8$, $R_9$, $R_{10}$, and $R_{11}$ are each independently selected from H, OH, $CH_3$, $CH_2CH_3$, F, Cl, $CF_3$, $OCF_3$, $C_1$-$C_6$ haloalkyl, $OCH_3$, $O(C_1$-$C_6$ alkyl), $OCH_2CH_2OH$, $O(C_1$-$C_6$ alkyl)OH, aryl, heteroaryl, $C_{3-7}$ cycloalkyl, alkylaryl, $CO_2R'$, $CONR'_2$, $S(O)_nNR'_2$, $S(O)_nR'$, $C(O)O(C_{1-4}$ alkyl), OC(O)N(R')$_2$, and C(O)NH(C$_4$ alkyl); where n=0, 1, or 2; R' are each independently H, C$_1$-C$_6$ alkyl, C$_1$-C$_6$ haloalkyl, aryl, alkylaryl, or C$_{1-6}$ alkoxy; and a pharmaceutically acceptable carrier.

In another embodiment, a composition is provided comprising a compound, or pharmaceutically acceptable salt thereof, according to Formula I, and a pharmaceutically acceptable carrier, wherein R$_7$, R$_{10}$, R$_{11}$ are each H; R$_3$ and R$_4$ are each independently selected from H, F, Cl, S(O)$_n$R', C(O)R', wherein n=2, and R' is selected from CH$_3$, piperazin-1-yl, piperidin-1-yl, morpholinyl; R$_8$ is selected from OH, OCH$_3$, OCH(CH$_3$)$_2$, OCH$_2$CH(CH$_3$)$_2$, or OC(CH$_3$)$_3$; and R$_9$ is OH; and a pharmaceutically acceptable carrier.

In another embodiment, a composition is provided comprising a compound, or pharmaceutically acceptable salt thereof, according to Formula I, and a pharmaceutically acceptable carrier, wherein the compound, or pharmaceutically acceptable salt thereof, is selected from the group consisting of:

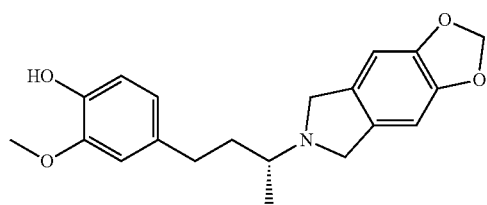

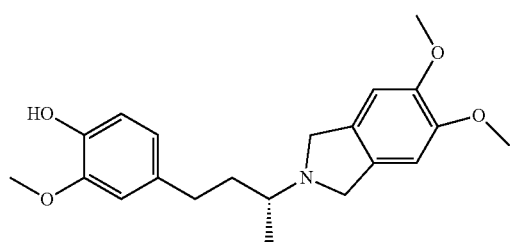

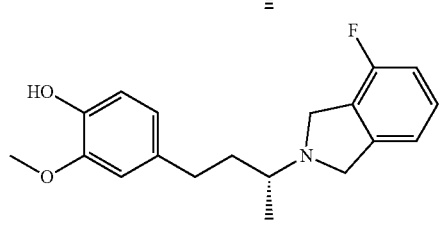

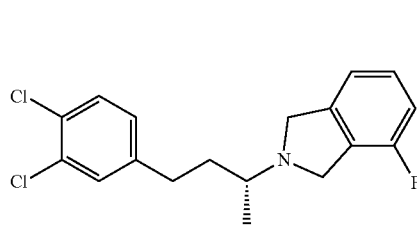

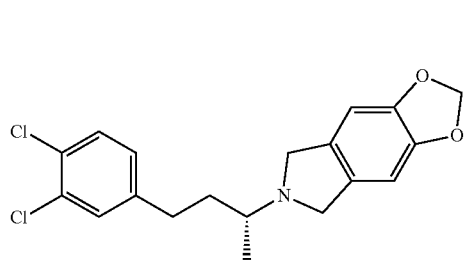

-continued

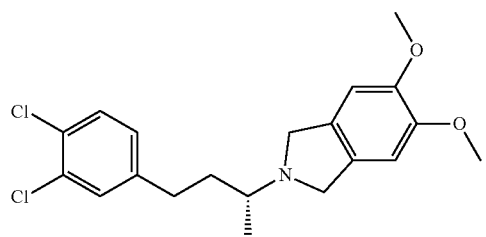

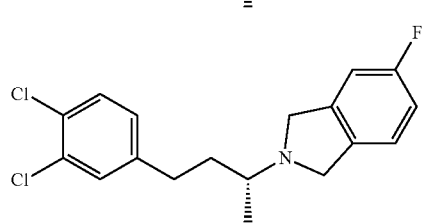

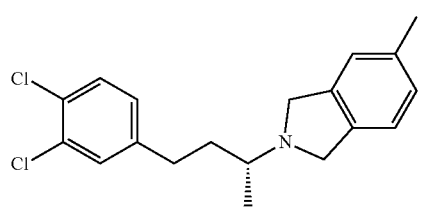

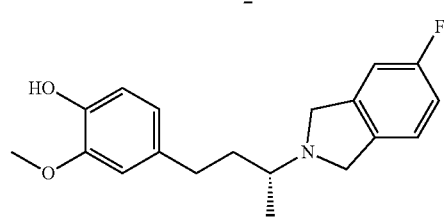

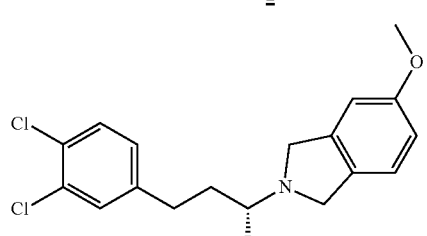

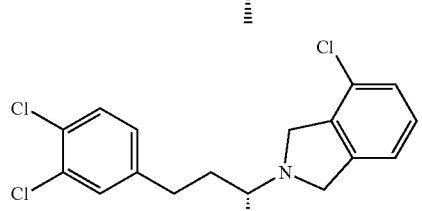

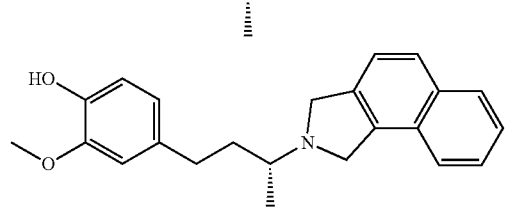

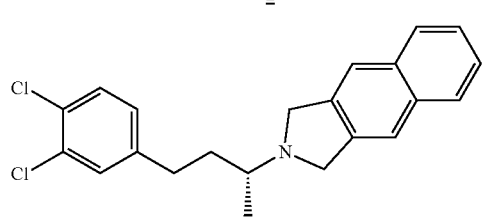

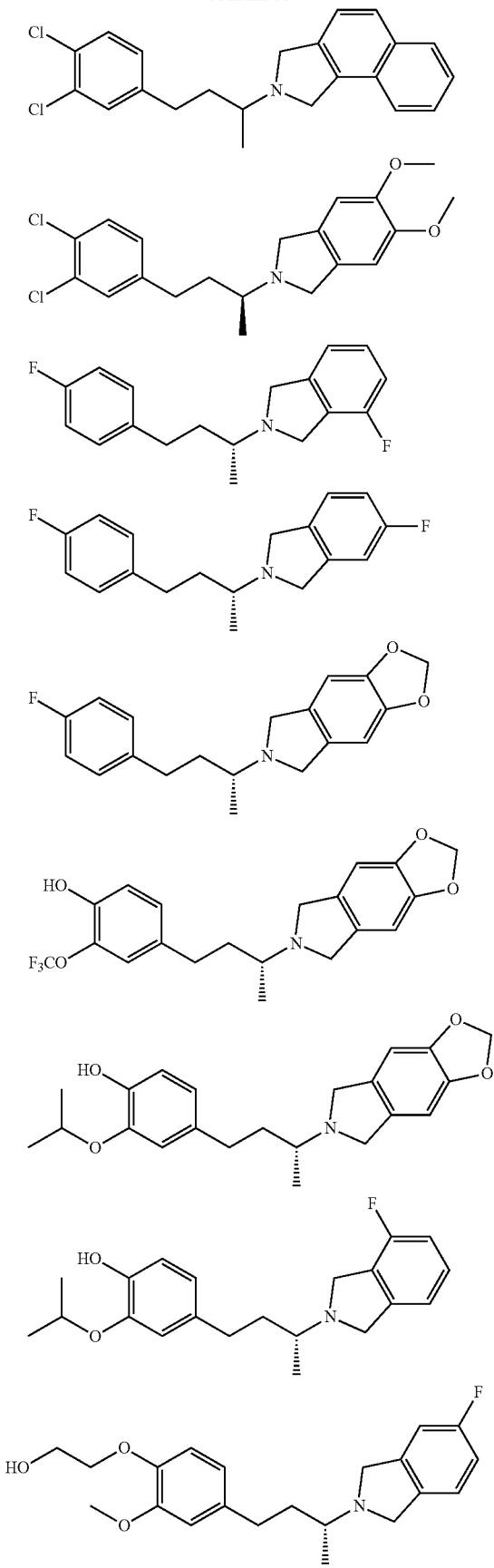
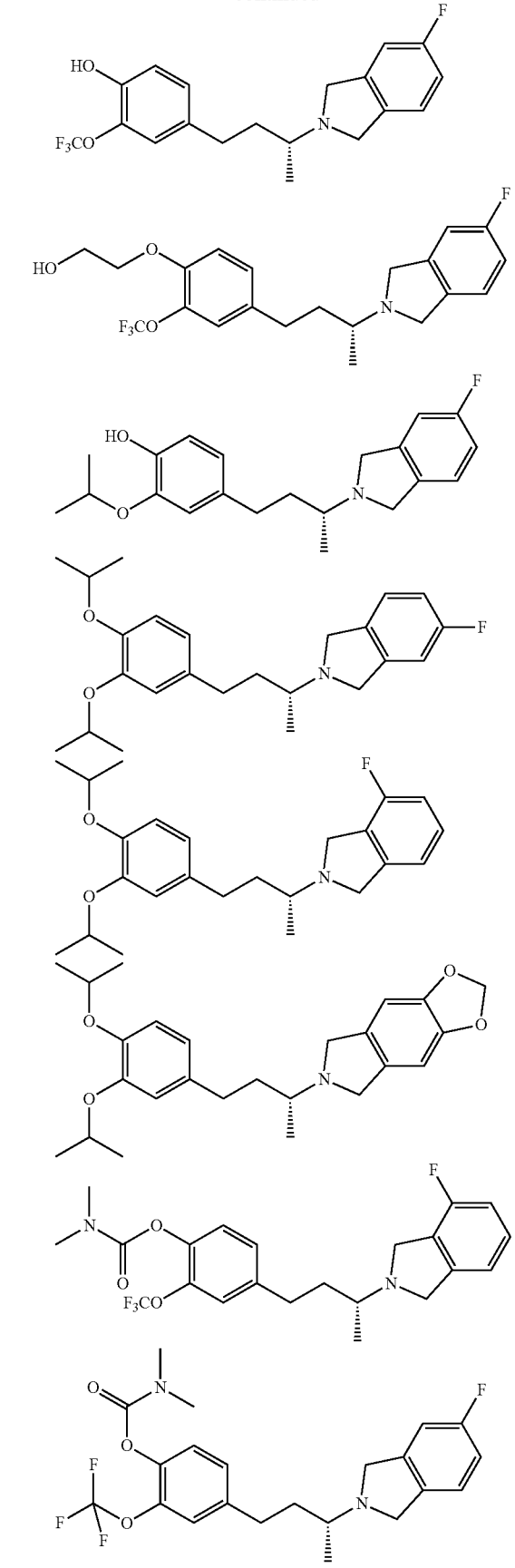

-continued

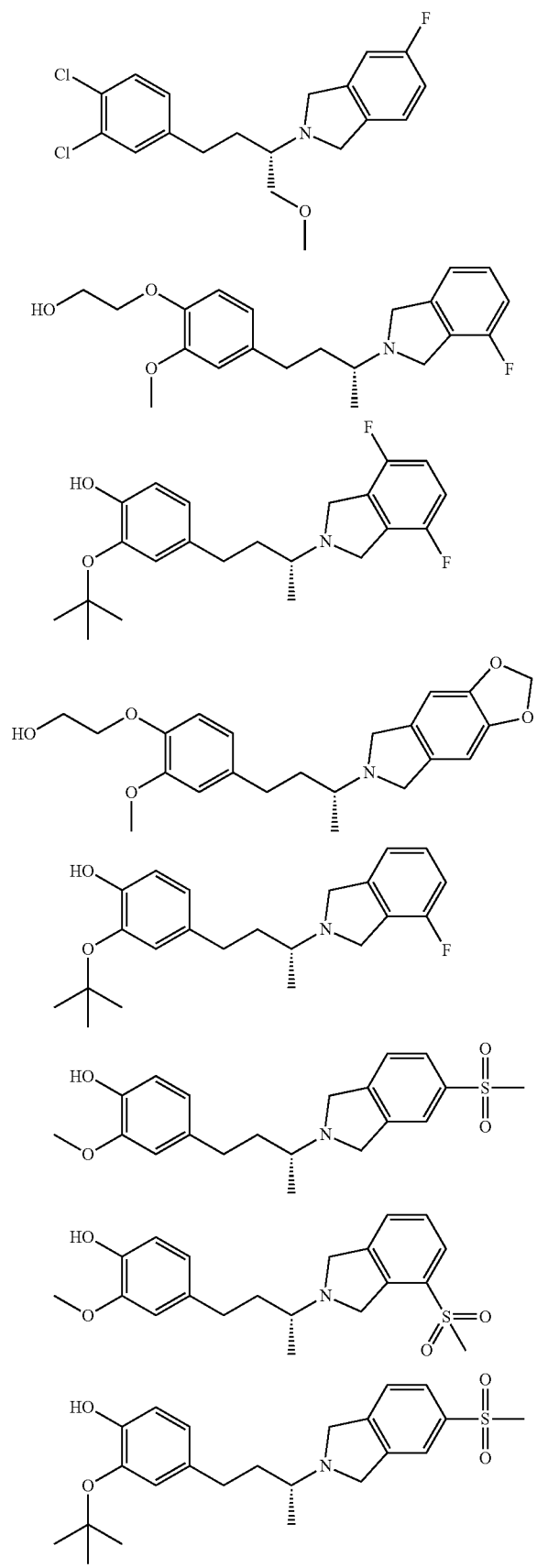

-continued

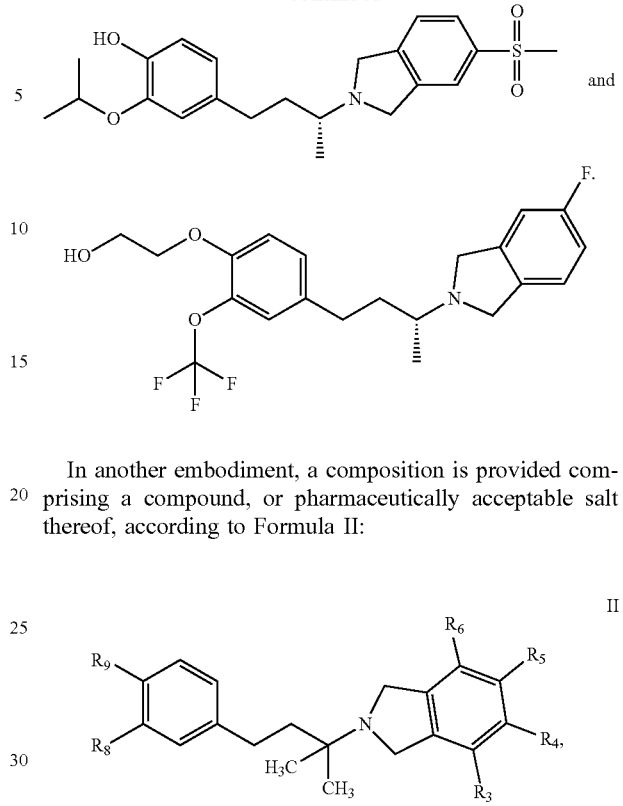

In another embodiment, a composition is provided comprising a compound, or pharmaceutically acceptable salt thereof, according to Formula II:

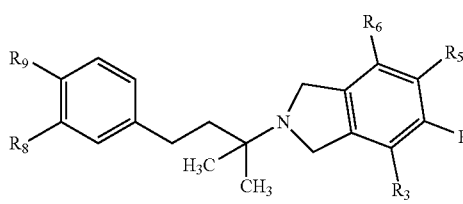

wherein $R_3$, $R_4$, $R_5$, and $R_6$ are each independently selected from H, Cl, F, OH, $CH_3$, $C_{1-6}$ alkyl, $OCH_3$, $OCH(CH_3)_2$, $OCH_2CH(CH_3)_2$, $OC(CH_3)_3$, $OC_{1-6}$ alkyl, aryl, heteroaryl, heterocycloalkyl, $CO_2R'$, $CONR'_2$, $NC(O)R'$, $NS(O)_nR'$, $S(O)_nNR'_2$, $S(O)_nR'$, $C(O)R'$, $OC(O)N(R')_2$, or $C(O)NH(C_{1-4}$ alkyl), wherein n=0, 1, or 2; and R' are each independently H, $C_1$-$C_6$ alkyl, $C_1$-$C_6$ haloalkyl or optionally substituted aryl, alkylaryl, piperazin-1-yl, piperidin-1-yl, morpholinyl, heterocycloalkyl, heteroaryl, $C_{1-6}$ alkoxy, $NH(C_{1-4}$ alkyl), or $NH(C_{1-4}$ alkyl)$_2$, wherein optionally substituted group is selected from $C_1$-$C_6$ alkyl or $C_2$-$C_7$ acyl; or $R_3$ and $R_4$, together with the C atom to which they are attached, form a 6-membered aryl; or $R_3$ and $R_4$ are linked together to form a —O—$C_{1-2}$ methylene-O— group; or $R_4$ and $R_5$, together with the C atom to which they are attached, form a 6-membered aryl; or $R_4$ and $R_5$ are linked together to form a —O—$C_{1-2}$ methylene-O— group; and $R_8$ and $R_9$ are each independently selected from H, Cl, F, OH, $CH_3$, $C_{1-6}$ alkyl, $OCH_3$, $OCH(CH_3)_2$, $OCH_2CH(CH_3)_2$, $OC(CH_3)_3$, $OC_{1-6}$ alkyl, aryl, heteroaryl, heterocycloalkyl, $CO_2R'$, $CONR'_2$, $NC(O)R'$, $NS(O)_nR'$, $S(O)_nNR'_2$, $S(O)_nR'$, $OC(O)N(R')_2$, or $C(O)NH(C_{1-4}$ alkyl); and a pharmaceutically acceptable carrier.

In another embodiment, a composition is provided comprising a compound, or pharmaceutically acceptable salt thereof, according to Formula II, wherein $R_3$ and $R_4$ are each independently selected from H, F, Cl, $S(O)_nR'$, $C(O)R'$, wherein n=2, and R' is selected from $CH_3$, piperazin-1-yl, piperidin-1-yl, or morpholinyl; $R_5$ and $R_6$ are each H; $R_8$ is selected from OH, $OCH_3$, $OCH(CH_3)_2$, $OCH_2CH(CH_3)_2$, or $OC(CH_3)_3$; and $R_9$ is OH; and a pharmaceutically acceptable carrier.

In a further embodiment, a composition is provided comprising a compound, or pharmaceutically acceptable salt thereof, and a pharmaceutically acceptable carrier, wherein the compound or salt is selected from the group consisting of:
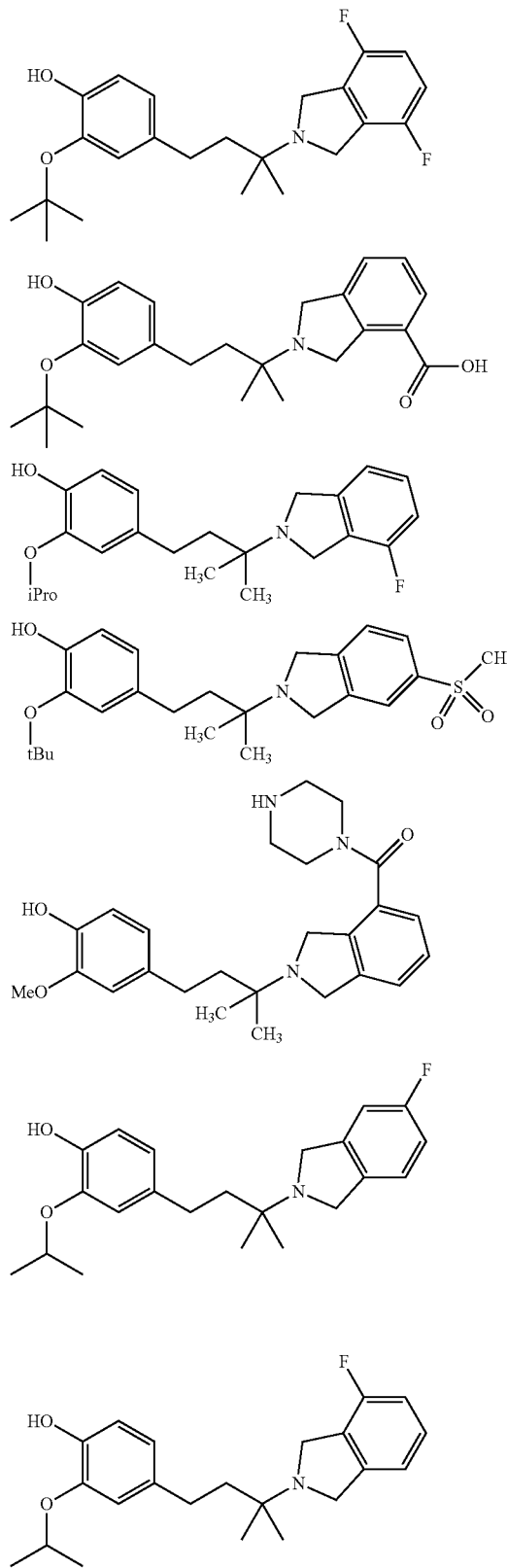
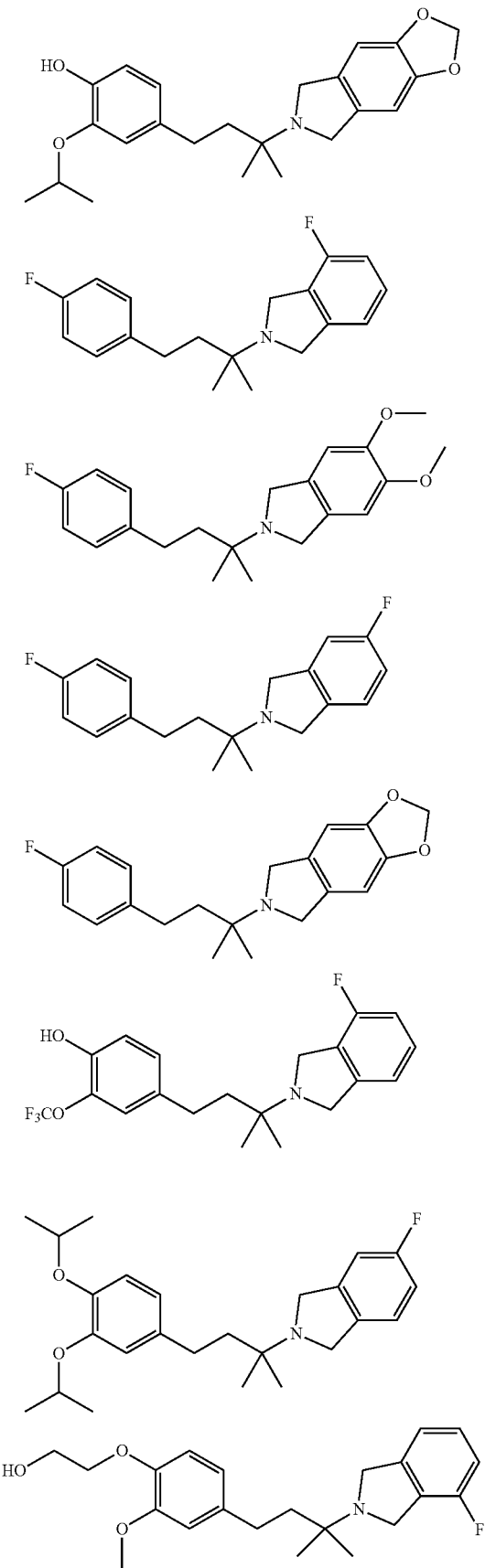

35
-continued
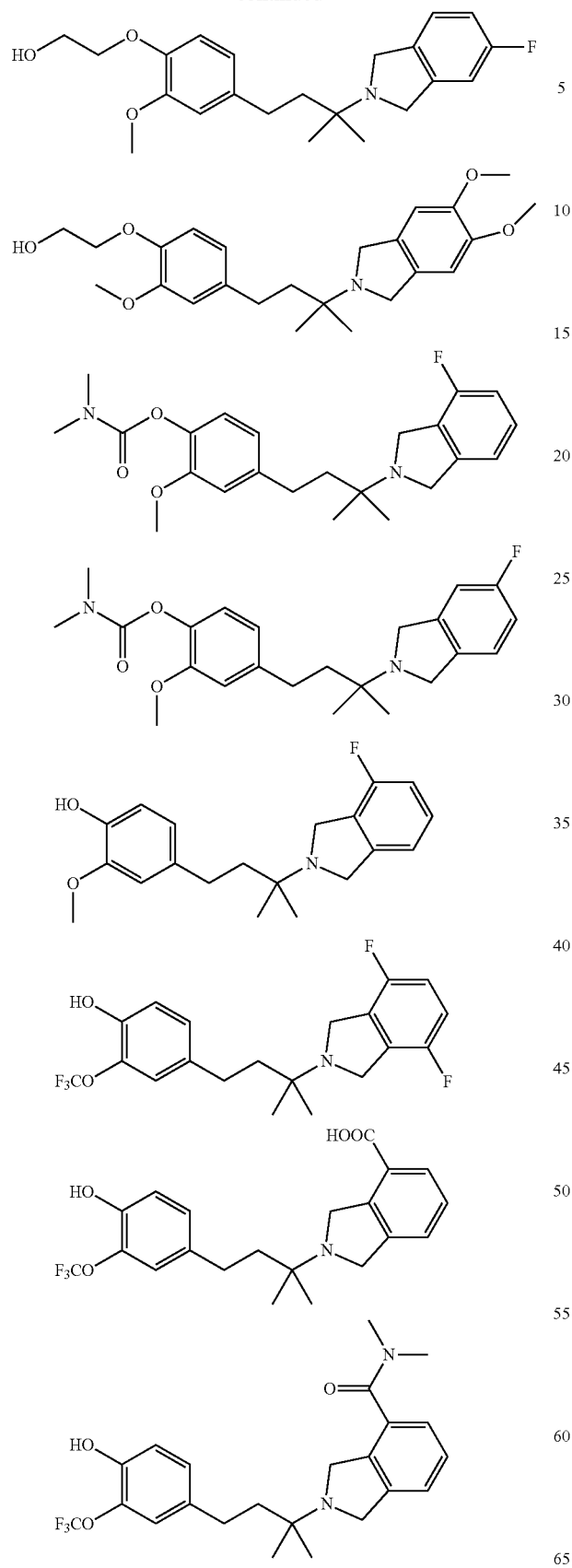
36
-continued
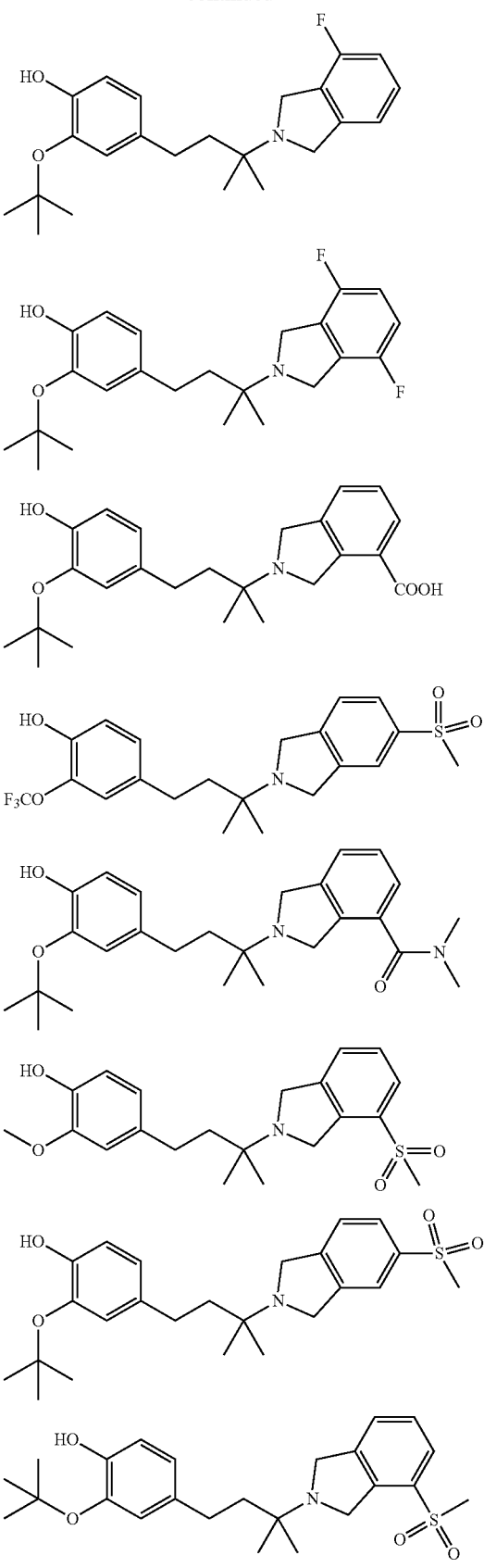

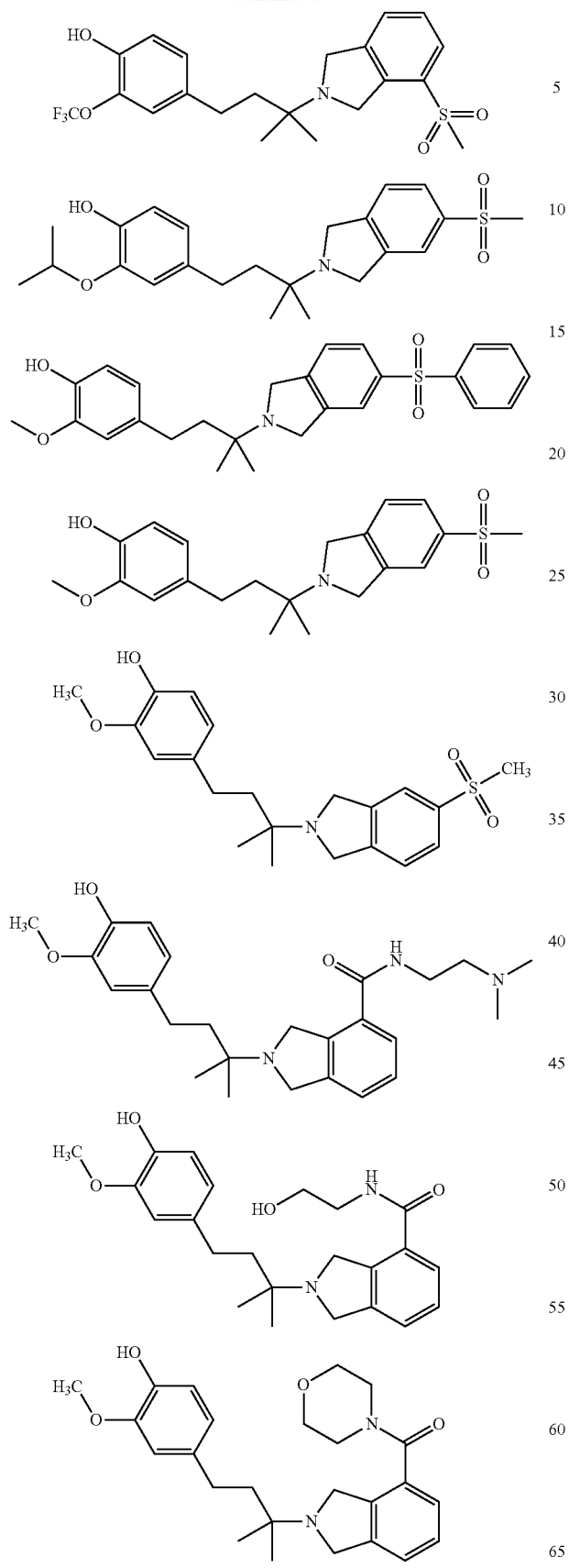
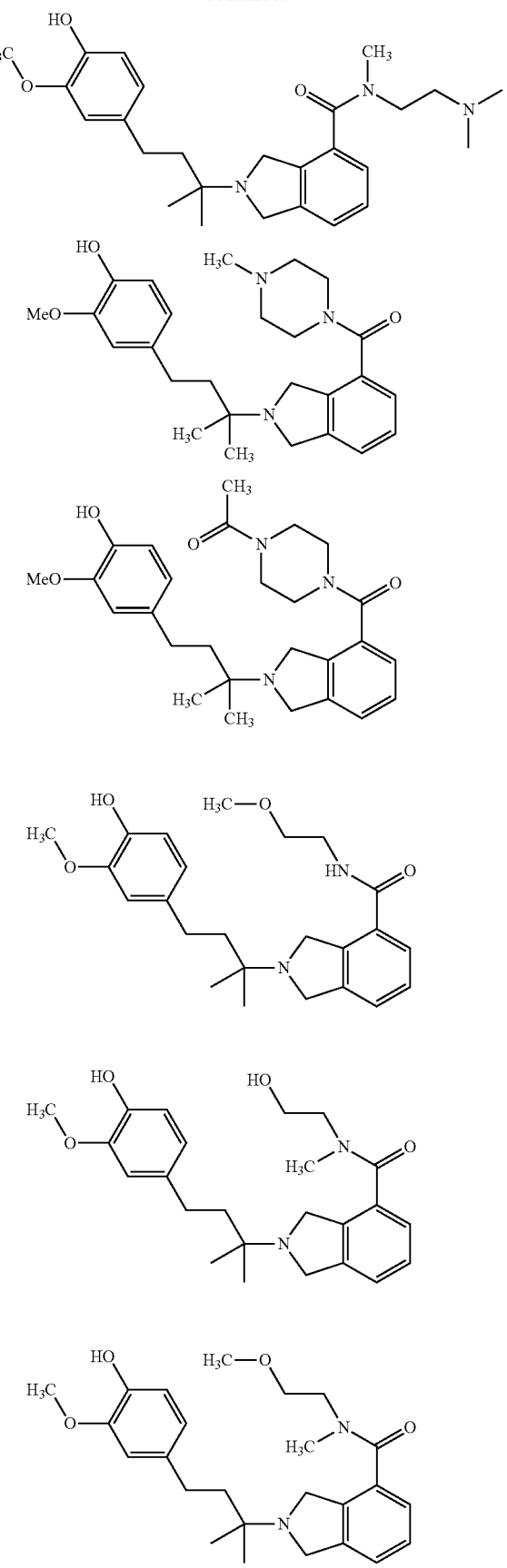

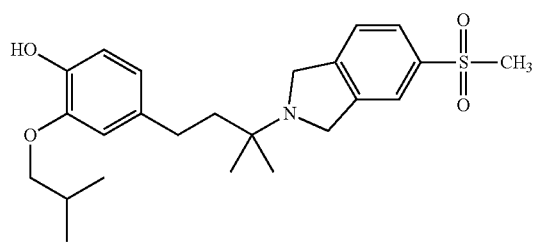
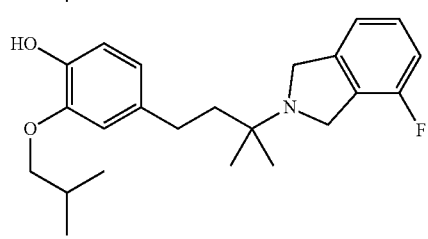
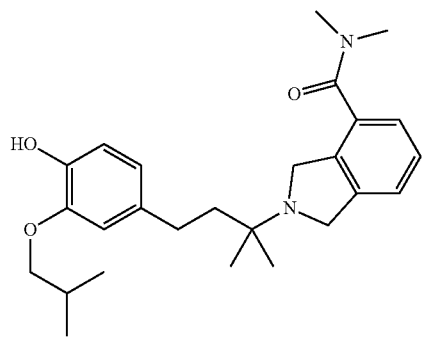
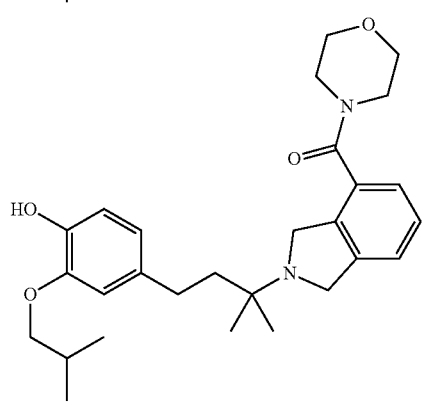
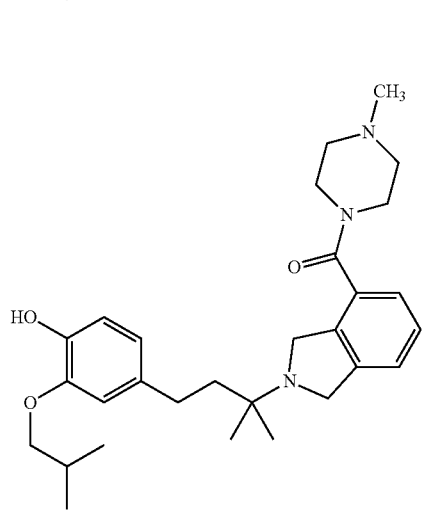
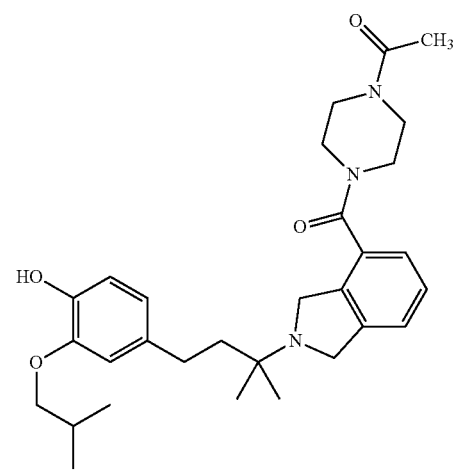
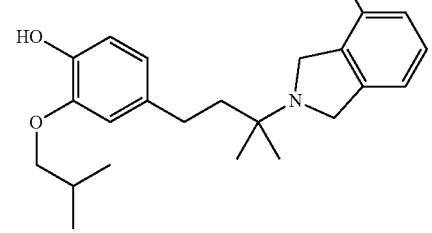
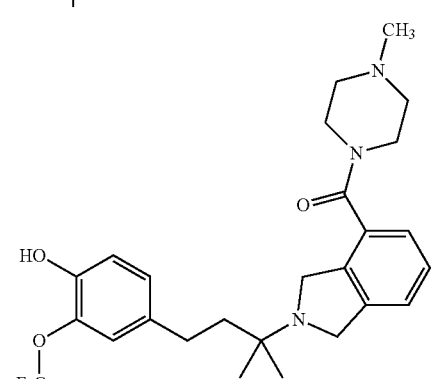
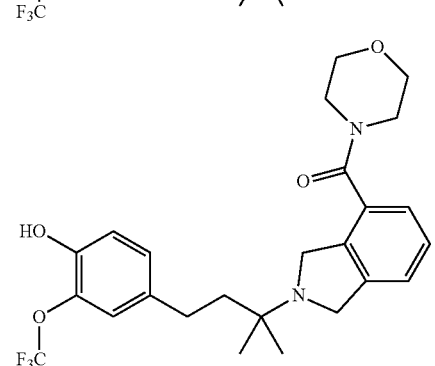
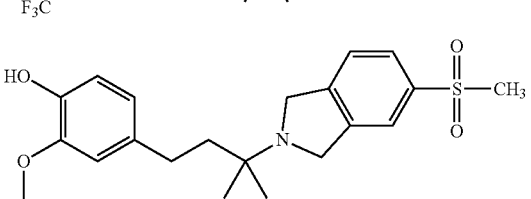
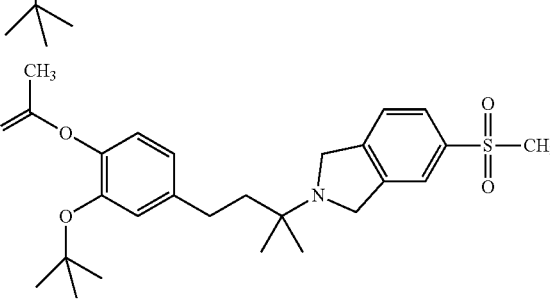

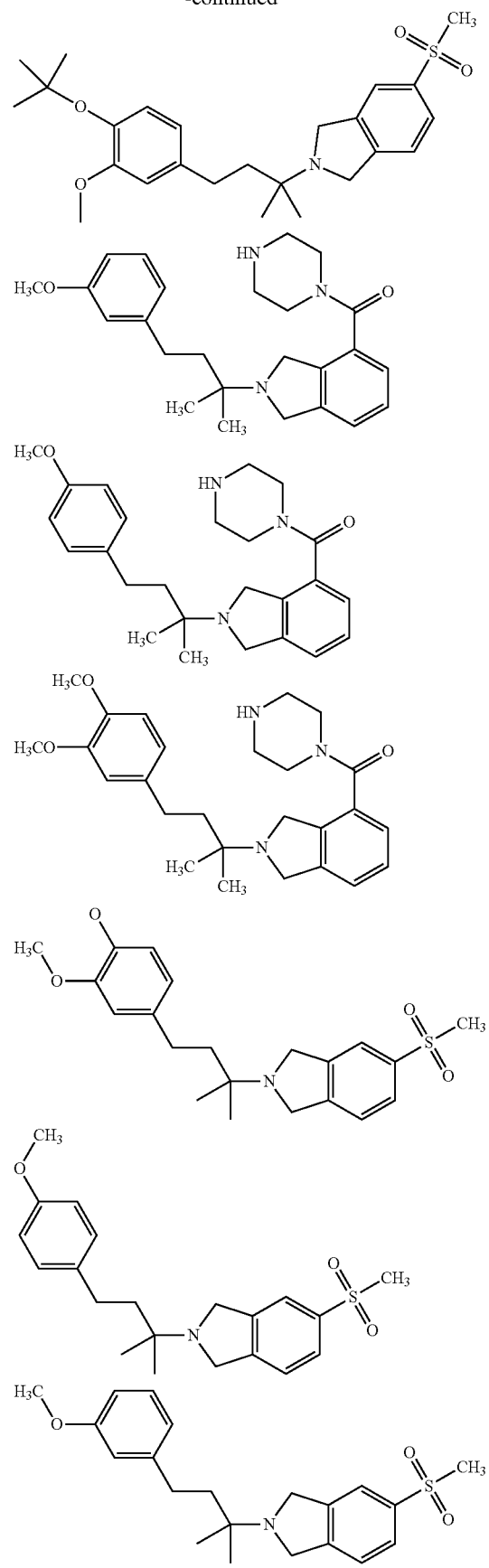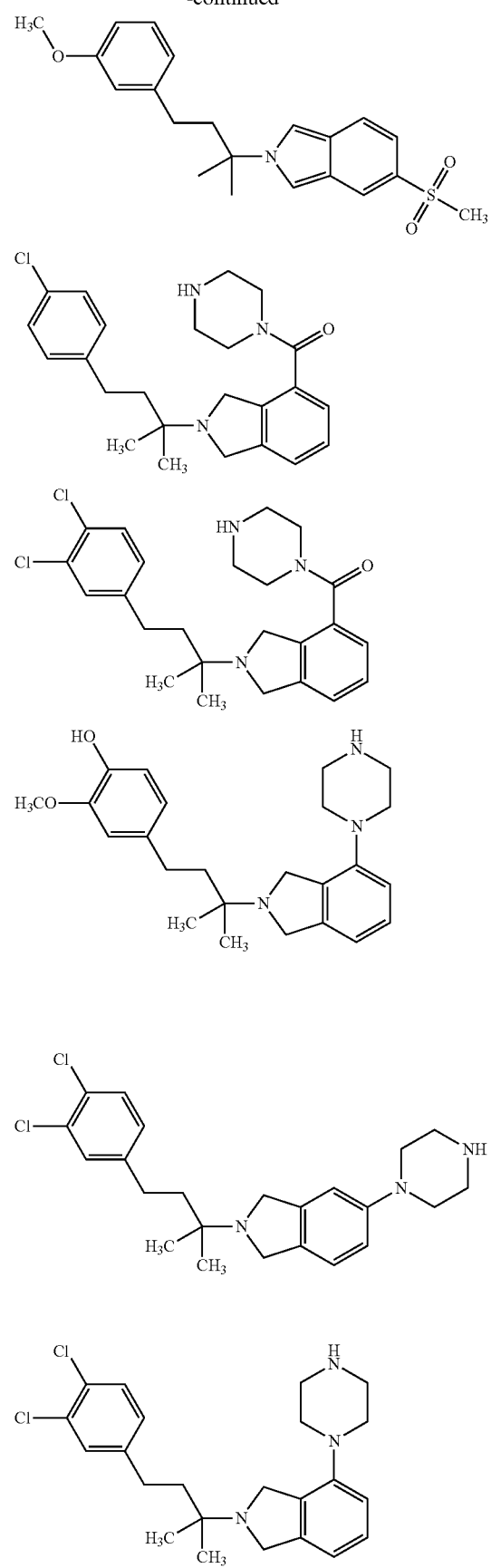

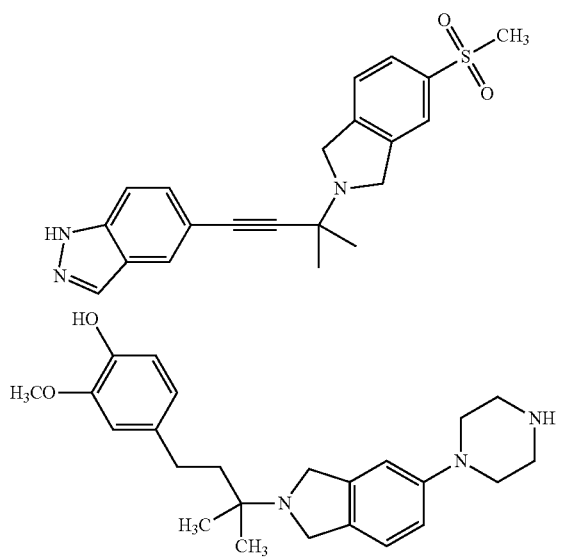
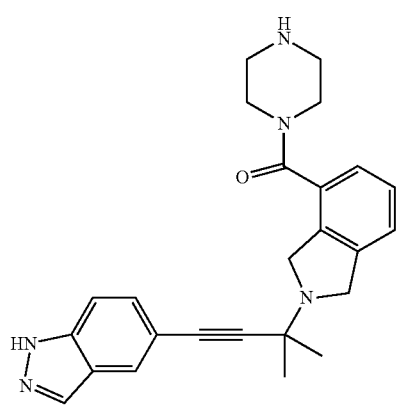
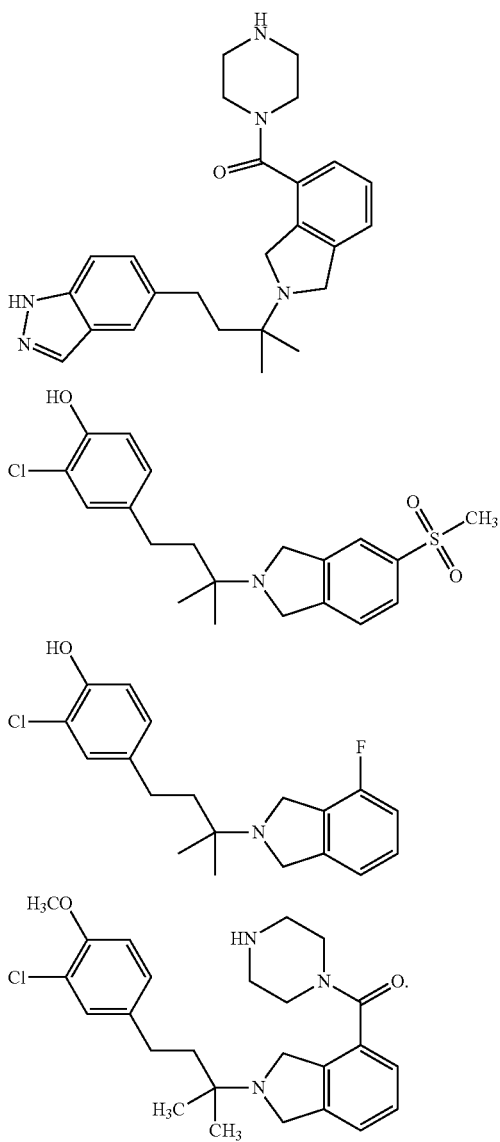
In a further embodiment, a composition is provided comprising a compound, or pharmaceutically acceptable salt thereof, and a pharmaceutically acceptable carrier, wherein the compound or salt is selected from the group consisting of:

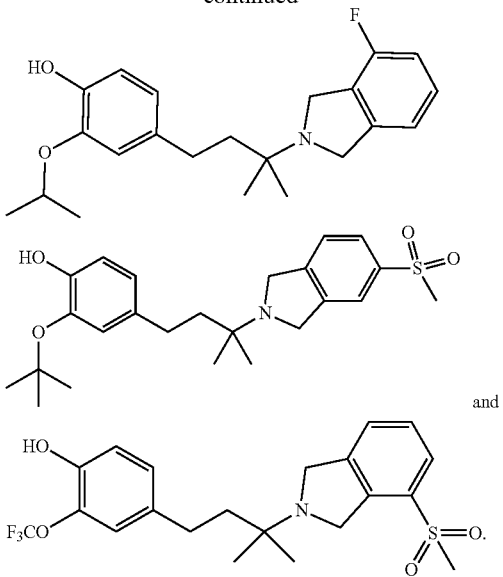

In a further embodiment, a composition is provided comprising a compound, or pharmaceutically acceptable salt thereof, and a pharmaceutically acceptable carrier, wherein the compound or salt is selected from the group consisting of:

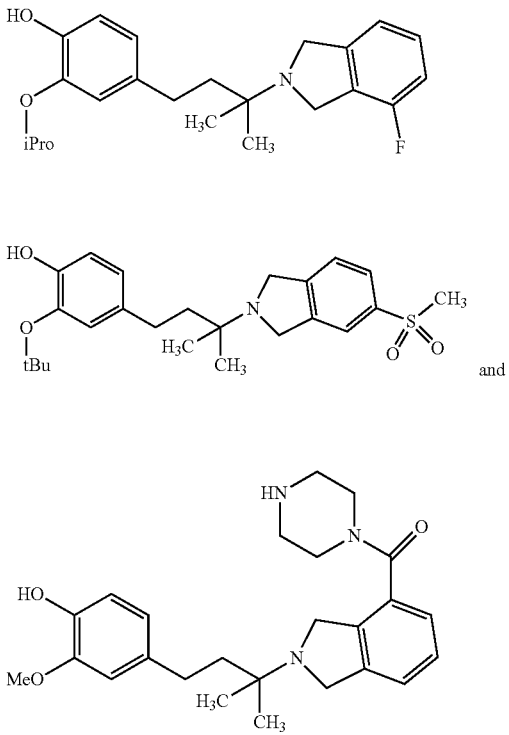

In one embodiment, a method/use is provided for inhibiting an amyloid beta effect on a neuronal cell comprising administering an effective amount of a composition comprising a selective sigma-2 receptor antagonist compound, or a pharmaceutically acceptable salt thereof, according to formula I:

I wherein:
$R_1$ and $R_2$ are each independently selected from H, $C_1$-$C_6$alkyl, or $CH_2OR'$; where $R'$=H or $C_1$-$C_6$ alkyl;

$R_3$, $R_4$, $R_5$, and $R_6$ are each independently selected from H, $C_1$-$C_6$ alkyl, OH, $OCH_3$, $OCH(CH_3)_2$, $OCH_2CH(CH_3)_2$, $OC(CH_3)_3$, $O(C_1$-$C_6$ alkyl), $OCF_3$, $OCH_2CH_2OH$, $O(C_1$-$C_6$ alkyl)OH, $O(C_1$-$C_6$ haloalkyl), F, Cl, Br, I, $CF_3$, CN, $NO_2$, $NH_2$, $C_1$-$C_6$ haloalkyl, $C_1$-$C_6$ hydroxyalkyl, $C_{1-6}$ alkoxy $C_{1-6}$alkyl, aryl, heteroaryl, $C_{3-7}$ cycloalkyl, heterocycloalkyl, alkylaryl, heteroaryl, $CO_2R'$, $C(O)R'$, $NH(C_{1-4}$ alkyl), $N(C_{1-4}$ alkyl$)_2$, $NH(C_{3-7}$ cycloalkyl), $NHC(O)(C_{1-4}$ alkyl), $CONR'_2$, $NC(O)R'$, $NS(O)_nR'$, $S(O)_nNR'_2$, $S(O)_nR'$, $C(O)R'$, $C(O)O(C_{1-4}$ alkyl), $OC(O)N(R')_2$, $C(O)$ ($C_{1-4}$ alkyl), and $C(O)NH(C_{1-4}$ alkyl); where n=0, 1, or 2; R' are each independently H, $CH_3$, $CH_2CH_3$, $C_3$-$C_6$ alkyl, $C_1$-$C_6$ haloalkyl; or optionally substituted aryl, alkylaryl, piperazin-1-yl, piperidin-1-yl, morpholinyl, heterocycloalkyl, heteroaryl, $C_{1-6}$ alkoxy, $NH(C_{1-4}$ alkyl), or $NH(C_{1-4}$ alkyl$)_2$, wherein optionally substituted group is selected from $C_1$-$C_6$ alkyl or $C_2$-$C_7$ acyl;

or $R_3$ and $R_4$, together with the C atom to which they are attached form a form a 4-, 5-, 6- 7- or 8-membered cycloalkyl, aryl, heteroaryl, or heterocycloalkyl that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^3$ and $R^4$, or $R^4$ and $R^5$, are each independently selected from a bond, C, N, S, and O; or $R_3$ and $R_4$ are linked together to form a —O—$C_{1-2}$ methylene-O— group;

or $R_4$ and $R_5$, together with the C atom to which they are attached form a form a 4-, 5-, 6- 7- or 8-membered cycloalkyl, aryl, heteroaryl, or heterocycloalkyl that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^3$ and $R^4$, or $R^4$ and $R^5$, are each independently selected from a bond, C, N, S, and O; or $R_4$ and $R_5$ are linked together to form a —$C_{1-2}$ methylene-O— group;

$R_7$, $R_8$, $R_9$, $R_{10}$, and $R_{11}$ are each independently selected from H, $C_1$-$C_6$ alkyl, OH, $OCH_3$, $OCH(CH_3)_2$, $OCH_2CH(CH_3)_2$, $OC(CH_3)_3$, $O(C_1$-$C_6$ alkyl), $OCF_3$, $OCH_2CH_2OH$, $O(C_1$-$C_6$ alkyl)OH, $O(C_1$-$C_6$ haloalkyl), F, Cl, Br, I, $CF_3$, CN, $NO_2$, $NH_2$, $C_1$-$C_6$ haloalkyl, $C_1$-$C_6$ hydroxyalkyl, $C_{1-6}$ alkoxy $C_{1-6}$alkyl, aryl, heteroaryl, $C_{3-7}$ cycloalkyl, heterocycloalkyl, alkylaryl, heteroaryl, $CO_2R'$, $C(O)R'$, $NH(C_{1-4}$ alkyl), $N(C_{1-4}$ alkyl$)_2$, $NH(C_{3-7}$ cycloalkyl), $NHC(O)(C_{1-4}$ alkyl), $CONR'_2$, $NC(O)R'$, $NS(O)_nR'$, $S(O)_nNR'_2$, $S(O)_nR'$, $C(O)O(C_4$ alkyl), $OC(O)N(R')_2$, $C(O)$ ($C_{1-4}$ alkyl), and $C(O)NH(C_{1-4}$ alkyl); where n=0, 1, or 2; R' are each independently H, $CH_3$, $CH_2CH_3$, $C_3$-$C_6$ alkyl, $C_1$-$C_6$ haloalkyl; or optionally substituted aryl, alkylaryl, piperazin-1-yl, piperidin-1-yl, morpholinyl, heterocycloalkyl, heteroaryl, $C_{1-6}$ alkoxy, NH(C$_{1-4}$ alkyl), or NH(C$_{1-4}$ alkyl)$_2$, wherein optionally substituted group is selected from C$_1$-C$_6$ alkyl or C$_2$-C$_7$ acyl;

or R$_7$ and R$_8$, together with the N or C atoms to which they are attached form a form a 4-, 5-, 6- 7- or 8-membered cycloalkyl, aryl, heterocycloalkyl or heteroaryl group that is optionally substituted with 1, 2, 3, 4, or 5 substituents independently selected from OH, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl, and heterocycloalkyl and R$^9$ and R$^{10}$ are each independently selected from a bond, C, N, S, and O; or R$_7$ and R$_8$ are linked together to form a —O—C$_{1-2}$ methylene-O— group;

or R$_8$ and R$_9$, together with the N or C atoms to which they are attached form a form a 4-, 5-, 6- 7- or 8-membered cycloalkyl, aryl, heterocycloalkyl or heteroaryl group that is optionally substituted with 1, 2, 3, 4, or 5 substituents independently selected from OH, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl, and heterocycloalkyl and R$^9$ and R$^{10}$ are each independently selected from a bond, C, N, S, and O; or R$_8$ and R$_9$ are linked together to form a —O—C$_{1-2}$ methylene-O— group, wherein each of the O, C$_{1-6}$ alkyl, C$_{1-6}$ haloalkyl, heteroaryl, aryl, heteroaryl, heterocycloalkyl, and cycloalkyl is optionally independently substituted with 1, 2, 3, 4, or 5 substituents independently selected from OH, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl and heterocycloalkyl;

with the proviso that the following compounds are excluded:

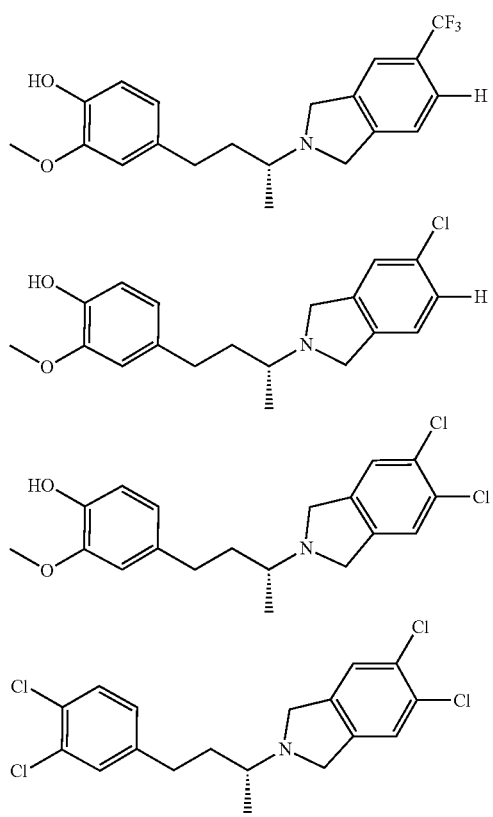

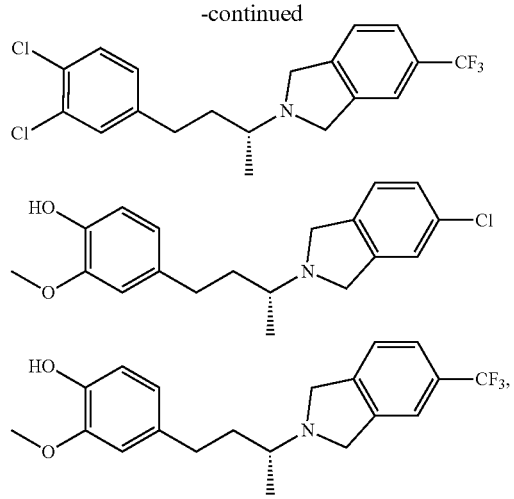

wherein the compound, or pharmaceutically acceptable salt thereof, is in an amount effective to inhibit amyloid beta oligomer binding in said cell; and a pharmaceutically acceptable carrier.

In another embodiment, a method/use is provided for inhibiting an amyloid beta effect on a neuronal cell comprising administering an effective amount of a composition comprising a selective sigma-2 receptor antagonist compound, or a pharmaceutically acceptable salt thereof, according to formula I, wherein the compound, or pharmaceutically acceptable salt thereof, is administered in an amount also effective to inhibit membrane trafficking deficits in said cell, said membrane trafficking effects being associated with exposure of said cell to soluble amyloid beta oligomers.

In another embodiment, a method/use is provided for inhibiting an amyloid beta effect on a neuronal cell comprising administering an effective amount of a composition comprising a selective sigma-2 receptor antagonist compound, or a pharmaceutically acceptable salt thereof, according to formula I, wherein the compound, or pharmaceutically acceptable salt thereof, is administered in an amount effective to inhibit both the oligomer binding and synapse loss associated with exposure of the cell to soluble amyloid beta oligomer in said cell.

In another embodiment, a method/use is provided for inhibiting an amyloid beta effect on a neuronal cell comprising administering a composition comprising an effective amount of a compound according to formula I, or a pharmaceutically acceptable salt thereof, and a pharmaceutically acceptable carrier, wherein the compound, or pharmaceutically acceptable salt thereof, is administered in an amount effective to inhibit a soluble amyloid beta oligomer-mediated cognitive effect. In one aspect, the cognitive effect is cognitive decline as tested in an animal model of cognitive decline. In another aspect, the cognitive decline is a decline in learning as tested by a fear conditioning assay. In a further aspect, the cognitive decline is a decline in spatial learning and memory as tested by a Morris water maze test. In another aspect, the cognitive decline is hippocampal-based spatial learning and memory decline as tested in a transgenic animal model of Alzheimer's disease.

In another embodiment, a method/use is provided for inhibiting an amyloid beta effect on a neuronal cell comprising administering a composition comprising an effective amount of a compound according to formula I, or a pharmaceutically acceptable salt thereof, wherein:

$R_1$ and $R_2$ are each independently selected from H or $CH_3$; $R_3$, $R_4$, $R_5$, and $R_6$ are each independently selected from H, $C_1$-$C_6$ alkyl, OH, $OCH_3$, $O(C_1$-$C_6$ alkyl), $O(C_1$-$C_6$ haloalkyl), F, Cl, $CF_3$, aryl, heteroaryl, $C_{3-7}$ cycloalkyl, $CO_2R'$, $C(O)R'$, $OC(O)N(R')_2$, $CONR'_2$, $NC(O)R'$, $NS(O)_nR'$, $S(O)_nNR'_2$, $S(O)_nR'$; where n=0, 1, or 2; R' are each independently H, $CH_3$, $CH_2CH_3$, $C_3$-$C_6$ alkyl, $C_1$-$C_6$ haloalkyl, piperazin-1-yl, piperidin-1-yl, morpholinyl, heterocycloalkyl, or aryl; or $R_3$ and $R_4$, together with the C atom to which they are attached, form a 5-, or 6-membered $C_{3-7}$cycloalkyl, or aryl; or $R_4$ and $R_5$, together with the C atom to which they are attached, form a $C_{3-7}$cycloalkyl, or a 5- or 6-membered aryl; or $R_3$ and $R_4$ are linked together to form a —O—$C_{1-2}$ methylene-O— group; or $R_4$ and $R_5$ are linked together to form a —O—$C_{1-2}$ methylene-O— group; and $R_7$, $R_8$, $R_9$, $R_{10}$, and $R_{11}$ are each independently selected from H, OH, $CH_3$, $CH_2CH_3$, F, Cl, $CF_3$, $OCF_3$, $C_1$-$C_6$ haloalkyl, $OCH_3$, $O(C_1$-$C_6$ alkyl), $OCH_2CH_2OH$, $O(C_1$-$C_6$ alkyl)OH, aryl, heteroaryl, $C_{3-7}$ cycloalkyl, alkylaryl, $CO_2R'$, $CONR'_2$, $S(O)_nNR'_2$, $S(O)_nR'$, $C(O)O(C_4$ alkyl), $OC(O)N(R')_2$, and $C(O)NH(C_{1-4}$ alkyl); where n=0, 1, or 2; R' are each independently H, $C_1$-$C_6$ alkyl, $C_1$-$C_6$ haloalkyl, aryl, alkylaryl, or $C_{1-6}$ alkoxy; and a pharmaceutically acceptable carrier.

In another embodiment, a method/use is provided for inhibiting an amyloid beta effect on a neuronal cell comprising administering a composition comprising an effective amount of a compound according to formula I, or a pharmaceutically acceptable salt thereof, wherein $R_7$, $R_{10}$, $R_{11}$ are each H; $R_3$ and $R_4$ are each independently selected from H, F, Cl, $S(O)_nR'$, $C(O)R'$, wherein n=2, and R' is selected from $CH_3$ or optionally substituted piperazin-1-yl, piperidin-1-yl, or morpholinyl, wherein optionally substituted group is selected from $C_1$-$C_6$ alkyl or $C_2$-$C_7$ acyl; $R_8$ is selected from OH, $OCH_3$, $OCH(CH_3)_2$, $OCH_2CH(CH_3)_2$, or $OC(CH_3)_3$; and $R_9$ is OH; and a pharmaceutically acceptable carrier.

In another embodiment, a method/use is provided for inhibiting an amyloid beta effect on a neuronal cell comprising administering a composition comprising an effective amount of a compound, or pharmaceutically acceptable salt thereof, selected from the group consisting of:

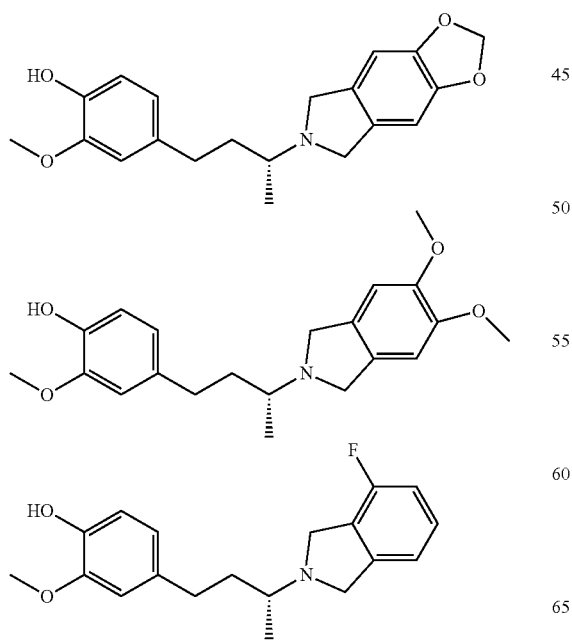

-continued

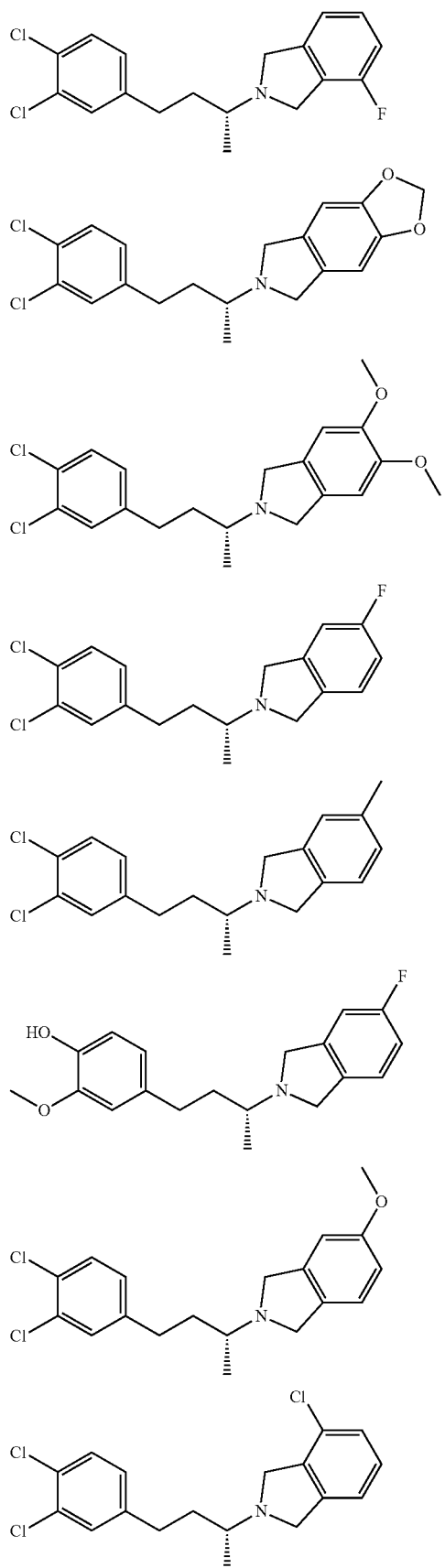

51
-continued
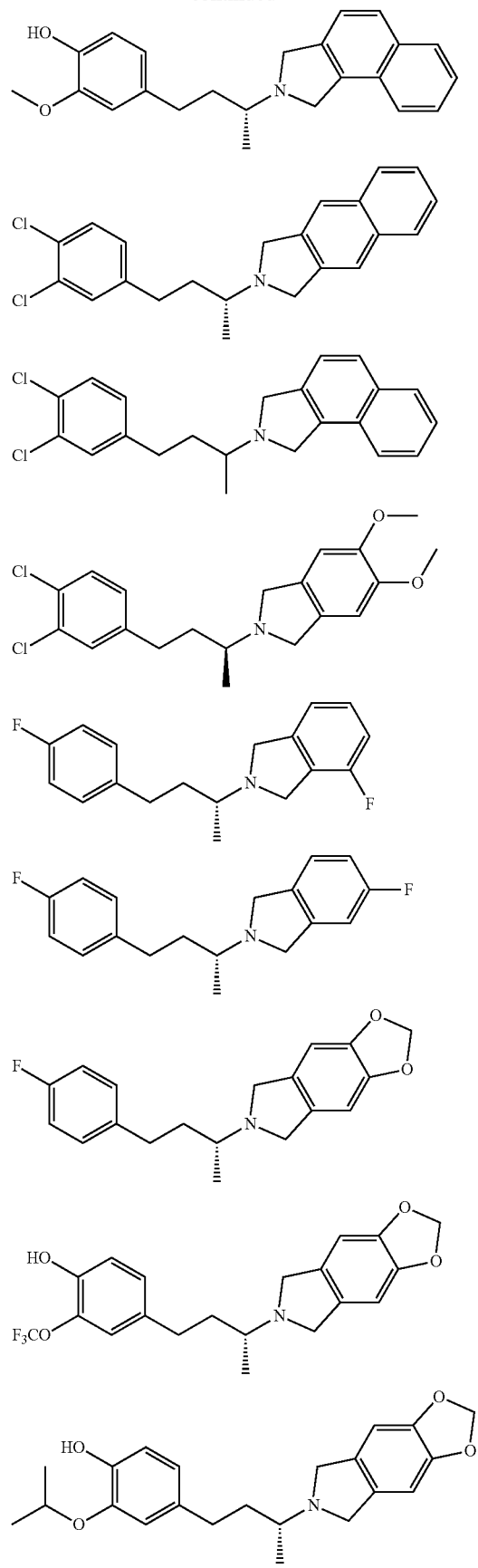
52
-continued
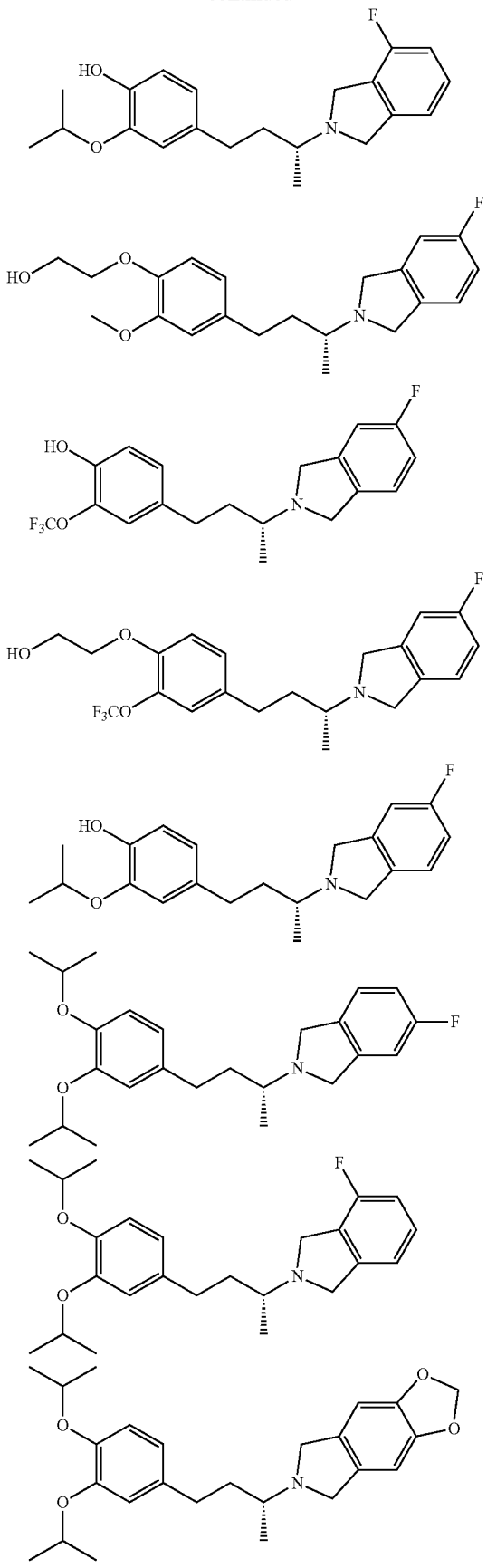

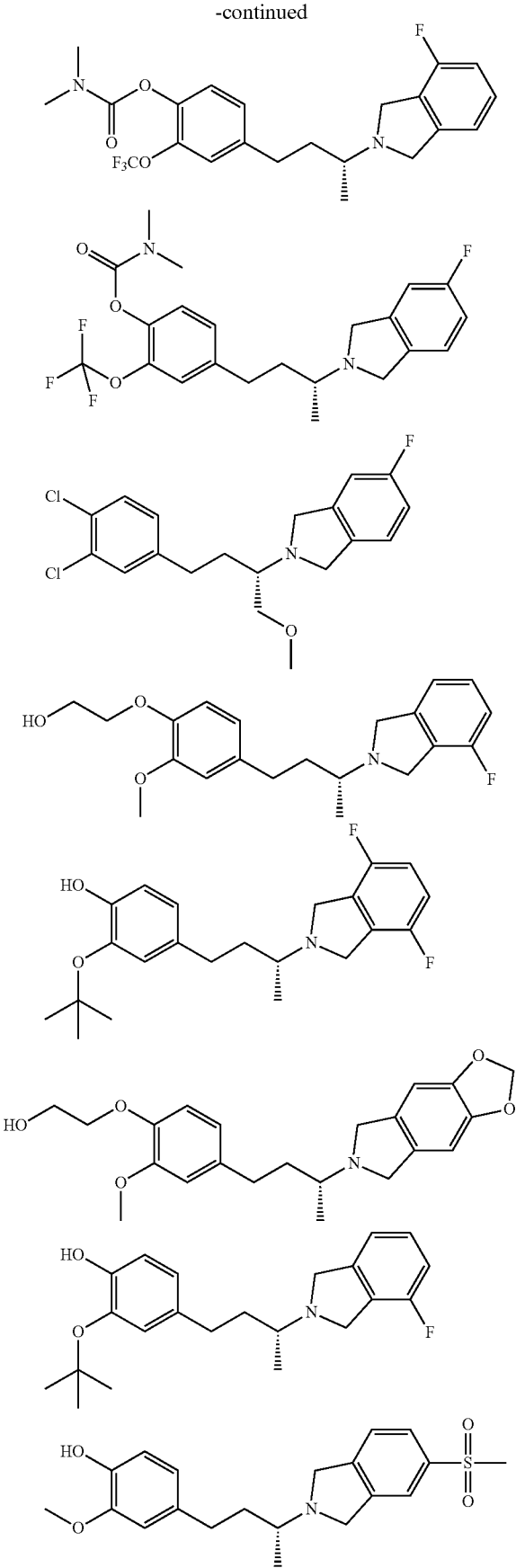

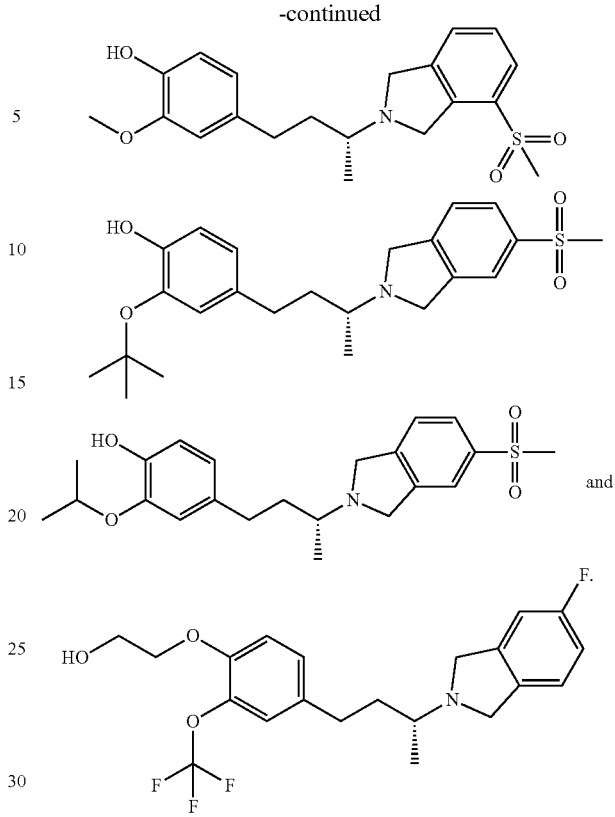

In another embodiment, a method/use is provided for inhibiting an amyloid beta effect on a neuronal cell comprising administering a composition comprising an effective amount of a compound, or pharmaceutically acceptable salt thereof, according to formula II:

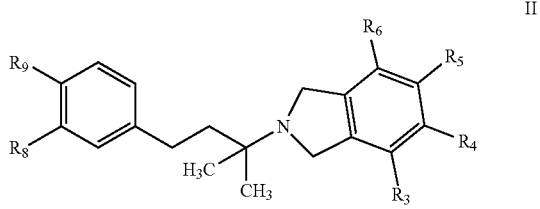

wherein $R_3$, $R_4$, $R_5$, and $R_6$ are each independently selected from H, Cl, F, OH, $CH_3$, $C_{1-6}$ alkyl, $OCH_3$, $OCH(CH_3)_2$, $OCH_2CH(CH_3)_2$, $OC(CH_3)_3$, $OC_{1-6}$ alkyl, aryl, heteroaryl, heterocycloalkyl, $CO_2R'$, $CONR'_2$, $NC(O)R'$, $NS(O)_nR'$, $S(O)_nNR'_2$, $S(O)_nR'$, $C(O)R'$, $OC(O)N(R')_2$, or $C(O)NH$ ($C_{1-4}$ alkyl), wherein n=0, 1, or 2; and R' are each independently H, $C_1$-$C_6$ alkyl, $C_1$-$C_6$ haloalkyl or optionally substituted aryl, alkylaryl, piperazin-1-yl, piperidin-1-yl, morpholinyl, heterocycloalkyl, heteroaryl, $C_{1-6}$ alkoxy, $NH(C_{1-4}$ alkyl), or $NH(C_{1-4}$ alkyl)$_2$, wherein optionally substituted group is selected from $C_1$-$C_6$ alkyl or $C_2$-$C_7$ acyl; or $R_3$ and $R_4$, together with the C atom to which they are attached, form a 6-membered aryl; or $R_3$ and $R_4$ are linked together to form a —O—$C_{1-2}$ methylene-O— group; or $R_4$ and $R_5$, together with the C atom to which they are attached, form a 6-membered aryl; or $R_4$ and $R_5$ are linked together to form a —O—$C_{1-2}$ methylene-O— group; and $R_8$ and $R_9$ are each independently selected from H, Cl, F, OH, $CH_3$, $C_{1-6}$ alkyl, $OCH_3$, $OCH(CH_3)_2$, $OCH_2CH(CH_3)_2$, $OC(CH_3)_3$, $OC_{1-6}$ alkyl, aryl, heteroaryl, heterocycloalkyl, $CO_2R'$, $CONR'_2$, $NC(O)R'$, $NS(O)_nR'$, $S(O)_nNR'_2$, $S(O)_nR'$, $OC(O)N(R')_2$, or $C(O)NH(C_{1-4}$ alkyl); and a pharmaceutically acceptable carrier.

In another embodiment, a method/use is provided for inhibiting an amyloid beta effect on a neuronal cell comprising administering a composition comprising an effective amount of a compound, or pharmaceutically acceptable salt thereof, according to formula II, wherein at least one of $R_3$, $R_4$, $R_5$ and $R_6$ is not H; and at least one of $R_8$ and $R_9$ is not H.

In another embodiment, a method/use is provided for inhibiting an amyloid beta effect on a neuronal cell comprising administering a composition comprising an effective amount of a compound, or pharmaceutically acceptable salt thereof, according to formula II, wherein $R_3$ and $R_4$ are each independently selected from H, F, Cl, $S(O)_nR'$, $C(O)R'$, wherein n=2, and R' is selected from $CH_3$, piperazin-1-yl, piperidin-1-yl, or morpholinyl; $R_5$ and $R_6$ are each H; $R_8$ is selected from OH, $OCH_3$, $OCH(CH_3)_2$, $OCH_2CH(CH_3)_2$, or $OC(CH_3)_3$; and $R_9$ is OH.

In another embodiment, a method/use is provided for inhibiting an amyloid beta effect on a neuronal cell comprising administering a composition comprising an effective amount of a compound, or pharmaceutically acceptable salt thereof, and a pharmaceutically acceptable carrier, wherein the compound or salt thereof, is selected from the group consisting of:

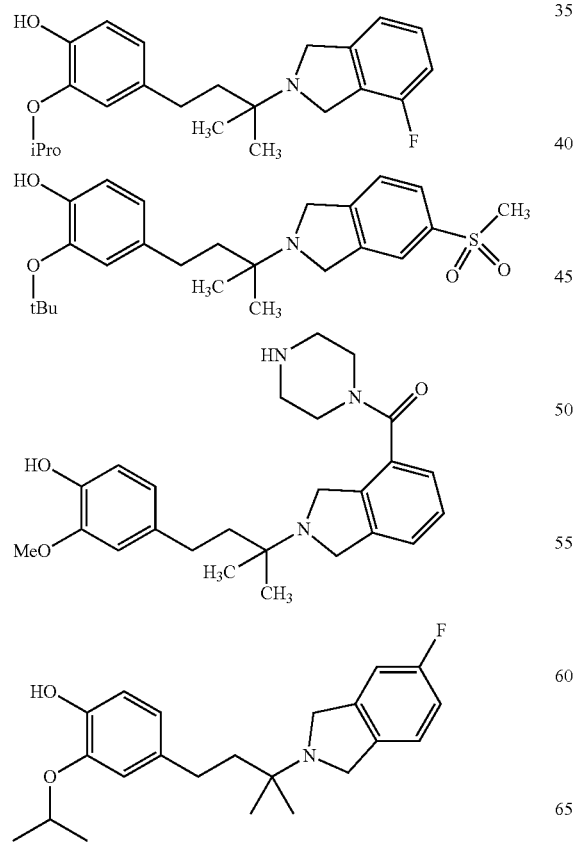

-continued

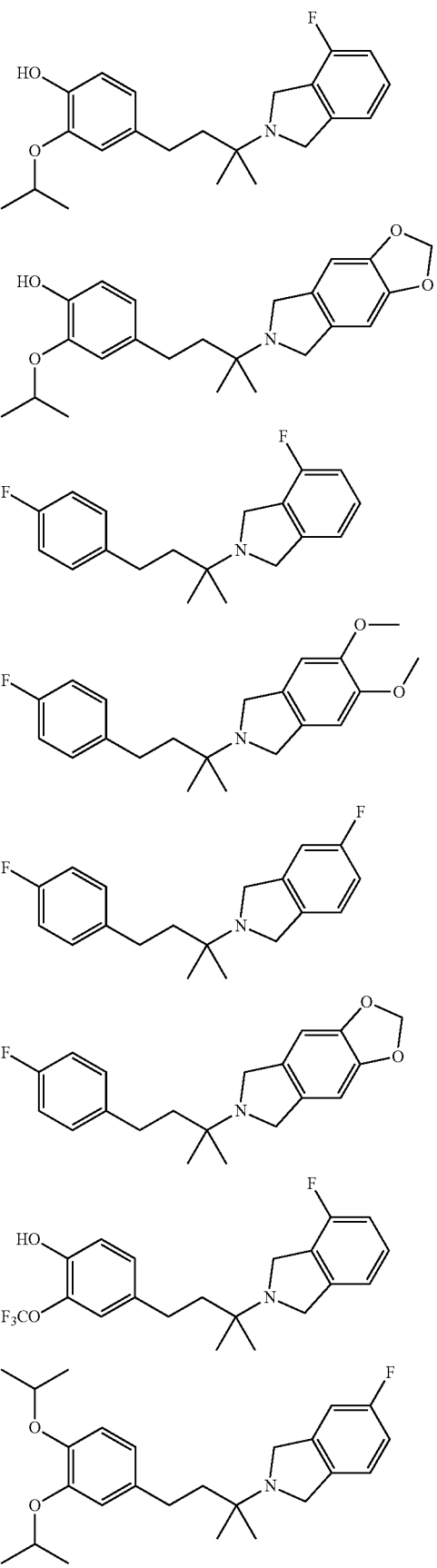

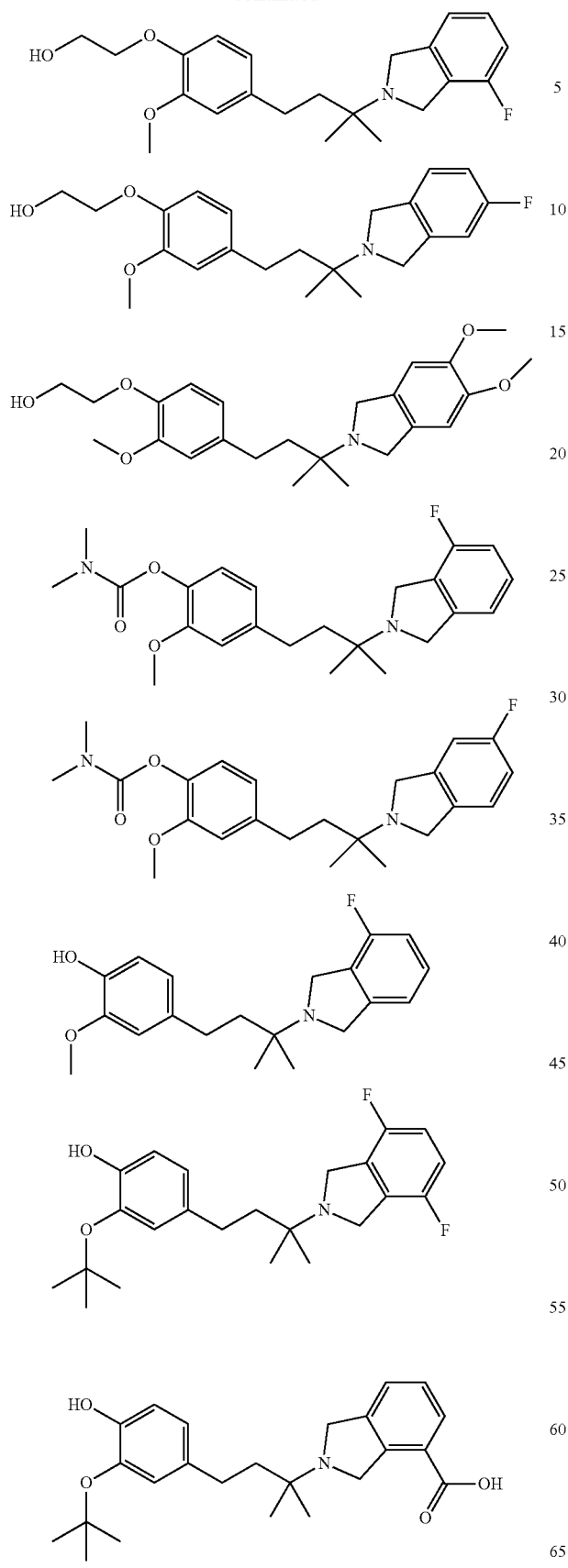
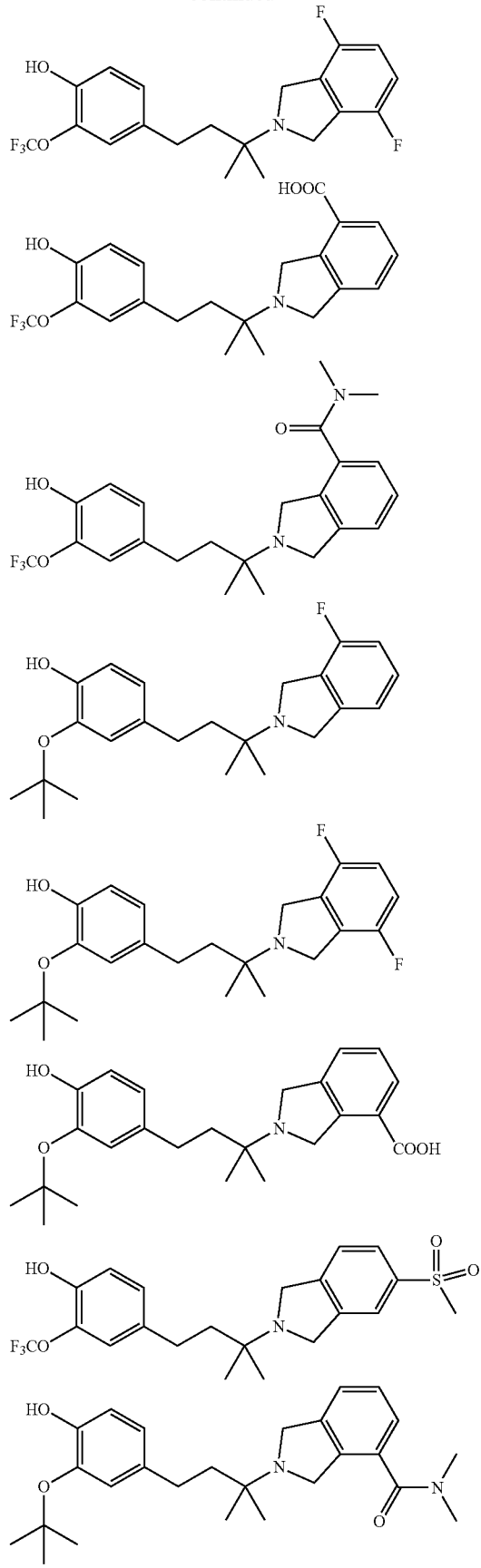

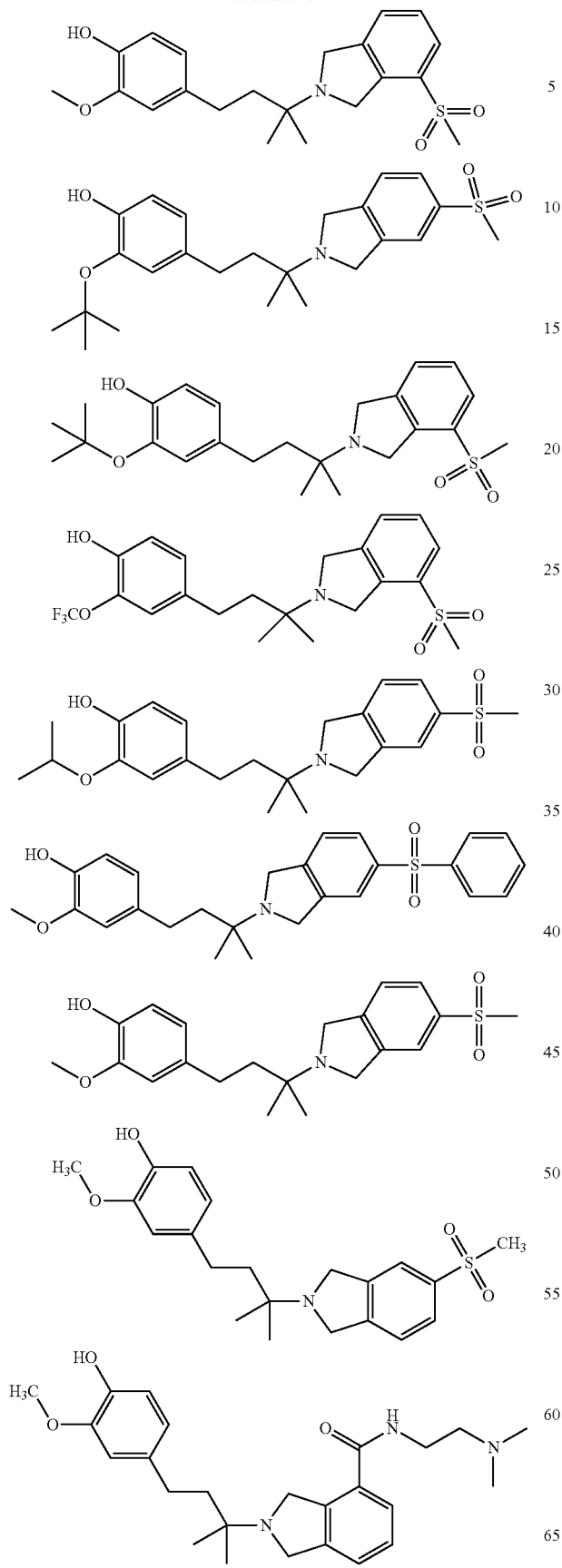
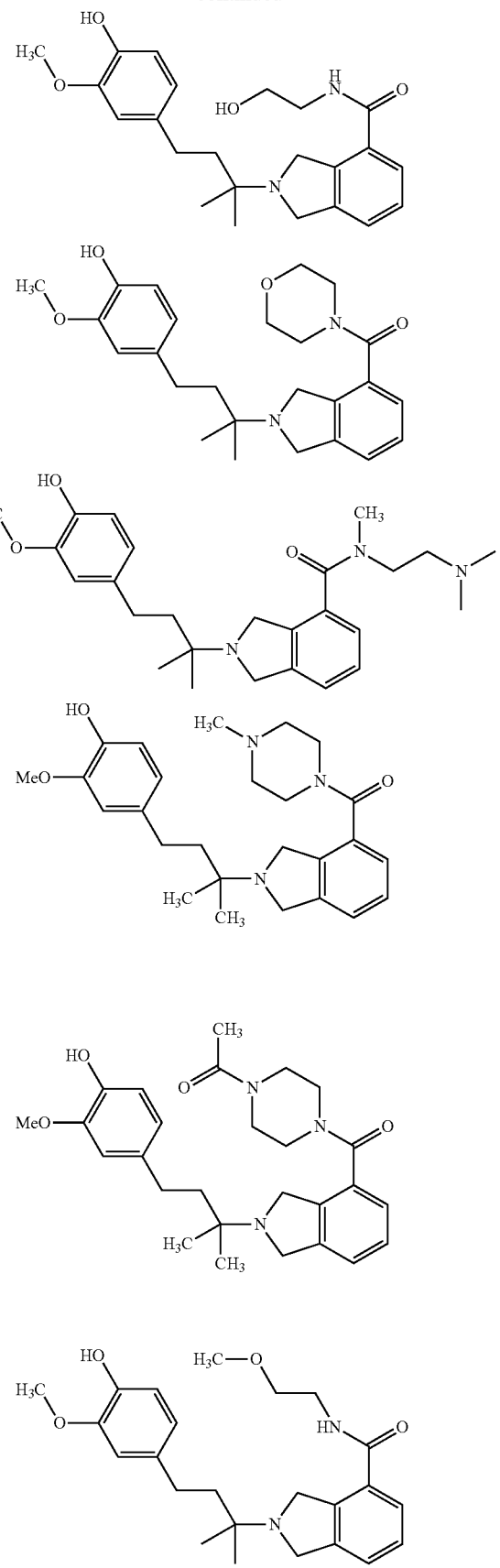

61
-continued
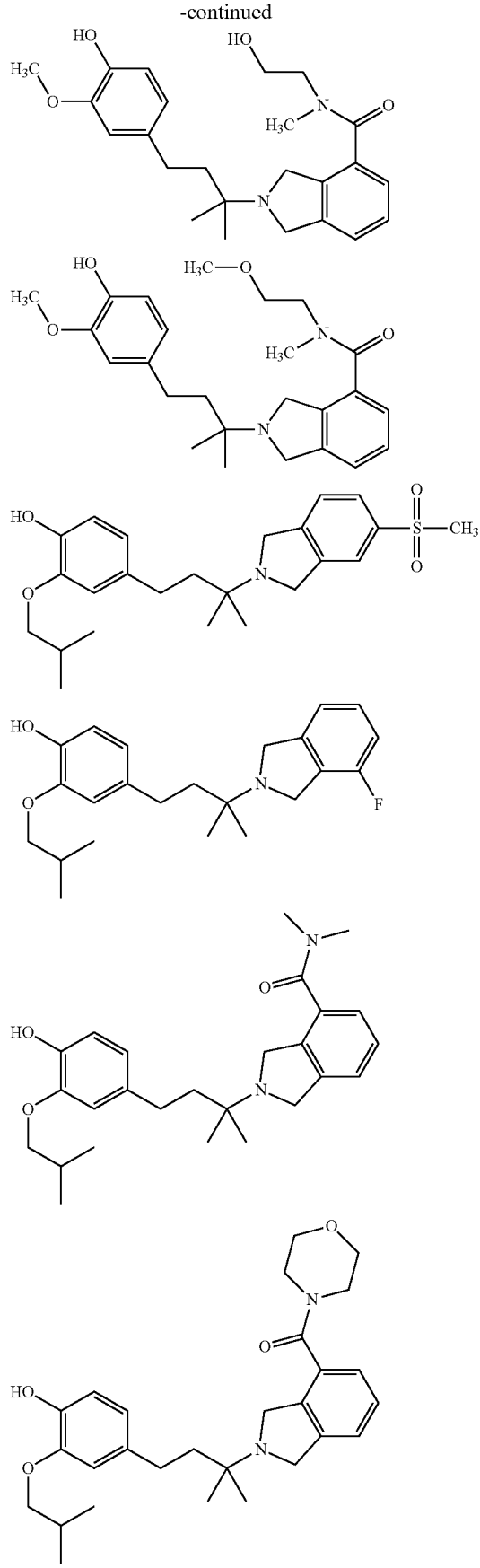
62
-continued
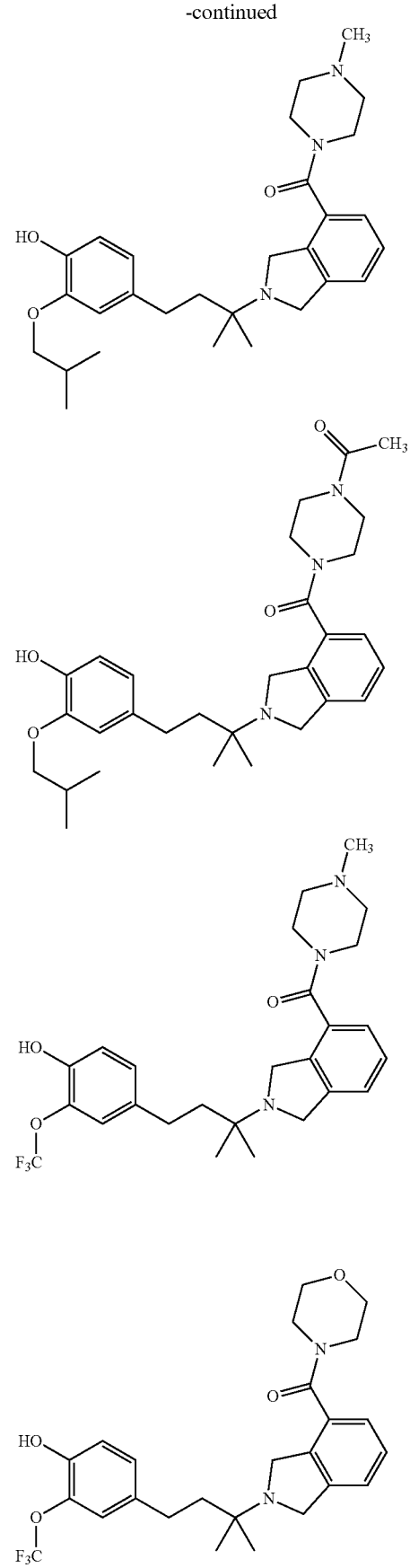

-continued
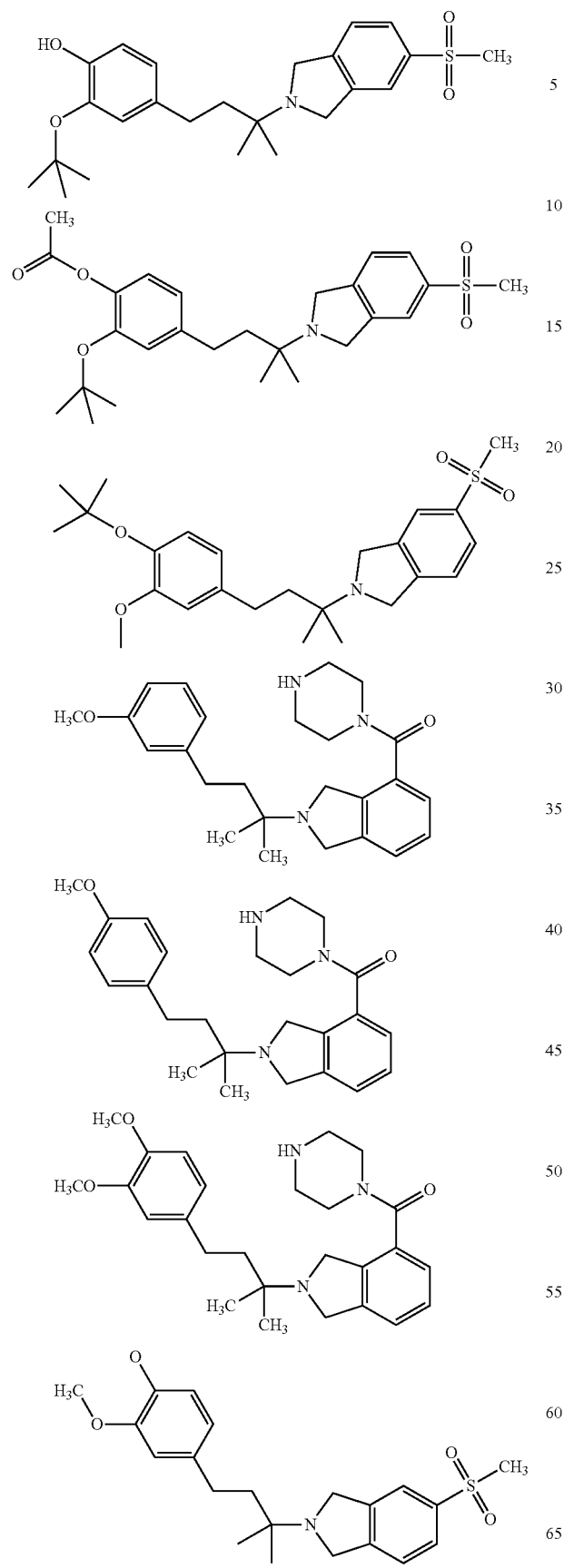
-continued
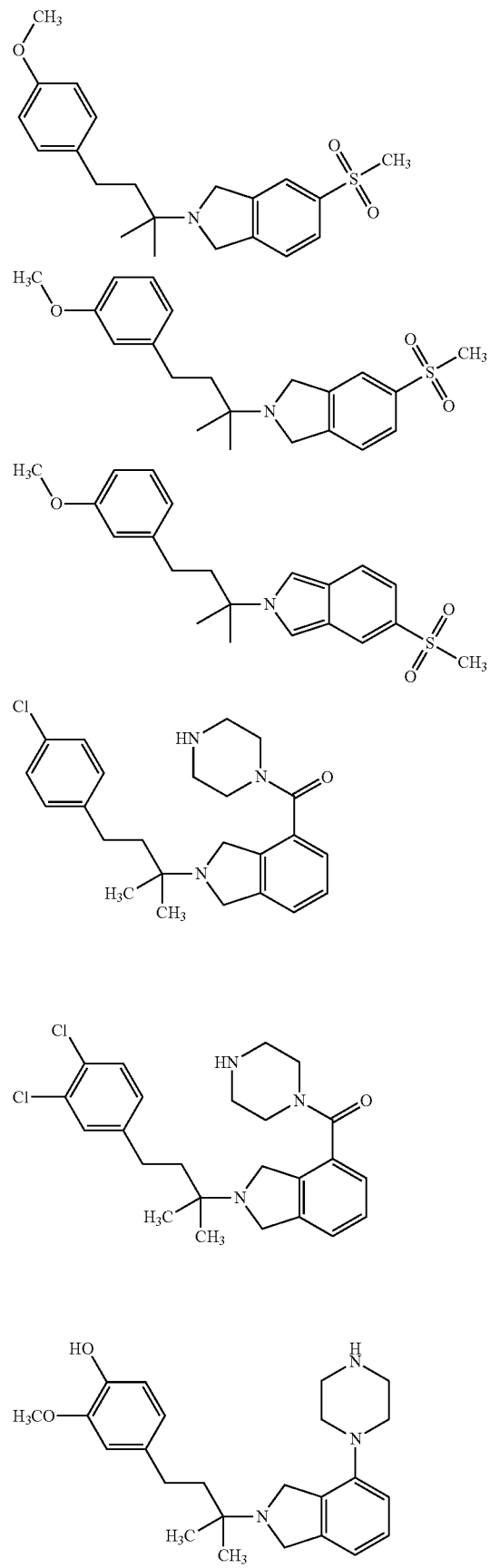

65
-continued

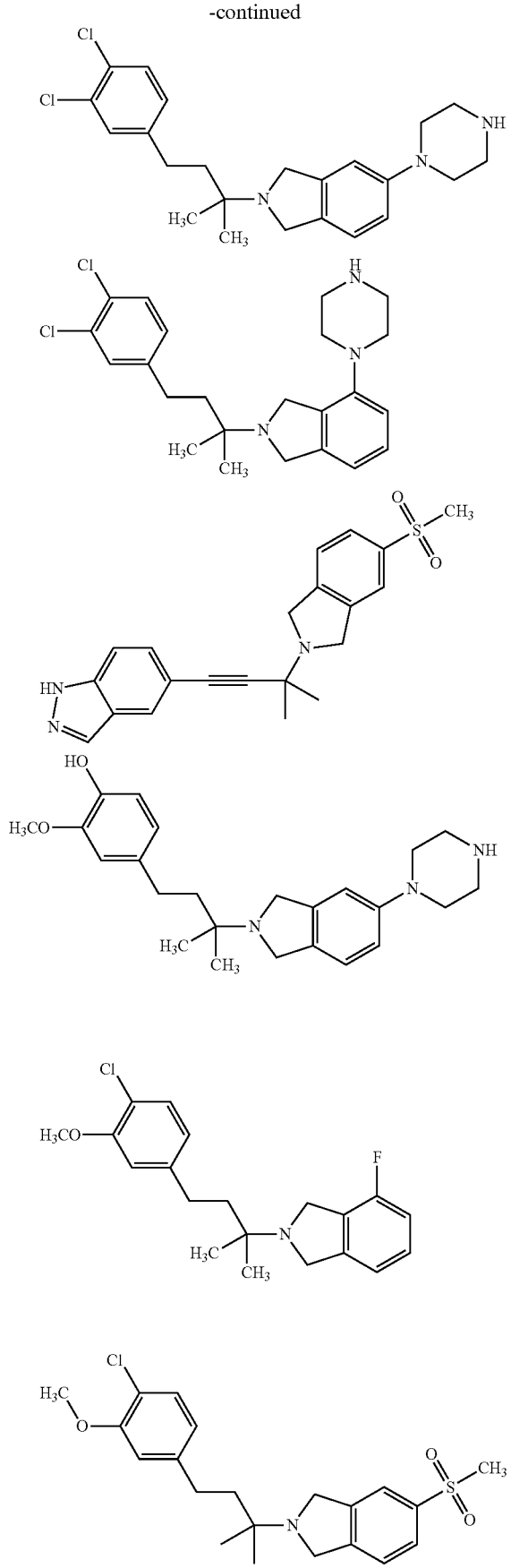

66
-continued

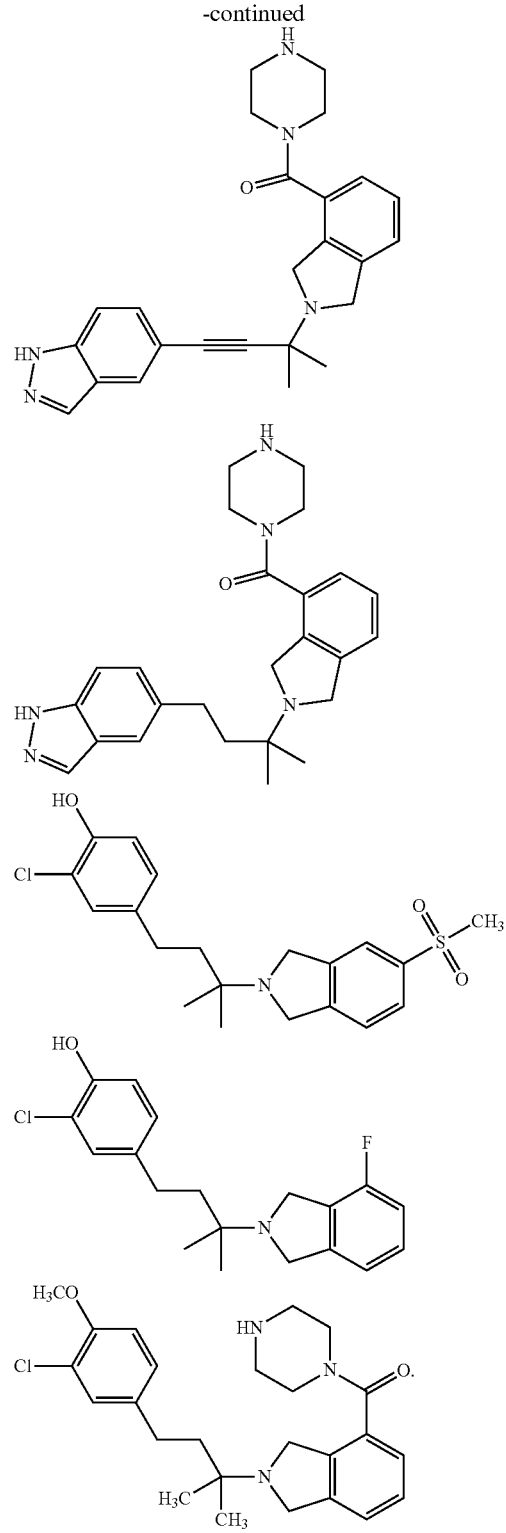

In another embodiment, a method/use is provided for inhibiting an amyloid beta effect on a neuronal cell comprising administering a composition comprising an effective amount of a compound, or pharmaceutically acceptable salt thereof, and a pharmaceutically acceptable carrier, wherein the compound, or salt thereof, is selected from the group consisting of:

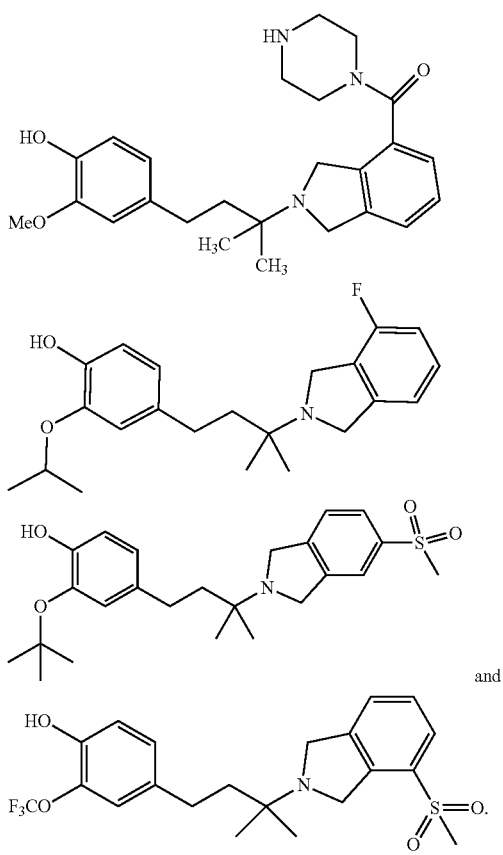

In another embodiment, a method/use is provided for inhibiting an amyloid beta effect on a neuronal cell comprising administering a composition comprising an effective amount of a compound, or pharmaceutically acceptable salt thereof, and a pharmaceutically acceptable carrier, wherein the compound, or salt thereof, is selected from the group consisting of:

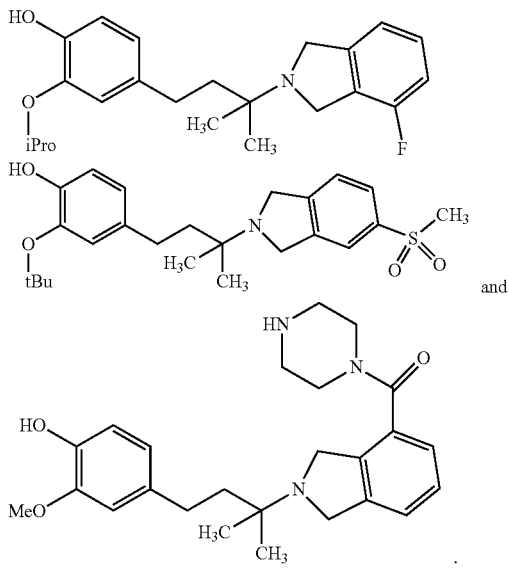

In another embodiment, a method/use is provided for inhibiting suppression of long term potentiation in a subject in need thereof comprising administering to the subject a therapeutically effective amount of a composition comprising a sigma-2 receptor antagonist compound, or pharmaceutically acceptable salt thereof, according to Formula I and/or Formula II; and a pharmaceutically acceptable carrier.

In another embodiment, a method/use is provided for inhibiting cognitive decline in a subject exhibiting, or at risk of exhibiting, cognitive decline, comprising administering to the subject a therapeutically effective amount of a composition comprising a sigma-2 receptor antagonist compound, or pharmaceutically acceptable salt thereof, according to Formula I and/or Formula II; and a pharmaceutically acceptable carrier.

In another embodiment, a method/use is provided for inhibiting cognitive decline in a subject associated with an amyloid beta oligomer effect on central neurons comprising administering to the subject afflicted with said cognitive decline a therapeutically effective amount of the composition comprising a sigma-2 receptor antagonist compound, or pharmaceutically acceptable salt thereof, according to Formula I and/or Formula II; and a pharmaceutically acceptable carrier.

In another embodiment, a method/use is provided for the treatment of mild cognitive impairment in Alzheimer's disease in a subject in need thereof, comprising administering to the subject a therapeutically effective amount of the composition comprising a sigma-2 receptor antagonist compound, or pharmaceutically acceptable salt thereof, according to Formula I and/or Formula II; and a pharmaceutically acceptable carrier.

In a further embodiment, isoindoline compounds are provided according to formula I and/or formula II, or pharmaceutically acceptable salts thereof, that act as sigma-2 antagonists by binding to a sigma-2 receptor and inhibiting the binding of Aβ oligomers to neurons, and particularly to synapses. In some embodiments, the sigma-2 antagonist competes with Aβ oligomer binding to neurons and specifically synapses, or otherwise disrupts the ability of Aβ oligomer to bind to neurons, such as by interfering with Aβ oligomer formation or binding to Aβ oligomer or possibly interfering with the ability of Aβ oligomer to set in motion signal transduction mechanisms attendant to its binding to neurons. In certain embodiments, the sigma-2 antagonists thus inhibit a non-lethal Aβ pathologic effect ("non-lethal Aβ pathology" or "non-lethal amyloid beta pathology), including a defect in membrane trafficking, synaptic dysfunction, a memory and learning defect in an animal, reduction in synapse number, change in dendritic spine length or spine morphology, or a defect in long term potentiation (LTP), among others.

In other embodiments, isoindoline sigma-2 antagonists provided herein that are active in other assays as illustrated herein, possess an ability to restore neurons to a normal state or interfere with Aβ oligomer-induced synaptic dysfunction. Without being bound by theory, sigma-2 antagonists provided herein interfere with one or more of Aβ oligomer structure, Aβ oligomer binding to neurons or Aβ oligomer-induced molecular signaling mechanisms which is useful in counteracting the nonlethal effects of Aβ oligomers and in treating early stages of soluble Aβ oligomer-associated pathologies.

In one embodiment, sigma-2 antagonists are provided according to formula I and/or formula II, or pharmaceutically acceptable salts thereof, that are functional neuronal antagonists and are used in a method of inhibiting synapse loss in a neuronal cell, the loss being associated with exposure of the cell to one or more Abeta oligomers or other Abeta complexes or, more generally, Abeta species including Abeta peptides in monomeric or oligomeric or otherwise soluble complexed form (as defined below), the method comprising contacting said cell with an amount of one or more sigma-2 antagonists in an amount effective to avert or reduce said loss or to partially or completely restore synapse number in said cell to pre-exposure levels.

In another embodiment, a method is provided for modulating a membrane trafficking change in a neuronal cell, said change being associated with exposure of said cell to one or more Abeta species, the method comprising contacting said cell with an amount of one or more sigma-2 antagonists according to formula I and/or formula II, or a pharmaceutically acceptable salt thereof, in an amount effective to avert or reduce said membrane trafficking change, or have it remain at or closer to levels observed prior to exposure of said cell to said Abeta species.

In another embodiment, sigma-2 antagonists are provided according to formula I and/or formula II, or pharmaceutically acceptable salts thereof, that are used in a method for treating cognitive decline comprising administering to a subject one or more of the sigma-2 antagonists of the disclosure.

In another embodiment, a method is provided for treating cognitive decline in a subject in need thereof comprising administering to the subject an effective amount of one or more sigma-2 antagonists according to formula I and/or formula II, or pharmaceutically acceptable salts thereof.

In yet another embodiment, the sigma-2 antagonists according to formula I and/or formula II, or pharmaceutically acceptable salts thereof, are functional neuronal sigma-2 antagonists used in a method for treating a cognitive decline or neurodegenerative disorder or a defect in synapse function and/or number comprising administering to a subject one or more of the sigma-2 antagonists of the disclosure.

In yet another embodiment, a method is provided for treating a cognitive decline or neurodegenerative disorder or a defect in synapse function and/or number in a subject comprising administering to a subject one or more of the sigma-2 antagonists according to formula I and/or formula II, or pharmaceutically acceptable salts thereof, that are functional neuronal sigma-2 antagonists.

In a further embodiments, methods are provided comprising administering one or more sigma-2 receptor antagonists according to formula I and/or formula II, or pharmaceutically acceptable salts thereof, to a subject in need thereof in an amount effective for inhibiting amyloid beta oligomer-induced synaptic dysfunction of a neuronal cell; and/or for inhibiting suppression of hippocampal long term potention caused by exposure of neurons to Abeta oligomers.

DETAILED DESCRIPTION

Before compounds, compositions and methods are described in detail, it is to be understood that this disclosure is not limited to the particular processes, compositions, or methodologies described, as these may vary. It is also to be understood that the terminology used in the description is for the purpose of describing the particular versions or embodiments only, and is not intended to limit the scope of the disclosure which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the disclosure, the preferred methods, devices, and materials are now described.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

Definitions

The singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of a given value. For example, "about 50%" means in the range of 45%-55%.

"Sigma-2 ligand" refers to a compound that binds to a sigma-2 receptor and includes agonists, antagonists, partial agonists, inverse agonists and simply competitors for other ligands of this receptor or protein.

The term "agonist" refers to a compound, the presence of which results in a biological activity of a receptor that is the same as the biological activity resulting from the presence of a naturally occurring ligand for the receptor.

The term "partial agonist" refers to a compound the presence of which results in a biological activity of a receptor that is of the same type as that resulting from the presence of a naturally occurring ligand for the receptor, but of a lower magnitude.

The term "antagonist" refers to an entity, e.g., a compound, antibody or fragment, the presence of which results in a decrease in the magnitude of a biological activity of a receptor. In certain embodiments, the presence of an antagonist results in complete inhibition of a biological activity of a receptor. As used herein, the term "sigma-2 receptor antagonist" is used to describe a compound that acts as a "functional antagonist" at the sigma-2 receptor in that it blocks Abeta effects, for example, Abeta oligomer-induced synaptic dysfunction, for example, as seen in an in vitro assay, such as a membrane trafficking assay, or a synapse loss assay, or Abeta oligomer mediated sigma-2 receptor activation of caspase-3, or in a behavioral assay, or in a patient in need thereof. The functional antagonist may act directly by inhibiting binding of, for example, an Abeta oligomer to a sigma-2 receptor, or indirectly, by interfering with downstream signaling resultant from Abeta oligomer binding the sigma-2 receptor.

The term "sigma-2 receptor antagonist compound" refers to a molecule that binds to a sigma-2 receptor in a measurable amount and acts as a functional antagonist with respect to Abeta effects oligomer induced synaptic dysfunction resultant from sigma-2 receptor binding.

The term "selectivity" or "selective" refers to a difference in the binding affinity of a compound ($K_i$) for a sigma receptor, for example, a sigma-2 receptor, compared to a non-sigma receptor. The sigma-2 antagonists possess high selectivity for a sigma receptor in synaptic neurons. The $K_i$ for a sigma-2 receptor or both a sigma-2 and a sigma-1 receptor is compared to the $K_i$ for a non-sigma receptor. In some embodiments, the selective sigma-2 receptor antagonist, or sigma-1 receptor ligand, has at least 10-fold, 20-fold, 30-fold, 50-fold, 70-fold, 100-fold, or 500-fold higher affinity, or more, for binding to a sigma receptor compared to a non-sigma receptor as assessed by a comparison of binding dissociation constant Ki values, or $IC_{50}$ values, or binding constant, at different receptors. Any known assay protocol can be used to assess the Ki or $IC_{50}$ values at different receptors, for example, by monitoring the competitive displacement from receptors of a radiolabeled compound with a known dissociation constant, for example, by the method of Cheng and Prusoff (1973) (Biochem. Pharmacol. 22, 3099-3108), or specifically as provided herein. In some embodiments, the sigma-2 antagonist compound is an antibody, or active binding fragment thereof, specific for binding to a sigma-2 receptor compared to a non-sigma receptor. In the case of an antibody, or fragment, binding constants at a sigma-2 receptor, or fragment, can be calculated and compared to binding constants at a non-sigma receptor by any means known in the art, for example, by the method of Beatty et al., 1987, J Immunol Meth, 100(1-2):173-179, or the method of Chalquest, 1988, J. Clin. Microbiol. 26(12): 2561-2563. The non-sigma receptor is, for example, selected from a muscarinic M1-M4 receptor, serotonin (5-HT) receptor, alpha adrenergic receptor, beta adrenergic receptor, opioid receptor, serotonin transporter, dopamine transporter, adrenergic transporter, dopamine receptor, or NMDA receptor.

In the present application, the term "high affinity" is intended to mean a compound which exhibits a $K_i$ value of less than 600 nM, 500 nM, 400 nM, 300 nM, 200 nM, less than 150 nM, less than 100 nM, less than 80 nM, less than 60 nM, or preferably less than 50 nM in a sigma receptor binding assay, for example against [$^3$H]-DTG, as disclosed by Weber et al., Proc. Natl. Acad. Sci (USA) 83: 8784-8788 (1986), incorporated herein by reference, which measures the binding affinity of compounds toward both the sigma-1 and sigma-2 receptor sites. Especially preferred sigma ligands exhibit Ki values of less than about 150 nM, preferably less than 100 nM, less than about 60 nM, less than about 10 nM, or less than about 1 nM against [3H]-DTG.

The term "therapeutic phenotype" is used to describe a pattern of activity for compounds in the in vitro assays that is predictive of behavioral efficacy. A compound that (1) selectively binds with high affinity to a sigma-2 receptor, and (2) acts as a functional antagonist with respect to Abeta oligomer-induced effects in a neuron, is said to have the "therapeutic phenotype" if (i) it blocks or reduces Aβ-induced membrane trafficking deficits; (ii) it blocks or reduces Aβ-induced synapse loss and (iii) it does not affect trafficking or synapse number in the absence of Abeta oligomer. This pattern of activity in the in vitro assays is termed the "therapeutic phenotype" and is predictive of behavioral efficacy.

The term "therapeutic profile" is used to describe a compound that meets the therapeutic phenotype, and also has good brain penetrability (the ability to cross the blood brain barrier), good plasma stability and good metabolic stability.

The term "drug-like properties" is used herein to describe the pharmacokinetic and stability characteristics of the sigma-2 receptor ligands upon administration; including brain penetrability, metabolic stability and/or plasma stability.

"Abeta species" or "Aβ" shall include compositions comprising soluble amyloid peptide-containing components such as Abeta monomers, Abeta oligomers, or complexes of Abeta peptide (in monomeric, dimeric or polymeric form) with other soluble peptides or proteins as well as other soluble Abeta assemblies, including any processed product of amyloid precursor protein. Soluble Aβ oligomers are known to be neurotoxic. Even $Aβ_{1-42}$ dimers are known to impair synaptic plasticity in mouse hippocampal slices. In one theory known in the art, native $Aβ_{1-42}$ monomers are considered neuroprotective, and self-association of Aβ monomers into soluble Abeta oligomers is required for neurotoxicity. However, certain Aβ mutant monomers (arctic mutation (E22G) are reported to be associated with familial AD. See, for example, Giuffrida et al., β-*Amyloid monomers are neuroprotective*. J. Neurosci. 2009 29(34): 10582-10587. Nonlimiting examples of preparations comprising Abeta species are disclosed in U.S. patent application Ser. No. 13/021,872; U.S. Patent Publication 2010/0240868; International Patent Application WO/2004/067561; International Patent Application WO/2010/011947; U.S. Patent Publication 20070098721; U.S. Patent Publication 20100209346; International Patent Application WO/2007/005359; U.S. Patent Publication 20080044356; U.S. Patent Publication 20070218491; WO/2007/126473; U.S. Patent Publication 20050074763; International Patent Application WO/2007/126473, International Patent Application WO/2009/048631, and U.S. Patent Publication 20080044406, each of which is incorporated herein by reference.

"Administering," when used in conjunction with the compounds of the disclosure, means to administer a compound directly into or onto a target tissue or to administer a compound systemically or locally to a patient or other subject.

The term "animal" as used herein includes, but is not limited to, humans and non-human vertebrates such as wild, experimental, domestic and farm animals and pets.

As used herein, the terms "subject," "individual," and "patient," are used interchangeably and refer to any animal, including mammals, mice, rats, other rodents, rabbits, dogs, cats, swine, cattle, sheep, horses, primates, non-human primates, humans, and the like.

As used herein, the term "contacting" refers to the bringing together or combining of molecules (or of a molecule with a higher order structure such as a cell or cell membrane) such that they are within a distance that allows for intermolecular interactions such as the non-covalent interaction between two peptides or one protein and another protein or other molecule, such as a small molecule. In some embodiments, contacting occurs in a solution in which the combined or contacted molecules are mixed in a common solvent and are allowed to freely associate. In some embodiments, the contacting can occur at or otherwise within a cell or in a cell-free environment. In some embodiments, the cell-free environment is the lysate produced from a cell. In some embodiments, a cell lysate may be a whole-cell lysate, nuclear lysate, cytoplasm lysate, and combinations thereof. In some embodiments, the cell-free lysate is lysate obtained from a nuclear extraction and isolation wherein the nuclei of a cell population are removed from the cells and then lysed. In some embodiments, the nuclei are not lysed, but are still considered to be a cell-free environment. The molecules can be brought together by mixing such as vortexing, shaking, and the like.

The term "improves" is used to convey that the disclosure changes either the characteristics and/or the physical attributes of the tissue to which it is being provided, applied or administered. The term "improves" may also be used in conjunction with a disease state such that when a disease state is "improved" the symptoms or physical characteristics associated with the disease state are diminished, reduced, eliminated, delayed or averted.

The term "inhibiting" includes the blockade, aversion of a certain result or process, or the restoration of the converse result or process. In terms of prophylaxis or treatment by administration of a compound of the disclosure, "inhibiting" includes protecting against (partially or wholly) or delaying the onset of symptoms, alleviating symptoms, or protecting against, diminishing or eliminating a disease, condition or disorder.

The term "inhibiting trafficking deficits" refers to the ability to block soluble Ab oligomer-induced membrane trafficking deficits in a cell, preferably a neuronal cell. A compound capable of inhibiting trafficking deficits has an EC50<20 µM, less than 15 µM, less than 10 µM, less than 5 µM, and preferably less than 1 µM in the membrane trafficking assay, and further is capable of at least 50%, preferably at least 60%, and more preferably at least 70% maximum inhibition of the Abeta oligomer effects of soluble Abeta oligomer-induced membrane trafficking deficits, for example, as described in Example 6.

The term "log P" refers to the partition coefficient of a compound. The partition coefficient is the ratio of concentrations of un-ionized compound in each of two solution phases, for example, octanol and water. To measure the partition coefficient of ionizable solute compounds, the pH of the aqueous phase is adjusted such that the predominant form of the compound is un-ionized. The logarithm of the ratio of concentrations of the un-ionized solute compound in the solvents is called log P. The log P is a measure of lipophilicity. For example, $$\log P_{oct/wat} = \log([\text{solute}]_{octanol}[\text{solute}]_{un\text{-}ionized,water}).$$

At various places in the present specification, substituents of compounds of the disclosure are disclosed in groups or in ranges. It is specifically intended that embodiments of the disclosure include each and every individual subcombination of the members of such groups and ranges. For example, the term "$C_{1-6}$ alkyl" is specifically intended to individually disclose e.g. methyl ($C_1$ alkyl), ethyl ($C_2$ alkyl), $C_3$ alkyl, $C_4$ alkyl, $C_5$ alkyl, and $C_6$ alkyl as well as, e.g. $C_1$-$C_2$ alkyl, $C_1$-$C_3$ alkyl, $C_1$-$C_4$ alkyl, $C_2$-$C_3$ alkyl, $C_2$-$C_4$ alkyl, $C_3$-$C_6$ alkyl, $C_4$-$C_5$ alkyl, and $C_5$-$C_6$ alkyl.

For compounds of the disclosure in which a variable appears more than once, each variable can be a different moiety selected from the Markush group defining the variable. For example, where a structure is described having two R groups that are simultaneously present on the same compound, then the two R groups can represent different moieties selected from the Markush group defined for R.

The term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

As used herein, the term "alkyl" is meant to refer to a saturated hydrocarbon group which is straight-chained or branched. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylene" refers to a divalent alkyl linking group. An example of alkylene is methylene ($CH_2$).

As used herein, "alkenyl" refers to an alkyl group having one or more double carbon-carbon bonds. Example alkenyl groups include, but are not limited to, ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include, but are not limited to, ethynyl, propynyl, and the like. The term "alkynylenyl" refers to a divalent linking alkynyl group.

As used herein, "haloalkyl" refers to an alkyl group having one or more halogen substituents selected from F, Cl, Br, and/or I. Example haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. In some embodiments, aryl groups have from 6 to about 10 carbon atoms.

As used herein, "cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic (e.g., having 2, 3 or 4 fused rings) ring systems as well as spiro ring systems. A cycloalkyl group can contain from 3 to about 15, from 3 to about 10, from 3 to about 8, from 3 to about 6, from 4 to about 6, from 3 to about 5, or from 5 to about 6 ring-forming carbon atoms. Ring-forming carbon atoms of a cycloalkyl group can be optionally substituted by oxo or sulfido. Example of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl). Preferably, "cycloalkyl" refers to cyclized alkyl groups that contain up to 20 ring-forming carbon atoms. Examples of cycloalkyl preferably include cyclopropyl, cyclobutyl, cyclopentyl, cyclohexyl, cycloheptyl, adamantyl, and the like As used herein, "heteroaryl" groups refer to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms each independently selected from sulfur, oxygen, and nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 1 to about 5, from about 1 to about 4, from about 1 to about 3, from about 1 to about 2, carbon atoms as ring-forming atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles having up to 20 ring-forming atoms including cyclized alkyl, alkenyl, and alkynyl groups where one or more of the ring-forming carbon atoms is replaced by a heteroatom such as an O, N, or S atom. Heterocycloalkyl groups can be mono or polycyclic (e.g., both fused and spiro systems). Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, pyrrolidin-2-one-3-yl, and the like. Ring-forming carbon atoms and heteroatoms of a heterocycloalkyl group can be optionally substituted by oxo or sulfido. For example, a ring-forming S atom can be substituted by 1 or 2 oxo [i.e., form a S(O) or S(O)$_2$]. For another example, a ring-forming C atom can be substituted by oxo (i.e., form carbonyl). Also included in the definition of heterocycloalkyl are moieties that have one or more aromatic rings fused (i.e., having a bond in common with) to the nonaromatic heterocyclic ring, for example pyridinyl, thiophenyl, phthalimidyl, naphthalimidyl, and benzo derivatives of heterocycles such as indoline, isoindoline, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. Ring-forming carbon atoms and heteroatoms of the heterocycloalkyl group can be optionally substituted by oxo or sulfido. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-haloalkyl group. An example haloalkoxy group is OCF$_3$. As used herein, "trihalomethoxy" refers to a methoxy group having three halogen substituents. Examples of trihalomethoxy groups include, but are not limited to, —OCF$_3$, —OCCF$_2$, —OCCl$_3$, and the like.

As used herein, "arylalkyl" refers to a C$_{1-6}$ alkyl substituted by aryl and "cycloalkylalkyl" refers to C$_{1-6}$ alkyl substituted by cycloalkyl.

As used herein, "heteroarylalkyl" refers to a C$_{1-6}$ alkyl group substituted by a heteroaryl group, and "heterocycloalkylalkyl" refers to a C$_{1-6}$ alkyl substituted by heterocycloalkyl.

As used herein, "amino" refers to NH$_2$.

As used herein, "alkylamino" refers to an amino group substituted by an alkyl group.

As used herein, "dialkylamino" refers to an amino group substituted by two alkyl groups.

As used here, C(O) refers to C(═O).

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valence of the designated atom or moiety is not exceeded, and that the substitution results in a stable compound. For example, if a methyl group (i.e., CH$_3$) is optionally substituted, then 3 hydrogen atoms on the carbon atom can be replaced with substituent groups, in indicated.

As used herein, an "amyloid beta effect", for example, a "nonlethal amyloid beta effect", or "Abeta oligomer effect", refers to an effect, particularly a nonlethal effect, on a cell that is contacted with an Abeta species. For example, it has been found that when a neuronal cell is contacted with a soluble Amyloid-beta ("Abeta") oligomer, the oligomers bind to a subset of synapses on a subset of neuronal cells in vitro. This binding can be quantified in an assay measuring Abeta oligomer binding in vitro for example. Another documented effect of Abeta species is a reduction in synapse number, which has been reported to be about 18% in the human hippocampus (Scheff et al, 2007) and can be quantified (for example, in an assay measuring synapse number). As another example, it has been found that, when a neuronal cell is contacted with an Amyloid-beta ("Abeta") oligomer, membrane trafficking is modulated and alteration of membrane trafficking ensues. This abnormality can be visualized with many assays, including but not limited to, an MTT assay. For example, yellow tetrazolium salts are endocytosed by cells and the salts are reduced to insoluble purple formazan by enzymes located within vesicles in the endosomal pathway. The level of purple formazan is a reflection of the number of actively metabolizing cells in culture, and reduction in the amount of formazan is taken as a measure of cell death or metabolic toxicity in culture. When cells that are contacted with a yellow tetrazolium salt are observed through a microscope, the purple formazan is first visible in intracellular vesicles that fill the cell. Over time, the vesicles are exocytosed and the formazan precipitates as needle-shaped crystals on the outer surface of the plasma membrane as the insoluble formazan is exposed to the aqueous media environment. Still other effects of Abeta species include cognitive decline, such as a decline in the ability to form new memories and memory loss which can be measured in assays using animal models in vivo. In some embodiments, an Abeta effect is selected from Abeta oligomer-induced synaptic dysfunction, for example, as seen in an in vitro assay, such as a membrane trafficking assay, or a synapse loss assay, or Abeta oligomer mediated sigma-2 receptor activation of caspase-3, or Abeta induced neuronal dysfunction, Abeta mediated decrease in long term potentiation (LTP), or in cognitive decline in a behavioral assay, or in a patient in need thereof.

In some embodiments, a test compound is said to be effective to treat cognitive decline or a disease associated therewith when it can inhibit an effect associated with soluble Abeta oligomer species on a neuronal cell more than about 10%, preferably more than 15%, and preferably more than 20% as compared to a negative control. In some embodiments, a test agent is said to be effective when it can inhibit a processed product of amyloid precursor protein-mediated effect more than about 10%, preferably more than 15%, and preferably more than 20% as compared to a positive control. For example, as shown in the Examples below, inhibition of Abeta oligomer binding by only 18% inhibits synapse reduction completely. Although the present specification focuses on inhibition of nonlethal effects of Abeta species, such as abnormalities in neuronal metabolism and synapse number reduction, these are shown to correlate with cognitive function and are furthermore expected, over time, to result in reduction (compared to untreated subjects) of downstream measurable symptoms of amyloid pathology, notably clinical symptoms such as 1) fibril or plaque accumulation measured by amyloid imaging agents such as fluorbetapir, PittB or any other imaging agent, 2) synapse loss or cell death as measured by glucose hypometabolism detected with FDG-PET, or 3) changes in protein expression or metabolite amount in the brain or body detectable by imaging or protein/metabolite detection in cerebrospinal fluid, brain biopsies or plasma obtained from patients by ELISA, (such as changes in levels and or ratios of Abeta 42, phosphorylated tau, total tau measured by ELISA, or patterns of protein expression changes detectable in an ELISA panel (see reference: Wyss-Coray T. et al. Modeling of pathological traits in Alzheimer's disease based on systemic extracellular signaling proteome. *Mol Cell Proteomics* 2011 Jul. 8, which is hereby incorporated by reference in its entirety), 4) cerebral vascular abnormalities as measured by the presence of vascular edema or microhemorrhage detectable by MRI and any other symptoms detectable by imaging techniques, and 5) cognitive loss as measured by any administered cognitive test such as ADAS-Cog, MMSE, CBIC or any other cognitive testing instrument.

As used herein, the term "a neuronal cell" can be used to refer to a single cell or to a population of cells. In some embodiments, the neuronal cell is a primary neuronal cell. In some embodiments, the neuronal cell is an immortalized or transformed neuronal cell or a stem cell. A primary neuronal cell is a neuronal cell that cannot differentiate into other types of neuronal cells, such as glia cells. A stem cell is one that can differentiate into neurons and other types of neuronal cells such as glia. In some embodiments, assays utilize a composition comprising at least one neuronal cell is free of glia cells. In some embodiments, the composition comprises less than about 30%, 25%, 20%, 15%, 10%, 5%, or 1% of glia cells, which are known to internalize and accumulate Abeta. The primary neuronal cell can be derived from any area of the brain of an animal. In some embodiments, the neuronal cell is a hippocampal or cortical cell. The presence of glia cells can be determined by any method. In some embodiments, glia cells are detected by the presence of GFAP and neurons can be detected by staining positively with antibodies directed against MAP2.

The phrase "pharmaceutically acceptable" refers to molecular entities and compositions that are generally regarded as safe and nontoxic. In particular, pharmaceutically acceptable carriers, diluents or other excipients used in the pharmaceutical compositions of this disclosure are physiologically tolerable, compatible with other ingredients, and do not typically produce an allergic or similar untoward reaction (for example, gastric upset, dizziness and the like) when administered to a patient. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The phrase "pharmaceutically acceptable salt(s)", as used herein, includes those salts of compounds of the disclosure that are safe and effective for use in mammals and that possess the desired biological activity. Pharmaceutically acceptable salts include salts of acidic or basic groups present in compounds of the disclosure or in compounds identified pursuant to the methods of the disclosure. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the disclosure can form pharmaceutically acceptable salts with various amino acids. Suitable base salts include, but are not limited to, aluminum, calcium, lithium, magnesium, potassium, sodium, zinc, iron and diethanolamine salts. Pharmaceutically acceptable base addition salts are also formed with amines, such as organic amines. Examples of suitable amines are N,N'-dibenzylethylenediamine, chloroprocaine, choline, diethanolamine, dicyclohexylamine, ethylenediamine, N-methylglucamine, and procaine.

As used herein, the term "therapeutic" means an agent utilized to treat, combat, ameliorate, protect against or improve an unwanted condition or disease of a subject.

As used herein, the term "effective amount" refers to an amount that results in measurable inhibition of at least one symptom or parameter of a specific disorder or pathological process. For example, an amount of a sigma-2 ligand of the disclosure that provides a measurably lower synapse reduction in the presence of Abeta oligomer qualifies as an effective amount because it reduces a pathological process even if no clinical symptoms of amyloid pathology are altered, at least immediately.

A "therapeutically effective amount" or "effective amount" of a compound or composition of the disclosure is a predetermined amount which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect or physician observes a change). An effective amount of a compound of the disclosure may broadly range from about 0.01 mg/Kg to about 500 mg/Kg, about 0.1 mg/Kg to about 400 mg/Kg, about 1 mg/Kg to about 300 mg/Kg, about 0.05 to about 20 mg/Kg, about 0.1 mg/Kg to about 10 mg/Kg, or about 10 mg/Kg to about 100 mg/Kg. The effect contemplated herein includes both medical therapeutic and/or prophylactic treatment, as appropriate. The specific dose of a compound administered according to this disclosure to obtain therapeutic and/or prophylactic effects will, of course, be determined by the particular circumstances surrounding the case, including, for example, the compound administered, the route of administration, the co-administration of other active ingredients, the condition being treated, the activity of the specific compound employed, the specific composition employed, the age, body weight, general health, sex and diet of the patient; the time of administration, route of administration, and rate of excretion of the specific compound employed and the duration of the treatment. The effective amount administered will be determined by the physician in the light of the foregoing relevant circumstances and the exercise of sound medical judgment. A therapeutically effective amount of a compound of this disclosure is typically an amount such that when it is administered in a physiologically tolerable excipient composition, it is sufficient to achieve an effective systemic concentration or local concentration in the tissue. The total daily dose of the compounds of this disclosure administered to a human or other animal in single or in divided doses can be in amounts, for example, from 0.01 mg/Kg to about 500 mg/Kg, about 0.1 mg/Kg to about 400 mg/Kg, about 1 mg/Kg to about 300 mg/Kg, about 10 mg/Kg to about 100 mg/Kg, or more usually from 0.1 to 25 mg/kg body weight per day. Single dose compositions may contain such amounts or submultiples thereof to make up the daily dose.

In general, treatment regimens according to the disclosure comprise administration to a patient in need of such treatment will usually include from about 1 mg to about 5000 mg, 10 mg to about 2000 mg of the compound(s), 20 to 1000 mg, preferably 20 to 500 mg and most preferably about 50 mg, of a compound according to Formula I, and/or Formula II, or a pharmaceutically acceptable salt thereof, per day in single or multiple doses.

The terms "treat", "treated", or "treating" as used herein refers to both therapeutic treatment and prophylactic or preventative measures, wherein the object is to protect against (partially or wholly) or slow down (e.g., lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this disclosure, beneficial or desired clinical results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease. Treatment seeks to elicit a clinically significant response without excessive levels of side effects. Treatment also includes prolonging survival as compared to expected survival if not receiving treatment.

Generally speaking, the term "tissue" refers to any aggregation of similarly specialized cells which are united in the performance of a particular function.

As used herein, "cognitive decline" can be any negative change in an animal's cognitive function. For example cognitive decline, includes but is not limited to, memory loss (e.g. behavioral memory loss), failure to acquire new memories, confusion, impaired judgment, personality changes, disorientation, or any combination thereof. A compound that is effective to treat cognitive decline can be thus effective by restoring long term neuronal potentiation (LTP) or long term neuronal depression (LTD) or a balance of synaptic plasticity measured electrophysiologically; inhibiting, treating, and/or abatement of neurodegeneration; inhibiting, treating, and/or abatement of general amyloidosis; inhibiting, treating, abatement of one or more of amyloid production, amyloid assembly, amyloid aggregation, and amyloid oligomer binding; inhibiting, treating, and/or abatement of a nonlethal effect of one or more of Abeta species on a neuron cell (such as synapse loss or dysfunction and abnormal membrane trafficking); and any combination thereof. Additionally, that compound can also be effective in treating Abeta related neurodegenerative diseases and disorders including, but not limited to dementia, including but not limited to Alzheimer's Disease (AD) including mild Alzheimer's disease, Down's syndrome, vascular dementia (cerebral amyloid angiopathy and stroke), dementia with Lewy bodies, HIV dementia, Mild Cognitive Impairment (MCI); Age-Associated Memory Impairment (AAMI); Age-Related Cognitive Decline (ARCD), preclinical Alzheimer's Disease (PCAD); and Cognitive Impairment No Dementia (CIND).

As used herein, the term "natural ligand" refers to a ligand present in a subject that can bind to a protein, receptor, membrane lipid or other binding partner in vivo or that is replicated in vitro. The natural ligand can be synthetic in origin, but must also be present naturally and without human intervention in the subject. For example, Abeta oligomers are known to exist in human subjects. Therefore the Abeta oligomers found in a subject would be considered natural ligands. The binding of Abeta oligomers to a binding partner can be replicated in vitro using recombinant or synthetic techniques, but the Abeta oligomer would still be considered a natural ligand regardless of how the Abeta oligomer is prepared or manufactured. A synthetic small molecule that can also bind to the same binding partner is not a natural ligand if it does not exist in a subject. For example, isoindoline compounds which are described herein, are not normally present in a subject, and, therefore, would not be considered natural ligands.

Human Amyloid Beta

Overproduction and accumulation of amyloid beta is a pathologic feature of Alzheimer's disease. Human amyloid beta (Abeta) is the main component of insoluble amyloid plaques-deposits found in the brain of patients with Alzheimer's disease. The plaques are composed of fibrillar aggregates of Abeta. Amyloid beta fibrils have been associated with the advanced stages of Alzheimer's disease.

The cognitive hallmark of early Alzheimer's disease (AD) is an extraordinary inability to form new memories. Early memory loss is considered a synapse failure caused by soluble Aβ oligomers. These oligomers block long-term potentiation, a classic experimental paradigm for synaptic plasticity, and they are strikingly elevated in AD brain tissue and transgenic AD models. It has been hypothesized that early memory loss stems from synapse failure before neuron death and that synapse failure derives from actions of soluble Aβ oligomers rather than fibrils. Lacor et al., Synaptic targeting by *Alzheimer's-related amyloid β oligomers*, J. Neurosci. 2004, 24(45):10191-10200.

Abeta is a cleavage product of an integral membrane protein, amyloid precursor protein (APP), found concentrated in the synapses of neurons. Soluble forms of Abeta are present in the brains and tissues of Alzheimer's patients, and their presence correlates with disease progression. Yu et al., 2009, *Structural characterization of a soluble amyloid beta-peptide oligomer*, Biochemistry, 48(9):1870-1877. Soluble amyloid β oligomers have been demonstrated to induce changes in neuronal synapses that block learning and memory.

Smaller, soluble Aβ oligomers interfere with a number of signaling pathways critical for normal synaptic plasticity, ultimately resulting in spine and synapse loss. Selkoe et al., 2008, *Soluble oligomers of the amyloid beta-protein impair synaptic plasticity and behavior*, Behav Brain Res 192(1): 106-113. Alzheimer's begins and persists as a synaptic plasticity disease.

The presence of soluble Aβ oligomers is believed to be to be responsible for early cognitive decline in the pre-Alzheimer's diseased brain. It is known that amyloid beta oligomers bind at neuronal synapses and that sigma-2 receptors are present in significant amounts in neurons and glia.

Sigma-2 Receptors

The sigma receptors are multifunctional adapter/chaperone proteins that participate in several distinct protein signaling complexes in a tissue and state-related manner. The sigma-2 receptor is expressed in brain and various peripheral tissues at low levels. (Walker et al., 1990 *Sigma receptors: biology and function*. Pharmacol. Rev. 42:355-402). Sigma-2 receptors are present in human hippocampus and cortex. The sigma-2 receptor was also previously validated as a biomarker for tumor cell proliferation. (Mach et al.,

*Sigma-2 receptors as potential biomarkers of proliferation in breast cancer.* Cancer Res. 57:156-161, 1997).

Sigma-2 receptors are implicated in many signaling pathways such as heme binding, Cytochrome P450 metabolism, cholesterol synthesis, progesterone signaling, apoptosis and membrane trafficking. Only a subset of sigma receptor binding sites/signaling pathways are relevant to oligomer signaling in AD. No sigma-2 receptor knock-outs are currently available and human mutations in sigma-2 sequence have not been studied in a neurodegeneration context.

A sigma-2 receptor was recently identified as the progesterone receptor membrane component 1 (PGRMC1) in rat liver by use of a photoaffinity probe WC-21, which irreversibly labels sigma-2 receptors in rat liver. Xu et al. *Identification of the PGRMC1 protein complex as the putative sigma-2 receptor binding site.* Nature Communications 2, article number 380, Jul. 5, 2011, incorporated herein by reference. PGRMC1 (progesterone receptor membrane component 1) was identified as the critical 25 kDa component of sigma-2 receptor activity in August 2011 by Xu et al. PGRMC1 is a single transmembrane protein with no homology to sigma-1 protein; family members include PGRMC2 and neudesin. PGRMC1 contains a cytochrome b5 heme-binding domain. PGRMC1 is a single transmembrane protein with no homology to S1 protein; family members include PGRMC2 and neudesin. PGRMC1 contains a cytochrome b5 heme-binding domain. Endogenous PGRMC1 ligands include progesterone/steroids, cholesterol metabolites, glucocorticoids, and heme. PGRMC1 functions as chaperone/adapter associated with different protein complexes in different subcellular locations (Cahill 2007. *Progesterone receptor membrane component 1: an integrative review.* J. Steroid Biochem. Mol. Biol. 105:16-36). PGRMC1 binds heme with reducing activity, complexes with CYP450 proteins (regulated redox reactions), associates with PAIRBP1 and mediates progesterone block of apoptosis, and associates with Insig-1 and SCAP to induce SRE-related gene transcription in response to low cholesterol. The *C. elegans* homolog VEM1 associates with UNC-40/DCC to mediate axon guidance. PGRMC1 contains two SH2 target sequences, an SH3 target sequence, a tyrosine kinase site, two acidophilic kinase sites (CK2), and consensus binding sites for ERK1 and PDK1. PGRMC1 contains several ITAM sequences involved in membrane trafficking (vesicle transport, clathrin-dependent endocytosis of calveolin-containing pits).

Sigma-2 receptor therapeutics have reached human Phase II clinical trials for other CNS indications, but not for treatment of AD. Many of the sigma-2 receptor ligands are not very selective and have high affinity for other non-sigma CNS receptors. For example, Cyr-101/MT-210 (Cyrenaic Pharmaceuticals; Mitsubishi) is a sigma-2 receptor antagonist in phase IIa clinical trials for schizophrenia, but has multiple other receptor interactions including at 5HT2a, ADRA1, and histamine H1. Siramesine (Lundbeck, Forest Lu28179) is a sigma-2 receptor agonist that previously was in clinical trials for anxiety, but was discontinued. Sigma-1 receptor ligands are in clinical trials for various CNS indications. Cutamesine dihydrochloride (AGY SA4503, M's Science Corp.) is a sigma-1 receptor agonist that was in phase II clinical trials for stroke, and phase II trials for depression. Anavex 2-73 is a sigma-1 receptor agonist that also acts as at muscarinic cholinergic receptors as M2/3 antagonist, M1 agonist, and is an antagonist with respect to various ion channels (NMDAR, Na+, Ca++). Anavex 2-73 entered phase IIa clinical trials for patients with AD and mild cognitive impairment. There are no previous clinical trials with highly selective sigma-2 receptor ligand therapeutics in AD.

Sigma-2 Antagonists

While not being bound by theory, it is proposed that the sigma-2 receptor is a receptor for Abeta oligomer in neurons. Various receptors have been proposed in the literature for soluble Abeta oligomers including prion protein, insulin receptor, beta adrenergic receptor and RAGE (receptor for advanced glycation end products). Laurén, J. et al, 2009, Nature, 457(7233): 1128-1132; Townsend, M. et al, J. Biol. Chem. 2007, 282:33305-33312; Sturchler, E. et al, 2008, J. Neurosci. 28(20):5149-5158. Indeed many investigators believe that Abeta oligomer may bind to more than one receptor protein. Without being bound by theory, on the basis of evidence presented herein, the present inventors postulate an additional receptor for Abeta oligomer located (not necessarily exclusively) in neurons.

Without being bound by theory, Abeta oligomers are sigma receptor agonists that bind to sigma protein complexes and cause aberrant trafficking and synapse loss. It is demonstrated herein that high affinity sigma-2 ligands that antagonize this interaction and/or sigma receptor function in neurons will compete or otherwise interfere with Abeta oligomers and return neuronal responses to normal. Such ligands are considered functional sigma-2 receptor antagonists and are referred to as such or more simply as sigma-2 receptor antagonists or as sigma-2 antagonists.

In some embodiments, the sigma-2 receptor antagonist according to Formula I and/or Formula II, or a pharmaceutically acceptable salt thereof, acts as a functional antagonist in a neuronal cell with respect to inhibiting soluble A oligomer induced synapse loss, and inhibiting soluble Aβ oligomer induced deficits in a membrane trafficking assay; exhibiting high affinity at a sigma-2 receptor; as well as having high selectivity for one or more sigma receptors compared to any other non-sigma receptor; and exhibiting good drug-like properties.

In some embodiments, a sigma-2 receptor functional antagonist meeting certain in vitro assay criteria detailed herein will exhibit behavioral efficacy, or be predicted to have behavioral efficacy, in one or more relevant animal behavioral models as disclosed in this specification. In some embodiments, behavioral efficacy is determined at 10 mg/kg p.o., or less.

In some embodiments, the disclosure provides an in vitro assay platform predictive of behavioral efficacy for high affinity sigma-2 receptor ligands. In accordance with the in vitro assay platform, the ligand binds with high affinity to a sigma-2 receptor; acts as a functional antagonist with respect to Abeta oligomer-induced effects in a neuron; inhibits Abeta oligomer-induced synapse loss in a central neuron or reduces Abeta oligomer binding to neurons to inhibit synapse loss; and does not affect trafficking or synapse number in the absence of Abeta oligomer. This pattern of activity in the in vitro assays is termed the "therapeutic phenotype". The ability of a sigma-2 receptor antagonist to block Abeta oligomer effects in mature neurons without affecting normal function in the absence of Abeta oligomers meets the criteria for the therapeutic phenotype. It is now disclosed that a selective sigma-2 antagonist having a therapeutic phenotype, can block Abeta oligomer-induced synaptic dysfunction.

In some embodiments, high affinity, selective sigma-2 antagonists are provided having the therapeutic phenotype that also possess the following characteristics are suitable as a therapeutic candidates for treating Abeta oligomer induced synaptic dysfunction in a patient in need thereof: high affinity at sigma receptors; high selectivity for sigma receptors compared to other non-sigma CNS receptors; higher affinity for a sigma-2 receptor, or comparable affinity, for example within an order of magnitude, at sigma-2 and sigma-1 receptors; selectivity for sigma receptors as opposed to other receptors relevant in the central nervous system and good drug-like properties. Drug-like properties include acceptable brain penetrability (the ability to cross the blood brain barrier), good stability in plasma and good metabolic stability, for example, as measured by exposure to liver microsomes. Without being bound by theory, high affinity sigma-2 receptor antagonists compete with Abeta oligomers, and/or stop pathological sigma receptor signaling, that leads to Alzheimer's disease.

In some embodiments, the antagonist of the disclosure may bind with greater affinity to sigma-1 receptor than to a sigma-2 receptor, but must still behave as a functional neuronal antagonist with respect to blocking or inhibiting an Abeta oligomer-induced effect (Abeta effect).

In some embodiments, a sigma-2 antagonist having the therapeutic phenotype that also possesses the following characteristics is suitable as a therapeutic candidate for treating Abeta oligomer induced synaptic dysfunction in a patient in need thereof: high affinity at sigma receptors; high selectivity for sigma receptors compared to other non-sigma CNS receptors; high affinity for a sigma-2 receptor, or comparable affinity at sigma-2 and sigma-1 receptors; and good drug-like properties. Drug-like properties include high brain penetrability, plasma stability, and metabolic stability.

In some embodiments, in the binding activity studies, an $IC_{50}$ or Ki value of at most about 600 nM, 500 nM, 400 nM, 300 nM, 200 nM, 150 nM, 100 nM, preferably at most about 75 nM, preferably at most about 60 nM, preferably at most about 40 nM, more preferably at most 10 nM, most preferably at most 1 nM indicates a high binding affinity with respect to the sigma receptor binding sites.

In some embodiments, a sigma-2 receptor antagonist with high affinity (preferably Ki less than about 600 nM, 500 nM, 400 nM, 300 nM, 200 nM, 150 nM, 100 nM, 70 nM, 60 nM, 50 nM, 30 nM, or 10 nM) at sigma-2 receptors that have greater than about 20-fold, 30-fold, 50-fold, 70-fold, or preferably greater than 100-fold selectivity for sigma receptors compared to other non-sigma CNS or target receptors, and have good drug-like properties including brain penetrability and good metabolic and/or plasma stability, and that possess the therapeutic phenotype, are predicted to have behavioral efficacy and can be used to treat Abeta oligomer-induced synaptic dysfunction in a patient in need thereof.

As used herein the term "brain penetrability" refers to the ability of a drug, antibody or fragment, to cross the blood-brain barrier. In some embodiments, an animal pharmacokinetic (pK) study, for example, a mouse pharmacokinetic/blood-brain barrier study can be used to determine or predict brain penetrability. In some embodiments various concentrations of drug can be administered, for example at 3, 10 and 30 mg/kg, for example p.o. for 5 days and various pK properties are measured, e.g., in an animal model. In some embodiments, dose related plasma and brain levels are determined. In some embodiments, brain Cmax >100, 300, 600, 1000, 1300, 1600, or 1900 ng/mL. In some embodiments good brain penetrability is defined as a brain/plasma ratio of >0.1, >0.3, >0.5, >0.7, >0.8, >0.9, preferably >1, and more preferably >2, >5, or >10. In other embodiments, good brain penetrability is defined as greater than about 0.1%, 1%, 5%, greater than about 10%, and preferably greater than about 15% of an administered dose crossing the BBB after a predetermined period of time. In certain embodiments, the dose is administered orally (p.o.). In other embodiments, the dose is administered intravenously (i.v.), prior to measuring pK properties. Pharmacokinetic ssays and brain penetrability are described in Example 7.

As used herein the term "plasma stability" refers to the degradation of compounds in plasma, for example, by enzymes such as hydrolases and esterases. Any of a variety of in vitro assays can be employed. Drugs are incubated in plasma over various time periods. The percent parent compound (analyte) remaining at each time point reflects plasma stability. Poor stability characteristics can tend to have low bioavailability. Good plasma stability can be defined as greater than 50% analyte remaining after 30 min, greater than 50% analyte remaining after 45 minutes, and preferably greater than 50% analyte remaining after 60 minutes.

As used herein the term "metabolic stability" refers to the ability of the compound to survive first-pass metabolism (intestinal and hepatic degradation or conjugation of a drug administered orally). This can be assessed, for example, in vitro by exposure of the compounds to mouse or human hepatic microsomes. In some embodiments, good metabolic stability refers to a $t_{1/2}$ >5 min, >10 min, >15 minutes, >20 minutes, and preferably >30 min upon exposure of a compound to mouse or human hepatic microsomes. In some embodiments, good metabolic stability refers to an Intrinsic Clearance Rate ($Cl_{int}$) of <300 uL/min/mg, preferably ≤200 uL/min/mg, and more preferably ≤100 uL/min/mg.

In some embodiments, excluded are certain compounds of the prior art. In some embodiments, the compounds described in Table 1 are disclosed in WO2013/029057 and/or WO2013/029060, each of which is incorporated by reference herein, and are disclaimed with respect to compositions or methods provided herein.

TABLE 1

Disclaimed Compounds.

| Disclaimed Compound | Reference |
|---|---|
| 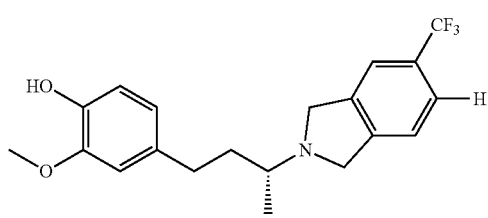 [SMILES: COc1cc(CC[C@@H](C)N2Cc3ccc(C(F)(F)F)cc3C2)ccc1O] | CogRx; Rishton, Catalano WO2013/029060, Table 1B, pp. 81-94; WO2013/029067, p. 48. |

TABLE 1-continued

Disclaimed Compounds.

| Disclaimed Compound | Reference |
| --- | --- |
| *[Structure: 4-hydroxy-3-methoxyphenyl propyl chain linked to 5-chloro-isoindoline]* | CogRx; Rishton, Catalano WO2013/029060, Table 1B, pp. 81-94; WO2013/029067, p. 47. |
| *[Structure: 4-hydroxy-3-methoxyphenyl propyl chain linked to 5,6-dichloro-isoindoline]* | CogRx; Rishton, Catalano WO2013/029060, Table 1B, pp. 81-94; WO2013/029067, p. 48. |
| *[Structure: 3,4-dichlorophenyl propyl chain linked to 5,6-dichloro-isoindoline]* | CogRx; Rishton, Catalano WO2013/029060, Table 1B, pp. 81-94; WO2013/029067, p. 182. |
| *[Structure: 3,4-dichlorophenyl propyl chain linked to 5-trifluoromethyl-isoindoline]* | CogRx; Rishton, Catalano WO2013/029060, Table 1B, pp. 81-94; WO2013/029067, pp. 55, 184. |
| *[Structure: 4-hydroxy-3-methoxyphenyl propyl chain linked to 5-chloro-isoindoline]* | CogRx; Rishton, Catalano WO2013/029060, Table 1B, pp. 81-94; WO2013/029067, p. 47. |
| *[Structure: 4-hydroxy-3-methoxyphenyl propyl chain linked to 5-trifluoromethyl-isoindoline]* | CogRx; Rishton, Catalano WO2013/029060, Table 1B, pp. 81-94; WO2013/029067, p. 48. |

Isoindoline compounds provided herein act as high affinity, selective sigma-2 functional antagonists having the therapeutic phenotype, and good drug-like properties, and thus can be used to treat Abeta oligomer-induced synaptic dysfunction.

In certain embodiments, the compositions are provided comprising isoindoline compounds of formula I as selective sigma-2 functional antagonists that have high binding affinity to the sigma receptors. In some embodiments, the sigma receptors include both the sigma-1 and sigma-2 subtypes. See Hellewell, S. B. and Bowen, W. D., Brain Res. 527: 224-253 (1990); and Wu, X.-Z. et al., J. Pharmacol. Exp. Ther. 257: 351-359 (1991). A sigma receptor binding assay which quantitates the binding affinity of a putative ligand for both sigma sites (against 3H-DTG, which labels both sites with about equal affinity) is disclosed by Weber et al., Proc. Natl. Acad. Sci (USA) 83: 8784-8788 (1986). Alternatively, [$^3$H]pentozocine may be used to selectively label the sigma-1 binding site in a binding assay. A mixture of [$^3$H]DTG and unlabeled (+)pentazocine is used to selectively label the sigma-2 site in a binding assay. The disclosure is also directed to compositions comprising certain ligands which are selective for the sigma-1 and sigma-2 receptors and act as sigma-2 functional antagonists as well as use of these compositions to treat Abeta oligomer-induced synaptic dysfunction. The discovery of such ligands which are selective for one of the two sigma receptor subtypes may be an important factor in identifying compounds which are efficacious in treating central nervous system disorders with minimal side effects.

In some embodiments, isoindoline compounds of Formula (I) exhibit sigma-2 antagonist activity, high affinity for the sigma-2 receptor, and the ability to block soluble Abeta oligomer binding or Abeta oligomer-induced synaptic dysfunction.

In some embodiments, the sigma-2 antagonists, are designed to enhance the ability to cross the blood-brain barrier.

In some embodiments, the specific sigma-2 receptor antagonist compound blocks binding between soluble Abeta oligomers and a sigma-2 receptor.

In some embodiments, the sigma-2 antagonist compound exhibits high affinity for the sigma-2 receptor.

Sigma-2 Receptor Ligands for Selection as Sigma-2 Receptor Antagonists

In some embodiments, sigma-2 receptor antagonists for use in the present disclosure are selected from among sigma-2 receptor ligand compounds that also meet additional selection criteria. Additional criteria are used to select sigma-2 receptor antagonists for use in the present disclosure from among sigma-2 receptor ligands. Additional selection criteria include: acting as a functional antagonist in a neuronal cell with respect to inhibiting soluble Aβ oligomer induced synapse loss, and inhibiting soluble Aβ oligomer induced deficits in a membrane trafficking assay; having high selectivity for one or more sigma receptors compared to any other non-sigma receptor; exhibiting high affinity at a sigma-2 receptor; and exhibiting good drug-like properties including good brain penetrability, good metabolic stability and good plasma stability. In some embodiments, the sigma-2 receptor antagonist is further selected on the basis of exhibiting one or more of the additional following properties: does not affect trafficking or synapse number in the absence of Abeta oligomer; does not induce caspase-3 activity in a neuronal cell; inhibits induction of caspase-3 activity by a sigma-2 receptor agonist; and/or decreases or protects against neuronal toxicity in a neuronal cell caused by a sigma-2 receptor agonist.

In some embodiments, certain sigma-2 receptor ligand compounds subject to further selection criteria are selected from compounds described herein and can be synthesized according to the methods described herein or in WO 2011/014880 (Application No. PCT/US2010/044136), WO 2010/118055 (Application No. PCT/US2010/030130), Application No. PCT/US2011/026530, WO 2012/106426 (Application No. PCT/US2012/023483), WO 2013/029057 (Application No. PCT/US2012/052572), and WO 2013/029060 (Application No. PCT/US2012/052578), each of which is incorporated herein by reference in its entirety. Additional options for preparing these compounds are discussed in detail below.

In some embodiments, the sigma-2 ligand comprises a compound of Formula I:

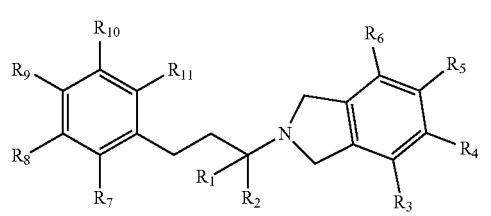

(I)

or a pharmaceutically acceptable salt thereof, wherein:

$R^1$ and $R^2$ are each independently selected from H, $C_1$-$C_6$alkyl, or $CH_2OR'$; where $R'$=H or $C_1$-$C_6$ alkyl;

$R_3$, $R_4$, $R_5$, and $R_6$ are each independently selected from H, $C_1$-$C_6$ alkyl, OH, $OCH_3$, $OCH(CH_3)_2$, $OCH_2CH(CH_3)_2$, $OC(CH_3)_3$, $O(C_1$-$C_6$ alkyl), $OCF_3$, $OCH_2CH_2OH$, $O(C_1$-$C_6$ alkyl)OH, $O(C_1$-$C_6$ haloalkyl), F, Cl, Br, I, $CF_3$, CN, $NO_2$, $NH_2$, $C_1$-$C_6$ haloalkyl, $C_1$-$C_6$ hydroxyalkyl, $C_{1-6}$ alkoxy $C_{1-6}$alkyl, aryl, heteroaryl, $C_{3-7}$ cycloalkyl, heterocycloalkyl, alkylaryl, heteroaryl, $CO_2R'$, $C(O)R'$, $NH(C_{1-4}$ alkyl), $N(C_{1-4}$ alkyl)$_2$, $NH(C_{3-7}$ cycloalkyl), $NHC(O)(C_{1-4}$ alkyl), $CONR'_2$, $NC(O)R'$, $NS(O)_nR'$, $S(O)_nNR'_2$, $S(O)_nR'$, $C(O)O(C_{1-4}$ alkyl), $OC(O)N(R')_2$, $C(O)$ $(C_{1-4}$ alkyl), and $C(O)NH(C_{1-4}$ alkyl); where n=0, 1, or 2; R' are each independently H, $CH_3$, $CH_2CH_3$, $C_3$-$C_6$ alkyl, $C_1$-$C_6$ haloalkyl; or optionally substituted aryl, alkylaryl, piperazin-1-yl, piperidin-1-yl, morpholinyl, heterocycloalkyl, heteroaryl, $C_{1-6}$ alkoxy, $NH(C_{1-4}$ alkyl), or $NH(C_{1-4}$ alkyl)$_2$, wherein optional substituted group is selected from $C_1$-$C_6$ alkyl or $C_2$-$C_7$ acyl;

or $R_3$ and $R_4$, together with the C atom to which they are attached form a form a 4-, 5-, 6- 7- or 8-membered cycloalkyl, aryl, heteroaryl, or heterocycloalkyl that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^3$ and $R^4$, or $R^4$ and $R^5$, are each independently selected from a bond, C, N, S, and O; or $R_3$ and $R_4$ are linked together to form a —O—$C_{1-2}$ methylene-O— group;

or $R_4$ and $R_5$, together with the C atom to which they are attached form a form a 4-, 5-, 6- 7- or 8-membered cycloalkyl, aryl, heteroaryl, or heterocycloalkyl that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^3$ and $R^4$, or $R^4$ and $R^5$, are each independently selected from a bond, C, N, S, and O; or $R_4$ and $R_5$ are linked together to form a —$C_{1-2}$ methylene-O— group;

$R_7$, $R_8$, $R_9$, $R_{10}$, and $R_{11}$ are each independently selected from H, $C_1$-$C_6$ alkyl, OH, $OCH_3$, $OCH(CH_3)_2$, $OCH_2CH(CH_3)_2$, $OC(CH_3)_3$, $O(C_1$-$C_6$ alkyl), $OCF_3$, $OCH_2CH_2OH$, $O(C_1$-$C_6$ alkyl)OH, $O(C_1$-$C_6$ haloalkyl), F, Cl, Br, I, $CF_3$, CN, $NO_2$, $NH_2$, $C_1$-$C_6$ haloalkyl, $C_1$-$C_6$ hydroxyalkyl, $C_{1-6}$ alkoxy $C_{1-6}$alkyl, aryl, heteroaryl, $C_{3-7}$ cycloalkyl, heterocycloalkyl, alkylaryl, heteroaryl, $CO_2R'$, $C(O)R'$, $NH(C_{1-4}$ alkyl), $N(C_{1-4}$ alkyl)$_2$, $NH(C_{3-7}$ cycloalkyl), $NHC(O)(C_{1-4}$ alkyl), $CONR'_2$, $NC(O)R'$, $NS(O)_nR'$, $S(O)_nNR'_2$, $S(O)_nR'$, $C(O)O(C_4$ alkyl), $OC(O)N(R')_2$, $C(O)$ $(C_{1-4}$ alkyl), and $C(O)NH(C_{1-4}$ alkyl); where n=0, 1, or 2; R' are each independently H, $CH_3$, $CH_2CH_3$, $C_3$-$C_6$ alkyl, $C_1$-$C_6$ haloalkyl, aryl, alkylaryl, piperazin-1-yl, piperidin-1-yl, morpholinyl, heterocycloalkyl, heteroaryl, $C_{1-6}$ alkoxy, $NH(C_{1-4}$ alkyl), or $NH(C_{1-4}$ alkyl)$_2$;

or $R_7$ and $R_8$, together with the N or C atoms to which they are attached form a form a 4-, 5-, 6- 7- or 8-membered cycloalkyl, aryl, heterocycloalkyl or heteroaryl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^9$ and $R^{10}$ are each independently selected from a bond, C, N, S, and O; or $R_7$ and $R_8$ are linked together to form a —O—$C_{1-2}$ methylene-O— group;

or $R_8$ and $R_9$, together with the N or C atoms to which they are attached form a form a 4-, 5-, 6- 7- or 8-membered cycloalkyl, aryl, heterocycloalkyl or heteroaryl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl and $R^9$ and $R^{10}$ are each independently selected from a bond, C, N, S, and O; or $R_8$ and $R_9$ are linked together to form a —O—$C_{1-2}$ methylene-O— group;

wherein each of the O, $C_{1-6}$ alkyl, $C_{1-6}$ haloalkyl, heteroaryl, aryl, heteroaryl, heterocycloalkyl, and cycloalkyl is optionally independently substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

with the proviso that the following compounds are excluded:

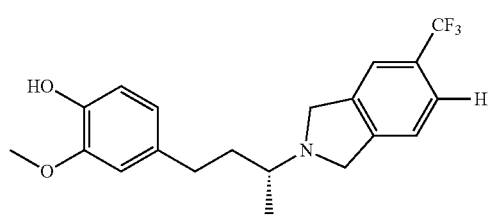 [SMILES: COc1cc(CC[C@@H](C)N2Cc3ccc(Cl)cc3C2)ccc1O]

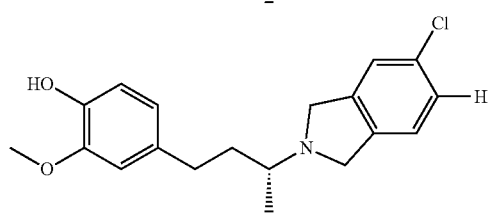

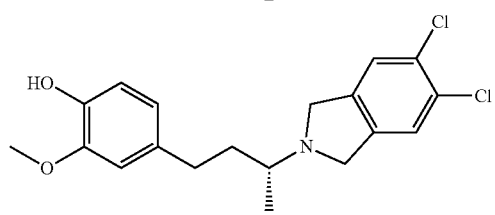 [SMILES: COc1cc(CC[C@@H](C)N2Cc3cc(Cl)c(Cl)cc3C2)ccc1O]

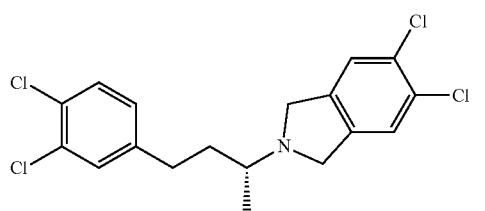 [SMILES: C[C@H](CCc1ccc(Cl)c(Cl)c1)N1Cc2cc(Cl)c(Cl)cc2C1]

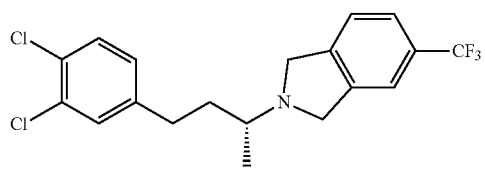 [SMILES: C[C@H](CCc1ccc(Cl)c(Cl)c1)N1Cc2ccc(C(F)(F)F)cc2C1]

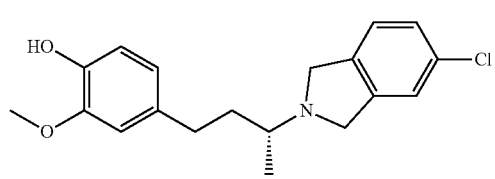 [SMILES: COc1cc(CC[C@@H](C)N2Cc3ccc(Cl)cc3C2)ccc1O]

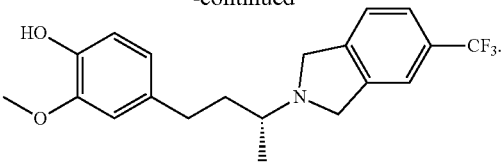

In some embodiments, the sigma-2 ligand comprises a racemic mixture or an enantiomer of compound of Formula I, wherein $R_1$, $R_2$, $R_3$, $R_4$, $R_5$, $R_6$, $R_7$, $R_8$, $R_9$, $R_{10}$, and $R_{11}$ are as described above.

In some embodiments, an isolated compound is provided according to Formula I:

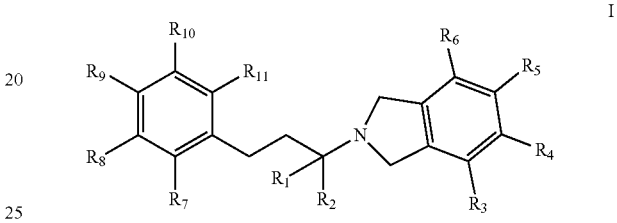

I or a pharmaceutically acceptable salt thereof, wherein $R_1$, $R_2$, $R_3$, $R_4$, $R_5$, $R_6$, $R_7$, $R_8$, $R_9$, $R_{10}$, and $R_{11}$ are as defined herein, with the proviso that when $R_1$, $R_3$, $R_6$, $R_7$, $R_{10}$ and $R_{11}$ are each H; $R_2$ is $CH_3$; $R_8$ is $OCH_3$ or Cl; and $R_9$ is OH or Cl; then $R_4$ is not Cl or $CF_3$, and $R_5$ is not Cl or $CF_3$.

In other embodiments, an isolated compound, or composition thereof, or method comprising administration of, is provided according to Formula I:

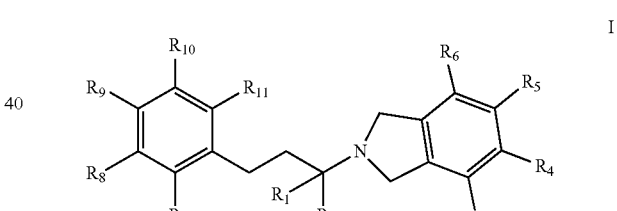

I or a pharmaceutically acceptable salt thereof, wherein $R_1$, $R_2$, $R_3$, $R_4$, $R_5$, $R_6$, $R_7$, $R_8$, $R_9$, $R_{10}$, and $R_{11}$ are as defined herein, with the proviso that a compound according to Formula I wherein $R_1$, $R_3$, $R_6$, $R_7$, $R_{10}$ and $R_{11}$ are each H; $R_2$ is $CH_3$; $R_8$ is $OCH_3$ or Cl; and $R_9$ is OH or Cl; $R_4$ is Cl or $CF_3$, and $R_5$ is Cl or $CF_3$, is not a preferred compound.

In another embodiment, a pharmaceutical composition is provided for inhibiting an amyloid beta effect on a neuronal cell comprising a compound according to Formula I:

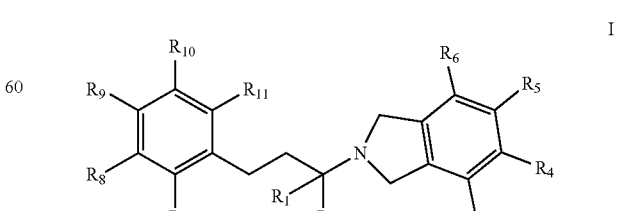

I or a pharmaceutically acceptable salt thereof, and a pharmaceutically acceptable carrier, wherein $R_1$, $R_2$, $R_3$, $R_4$, $R_5$, $R_6$, $R_7$, $R_8$, $R_9$, $R_{10}$, and $R_{11}$ are as defined herein, with the proviso that when $R_1$, $R_3$, $R_6$, $R_7$, $R_{10}$ and $R_{11}$ are each H; $R_2$ is $CH_3$; $R_8$ is $OCH_3$ or Cl; and $R_9$ is OH or Cl; then $R_4$ is not Cl or $CF_3$, and $R_5$ is not Cl or $CF_3$.

In another embodiment, a method/use is provided for inhibiting an amyloid beta effect on a neuronal cell comprising administering an effective amount of a composition comprising a selective sigma-2 receptor antagonist compound according to formula I:

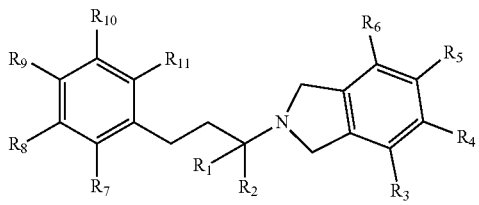

I or a pharmaceutically acceptable salt thereof, and a pharmaceutically acceptable carrier, wherein $R_1$, $R_2$, $R_3$, $R_4$, $R_5$, $R_6$, $R_7$, $R_8$, $R_9$, $R_{10}$, and $R_{11}$ are as defined herein, with the proviso that when $R_1$, $R_3$, $R_6$, $R_7$, $R_{10}$ and $R_{11}$ are each H; $R_2$ is $CH_3$; $R_8$ is $OCH_3$ or Cl; and $R_9$ is OH or Cl; then $R_4$ is not Cl or $CF_3$, and $R_5$ is not Cl or $CF_3$, and wherein the compound or salt thereof is present in the composition in an amount effective to inhibit amyloid beta oligomer binding in said cell; and a pharmaceutically acceptable carrier.

In some embodiments, the sigma-2 ligand comprises a racemic mixture or an enantiomer of compound of Formula II:

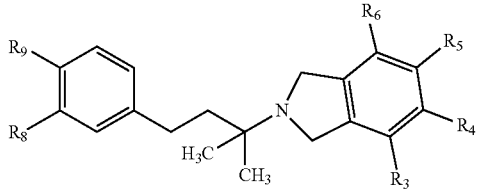

II wherein $R_3$, $R_4$, $R_5$, $R_6$, $R_8$, and $R_9$ are as described herein.

In another embodiment, a compound, or pharmaceutically acceptable salt thereof, is provided according to Formula III, wherein $R_3$, $R_4$, $R_5$, $R_6$, $R_7$, $R_8$, $R_9$, $R_{10}$ and $R_{11}$ are as provided herein and wherein ≡≡≡ are each independently selected from a single, double or triple bond.

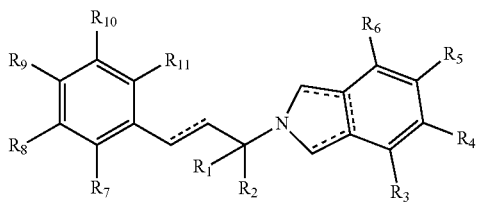

III

In some aspects, a compound according to Formula III is selected from:

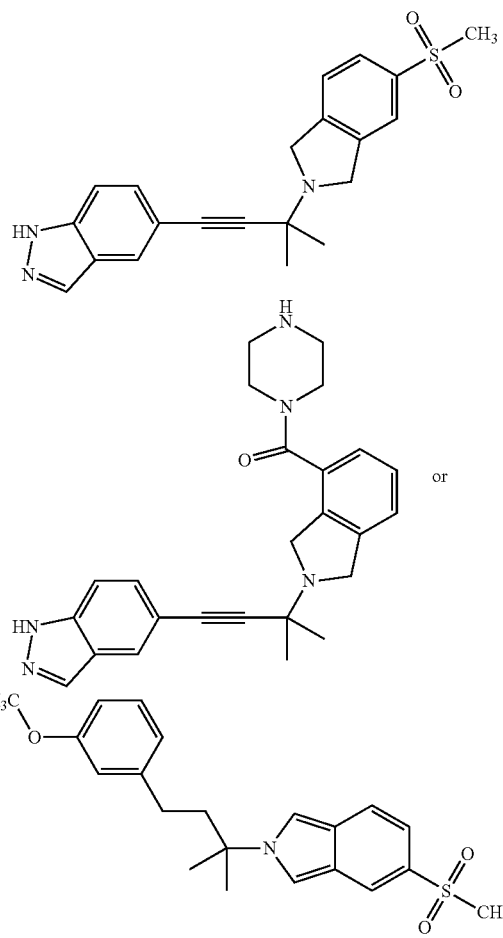

or a pharmaceutically acceptable salt thereof.

In some embodiments, the sigma-2 ligand comprises a racemic mixture or an enantiomer of a compound of Formula I, wherein $R_3$, $R_4$, $R_5$, $R_6$, $R_8$, and $R_9$ are as described herein.

In some embodiments, the sigma-2 ligand is a compound or a pharmaceutically acceptable salt of Formula I, wherein $R_8$ and $R_9$ are independently selected from OH, $C_{1-6}$ alkoxy, and hydroxy $C_{1-6}$ alkoxy.

In some embodiments, the sigma-2 ligand is a compound or a pharmaceutically acceptable salt of Formula I, wherein $R_8$ and $R_9$ are independently selected from OH and NH($C_{1-4}$ alkyl).

In some embodiments, the sigma-2 ligand is a compound or a pharmaceutically acceptable salt of Formula I, wherein $R_8$ and $R_9$ are independently selected from H, halo, $C_{1-6}$ haloalkyl, and $C_{1-6}$ haloalkoxy.

In some embodiments, the sigma-2 ligand is a compound or a pharmaceutically acceptable salt of Formula I, wherein $R_8$ and $R_9$ are each independently selected from OH, halo, $C_{1-6}$ alkoxy and $C_{1-6}$ haloalkoxy and $R_1$ and $R_2$ are each independently $C_{1-6}$ alkyl.

In some embodiments, the sigma-2 ligand is a compound or a pharmaceutically acceptable salt of Formula I, wherein $R_1$ and $R_2$ are each methyl.

In some embodiments, the sigma-2 ligand is a compound or a pharmaceutically acceptable salt of Formula I, wherein one of $R_1$ and $R_2$ is methyl and the other is H.

In some embodiments, the sigma-2 ligand is a compound or a pharmaceutically acceptable salt of Formula I, wherein $R_8$ and $R_9$ are each independently selected from OH and $C_{1-6}$ alkoxy and $R_1$ and $R_2$ are each independently methyl.

In some embodiments, the sigma-2 ligand is a compound or a pharmaceutically acceptable salt of Formula I, wherein $R_8$ and $R_9$ are independently selected from H, halo, and $C_{1-6}$ haloalkyl, and $R_1$ and $R_2$ are each methyl.

In some embodiments, the sigma-2 ligand is a compound or a pharmaceutically acceptable salt of Formula I, wherein $R^1$ and $R^9$ are each independently selected from H, halo and $C_{1-6}$ haloalkyl.

In some embodiments, the sigma-2 ligand is a compound or a pharmaceutically acceptable salt of Formula I, wherein $R_7$ and $R_{11}$ are each H.

In some embodiments, the sigma-2 ligand is a compound or a pharmaceutically acceptable salt of Formula I, wherein $R_3$, $R_4$, $R_5$, and $R_6$ are each independently selected from H, halo, $C_{1-6}$alkyl, $C_{1-6}$haloalkyl and $C_{1-6}$ alkoxy.

In some embodiments, the sigma-2 ligand is a compound or a pharmaceutically acceptable salt of Formula I, wherein $R_3$, $R_4$ and $R_5$ are each independently selected from H, halo, $C_{1-6}$alkyl, $C_{1-6}$haloalkyl and $C_{1-6}$ alkoxy.

In some embodiments, the sigma-2 ligand is a compound or a pharmaceutically acceptable salt of Formula I, wherein $R_3$, $R_4$, $R_5$, and $R_6$ are each independently selected from H, halo, $S(O)_nR'$, $C(O)OR'$, $C(O)N(R')_2$, and $C(O)R'$; where n=2; R' are each independently H, $CH_3$, $CH_2CH_3$, $C_3$-$C_6$ alkyl, $C_1$-$C_6$ haloalkyl, or optionally $C_1$-$C_6$ alkyl or $C_2$-$C_7$ acyl substituted aryl, alkylaryl, piperazinyl, piperidinyl, morpholinyl, heterocycloalkyl, and heteroaryl.

In some embodiments, the sigma-2 ligand is a compound or a pharmaceutically acceptable salt of Formula I, wherein $R_3$, $R_4$ and $R_5$ are each independently selected from H, halo, $S(O)_nR'$, and $C(O)R'$; where n=2; R' are each independently $CH_3$, $CH_2CH_3$, $C_3$-$C_6$ alkyl, aryl, piperazin-1-yl, piperidin-1-yl, and morpholinyl-4-yl.

In some embodiments, the sigma-2 ligand is a compound or a pharmaceutically acceptable salt of Formula I, wherein $R_3$, $R_4$ and $R_5$ are each independently selected from H, halo, $S(O)_nR'$, and $C(O)R'$; where n=2; R' are each independently $CH_3$, $CH_2CH_3$, $C_3$-$C_6$ alkyl, aryl, piperazin-1-yl, piperidin-1-yl, and morpholinyl-4-yl; $R_8$ and $R_9$ are each independently selected from OH, halo, $C_{1-6}$ alkoxy and $C_{1-6}$ haloalkoxy; and $R_1$ and $R_2$ are each methyl.

In some embodiments, the sigma-2 ligand is a compound or a pharmaceutically acceptable salt of Formula I, wherein $R_3$ and $R_4$ or $R_4$ and $R_5$ together with the C atom to which they are attached form a 6-membered cycloalkyl, or a heterocycloalkyl, aryl or heteroaryl ring.

In some embodiments, the sigma-2 ligand is a compound or a pharmaceutically acceptable salt of Formula I, wherein $R_3$ and $R_4$ or $R_4$ and $R_5$ are O, and are linked together to form a —O—$C_{1-2}$ methylene-O— group.

In some embodiments, the sigma-2 ligand is a compound or a pharmaceutically acceptable salt of Formula I, wherein $R^2$ and $R^3$ are independently selected from H, OH, halo, $C_{1-6}$ alkoxy and $C_{1-6}$ haloalkyl.

In some embodiments, the sigma-2 ligand is a compound or a pharmaceutically acceptable salt of Formula II, wherein $R_3$ and $R_4$ are independently selected from H, Cl, F, —OMe, —$CF_3$, $S(O)_nR'$, and $C(O)R'$; where n=2; R' are each independently H, $CH_3$, $CH_2CH_3$, $C_3$-$C_6$ alkyl, aryl, piperazin-1-yl, piperidin-1-yl, and morpholinyl-4-yl; $R_8$ and $R_9$ are each independently selected from OH and $C_{1-6}$ alkoxy.

In some embodiments, the sigma-2 ligand is a compound or a pharmaceutically acceptable salt of Formula I, wherein $R^2$ and $R^3$ are independently selected from H, OH, Cl, F, —OMe, and —$CF_3$, wherein $R^7$ and $R^8$ are each independently selected from H and $C_{1-6}$ alkyl, wherein $R^9$ is H, and wherein $R^5$ and $R^6$ are each independently selected from H and $C_{1-6}$ haloalkyl.

Preferred salts for use in the disclosure include the hydrochloride salts of the above compounds.

These have been synthesized in accordance with general methods provided herein and specific synthetic examples with any additional steps being well within the skill in the art. Several of these compounds have been tested in various assays as detailed herein and have been found active. Tested compounds also display increased bioavailability by reference to compounds disclosed in WO 2010/110855.

In some embodiments, each of the general formulae above may contain a proviso to remove one or more of the following compounds:

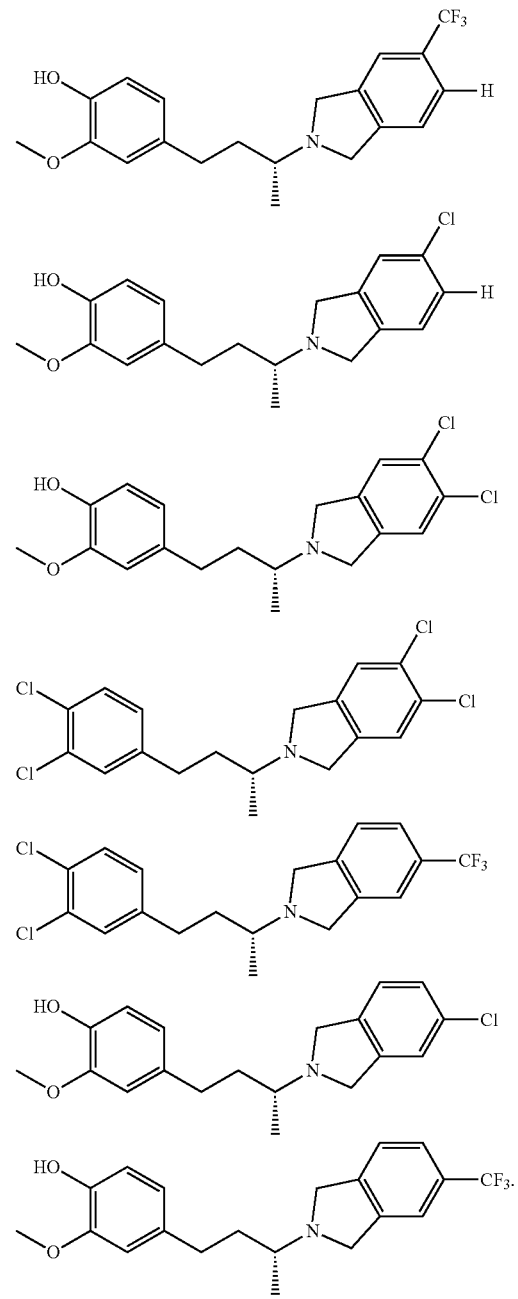

Compounds according to Formula I and/or Formula II have been synthesized in accordance with general methods provided herein and specific synthetic examples with any additional steps being well within the skill in the art. Several of these compounds have been tested in various assays as detailed herein and have been found active. Tested compounds also display increased bioavailability by reference to compounds disclosed in WO 2010/110855, incorporated herein by reference.

As used herein, the term "hydrogen bond acceptor group" refers to a group capable of accepting a hydrogen bond. Examples of hydrogen bond acceptor groups are known and include, but are not limited to, alkoxy groups, oxazolidin-2-one groups, —O—C(O)—N—; —C(O)—N—; —O—; the hetero atom (e.g. oxygen) in a cycloheteroalkyl; —N—SO$_2$— and the like. The groups can be bound in either direction and can be connected to another carbon or heteroatom. A hydrogen bond acceptor group can also be present in or near a hydrophobic aliphatic group. For example, a tetrahydrofuran group comprises both a hydrogen bond acceptor group and a hydrophobic aliphatic group. The oxygen present in the tetrahydrofuran ring acts as a hydrogen bond acceptor and the carbons in the tetrahydrofuran ring act as the hydrophobic aliphatic group.

As used herein, the term "hydrophobic aliphatic group" refers to a carbon chain or carbon ring. The carbon chain can be present in a cycloheteroalkyl, but the hydrophobic aliphatic group does not include the heteroatom. The tetrahydrofuran example provided above is one such example, but there are many others. In some embodiments, the hydrophobic aliphatic group is an optionally substituted C1-C6 alkyl, cycloalkyl, or C1-C6 carbons of a heterocycloalkyl. A "hydrophobic aliphatic group" is not a hydrophobic aromatic group.

As used herein, the term "positive ionizable group" refers to an atom or a group of atoms present in a structure that can be positively charged under certain conditions such as biological conditions present in solution or in a cell. In some embodiments, the positive ionizable group is a nitrogen. In some embodiments, the positive ionizable group is a nitrogen present in a cycloheteroalkyl ring. For example, in a piperazine group, the two nitrogens would be considered two positive ionizable groups. However, in some embodiments, the carbons linked to a positive ionizable group are not considered a hydrophobic aliphatic group. In some embodiments, the positive ionizable group is a nitrogen containing ring. Examples of nitrogen containing rings include, but are not limited to, piperazine, piperadine, triazinane, tetrazinane, and the like. In some embodiments with respect to the positive ionizable group, a nitrogen containing ring comprises 1, 2, 3, or 4 nitrogens. In some embodiments, the positive ionizable group is not the nitrogen present in a —N—SO$_2$— group In some embodiments, a group comprises both a hydrogen bond acceptor and a positive ionizable group. For example, a morpholine group comprises both a hydrogen bond acceptor in the oxygen group and a positive ionizable group in the nitrogen.

As used herein, the term "hydrogen bond donor" refers to a group that is capable of donating a hydrogen bond. Examples of a hydrogen bond donor group include, but are not limited to, —OH, and the like.

Salts, Solvates, Stereoisomers, Derivatives, Prodrugs and Active Metabolites of the Novel Compounds.

The disclosure further encompasses salts, solvates, stereoisomers, prodrugs and active metabolites of the compounds of any of the formulae above.

The term "salts" can include acid addition salts or addition salts of free bases. Preferably, the salts are pharmaceutically acceptable. Examples of acids which may be employed to form pharmaceutically acceptable acid addition salts include, but are not limited to, salts derived from nontoxic inorganic acids such as nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, et al. "Pharmaceutical Salts," *J. Pharma. Sci.* 1977; 66:1).

The acid addition salts of the compounds of any of the formulae above may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the disclosure.

Also included are both total and partial salts, that is to say salts with 1, 2 or 3, preferably 2, equivalents of base per mole of acid of a, e.g., formula I compound or salt, with 1, 2 or 3 equivalents, preferably 1 equivalent, of acid per mole of base of a any of the formulae above compound.

For the purposes of isolation or purification it is also possible to use pharmaceutically unacceptable salts. However, only the pharmaceutically acceptable, non-toxic salts are used therapeutically and they are therefore preferred.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of said acidic compounds are prepared by contacting the free acid form with a sufficient amount of the desired base to produce the salt in the conventional manner. The free acid form may be regenerated by contacting the salt form with an acid and isolating the free acid.

Compounds of the disclosure may have both a basic and an acidic center and may therefore be in the form of zwitterions or internal salts.

Typically, a pharmaceutically acceptable salt of a compound of any of the formulae above may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of any of the formulae above and the resulting mixture evaporated to dryness (lyophilized) to obtain the acid addition salt as a solid. Alternatively, a compound of any of the formulae above may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the disclosure are within the scope of the disclosure. The salts of the compound of any of the formulae above may form solvates (e.g., hydrates) and the disclosure also includes all such solvates. The meaning of the word "solvates" is well known to those skilled in the art as a compound formed by interaction of a solvent and a solute (i.e., solvation). Techniques for the preparation of solvates are well established in the art (see, for example, Brittain. *Polymorphism in Pharmaceutical solids*. Marcel Decker, New York, 1999).

The disclosure also encompasses N-oxides of the compounds of formulas I. The term "N-oxide" means that for heterocycles containing an otherwise unsubstituted $sp^2$ N atom, the N atom may bear a covalently bound O atom, i.e., —N→O. Examples of such N-oxide substituted heterocycles include pyridyl N-oxides, pyrimidyl N-oxides, pyrazinyl N-oxides and pyrazolyl N-oxides.

Compounds of any of the formulae above may have one or more chiral centers and, depending on the nature of individual substituents, they can also have geometrical isomers. Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has a chiral center, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomer respectively). A chiral compound can exist as either an individual enantiomer or as a mixture of enantiomers. A mixture containing equal proportions of the enantiomers is called a "racemic mixture". A mixture containing unequal portions of the enantiomers is described as having an "enantiomeric excess" (ee) of either the R or S compound. The excess of one enantiomer in a mixture is often described with a % enantiomeric excess (% ee) value determined by the formula:

% $ee=(R)-(S)/(R)+(S)$

The ratio of enantiomers can also be defined by "optical purity" wherein the degree at which the mixture of enantiomers rotates plane polarized light is compared to the individual optically pure R and S compounds. Optical purity can be determined using the following formula:

Optical purity=$enant._{major}/(enant._{major}+enant._{minor})$

The compounds can also be a substantially pure (+) or (−) enantiomer of the compounds described herein. In some embodiments, a composition comprising a substantially pure enantiomer comprises at least 90, 91, 92, 93, 94, 95, 96, 97, 98, or 99% of one enantiomer. In some embodiments, a composition comprising a substantially pure enantiomer is at least 99.5% one enantiomer. In some embodiments, the composition comprises only one enantiomer of a compound described herein.

The disclosure encompasses all individual isomers of the compounds of any of the formulae above. The description or naming of a particular compound in the specification and claims is intended to include both individual enantiomers and mixtures, racemic or otherwise, thereof. Methods for the determination of stereochemistry and the resolution or stereotactic synthesis of stereoisomers are well-known in the art. Specifically, there is a chiral center shown in the compounds of any of the formulae above which gives rise to one set of enantiomers. Additional chiral centers may be present depending on the substituents.

For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions. Those of skill in the art will further recognize that disclosure compounds may exist in polymorphic forms wherein a compound is capable of crystallizing in different forms. Suitable methods for identifying and separating polymorphisms are known in the art.

Diastereomers differ in both physical properties and chemical reactivity. A mixture of diastereomers can be separated into enantiomeric pairs based on solubility, fractional crystallization or chromatographic properties, e.g., thin layer chromatography, column chromatography or HPLC.

Purification of complex mixtures of diastereomers into enantiomers typically requires two steps. In a first step, the mixture of diastereomers is resolved into enantiomeric pairs, as described above. In a second step, enantiomeric pairs are further purified into compositions enriched for one or the other enantiomer or, more preferably resolved into compositions comprising pure enantiomers. Resolution of enantiomers typically requires reaction or molecular interaction with a chiral agent, e.g., solvent or column matrix. Resolution may be achieved, for example, by converting the mixture of enantiomers, e.g., a racemic mixture, into a mixture of diastereomers by reaction with a pure enantiomer of a second agent, i.e., a resolving agent. The two resulting diastereomeric products can then be separated. The separated diastereomers are then reconverted to the pure enantiomers by reversing the initial chemical transformation.

Resolution of enantiomers can also be accomplished by differences in their non-covalent binding to a chiral substance, e.g., by chromatography on homochiral adsorbants. The noncovalent binding between enantiomers and the chromatographic adsorbant establishes diastereomeric complexes, leading to differential partitioning in the mobile and bound states in the chromatographic system. The two enantiomers therefore move through the chromatographic system, e.g., column, at different rates, allowing for their separation.

Chiral resolving columns are well known in the art and are commercially available (e.g., from MetaChem Technologies Inc., a division of ANSYS Technologies, Inc., Lake Forest, Calif.). Enantiomers can be analyzed and purified using, for example, chiral stationary phases (CSPs) for HPLC. Chiral HPLC columns typically contain one form of an enantiomeric compound immobilized to the surface of a silica packing material.

D-phenylglycine and L-leucine are examples of Type I CSPs and use combinations of π-π interactions, hydrogen bonds, dipole-dipole interactions, and steric interactions to achieve chiral recognition. To be resolved on a Type I column, analyte enantiomers must contain functionality complementary to that of the CSP so that the analyte undergoes essential interactions with the CSP. The sample should preferably contain one of the following functional groups: π-acid or π-base, hydrogen bond donor and/or acceptor, or an amide dipole. Derivatization is sometimes used to add the interactive sites to those compounds lacking them. The most common derivatives involve the formation of amides from amines and carboxylic acids.

The MetaChiral ODM™ is an example of a type II CSP. The primary mechanisms for the formation of solute-CSP complexes is through attractive interactions, but inclusion complexes also play an important role. Hydrogen bonding, π-π interactions, and dipole stacking are important for chiral resolution on the MetaChiral™ ODM. Derivatization maybe necessary when the solute molecule does not contain the groups required for solute-column interactions. Derivatization, usually to benzylamides, may be required for some strongly polar molecules like amines and carboxylic acids, which would otherwise interact strongly with the stationary phase through non-specific-stereo interactions.

Where applicable, compounds of any of the formulae above can be separated into diastereomeric pairs by, for example, separation by column chromatography or TLC on silica gel. These diastereomeric pairs are referred to herein as diastereomer with upper TLC Rf; and diastereomer with lower TLC Rf. The diastereomers can further be enriched for a particular enantiomer or resolved into a single enantiomer using methods well known in the art, such as those described herein.

The relative configuration of the diastereomeric pairs can be deduced by the application of theoretical models or rules (e.g. Cram's rule, the Felkin-Ahn model) or using more reliable three-dimensional models generated by computational chemistry programs. In many instances, these methods are able to predict which diastereomer is the energetically favored product of a chemical transformation. As an alternative, the relative configuration of the diastereomeric pairs can be indirectly determined by discovering the absolute configurations of a single enantiomer in one (or both) of the diastereomeric pair(s).

The absolute configuration of the stereocenters can be determined by very well known method to those skilled in the art (e.g. X-Ray diffraction, circular dichroism). Determination of the absolute configuration can be useful also to confirm the predictability of theoretical models and can be helpful to extend the use of these models to similar molecules prepared by reactions with analogous mechanisms (e.g. ketone reductions and reductive amination of ketones by hydrides).

The disclosure may also encompass stereoisomers of the Z-E type, and mixtures thereof due to $R_2$-$R_3$ substituents to the double bond not directly linked to the ring. Additional Z-E stereoisomers are encountered when m is not 1 and m and n are different. The Cahn-Ingold-Prelog priority rules are applied to determine whether the stereoisomers due to the respective position in the plane of the double bond of the doubly bonded substituents are Z or E. The stereoisomer is designated as Z (zusammen=together) if the 2 groups of highest priority lie on the same side of a reference plane passing through the C=C bond. The other stereoisomer is designated as E (entgegen=opposite).

Mixture of stereoisomers of E-Z type can be separated (and/or characterized) in their components using classical method of purification that are based on the different chemico-physical properties of these compounds. Included in these method are fractional crystallization, chromatography carried out by low, medium or high pressure techniques, fractional distillation and any other method very well known to those skilled in the art.

The disclosure also encompasses prodrugs of the compounds of any of the formulae above, i.e., compounds which release an active drug according to any of the formulae above in vivo when administered to a mammalian subject. A prodrug is a pharmacologically active or more typically an inactive compound that is converted into a pharmacologically active agent by a metabolic transformation. Prodrugs of a compound of any of the formulae above are prepared by modifying functional groups present in the compound of any of the formulae above in such a way that the modifications may be cleaved in vivo to release the parent compound. In vivo, a prodrug readily undergoes chemical changes under physiological conditions (e.g., are hydrolyzed or acted on by naturally occurring enzyme(s)) resulting in liberation of the pharmacologically active agent. Prodrugs include compounds of any of the formulae above wherein a hydroxy, amino, or carboxy group is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds of any of the formulae above or any other derivative which upon being brought to the physiological pH or through enzyme action is converted to the active parent drug. Conventional procedures for the selection and preparation of suitable prodrug derivatives are described in the art (see, for example, Bundgaard. Design of Prodrugs. Elsevier, 1985).

Prodrugs may be administered in the same manner as the active ingredient to which they convert or they may be delivered in a reservoir form, e.g., a transdermal patch or other reservoir which is adapted to permit (by provision of an enzyme or other appropriate reagent) conversion of a prodrug to the active ingredient slowly over time, and delivery of the active ingredient to the patient.

Unless specifically indicated, the term "active ingredient" is to be understood as referring to a compound of any of the formulae above as defined herein.

The disclosure also encompasses metabolites. "Metabolite" of a compound disclosed herein is a derivative of a compound which is formed when the compound is metabolized. The term "active metabolite" refers to a biologically active derivative of a compound which is formed when the compound is metabolized. The term "metabolized" refers to the sum of the processes by which a particular substance is changed in the living body. In brief, all compounds present in the body are manipulated by enzymes within the body in order to derive energy and/or to remove them from the body. Specific enzymes produce specific structural alterations to the compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics,* 9th Edition, McGraw-Hill (1996), pages 11-17. Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

Use of the Sigma-2 Receptor Antagonists

In some embodiments, the disclosure provides methods of inhibiting synapse number decline or membrane trafficking abnormalities associated with exposure of a neuronal cell to Abeta species by administration of a sigma-2 receptor antagonist. The disclosure also provides methods for treating cognitive decline and/or a neurodegenerative disease, e.g. Alzheimer's disease or mild cognitive impairment (MCI) in a patient comprising administering to the patient a sigma-2 antagonist described herein, e.g., those encompassed by any of the formulae described herein, or a pharmaceutically acceptable salt thereof. In some embodiments, the method of inhibiting, or treating, cognitive decline and/or a neurodegenerative disease, e.g. Alzheimer's disease comprises inhibiting, or treating one or more symptoms of cognitive decline selected from the group consisting of memory loss, confusion, impaired judgment, personality changes, disorientation, and loss of language skills. In some embodiments, the method comprises inhibiting, or treating, diseases or disorders or conditions mediated by or associated with Abeta oligomers. In some embodiments, the method of inhibiting, or treating, cognitive decline and/or a neurodegenerative disease, e.g. Alzheimer's disease, comprises one or more of: (i) restoration of long term potentiation (LTP), long term depression (LTD) or synaptic plasticity detectable by electrophysiological measurements or any of the other negative changes in cognitive function as mentioned in the definition of the term above; and/or (ii) inhibiting, or treating, neurodegeneration; and/or (iii) inhibiting, or treating, general amyloidosis; and/or (iv) inhibiting, or treating, one or more of amyloid production, amyloid assembly, amyloid aggregation, and amyloid oligomer binding, and amyloid deposition; and/or (v) inhibiting, treating, and/or abating an effect, notably a nonlethal effect, of one or more of Abeta oligomers on a neuron cell. In some embodiments, the method of inhibiting, treating, and/or abating cognitive decline and/or a neurodegenerative disease, e.g. Alzheimer's disease comprises inhibiting, treating, and/or abating one or more of amyloid production, amyloid assembly, the activity/effect of one or more of Abeta oligomers on a neuron cell, amyloid aggregation, amyloid binding, and amyloid deposition. In some embodiments, the method of inhibiting, treating, and/or abating cognitive decline and/or a neurodegenerative disease, e.g. Alzheimer's disease comprises inhibiting, treating, and/or abating one or more of the activity/effect of one or more of Abeta oligomers on a neuron cell.

In some embodiments, the activity/effect of one or more of Abeta oligomers on a neuron cell, amyloid aggregation and amyloid binding is the effect of Abeta oligomers on membrane trafficking or synapse number. In some embodiments, the sigma-2 antagonist inhibits the Abeta oligomer effect on membrane trafficking or synapse number or Abeta oligomer binding.

In some embodiments, the disclosure provides methods of treating a proteopathic disease associated with Abeta oligomer toxicity, specifically nonlethal Abeta oligomer effects. In some embodiments, the method comprises contacting a subject with such a proteopathic disease with a sigma-2 antagonist of the disclosure or a composition containing the same that binds the sigma-2 receptor.

In some embodiments, the proteopathic disease is a CNS proteopathy, characterized by an increase in Abeta protein, such as MCI, Down's Syndrome, macular degeneration or Alzheimer's disease, and the like.

In some embodiments, the disclosure provides methods of treating one or more mild cognitive impairment (MCI), or dementia by administering a sigma-2 antagonist in accordance with the disclosure. In some embodiments, the disclosure provides methods of treating MCI, and dementia.

In some embodiments, the disclosure provides methods of treating an individual with a sigma-2 antagonist according to the disclosure to restore, partially or totally, the subject's cells to a normal phenotype in terms of functions affected adversely by Abeta species, such as Abeta oligomers. Examples are synaptic number reduction and membrane trafficking abnormalities, which can be measured by various methods including assays described herein. The normal phenotype can be, for example, normal membrane trafficking. In some embodiments, the normal phenotype is normal cognitive ability. The "normal" phenotype can be determined by comparing a subject's results with a sample of normal subjects. The sample may be as small as 1 subject or 1 sample or may be more than 10 samples or subjects and the norm is an average that is calculated based upon a plurality of subjects.

In some embodiments, the method comprises administering to a subject afflicted with cognitive decline or with a neurodegenerative disease a compound or composition that binds a sigma-2 protein and inhibits a beta-amyloid pathology. In some embodiments, the beta-amyloid pathology is a membrane trafficking defect, a decrease in synapse number, a decrease in dendritic spine number, a change in dendritic spine morphology, a change in LTP, a change in LTD, a defect in measures of memory and learning in an animal, or any combination thereof, and the like. The foregoing uses result from evidence adduced by the inventors as follows:

Evaluation of Behavioral Efficacy: Abeta oligomer-induced memory deficits in mouse fear conditioning is a model established in the laboratory of Dr. Ottavio Arancio of Columbia University (Puzzo 2008). Several pharmaceutical companies use this same model in their discovery efforts. Contextual fear conditioning is an accepted model of associative memory formation which correlates to human cognitive function and specifically the creation of new memories (Delgado 2006). Abeta oligomers are injected into the hippocampus of wild-type animals immediately before conditioning training and memory is assessed via freezing behavior after 24 hours. This model system was chosen because intrahippocampal administration of oligomers allows rapid comparative assessment of compound activity and off-target toxicity.

Compounds also can be tested in vivo in two transgenic Alzheimer's models to show the compound's effect in reversing Abeta oligomer-associated memory loss. These behavioral studies collectively demonstrated that sigma-2 antagonist compounds cause improvement in learning and memory in two different behavioral tasks, with two different models of Alzheimer's disease, in both genders and following short or long-term administration and demonstrate that the in vitro assays correlate with in vivo activity.

As discussed herein, evidence suggests that Abeta oligomer-mediated reduction in neuronal surface receptor expression mediated by membrane trafficking are the basis for oligomer inhibition of electrophysiological measures of synaptic plasticity (LTP) and thus learning and memory (See Kamenetz F, Tomita T, Hsieh H, Seabrook G, Borchelt D, Iwatsubo T, Sisodia S, Malinow R. APP processing and synaptic function. Neuron. 2003 Mar. 27; 37(6):925-37; and Hsieh H, Boehm J, Sato C, Iwatsubo T, Tomita T, Sisodia S, Malinow R. AMPAR removal underlies Abeta oligomer-induced synaptic depression and dendritic spine loss. Neuron. 2006 Dec. 7; 52(5):831-43). Measuring membrane trafficking rate changes induced by oligomers via formazan morphological shifts has been used in cell lines to discover Abeta oligomer-blocking drugs [Maezawa I, Hong H S, Wu H C, Battina S K, Rana S, Iwamoto T, Radke G A, Pettersson E, Martin G M, Hua D H, Jin L W. A novel tricyclic pyrone compound ameliorates cell death associated with intracellular amyloid-beta oligomeric complexes. J Neurochem. 2006 July; 98(1):57-67; Liu Y, Schubert D. Cytotoxic amyloid peptides inhibit cellular 3-(4,5-dimethylthiazol-2-yl)-2, 5-diphenyltetrazolium bromide (MTT) reduction by enhancing MTT formazan exocytosis. J Neurochem. 1997 December; 69(6):2285-93; Liu Y, Dargusch R, Banh C, Miller C A, Schubert D. Detecting bioactive amyloid beta peptide species in Alzheimer's disease. J Neurochem. 2004 November; 91(3):648-56; Liu Y, Schubert D. Treating Alzheimer's disease by inactivating bioactive amyloid beta peptide. Curr Alzheimer Res. 2006 April; 3(2):129-35; Rana S, Hong H S, Barrigan L, Jin L W, Hua D H. Syntheses of tricyclic pyrones and pyridinones and protection of Abeta-peptide induced MC65 neuronal cell death. Bioorg Med Chem Lett. 2009 Feb. 1; 19(3):670-4. Epub 2008 Dec. 24; and Hong H S, Maezawa I, Budamagunta M, Rana S, Shi A, Vassar R, Liu R, Lam K S, Cheng R H, Hua D H, Voss J C, Jin L W. Candidate anti-Abeta fluorene compounds selected from analogs of amyloid imaging agents. Neurobiol Aging. 2008 Nov. 18. (Epub ahead of print)] that lower Abeta brain levels in rodents in vivo [Hong H S, Rana S, Barrigan L, Shi A, Zhang Y, Zhou F, Jin L W, Hua D H. Inhibition of Alzheimer's amyloid toxicity with a tricyclic pyrone molecule in vitro and in vivo. J Neurochem. 2009 February; 108(4):1097-1108]. Accordingly, the foregoing tests have established relevance in identifying compounds to treat early Alzheimer's disease and mild cognitive impairment.

In some embodiments, a compound of any of the formulae above has an $IC_{50}$ value of less than 100 μM, 50 μM, 20 μM, 15 μM, 10 μM, 5 μM, 1 μM, 500 nM, 100 nM, 50 nM, or 10 nM with respect to inhibition of one or more of the effect of Abeta oligomers on neurons (such as neurons in the brain), amyloid assembly or disruption thereof, and amyloid (including amyloid oligomer) binding, and amyloid deposition. In some embodiments, the compound has an $IC_{50}$ value of less than 100 μM, 50 μM, 20 μM, 15 μM, 10 μM, 5 μM, 1 μM, 500 nM, 100 nM, 50 nM, or 10 nM with respect to inhibition of the activity/effect of Abeta species such as oligomers on neurons (such as central nervous system neurons).

In some embodiments, percentage inhibition by the compound of the disclosure of one or more of the effects of Abeta species such as oligomers on neurons (such as neurons in the brain), such as amyloid (including amyloid oligomer) binding to synapses, and abnormalities in membrane trafficking mediated by Abeta oligomer was measured at a concentration of from 10 nM to 10 μM. In some embodiments, the percentage inhibition measured is about 1% to about 20%, about 20% to about 50%, about 1% to about 50%, or about 1% to about 80%. Inhibition can be assessed for example by quantifying synapse number of a neuron prior to and after exposure to an amyloid beta species or quantifying the number of synapses in the presence of both of a sigma-2 antagonist and the Abeta species wherein the sigma-2 antagonist is simultaneous with, or precedes or follows, Abeta species exposure. As another example, inhibition can be assessed by determining membrane trafficking and comparing one or more parameters that measure exocytosis rate and extent, endocytosis rate and extent, or other indicators of cell metabolism in the presence and absence of an Abeta species and in the presence and absence of a sigma-2 antagonist according to the disclosure. The present inventors have adduced biochemical assay evidence that compounds of the disclosure also inhibit amyloid aggregation (data not shown).

In some embodiments, the compounds described herein bind specifically to a sigma-2 receptor. A compound that binds specifically to a specific receptor refers to a compound that has a preference for one receptor over another. For example, although a compound may be capable of binding both sigma-1 and sigma-2 receptor, a compound can be said to be specific for a sigma-2 receptor when it binds with a binding affinity that is at least 10% greater than to the sigma-1 receptor. In some embodiments, the specificity is at least 10, 20, 30, 40, 50, 60, 70, 80, 90, 100, 200, 300, 400, 500, or 1000% greater for one binding partner (e.g. receptor) than a second binding partner.

In some embodiments, the disclosure provides methods of measuring beta-amyloid-associated cognitive decline in an animal using a labeled sigma-2 ligand. In some embodiments, the method comprises contacting the animal with a labeled sigma-2 ligand according to the disclosure and measuring sigma-2 activity or expression. In some embodiments, the method comprises comparing the sigma-2 activity or expression in the animal with an animal known to have beta-amyloid induced cognitive decline. If the activity or expression is the same as the animal known to have beta-amyloid induced cognitive decline the animal is said to have the same level of cognitive decline. The animals can be ranked according the similarities in known activity or expression of various stages of beta amyloid induced cognitive decline. Any of the sigma-2 ligands described herein can be labeled so that the labeled sigma-2 ligand can be used in vivo.

In determining whether a compound of any of the formulae above and other compounds described as sigma-2 antagonists above is effective in treating the various conditions described herein, in vitro assays can be used. The in vitro assays have been correlated with an in vivo effect using Compound II For example, if a compound of formulae III-IV which bears structural similarity to compound II is active, for example, in the in vitro assays described herein, it can also be used in vivo to treat or ameliorate the conditions described herein including inhibiting or restoring synapse loss, modulating a membrane trafficking change in neuronal cells, protecting against or restoring memory loss, and treating cognitive decline conditions, diseases and disorders such as MCI and Alzheimer's disease. The assays are based, in part, on the amyloid beta oligomers and their function in binding to neurons at the synapses and the effect that amyloid beta oligomers have on neurons in vitro. In some embodiments, an Abeta oligomer receptor in neurons which the present inventors believe includes a sigma-2 protein is contacted with an amyloid beta assembly as described herein and a compound according to Formula I, II, or III that binds to the sigma-2 protein will inhibit the binding of the amyloid beta assembly to the receptor. In competitive radioligand binding assays the present inventors have shown that the present compounds are specific for the sigma-2 receptor. The inventors have also shown that the compounds of the disclosure inhibit binding of Abeta oligomers to their heretofore unidentified receptor on the surface of neurons. In some embodiments, methods are provided to determine a compound of any above formula's sigma-2 ligand efficacy in neuronal signaling. In some embodiments, the method comprises contacting a cell, such as but not limited to, a primary neuron, with a sigma-2 ligand and measuring neuronal function. In some embodiments, the cell is contacted in vitro. In some embodiments the cell is contacted in vivo. The neuronal activity can be signaling activity, electrical activity, the production or release of synaptic proteins, and the like. A sigma-2 antagonist that enhances or restores the signaling is identified as a compound that is effective in modulating neuronal activity. In some embodiments, the cell is derived from a pathological sample. In some embodiments, the cell is derived from a subject having a neurodegenerative disease. In some embodiments, the neurodegenerative disease is MCI or Alzheimer's Disease, especially mild Alzheimer's disease.

Receptor Binding Assays and Compound Screening

In some embodiments, a test compound is contacted with the cell or cell membrane to determine if the test compound can bind to the sigma-2 receptor. In some embodiments, the test compound is dissolved in a carrier or vehicle, such as but not limited to, dimethyl sulfoxide. In some embodiments, the cells are cultured until confluent. In some embodiments, upon confluence, the cells can be detached by gentle scraping. In some embodiments, the cells are detached by trypsinization, or any other suitable detachment means.

In some embodiments, the binding of the test compound to the sigma-2 receptor can be determined by, for example, a competitive radioligand binding assay. Radioligand binding assays can be carried out on intact cells stably expressing human receptors or a tissue source. The detached cells or tissue can, for example, be washed, centrifuged, and/or resuspended in a buffer. The test compound can be radiolabeled according to any method including, but not limited to, those described herein. The radioligand can be used at a fixed concentration of 0.1 µCi in the absence and presence of various concentrations (the range can be, for example, $10^{10}$-$10^{3}$M OR $10^{11}$-$10^{4}$M of competing drugs. The drugs can be added to the tissue or cells (~ e.g., 50,000 cells) in a buffer and allowed to incubate. Nonspecific binding can be determined in the presence of broad spectrum activators or inhibitors or functional agonists or antagonists for each receptor subtype (for example, for sigma receptors, in the presence of e.g., 10 µM of an appropriate ligand for each receptor). Reactions can be terminated by rapid filtration, which can be followed by washes with ice-cold buffer twice. Radioactivity on the dried filter discs can be measured using any method, including but not limited to, a liquid scintillation analyzer. The displacement curves can be plotted and the Ki values of the test ligands for the receptor subtypes cam be determined using, for example, GraphPad Prism (GraphPad Software Inc., San Diego, Calif.). The percentage specific binding can be determined by dividing the difference between total bound (disintegrations per minute) and nonspecific bound (disintegrations per minute) by the total bound (disintegrations per minute).

In some embodiments, for binding studies in cell lines or tissues sources, varying concentrations of each drug were added in duplicate within each experiment, and the individual $IC_{50}$ values were determined using, for example, GraphPad Prism software. The Ki value of each ligand can be determined according to the equation described by Cheng and Prusoff (1973), and final data can presented as pKi±S.E.M., where in some embodiments, the number of tests is about 1-6.

In some embodiments, the method further comprises determining whether a compound that binds to a sigma-2 receptor acts as a functional antagonist at a sigma-2 receptor by inhibiting soluble Aβ oligomer induced neurotoxicity with respect to inhibiting soluble Aβ oligomer induced synapse loss, and inhibiting soluble Aβ oligomer induced deficits in a membrane trafficking assay. In some embodiments the method further determining that the sigma-2 receptor antagonist does not affect trafficking or synapse number in the absence of Abeta oligomer; does not induce caspase-3 activity in a neuronal cell; inhibits induction of caspase-3 activity by a sigma-2 receptor agonist; and/or decreases or protects against neuronal toxicity in a neuronal cell caused by a sigma-2 receptor agonist.

The testing can also include a functional assay to determine the effect of the test compound on the function of the binding partner, which can be, but is not limited to sigma-2 receptor. A variety of standard assay technologies can be used. For example, methods can be used to measure functional agonist-like or antagonist-like activity of compounds in living cells or tissues. Methods include, but are not limited to, TR-FRET to determine cAMP concentration and IP1 levels, real time fluorescence to monitor calcium flux, cellular dielectric spectroscopy to measure impedance modulation, ileum contraction, or tumor cell apoptosis. The specificity of the test compound can also be determined by, for example, determining if the compound binds to Sigma-1 receptor, Sigma-2 receptor, neither, or both. A method for determining if a test compound binds to a Sigma-1 receptor is described in Ganapathy, M. E et al. (1999) J. Pharmacol. Exp. Ther., 289: 251-260, which is hereby incorporated by reference in its entirety. A method for determining if a test compound binds to a Sigma-1 receptor is described in Bowen, W. D et al. (1993) Mol. Neuropharmacol., 3: 117-126, which is hereby incorporated by reference in its entirety, and also Xu, J. et al, Nature Communications, 2011, 2:380 DOI:10.1038/ncomms 1386 which is also hereby incorporated by reference here in its entirety.

In various embodiments, the disclosure provides assay protocols for identification of a selective, high affinity sigma-2 receptor ligands that can act as a functional antagonist at a sigma-2 receptor by inhibiting soluble Aβ oligomer-induced neurotoxicity with respect to inhibiting soluble Aβ oligomer induced synapse loss, that inhibits soluble Aβ oligomer induced deficits in a membrane trafficking assay, that does not affect trafficking or synapse number in the absence of Abeta oligomer; and that exhibits good drug like properties as described herein such that the selective, high affinity sigma-2 receptor antagonist compound thus identified can be used to treat soluble Aβ oligomer-induced synaptic dysfunction in vivo.

In some embodiments, the disclosure provides methods of determining whether a subject should be treated with a sigma-2 antagonist, wherein the subject is suspected of having cognitive decline or a neurodegenerative disease or other condition, disease or disorder described herein. In some embodiments, the method comprises contacting a sample derived from the patient with a sigma-2 antagonist and determining whether the sigma-2 modulating compound inhibits or ameliorates a beta-amyloid pathology present in the sample, wherein a sample that shows inhibition or amelioration of the beta-amyloid pathology present in the sample indicates that the subject should be treated with a sigma-2 antagonist.

Additionally, the disclosure includes methods to identify sigma-2 antagonists that inhibit an Aβ oligomer induced reduction in synapse number, and the like. In some embodiments, the methods can be used to identify sigma-2 antagonists for treating a beta-amyloid pathology. In some embodiments, the methods are used to determine the efficacy of a treatment to treat a beta-amyloid pathology. In some embodiments, the beta-amyloid pathology is a defect in membrane trafficking, synaptic dysfunction, memory and learning defect in an animal, reduction in synapse number, change in dendritic spine length or spine morphology, a defect in LTP, or an increase in the phosphorylation of Tau protein.

Amyloid Beta as Used in the Present Disclosure

Human amyloid β is the cleavage product of an integral membrane protein, amyloid precursor protein (APP), found concentrated in the synapses of neurons. Amyloid β self-associates to form metastable, oligomeric assemblies. At higher concentrations, Abeta will polymerize and assemble into linear-shaped fibrils, facilitated by lower pH. It is not presently clear whether fibrils are formed from oligomers. Amyloid β oligomers have been demonstrated to cause Alzheimer's disease in animal models by inducing changes in neuronal synapses that block learning and memory, and amyloid β fibrils have long been associated with the advanced stages Alzheimer's disease in animals and humans. In fact, the modern working hypothesis for Alzheimer's disease, and one that has gained a lot of support, is that Abeta assemblies and notably Abeta oligomers are at the center of early pathology associated with Alzheimer's as well as of pathologies associated with less grave dementias, such as MCI and mild AD. Cleary, James P. et al. "Natural oligomers of the amyloid-β protein specifically disrupt cognitive function." *Nature Neuroscience* Vol. 8 (2005): 79-84; Klyubin, I. et al. "Amyloid beta protein dimer-containing human CSF disrupts synaptic plasticity: prevention by systemic passive immunization." *J Neurosci.* Vol. 28 (2008): 4231-4237. However, very little is known about how oligomers form and the structural state of the oligomer. For example, the number of amyloid β subunits that associate to form the oligomer is currently unknown, as is the structural form of the oligomers, or which residues are exposed. There is evidence to suggest that more than one structural state of oligomer is neuroactive. Reed, Jess D. et al. "MALDI-TOF mass spectrometry of oligomeric food polyphenols." *Phytochemistry* 66:18 (September 2005): 2248-2263; Cleary, James P. et al. "Natural oligomers of the amyloid-β protein specifically disrupt cognitive function." *Nature Neuroscience* Vol. 8 (2005): 79-84.

Amyloid β has affinity for many proteins found in the brain, including ApoE and ApoJ. However, it is unclear whether chaperones or other proteins form associations with the protein that can affect its final structural state and/or its neuroactivity.

Soluble Abeta peptide is likely to play a key role during early stages of AD by perturbing synaptic dusfunction and cognitive processes. For example, Origlia et al. showed soluble Abeta (Abeta 42) impairs long term potentiation (LTP) in the entorhinal cortex through neuronal receptor for advanced glycation end products (RAGE)-mediated activation of p38MAPK. Origlia et al. 2008, Receptor for advanced glycation end product-dependnet activation of p38 mitogen-activated protein kinase contributes to amyloid-beta-mediated cortical synaptic dysfunction. J. Neuroscience 28(13):3521-3530, incorporated herein by reference.

Synaptic dysfunction is involved in early stages of Alzheimer's disease. Amyloid beta peptides have been shown to alter synaptic function. Puzzo et al reported that a synthetic fibrillar form of Abeta impairs the late protein synthesis dependent phase of LTP without affecting the early protein synthesis phase. The report is consistent with earlier reports that Abeta oligomers are highly toxic to cells and involved in synaptic dysfunction. Puzzo et al., 2006, Curr Alzheimer's Res 3(3):179-183, which is incorporated herein by reference. Abeta has been found to markedly impair hippocampal long-term potentiation (LTP) by various second messenger cascades including a nitric oxide cascade. NO/cGMP/cGK/CREB. Puzzo et al., J Neurosci. 2005, In some embodiments, the disclosure provides compositions and methods comprising sigma-2 receptor antagonists for inhibiting amyloid beta oligomer-induced synaptic dysfunction of a neuronal cell; and inhibiting suppression of hippocampal long term potention caused by exposure of neurons to Abeta oligomers.

Any form of amyloid β may be used in the practice of the screening methods and of the assays according to the disclosure, including amyloid β monomers, oligomers, fibrils, as well as amyloid β associated with proteins ("protein complexes") and more generally amyloid β assemblies. For example, screening methods can employ various forms of soluble amyloid β oligomers as disclosed, for example, in U.S. patent application Ser. No. 13/021,872; U.S. Patent Publication 2010/0240868; International Patent Application WO/2004/067561; International Patent Application WO/2010/011947; U.S. Patent Publication 20070098721; U.S. Patent Publication 20100209346; International Patent Application WO/2007/005359; U.S. Patent Publication 20080044356; U.S. Patent Publication 20070218491; WO/2007/126473; U.S. Patent Publication 20050074763; International Patent Application WO/2007/126473, International Patent Application WO/2009/048631, and U.S. Patent Publication 20080044406, U.S. Pat. Nos. 7,902,328 and 6,218,506, each of which is incorporated herein by reference.

Amyloid β forms, including monomers or oligomers of amyloid β may be obtained from any source. For example, in some embodiments, commercially available amyloid β monomers and/or amyloid β oligomers may be used in the aqueous solution, and in other embodiments, amyloid β monomers and/or amyloid β oligomers that are used in the aqueous protein solution can be isolated and purified by the skilled artisan using any number of known techniques. In general, the amyloid β monomers and/or amyloid β oligomers used in the preparation of the aqueous solution of proteins and amyloid β of various embodiments may be soluble in the aqueous solution. Therefore, both the proteins of the aqueous solution and the amyloid β may be soluble.

The amyloid β added may be of any isoform. For example, in some embodiments, the amyloid β monomers may be amyloid β 1-42, and in other embodiments the amyloid β monomers may be amyloid β 1-40. In still other embodiments, the amyloid β may be amyloid β 1-39 or amyloid β 1-41. Hence, the amyloid β of various embodiments may encompass any C-terminal isoform of amyloid β. Yet other embodiments include amyloid β in which the N-terminus has been frayed, and in some embodiments, the N-terminus of any of amyloid β C-terminal isomers described above may be amino acid 2, 3, 4, 5, or 6. For example, amyloid β 1-42 may encompass amyloid β 2-42, amyloid β 3-42, amyloid β 4-42, or amyloid β 5-42 and mixtures thereof, and similarly, amyloid β 1-40 may encompass amyloid β 2-40, amyloid β 3-40, amyloid β 4-40, or amyloid β 5-40.

The amyloid β forms used in various embodiments may be wild type, i.e. having an amino acid sequence that is identical to the amino acid sequence of amyloid β synthesized in vivo by the majority of the population, or in some embodiments, the amyloid β may be a mutant amyloid β. Embodiments are not limited to any particular variety of mutant amyloid β. For example, in some embodiments, the amyloid β introduced into the aqueous solution may include a known mutation, such as, for example, amyloid β having the "Dutch" (E22Q) mutation or the "Arctic" (E22G) mutation. Such mutated monomers may include naturally occurring mutations such as, for example, forms of amyloid β isolated from populations of individuals that are predisposed to, for example, Alzheimer's disease, familial forms of amyloid β. In other embodiments, mutant amyloid β monomers may be synthetically produced by using molecular techniques to produce an amyloid β mutant with a specific mutation. In still other embodiments, mutant amyloid β monomers may include previously unidentified mutations such as, for example, those mutants found in randomly generated amyloid β mutants. The term "amyloid β" as used herein is meant to encompass both wild type forms of amyloid β as well as any of the mutant forms of amyloid β.

In some embodiments, the amyloid β in the aqueous protein solution may be of a single isoform. In other embodiments, various C-terminal isoforms of amyloid β and/or various N-terminal isoforms of amyloid β may be combined to form amyloid β mixtures that can be provided in the aqueous protein solution. In yet other embodiments, the amyloid β may be derived from amyloid precursor protein (APP) that is added to the protein containing aqueous solution and is cleaved in situ, and such embodiments, various isoforms of amyloid β may be contained within the solution. Fraying of the N-terminus and/or removal of C-terminal amino acids may occur within the aqueous solution after amyloid β has been added. Therefore, aqueous solutions prepared as described herein may include a variety of amyloid β isoforms even when a single isoform is initially added to the solution.

The amyloid β monomers added to the aqueous solution may be isolated from a natural source such as living tissue, and in other embodiments, the amyloid β may be derived from a synthetic source such as transgenic mice or cultured cells. In some embodiments, the amyloid β forms, including monomers, oligomers, or combinations thereof are isolated from normal subjects and/or patients that have been diagnosed with cognitive decline or diseases associated therewith, such as, but not limited to, Alzheimer's disease. In some embodiments, the amyloid β monomers, oligomers, or combinations thereof are Abeta assemblies that have been isolated from normal subjects or diseased patients. In some embodiments, the Abeta assemblies are high molecular weight, e.g. greater than 100 KDa. In some embodiments, the Abeta assemblies are intermediate molecular weight, e.g. 10 to 100 KDa. In some embodiments, the Abeta assemblies are less than 10 kDa.

The amyloid β oligomers of some embodiments may be composed of any number of amyloid β monomers consistent with the commonly used definition of "oligomer." For example, in some embodiments, amyloid β oligomers may include from about 2 to about 300, about 2 to about 250, about 2 to about 200 amyloid β monomers, and in other embodiments, amyloid β oligomers may be composed from about 2 to about 150, about 2 to about 100, about 2 to about 50, or about 2 to about 25, amyloid β monomers. In some embodiments, the amyloid β oligomers may include 2 or more monomers. The amyloid β oligomers of various embodiments may be distinguished from amyloid β fibrils and amyloid β protofibrils based on the confirmation of the monomers. In particular, the amyloid β monomers of amyloid β oligomers are generally globular consisting of β-pleated sheets whereas secondary structure of the amyloid β monomers of fibrils and protofibrils is parallel β-sheets.

Identification of Subjects Having or at Risk of Having Alzheimer's Disease

Alzheimer's disease (AD) is defined histologically by the presence of extracellular β-amyloid (Aβ) plaques and intraneuronal neurofibrillary tangles in the cerebral cortex. Various diagnostic and prognostic biomarkers are known in the art, such as magnetic resonance imaging, single photon emission tomography, FDG PET, PiB PET, CSF tau and Abeta analysis, as well as available data on their diagnostic accuracy are discussed in Alves et al., 2012, Alzheimer's disease: a clinical practice-oriented review, Frontiers in Neurology, April, 2012, vol 3, Article 63, 1-20, which is incorporated herein by reference.

The diagnosis of dementia, along with the prediction of who will develop dementia, has been assisted by magnetic resonance imaging and positron emission tomography (PET) by using [(18)F]fluorodeoxyglucose (FDG). These techniques are not specific for AD. See, e.g., Vallabhajosula S. *Positron emission tomography radiopharmaceuticals for imaging brain Beta-amyloid*. Semin Nucl Med. 2011 July; 41(4):283-99. Another PET ligand recently FDA approved for imaging moderate to frequent amyloid neuritic plaques in patients with cognitive impairment is Florbetapir F 18 injection, (4-((1E)-2-(6-{2-(2-(2-(18F)fluoroethoxy)ethoxy)ethoxy}pyridin-3-yl)ethenyl)-N-methylbenzenamine, AMYVID®, Lilly). Florbetapir binds specifically to fibrillar Abeta, but not to neurofibrillary tangles. See, e.g., Choi S R, et al., *Correlation of amyloid PET ligand florbetapir F 18 binding with Aβ aggregation and neuritic plaque deposition in postmortem brain tissue*. Alzheimer Dis Assoc Disord. 2012 January; 26(1):8-16. The PET ligand florbetapir suffers from low specificity with respect to qualitative visual assessment of the PET scans. Camus et al., 2012, Eur J Nucl Med Mol Imaging 39:621-631. However, many people with neuritic plaques seem cognitively normal.

CSF markers for Alzheimer's disease include total tau, phosphor-tau and Abeta42. See, for example, Andreasen, Sjogren and Blennow, World J Biol Psyciatry, 2003, 4(4): 147-155, which is incorporated herein by reference. Reduced CSF levels of the 42 amino acid form of Abeta (Abeta42) and increased CSF levels of total tau in AD have been found in numerous studies. In addition, there are known genetic markers for mutations in the APP gene useful in the identification of subjects at risk for developing AD. See, for example, Goate et al., Segregation of a missense mutation in the amyloid precursor protein gene with familial Alzheimer's disease, Nature, 349, 704-706, 1991, which is incorporated herein by reference. In embodiments, any known diagnostic or prognostic method can be employed to identify a subject having or at risk of having Alzheimer's disease. Pharmaceutical Compositions Comprising a Sigma-2 Receptor Antagonist The sigma-2 receptor antagonist compounds provided herein can be administered in the form of pharmaceutical compositions. These compositions can be prepared in a manner well known in the pharmaceutical art, and can be administered by a variety of routes, depending upon whether local or systemic treatment is desired and upon the area to be treated.

Thus, another embodiment of the disclosure comprises pharmaceutical compositions comprising a pharmaceutically acceptable excipient or diluent and a therapeutically effective amount of a sigma-2 receptor antagonist compound of the disclosure, including an enantiomer, diastereomer, N-oxide or pharmaceutically acceptable salt thereof.

While it is possible that a compound may be administered as the bulk substance, it is preferable to present the active ingredient in a pharmaceutical formulation, e.g., wherein the active agent is in admixture with a pharmaceutically acceptable carrier selected with regard to the intended route of administration and standard pharmaceutical practice.

Accordingly, in one aspect, the disclosure provides a pharmaceutical composition comprising at least one compound, antibody or fragment, of any of the formulae above and other compounds described as sigma-2 receptor antagonists above described above or a pharmaceutically acceptable derivative (e.g., a salt or solvate) thereof, and, optionally, a pharmaceutically acceptable carrier. In particular, the disclosure provides a pharmaceutical composition comprising a therapeutically effective amount of at least one compound of any of the formulae above or a pharmaceutically acceptable derivative thereof, and, optionally, a pharmaceutically acceptable carrier.

Combinations

For the compositions and methods of the disclosure, a compound of any of the formulae above and other compounds described as sigma-2 receptor antagonists above described above may be used in combination with other therapies and/or active agents.

In some embodiments, the sigma-2 antagonist compound can be combined with one or more of a cholinesterase inhibitor, an N-methyl-D-aspartate (NMDA) glutamate receptor antagonist, a beta-amyloid specific antibody, a beta-secretase 1 (BACE1, beta-site amyloid precursor protein cleaving enzyme 1) inhibitor, a tumor necrosis factor alpha (TNF alpha) modulator, an intravenous immunoglobulin (IVIG), or a prion protein antagonist. In some embodiments the sigma-2 receptor antagonist is combined with a cholinesterase inhibitor selected from tacrine (COGNEX®; Sciele), donepezil (ARICEPT®; Pfizer), rivastigmine (EXELON®; Novartis), or galantamine (RAZADYNE®; Ortho-McNeil-Janssen). In some embodiments, the sigma-2 receptor antagonist is combined with a TNFalpha modulator that is perispinal etanercept (ENBREL®, Amgen/Pfizer). In some embodiments, the sigma-2 receptor antagonist is combined with a beta-amyloid specific antibody selected from bapineuzumab (Pfizer), solanezumab (Lilly), PF-04360365 (Pfizer), GSK933776(GaxoSmithKline), Gammagard (Baxter) or Octagam (Octapharma). In some embodiments, the sigma-2 receptor antagonist is combined with an NMDA receptor antagonist that is memantine (NAMENDA®; Forest). In some embodiments, the BACE1 inhibitor is MK-8931 (Merck). In some embodiments, the sigma-2 receptor antagonist is combined with IVIG as described in Magga et al., J Neuroinflam 2010, 7:90, Human intravenous immunoglobulin provides protection against Ab toxicity by multiple mechanisms in a mouse model of Alzheimer's disease, and Whaley et al., 2011, Human Vaccines 7:3, 349-356, Emerging antibody products and Nicotiana manufacturing; each of which is incorporated herein by reference. In some embodiments, the sigma-2 receptor antagonist is combined with a prion protein antagonist as disclosed in Strittmatter et al., US 2010/0291090, which is incorporated herein by reference.

Accordingly, the disclosure provides, in a further aspect, a pharmaceutical composition comprising at least one compound of any of the formulae above or a pharmaceutically acceptable derivative thereof, a second active agent, and, optionally a pharmaceutically acceptable carrier.

When combined in the same formulation it will be appreciated that the two or more compounds must be stable and compatible with each other and the other components of the formulation. When formulated separately they may be provided in any convenient formulation, conveniently in such manner as are known for such compounds in the art.

Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used.

With respect to combinations including biologics such as monoclonal antibodies or fragments, suitable excipients will be employed to prevent aggregation and stabilize the antibody or fragment in solution with low endotoxin, generally for parenteral, for example, intravenous, administration. For example, see Formulation and Delivery Issues for Monoclonal Antibody Therapeutics, Daugherty et al., in Current Trends in Monoclonal Antibody Development and Manufacturing, Part 4, 2010, Springer, New York pp 103-129.

The compounds of the disclosure may be milled using known milling procedures such as wet milling to obtain a particle size appropriate for tablet formation and for other formulation types. Finely divided (nanoparticulate) preparations of the compounds of the disclosure may be prepared by processes known in the art, for example see WO 02/00196 (SmithKline Beecham).

Routes of Administration and Unit Dosage Forms

The routes for administration (delivery) include, but are not limited to, one or more of: oral (e.g., as a tablet, capsule, or as an ingestible solution), topical, mucosal (e.g., as a nasal spray or aerosol for inhalation), parenteral (e.g., by an injectable form), gastrointestinal, intraspinal, intraperitoneal, intramuscular, intravenous, intracerebroventricular, or other depot administration etc. Administration of an antibody or fragment will generally be by parenteral means.

Therefore, the compositions of the disclosure include those in a form especially formulated for, the mode of administration. In certain embodiments, the pharmaceutical compositions of the disclosure are formulated in a form that is suitable for oral delivery. For example compound CB and compound CF are sigma-2 receptor antagonist compounds that are orally bioavailable in animal models and have been administered orally once per day and shown efficacy in a fear conditioning model, see for example FIG. 12B Orally bioavailable compounds as described herein can be prepared in an oral formulation. In some embodiments, the sigma-2 antagonist compound is an orally bioavailable compound, suitable for oral delivery. In other embodiments, the pharmaceutical compositions of the disclosure are formulated in a form that is suitable for parenteral delivery In some embodiments, the sigma-2 receptor antagonist compound is an antibody or fragment thereof, wherein the antibody or fragment is formulated in a parenteral composition. For example, an anti-sigma-2 receptor antibody such as an anti-PGRMC1 antibody that blocks binding of Abeta oligomers to the sigma-2 receptor can be formulated for parenteral delivery.

The compounds of the disclosure may be formulated for administration in any convenient way for use in human or veterinary medicine and the disclosure therefore includes within its scope pharmaceutical compositions comprising a compound of the disclosure adapted for use in human or veterinary medicine. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

There may be different composition/formulation requirements depending on the different delivery systems. It is to be understood that not all of the compounds need to be administered by the same route. Likewise, if the composition comprises more than one active component, then those components may be administered by different routes. By way of example, the pharmaceutical composition of the disclosure may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

The combination of a compound provided herein and an antibody or antibody fragment molecule can be formulated and administered by any of a number of routes and are administered at a concentration that is therapeutically effective in the indication or for the purpose sought. To accomplish this goal, the antibodies may be formulated using a variety of acceptable excipients known in the art. Typically, the antibodies are administered by injection, for example, intravenous injection. Methods to accomplish this administration are known to those of ordinary skill in the art. For example, Gokarn et al., 2008, J Pharm Sci 97(8):3051-3066, incorporated herein by reference, describe various high concentration antibody self buffered formulations. For example, monoclonal antibodies in self buffered formulation at e.g., 50 mg/mL mAb in 5.25% sorbitol, pH 5.0 or 60 mg/mL mAb in 5% sorbitol, 0.01% polysorbate 20, pH 5.2; or conventional buffered formulations, for example, 50 mg/mL mAb1 in 5.25% sorbitol, 25 or 50 mM acetate, glutamate or succinate, at pH 5.0; or 60 mg/mL in 10 mM acetate or glutamate, 5.25% sorbitol, 0.01% polysorbate 20, pH 5.2; other lower concentration formulations can be employed as known in the art.

Because the preferred sigma-2 receptor antagonist compounds of the disclosure cross the blood brain barrier they can be administered in a variety of methods including for example systemic (e.g., by iv, SC, oral, mucosal, transdermal route) or localized methods (e.g., intracranially). Where the compound of the disclosure is to be delivered mucosally through the gastrointestinal mucosa, it should be able to remain stable during transit though the gastrointestinal tract; for example, it should be resistant to proteolytic degradation, stable at acid pH and resistant to the detergent effects of bile. For example, the sigma-2 antagonist compounds selected from the sigma-2 ligands and prepared for oral administration described above may be coated with an enteric coating layer. The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

Where appropriate, the pharmaceutical compositions can be administered by inhalation, by use of a skin patch, orally in the form of tablets containing excipients such as starch or lactose, or in capsules or ovules either alone or in admixture with excipients, or in the form of elixirs, solutions or suspensions containing flavoring or coloring agents, or they can be injected parenterally, for example intravenously, intramuscularly or subcutaneously. For buccal or sublingual administration the compositions may be administered in the form of tablets or lozenges, which can be formulated in a conventional manner.

Where the composition of the disclosure is to be administered parenterally, such administration includes without limitation: intravenously, intraarterially, intrathecally, intraventricularly, intracranially, intramuscularly or subcutaneously administering the compound of the disclosure; and/or by using infusion techniques. Antibodies or fragments are typically administered parenterally, for example, intravenously.

Pharmaceutical compositions suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, or acsorbic acid. In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminum monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound of formulas I, with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the sigma-2 receptor antagonists and desired excipients for subsequent preparation of sterile solutions.

The compounds according to the disclosure may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing and/or dispersing agents. Alternatively the active ingredient may be in sterile powder form for reconstitution with a suitable vehicle, e.g., sterile, pyrogen-free water, before use.

The compounds of the disclosure can be administered in the form of tablets, capsules, troches, ovules, elixirs, solutions or suspensions, for immediate-, delayed-, modified-, sustained-, pulsed- or controlled-release applications.

The compounds of the disclosure may also be presented for human or veterinary use in a form suitable for oral or buccal administration, for example in the form of solutions, gels, syrups, or suspensions, or a dry powder for reconstitution with water or other suitable vehicle before use. Solid compositions such as tablets, capsules, lozenges, troches, pastilles, pills, boluses, powder, pastes, granules, bullets or premix preparations may also be used. Solid and liquid compositions for oral use may be prepared according to methods well-known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The compositions may be administered orally, in the form of rapid or controlled release tablets, microparticles, mini tablets, capsules, sachets, and oral solutions or suspensions, or powders for the preparation thereof. Oral preparations may optionally include various standard pharmaceutical carriers and excipients, such as binders, fillers, buffers, lubricants, glidants, dyes, disintegrants, odorants, sweeteners, surfactants, mold release agents, antiadhesive agents and coatings. Some excipients may have multiple roles in the compositions, e.g., act as both binders and disintegrants.

Examples of pharmaceutically acceptable disintegrants for oral compositions useful in the disclosure include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthine resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulphate.

Examples of pharmaceutically acceptable lubricants useful in the compositions of the disclosure include, but are not limited to, magnesium stearate, talc, polyethylene glycol, polymers of ethylene oxide, sodium lauryl sulphate, magnesium lauryl sulphate, sodium oleate, sodium stearyl fumarate, and colloidal silicon dioxide.

Examples of suitable pharmaceutically acceptable odorants for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Examples of useful pharmaceutically acceptable coatings for the oral compositions, typically used to facilitate swallowing, modify the release properties, improve the appearance, and/or mask the taste of the compositions include, but are not limited to, hydroxypropylmethylcellulose, hydroxypropylcellulose and acrylate-methacrylate copolymers.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulphate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

As indicated, the compounds of the disclosure can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the disclosure may be delivered for use in human or veterinary medicine via a nebulizer.

The pharmaceutical compositions of the disclosure may contain from 0.01 to 99% weight per volume of the active material. For topical administration, for example, the composition will generally contain from 0.01-10%, more preferably 0.01-1% of the active material.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage form of the disclosure may be administered according to a dosage and administration regimen defined by routine testing in the light of the guidelines given above in order to obtain optimal activity while minimizing toxicity or side effects for a particular patient. However, such fine tuning of the therapeutic regimen is routine in the light of the guidelines given herein.

The dosage of the compounds of the disclosure may vary according to a variety of factors such as underlying disease conditions, the individual's condition, weight, sex and age, and the mode of administration. An effective amount for treating a disorder can easily be determined by empirical methods known to those of ordinary skill in the art, for example by establishing a matrix of dosages and frequencies of administration and comparing a group of experimental units or subjects at each point in the matrix. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of urinary tract disorders is within the scope of the disclosure. Clinically significant attenuation or amelioration means perceptible to the patient and/or to the physician.

The amount of the compound to be administered can range between about 0.01 and about 25 mg/kg/day, usually between about 0.1 and about 10 mg/kg/day and most often between 0.2 and about 5 mg/kg/day. It will be understood that the pharmaceutical formulations of the disclosure need not necessarily contain the entire amount of the compound that is effective in treating the disorder, as such effective amounts can be reached by administration of a plurality of divided doses of such pharmaceutical formulations.

In a preferred embodiment of the disclosure, the compounds I are formulated in capsules or tablets, usually containing 10 to 200 mg of the compounds of the disclosure, and are preferably administered to a patient at a total daily dose of 10 to 300 mg, preferably 20 to 150 mg and most preferably about 50 mg.

A pharmaceutical composition for parenteral administration contains from about 0.01% to about 100% by weight of the active compound of the disclosure, based upon 100% weight of total pharmaceutical composition.

Generally, transdermal dosage forms contain from about 0.01% to about 100% by weight of the active compound versus 100% total weight of the dosage form.

The pharmaceutical composition or unit dosage form may be administered in a single daily dose, or the total daily dosage may be administered in divided doses. In addition, co-administration or sequential administration of another compound for the treatment of the disorder may be desirable. To this purpose, the combined active principles are formulated into a simple dosage unit.

Synthesis of the Compounds

Compounds of formulas I and II and enantiomers, diastereomers, N-oxides, and pharmaceutically acceptable salts thereof, may be prepared by the general methods outlined in, for example, WO2013/029057, incorporated herein by reference, or as described hereinafter, said methods constituting a further aspect of the disclosure.

It will be appreciated by those skilled in the art that it may be desirable to use protected derivatives of intermediates used in the preparation of the compounds. Protection and deprotection of functional groups may be performed by methods known in the art (see, for example, Green and Wuts *Protective Groups in Organic Synthesis*. John Wiley and Sons, New York, 1999). Hydroxy or amino groups may be protected with any hydroxy or amino protecting group. The amino protecting groups may be removed by conventional techniques. For example, acyl groups, such as alkanoyl, alkoxycarbonyl and aroyl groups, may be removed by solvolysis, e.g., by hydrolysis under acidic or basic conditions. Arylmethoxycarbonyl groups (e.g., benzyloxycarbonyl) may be cleaved by hydrogenolysis in the presence of a catalyst such as palladium-on-charcoal.

The synthesis of the target compounds is completed by removing any protecting groups which may be present in the penultimate intermediates using standard techniques, which are well-known to those skilled in the art. The deprotected final products are then purified, as necessary, using standard techniques such as silica gel chromatography, HPLC on silica gel and the like, or by recrystallization.

WORKING AND SYNTHESIS EXAMPLES

Examples 1 and 2 describe Abeta oligomer preparations that could be used for experiments such as those described herein. The particular preparations used in the membrane trafficking and oligomer bindin/synapse reduction assays as well as those used in the in vivo assays described below are each described in the example to which they pertain.

Example 1: Preparation of Amyloid β Oligomers

The conditions in which amyloid β may oligomerize in nervous tissue, a milieu of aqueous-soluble proteins with which it may associate, were re-created to identify the more disease-relevant structural state of amyloid β oligomers and fibrils. Aqueous soluble proteins were prepared from rat brain by ultracentrifugation. Specifically, 5 volumes of TBS buffer (20 mM Tris-HCL, pH 7.5, 34 mM NaCl and a complete protease inhibitor cocktail (Santa Cruz) per gram of brain tissue was added to the rat brain tissue on ice. Dounce homogenization was then carried out with a tight-fitting pestle. The homogenized brain tissues were then centrifuged at 150,000×g for 1 hour at 4° C. (40,000 rpm Ty65). The infranatant (between floating myelin and a half cm above the pellet) was then removed and aliquots were frozen at −75° C. The pellets were then resuspended in TBS to the original volume and frozen in aliquots at −75° C. Synthetic, monomeric human amyloid β 1-42 was added to this mixture to provide a final concentration of 1.5 uM amyloid β, and the solution was incubated for 24 hours at 4° C. Centrifugation of the mixture at 5,800 g for 10 minutes was performed to remove fibrillar assemblies and then Immunoprecipitation was performed using 6E10 conjugated agarose spin columns (Pierce Chemical Company) for 24 hours at 4° C. The eluted amyloid β oligomers were then subject to MALDI-T of mass spectroscopic analysis to identify the contents of the sample.

The amyloid β self-associated in the protein containing solution to form subunit assemblies of 22,599 Da, 5 subunit pentamers and 31,950 Da, 7 subunit, 7mers. Another peak at 49,291 Da may represent 12 subunit, 12mers, although this would not appear to be an accurate molecular weight for amyloid β 12mers. Notably, no peaks are observed at either 4518 Da or 9036 Da which would represent amyloid β monomers and dimers. However, peaks at 9,882 Da and 14,731 Da could represent amyloid β dimers associated with a 786 Da (or 2×393 Da) lipids or proteins and amyloid β trimers associated with 3×393 Da lipids or proteins, respectively. In addition, the presence of a peak at 19,686 Da is indicative of an assembly state possibly involving a trimer complex and a rat amyloid β fragment of 4954 Da. Accordingly these data may reflect the association of small lipids or proteins with dimers and trimers of amyloid β which may direct the assembly of conformational states unique to physiological systems.

Example 2: Preparation of Beta-Amyloid Oligomers

A solution of 1.5 uM monomeric human amyloid β 1-42 in a mixture of rat brain soluble proteins was incubated for 24 hours at 4° C. as described in Example 1. This solution was then treated with tri-fluoro ethanol (TFE) prior to taking the spectra. In TFE, assembled protein structures and non-covalently bound protein complexes dissociate into denatured proteins, and the peaks associated with assembled oligomers are expected to disappear. The majority of protein peaks observed in Example 1 disappeared including the 9822 Da, 14,731 Da, 31,950 Da, and 49,291 Da peaks identified above. However, an abundant peak is observed at 4518 Da which represents amyloid β monomer peak. A peak at 4954.7 is apparent which may represent a longer abeta fragment similar to amyloid β 1-46. An additional peak is observed at 7086 Da which was not present in the preparation described in Example 1, which may represent amyloid β monomers associated with a 2550 Da covalently bound protein.

Example 3: Isolation of Beta-Amyloid Oligomers from Human AD Brain Tissue

TBS soluble extracts: Samples of post-mortem brain tissue from human patients characterized via histopathological analysis as Braak Stage V/VI Alzheimer's disease (AD) were obtained from a hospital brain tissue bank. Age and gender matched AD and normal tissue specimens were diluted to 0.15 gm tissue/ml in 20 mM Tris-HCL, 137 mM NaCl, pH 7.6 containing 1 mM EDTA and 1 mg/ml complete protease inhibitor cocktail (Sigma P8340) and homogenized. Ultracentrifugation of the tissue homogenates was performed at 105,000 g for 1 hour in a Beckman Optima XL-80K Ultracentrifuge. The resulting TBS soluble fractions were immunodepleted using protein-A and protein-G agarose columns (Pierce Chemical) and then size fractionated with Amicon Ultra 3, 10 & 100 kDa NMWCO filters (Millipore Corporation).

Immunoprecipitation: Size fractionated and immunodepleted TBS soluble extracts were concentrated to approximately 200 ul in the appropriate NMWCO Amicon Ultra filters. The concentrated TBS soluble extracts were diluted up to 400 ul with TBS sample buffer (Pierce Chemical) and centrifuged for 10 minutes at 5,800 g to remove fibrils. The resulting supernatant was then immunoprecipitated with 6E10-conjugated agarose beads overnight at 4° C. followed by antigen elution using high osmotic strength Gentle elution buffers (Pierce Chemical) to isolate Abeta containing protein species.

MALDI-mass spectrometry: Immunoisolated beta amyloid was subjected to mass spectroscopic analysis using an Applied Biosystems (ABI) Voyager DE-Pro MALDI-Tof instrument. Samples were analyzed using various matrix types such as α-Cyano-4-hydroxycinnamic acid (CHCA), Sinapic acid (SA), or 6-Aza-2-thiothymine (ATT) depending on the target molecular weight range of the analysis. The instrument was run in a linear-positive ion mode along with a variable extraction delay. Non-accumulated spectra represented 100 shots of a "hot spot" per acquisition while accumulated spectra were represented by 12 separate areas of each spot with 200 laser shots per acquisition.

Data analysis: Data acquisition and analysis was performed using Voyager's Data Explorer software package. Standard processing of the mass spectra included smoothing of the spectrum and baseline subtraction functions in addition to variations in the signal to noise ratio.

ELISA for Ab quantification: Immunoprecipitated TBS soluble fractions were analyzed for both "total" Abeta and Abeta oligomer concentration using a modified sandwich ELISA technique. Briefly, 6E10 and 4G8 coated Nunc MaxiSorp 96-well plates were incubated with Abeta containing samples and then probed with a Biotinylated 4G8 detection antibody. Incubation with Streptavidin-HRP (Rockland) followed by development of a Tetramethyl benzidine (TMB) substrate allowed for colorimetric detection (OD 450) of abeta on a BioTEk Synergy HT plate reader. Monomeric Abeta 1-42 was used for generation of a standard curve and along with GEN 5 software allowed for quantification of Abeta levels in the immuno-precipitated samples.

Example 4: Receptor Binding Assays

Certain compounds are tested for interaction with several receptors by blocking the binding or action of their agonists or antagonists. Some compounds are tested to see whether they interact directly with known cellular receptor or signaling proteins. Compounds can be tested for the ability to displace binding of known agonists or antagonists of a given human receptor that was overexpressed in cell lines or isolated from tissue. Compounds can also be tested for the ability to block downstream signaling induced by agonists or antagonists of a given human receptor. Compounds can be tested for action at 100 known receptors, and it is desirable that specific activity will occur at only a small subset of CNS-relevant receptors. Compounds that bind the sigma-2 receptor with the highest affinity compared to other receptors, are labeled as sigma-2 receptor selective ligands.

Using the same protocol, some compounds for which membrane trafficking data are given in Table 2 are tested for recognition of sigma-2 receptor. Certain preferred compounds of Formula I are selective sigma-2 receptor ligands, i.e., preferentially bind to the sigma-2 receptor.

Competitive Radioligand Binding Assay.

Radioligand binding assays for Sigma-1 receptors and Sigma-2 receptors were carried out by a commercial contract research organization. For Sigma-1 binding, various concentrations of test compounds from 100 μM to 1 nM were used to displace 8 nM [$^3$H](+)pentazocine from endogenous receptors on Jurkat cell membranes (Ganapathy M E et al. 1991, J Pharmacol. Exp. Ther. 289:251-260). 10 μM Haloperidol was used to define non-specific binding. For Sigma-2 receptors various concentrations of test compounds from 100 μM to 1 nM were used to displace 5 nM [$^3$H] 1,3-Di-(2-tolyl)guanidine from endogenous receptors on membranes from rat cerebral cortex in the presence of 300 nM (+)pentazocine to mask Sigma-1 receptors. (Bowen W D, et al. 1993, Mol. Neuropharmcol 3:117-126). 10 μM Haloperidol was used to define non-specific binding. Reactions were terminated by rapid filtration through Whatman GF/C filters using a Brandel 12R cell harvester followed by two washes with ice-cold buffer. Radioactivity on the dried filter discs was measured using a liquid scintillation analyzer (Tri-Carb 2900TR; PerkinElmer Life and Analytical Sciences). The displacement curves were plotted and the Ki values of the test ligands for the receptor subtypes were determined using GraphPad Prism (GraphPad Software Inc., San Diego, Calif.). The percentage specific binding was determined by dividing the difference between total bound (disintegrations per minute) and nonspecific bound (disintegrations per minute) by the total bound (disintegrations per minute).

Affinities for Sigma-1 and Sigma-2 receptors are typically obtained from published studies using cerebral tissue homogenates with [$^3$H](+)pentazocine to measure displacement from Sigma-1 receptors and [$^3$H] 1,3-Di-(2-tolyl)guanidine in the presence of 300 nM (+)pentazocine to measure displacement from Sigma-2 receptors.

Competitive Radioligand Binding Assay 2.

The affinity of candidate sigma-2 ligand compounds at sigma-1 and sigma-2 receptors was also determined by displacement of different known labeled sigma-2 or sigma-1 ligands. Filtration assays were conducted according the previously published procedure (Xu, et al., 2005). Test compounds were dissolved in N,N-Dimethylformamide (DMF), dimethyl sulfoxide (DMSO) or ethanol and then diluted in 50 mM Tris-HCl pH 7.4 buffer containing 150 mM NaCl and 100 mM EDTA. Membrane homogenates were made from guinea pig brain for sigma-1 binding assay and rat liver for sigma-2 binding assay. Membrane homogenates were diluted with 50 mM Tris-HCl buffer, pH 8.0 and incubated at 25° C. in a total volume of 150 uL in 96 well plates with the radioligand and test compounds with concentrations ranging from 0.1 nM to 10 uM. After incubation was completed, the reactions were terminated by the addition of 150 uL of ice-cold wash buffer (10 mM Tris HCl, 150 mM NaCl, pH 7.4) using a 96 channel transfer pipette (Fisher Scientific, Pittsburgh, Pa.) and the samples harvested and filtered rapidly through 96 well fiber glass filter plate (Millipore, Billerica, Mass.) that had been presoaked with 100 uL of 50 mM Tris-HCl buffer. Each filter was washed four times with 200 uL of ice-cold wash buffer (10 mM Tris-HCl, 150 mM NaCl, pH 7.4). A Wallac 1450 MicroBeta liquid scintillation counter (Perkin Elmer, Boston, Mass.) was used to quantitate the bound radioactivity.

The sigma-1 receptor binding assays were conducted using guinea pig brain membrane homogenates (~300 ug protein) and ~5 nM [$^3$H](+)-pentazocine (34.9 Ci/mmol, Perkin Elmer, Boston, Mass.), incubation time was 90 min at room temperature. Nonspecific binding was determined from samples that contained 10 μM of cold haloperidol.

The sigma-2 receptor binding assays were conducted using rat liver membrane homogenates (~300 ug protein) and ~2 nM sigma-2 highly selective radioligand [$^3$H]RHM-1 only (no other blockers) (America Radiolabeled Chemicals Inc. St. Louis, Mo.), ~10 nM [$^3$H]DTG (58.1 Ci/mmol, Perkin Elmer, Boston, Mass.) or ~10 nM [$^3$H]Haloperidol (America Radiolabeled Chemicals Inc., St. Louis, Mo.) in the presence of 1 uM (+)-pentazocine to block sigma-1 sites, incubation times were 6 minutes for [$^3$H]RHM-1, 120 min for [$^3$H]DTG and [$^3$H]haloperidol at room temperature. Nonspecific binding was determined from samples that contained 10 uM of cold haloperidol.

Data from the competitive inhibition experiments were modeled using nonlinear regression analysis to determine the concentration of inhibitor that inhibits 50% of the specific binding of the radioligand ($IC_{50}$ value). The binding affinity, Ki values was calculated using the method of Cheng and Prusoff. The Kd value used for [$^3$H](+)-pentazocine in guinea pig brain was 7.89 nM, for [$^3$H]RHM-1 and [$^3$H]DTG in rat liver were 0.66 nM and 30.73 nM respectively. The standard compound haloperidol was used for quality assurance. Affinity data at the sigma-2 receptor for exemplary compounds of Examples 1-118 are shown in Table 2.

In some embodiments, isoindoline compounds according to formula I and/or formula II, as provided herein, or pharmaceutically acceptable salts thereof, exhibit sigma-2 receptor binding affinity Ki of not more than 1,000 nM, not more than 750 nM, not more than 500 nM, not more than 250 nM, not more than 100 nM, not more than 50 nM, not more than 25 nM, or not more than 10 nM, when tested according to a sigma-2 receptor binding assay protocol provided herein.

Example 5: Memory Loss in Transgenic Mice: Morris Swim Test

Selected compounds are tested to determine the ability to reverse memory loss seen in older transgenic mouse models of Alzheimer's disease, where oligomers build up with age. For this study hAPP mice expressing human APP751 Swedish (670/671) and London (717) mutations under the control of the murine Thy-1 promoter were chosen. These mice exhibit an age-dependent increase in the amount of Abeta, with plaques developing beginning at 3-6 months and exhibit established cognitive deficits by 8 month of age. In this study, rather than preventing deficits from occurring, deficits that were already established were treated. These studies were performed pursuant to a service contract by scientists who were blind to the experimental conditions. Test compound is infused at 0.5 and 0.1 mg/kg/day for one month in 8 month old female mice via subcutaneous minipump and cognitive performance is tested in the Morris water maze, a test of hippocampal-based spatial learning and memory. This mouse model does not exhibit neuronal loss so the restoration of memory cannot be attributed to aversion of apoptosis.

The swim speed is analyzed as part of the Morris measurements to determine if there were any motor or motivational deficits. The vehicle is a 5% DMSO/5% Solutol, 90% saline mixture. The transgenic animals are treated with a low dose (e.g., 0.1 mg/kg/day) and a high dose (e.g., 0.5 mg/kg/day) of compounds. The average of three daily trials on each of four consecutive days are determined. Typically, no significant motor deficits or abnormal behaviors are observed during the course of the study-below expected mortality levels at this age. In addition, a sentinel group of animals is maintained that had periodic blood draws to monitor plasma levels of compound.

Escape latency measurements from the Morris water test are taken. Typically, on the second day of testing a significant difference between wild-type and transgenic animals is observed, with the wild-type learning faster than transgenics. Typically, if on this day a significant improvement in transgenic performance at the higher compound dose vs. vehicle is observed, then it is concluded that the compound administered at the higher dose of, e.g., 0.5 mg/kg/day is capable of improving cognitive performance in transgenic models of AD.

Typically, Abeta 42 oligomers cause about an 18% decrease in synapse number; 100% of this loss can be eliminated by preferred test compounds. Other sigma-2 receptor antagonists also block synapse loss. Known prior art Sigma-2 receptor ligands NE-100 and haloperidol completely eliminated synapse loss, while SM-21, a selective Sigma 1 ligand was only weakly active in eliminating synapse loss (20% recovery).

Test Compounds can also be tested using a similar assay. The compound (e.g., 1 mg/kg/day, N=8 or 10 mg/kg/day, N=8) or vehicle (5% DMSO/5% Solutol/90% saline, N=15) can be systemically administered via subcutaneous dosing (Alzet minipump) to, e.g., 9 month old male hAPPSL transgenic mice (e.g., N=8) or nontransgenic littermates (e.g., N=6) for 20 days and spatial learning and memory of these mice can be evaluated in the Morris water maze. During the final four days of treatment, mice are tested to find the hidden platform in three trials/day. A computerized tracking system automatically quantifies escape latency, or swim length.

There is no significant difference in the performance of transgenic animals vs. nontransgenic animals on any day of the test (analysis restricted to these 2 groups; two-way (genotype and time) ANOVA with repeated measures followed by Bonferroni's post-hoc test). A similar analysis, when restricted to the transgenic groups (treatment and time), with transgenic animals treated with 10 mg/kg/day of a Test Compound, is expected to show treated animals perform significantly better than vehicle-treated transgenic animals after the first day of testing, when analyzed, e.g., by Student's t-test. It is expected that animals treated with the test compounds will exhibit improved transgenic animal performance compared to vehicle treatment over the test period.

Successful test compounds are capable of reversing established behavioral deficits in learning and memory in aged transgenic animals in a dose-dependent manner.

Example 6: Inhibition of Abeta Oligomer Effect on Neuronal Cells in Membrane Trafficking Assay Sigma-2 ligands provided herein were tested for their ability to inhibit an amyloid beta effect on the cells. The sigma-2 ligands generally were able to inhibit the amyloid beta effect as measured by a membrane trafficking/exocytosis assay (MTT assay). The results are indicated in Table 2. The rationale for this assay was as follows:

Since synaptic and memory deficits, and not widespread cell death, predominate at the earliest stages of Alzheimer's disease, assays that measure these changes are particularly well suited to discovering small molecule inhibitors of oligomer activity. The MTT assay is frequently used as a measure of toxicity in cultures. Yellow tetrazolium salts are endocytosed by cells and reduced to insoluble purple formazan in the endosomal pathway. The level of purple formazan is a reflection of the number of actively metabolizing cells in culture, and reduction in the amount of formazan is taken as a measure of cell death or metabolic toxicity in culture. When observed through a microscope, the purple formazan is first visible in intracellular vesicles that fill the cell. Over time, the vesicles are exocytosed and the formazan precipitates as needle-shaped crystals on the outer surface of the plasma membrane as the insoluble formazan is exposed to the aqueous media environment. Liu and Schubert ('97) discovered that cells respond to sublethal levels of Abeta oligomers by selectively accelerating the exocytosis rate of reduced formazan, while leaving endocytosis rate unaffected. The inventors have replicated these observations in mature primary neurons in culture and quantified these morphological shifts via automated microscopy and image processing. Under these circumstances, there is no overall change in the total amount of reduced formazan, simply a shift in its morphology reflective of changes in rate of its formation and/or expulsion from the cell. The inventors have confirmed previous findings that this assay is sensitive to low levels of oligomers that do not cause cell death (Liu and Schubert '04, Hong et al., '07). Indeed, low amounts of oligomers that lead to inhibition of LTP do not lead to cell death (Tong et al., '04) and are not expected to change total amounts of formazan in culture (or in brain slices).

Evidence adduced by other investigators suggests that Abeta oligomer-mediated reduction in neuronal surface receptor expression mediated by membrane trafficking is the basis for oligomer inhibition of electrophysiological measures of synaptic plasticity (LTP) and thus learning and memory (Kamenetz et al., '03, Hseih et al., '06). Measuring membrane trafficking rate changes induced by oligomers via formazan morphological shifts has been used in cell lines to discover Abeta oligomer-blocking drugs (Maezawa et al., '06, Liu and Schubert '97, '04, '06, Rana et al., '09, Hong et al., '08) that lower Abeta brain levels in rodents in vivo (Hong et al., '09). Similar procedures for exocytosis assays/ MTT assays can be found in the literature. See e.g., Liu Y, et. al., Detecting bioactive amyloid beta peptide species in Alzheimer's disease. J Neurochem. 2004 November; 91(3): 648-56; Liu Y, and Schubert D. "Cytotoxic amyloid peptides inhibit cellular 3-(4,5-dimethylthiazol-2-yl)-2,5-diphenyltetrazolium bromide (MTT) reduction by enhancing MTT formazan exocytosis." J Neurochem. 1997 December; 69(6):2285-93; and Liu Y, and Schubert D. "Treating Alzheimer's disease by inactivating bioactive amyloid beta peptide" Curr. Alzheimer Res. 2006 April; 3(2):129-35. Therefore the approach is valid.

The present exocytosis assay was adapted for use with mature primary neuronal cultures grown for 3 weeks in vitro. See WO 2011/106785, which is incorporated herein by reference in its entirety. Abeta oligomers cause a dose-dependent decrease in the amount of intracellular vesicles (puncta) filled with reduced purple formazan as measured via image processing using a Cellomics VTI automated microscopy system. Photomicrographs for a cultured neuronal cell exposed to vehicle alone show vesicles filled with formazan; wherein a photomicrograph of a neuronal cell exposed to vehicle plus Abeta oligomer shows considerably fewer vesicles filled with formazan and instead shows exocytosed formazan which, when encountering the extracellular environment, precipitates into crystals. Increasing the amount of Abeta oligomers eventually results in overt toxicity. Thus, the concentration of neuroactive Abeta oligomers used in the assay is much lower than that causing cell death. The inventors confirmed that the assay is operative by showing that the effects of Abeta oligomer are blocked upon addition of anti-Abeta antibody but antibody alone has no effect on its own (data not shown). When configured in this manner, the assay is able to detect compounds that inhibit nonlethal effects of Abeta oligomer whether these compounds act via disruption of oligomers, inhibition of oligomer binding to neurons, or counteraction of signal transduction mechanisms of action initiated by oligomer binding.

The methods used to generate the results were as follows in the Membrane Trafficking/Exocytosis (MTT) assay.

Primary hippocampal neurons from E18 Sprague-Dawley rat embryos were plated at optimized concentrations in 384 well plates in NB media (Invitrogen). Neurons were maintained in cultures for 3 weeks, with twice weekly feeding of NB media with $N_2$ supplement (Invitrogen). These neurons express the full complement of synaptic proteins characteristic of neurons in the mature brain, and exhibit a complex network of activity-dependent electrical signaling. Neurons and glia in such cultures have molecular signaling networks exhibiting excellent registration with intact brain circuitry, and for this reason have been used for over two decades as a model system for learning and memory (See e.g. Kaech S, Banker G. Culturing hippocampal neurons. Nat Protoc. 2006; 1(5):2406-15. Epub 2007 Jan. 11; See also Craig A M, Graf E R, Linhoff M W. How to build a central synapse: clues from cell culture. Trends Neurosci. 2006 January; 29(1):8-20. Epub 2005 Dec. 7. Review).

A test compound was added to cells at concentrations ranging from 100 uM to 0.001 nM followed by addition of vehicle or Abeta oligomer preparations (3 µM total Abeta protein concentration), and incubated for 1 to 24 hr at 37° C. in 5% $CO_2$. MTT reagent (3-(4,5-dimethylthizaol-2yl)-2, 5diphenyl tetrazolium bromide) (Roche Molecular Biochemicals) was reconstituted in phosphate buffered saline to 5 mg/mL. 10 µL of MTT labeling reagent is added to each well and incubated at 37° C. for 1 h, then imaged. Exocytosis was assessed by automated microscopy and image processing to quantify the amount of endocytosed and exocytosed formazan.

Each assay plate was formatted so that compounds are tested with and without Abeta oligomer on each plate. This design eliminates toxic or metabolically active compounds early on in the screening cascade (at the level of the primary screen). Reduced formazan was first visible in intracellular vesicles. Eventual formazan exocytosis was accelerated via Abeta oligomers. FIGS. 1A and 1B are examples of photomicrographs of neurons, the first of intracellular vesicles where formazan is first seen and the second of a neuron covered with insoluble purple dye that has been extruded via exocytosis. The dye precipitated in the aqueous environment of the culture and formed needle-shaped crystals on the surface of the neuron.

In the presence of an effective concentration of active Test Compound, the membrane traffic changes are blocked and the cell is indistinguishable from a vehicle-treated neuron. Furthermore, in some cases this effect of Test Compound appears to be independent of whether Test Compound is added before or after exposure of the cells to Abeta oligomer, which indicates a therapeutic as well as a prophylactic effect. Adequate concentration of active Test Compound blocks membrane trafficking effects of Abeta oligomer seen in this assay. Ascending doses of selective, high affinity sigma-2 receptor antagonist compounds stop oligomer effects and make the cultures look more like vehicle-treated cultures.

Based on these results, selective, high affinity sigma-2 receptor antagonist compounds as disclosed herein are that effective for inhibiting Abeta oligomer toxicity are promising as therapeutic and (in very early stages) prophylactic modalities for amyloid beta oligomer toxicity related cognitive decline such as that seen in Alzheimer's disease.

Synthetic Abeta oligomers were dosed in the membrane trafficking assay, where it exhibited an EC50 of 820 nM. Each concentration of Abeta was tested against several concentrations of each selective high affinity sigma-2 receptor antagonist Test Compound. Active compounds caused a rightward shift in the $EC_{50}$ by almost two orders of magnitude. When the data were fitted to classical linear and non linear models, the data were linear with a Schild analysis (Hill slope nH of 1), which indicates that the sigma-2 receptor compound compounds exhibit true pharmacological competition between oligomers and compound for targets that mediate membrane trafficking.

Abeta oligomers derived from Alzheimer's patient's brains can be dosed against Test compounds, and a rightward shift is also expected to be exhibited by compound exposure. Specifically, at effective doses, the active Test Compounds exhibit pharmacological competition with both synthetic and human Alzheimer's patient-derived oligomers. Selective high affinity sigma-2 receptor antagonist compound candidate drugs effectively make Abeta oligomers less synaptotoxic. Without being bound by theory, the simplest possibile mechanism of action is that the sigma-2 receptor compounds act as competitive receptor antagonists.

EXPERIMENTAL CONTROLS

Abeta 1-42 oligomers made according to published methods were used as positive controls. [See e.g. Dahlgren et al., "Oligomeric and fibrillar species of amyloid-beta peptides differentially affect neuronal viability" J Biol Chem. 2002 Aug. 30; 277(35):32046-53. Epub 2002 Jun. 10; LeVine H 3rd. "Alzheimer's beta-peptide oligomer formation at physiologic concentrations" Anal Biochem. 2004 Dec. 1; 335(1): 81-90; Shrestha et. al, "Amyloid beta peptide adversely affects spine number and motility in hippocampal neurons" Mol Cell Neurosci. 2006 November; 33(3):274-82. Epub 2006 Sep. 8; Puzzo et al., "Amyloid-beta peptide inhibits activation of the nitric oxide/cGMP/cAMP-responsive element-binding protein pathway during hippocampal synaptic plasticity" J Neurosci. 2005 Jul. 20; 25(29):6887-97; Barghorn et al., "Globular amyloid beta-peptide oligomer—a homogenous and stable neuropathological protein in Alzheimer's disease" J Neurochem. 2005 November; 95(3): 834-47. Epub 2005 Aug. 31; Johansson et al., Physiochemical characterization of the Alzheimer's disease-related peptides A beta 1-42 Arctic and A beta 1-42 wt. FEBS J. 2006 June; 2 73(12):2618-30] as well as brain-derived Abeta oligomers (See e.g. Walsh et al., Naturally secreted oligomers of amyloid beta protein potently inhibit hippocampal long-term potentiation in vivo. Nature (2002). 416, 535-539; Lesne et al., A specific amyloid-beta protein assembly in the brain impairs memory. Nature. 2006 Mar. 16; 440(7082): 352-7; Shankar et al, Amyloid-beta protein dimers isolated directly from Alzheimer's brains impair synaptic plasticity and memory. Nat Med. 2008 August; 14(8):837-42. Epub 2008 Jun. 22). It should be noted that any Abeta oligomer preparation can be used in this assay or as a control, including preparations described in the patent literature, cited above and incorporated by reference in their entirety.

Various different Abeta oligomer preparations were demonstrated to cause an Abeta effect in the membrane trafficking assay, including notably oligomer preparations isolated from the brain of Alzheimer's disease patients.

Oligomers were isolated from postmortem human hippocampus or prefrontal cortex without the use of detergents and inhibited membrane trafficking in a dose-dependent manner with a Kd of 6 pMolar. Human Alzheimer's disease patient-derived Abeta oligomers (137 μM, second bar FIG. 1J) produce a statistically significant inhibition of membrane trafficking compared to vehicle (first bar, FIG. 1J). Compound II (third bar) eliminates the membrane trafficking deficits induced by AD brain-derived Abeta oligomers, but does not affect trafficking when dosed in the absence of Abeta (fourth, hatched, bar). The data are averaged from 3 experiments (n=3).

Although potencies of various Abeta oligomer preparations differ (for example native Alzheimer's isolates are more potent than any of the synthetic preparations tested-data not shown), the results are qualitatively the same: pathologies mediated by oligomers are countered by compositions of the disclosure comprising a sigma-2 receptor antagonist compound.

Primary Neuronal Cultures

Optimal cell density is determined based on cellular response to Abeta oligomers using the exocytosis assay as a readout, and immunohistochemical analysis of the relative proportion of glia to neurons in the cultures. Cultures are monitored on a weekly basis with immunohistochemistry and image processing-based quantification to monitor the percentage of the cultures that are neurons vs. glia (Glial cells). Cultures containing more than 20% glia (positive for GFAP) vs. neurons (staining positively with (chicken polyclonal) antibodies (Millipore) directed against MAP2 at 1:5000 (concentration variable)) at the screening age of 21 days in vitro (21 DIV) are rejected.

Abeta Oligomer Preparations

Human amyloid peptide 1-42 was obtained from a number of commercial vendors such as California Peptide, with lot-choice contingent upon quality control analysis. Quality controls of oligomer preparations consist of Westerns to determine oligomer size ranges and relative concentrations, and the MTT assay to confirm exocytosis acceleration without toxicity. Toxicity was monitored in each image-based assay via quantification of nuclear morphology visualized with the DNA binding blue dye DAPI (Invitrogen). Nuclei that are fragmented are considered to be in late stage apoptosis (Majno and Joris '95) and the test would be rejected. Peptide lots producing unusual peptide size ranges or significant toxicity at a standard 1.5 μM concentration on neurons would also be rejected.

Plate-based controls—The assay optimization was considered complete when reformatted plates achieve a minimum of statistically significant two-fold separation between vehicle and Abeta oligomer-treated neurons (p<0.01, Student's t-test, unequal variance) on a routine basis, with no more than 10% CV between plates.

Statistical Software and Analysis:

Data handling and analysis were accomplished by Cellomics VTI image analysis software and STORE automated database software. Because of the low dynamic range and neuronal well-to-well variability after three weeks in culture, statistical comparisons are made via pairwise Tukey-Kramer analysis to determine the significance of the separation between compound+Abeta oligomers from Abeta alone, and between compound alone from vehicle. The ability of mature primary neurons to more closely approximate the electrophysiologically mediated signal transduction network of the adult brain justifies this screening strategy. Power analysis was set for a number of replicate screening wells that minimized false negatives (e.g. N=4). Test compounds of the disclosure significantly reverse the effects of Abeta oligomers on membrane trafficking but do not affect neuronal metabolism themselves.

Selected compounds according to Formula I and/or Formula II, were dosed in the MTT assay described herein prior to Abeta oligomer addition and were shown to block the Abeta oligomer-induced membrane trafficking deficits with the indicated $EC_{50}$. Specifically, these results indicate that compounds block/abate the activity/effect of Abeta oligomer on membrane trafficking of neuron cells at micromolar concentrations.

Combined Results for compounds of Formula I and or Formula II with respect to log P, psa ($Å^2$), membrane trafficking (uM), sigma-2 receptor affinity, microsomal stability in mouse liver microsomes (MLM) (t½, min), in vitro toxicity potassium channel hERG (IC50, nM), and neuronal phenotype are provided in Table 2.

TABLE 2

Sigma-2 Receptor Ligands: lipophilicity, ability to inhibit amyloid oligomer effects on membrane trafficking, binding to Sigma-2 Receptors, microsomal Stability, and in vitro toxicity.

| Ex. Cpd. | log P | psa ($Å^2$) | Membrane Trafficking EC50 (uM) | Sigma-1 Receptor Affinity, Ki (nM) | Sigma-2 Receptor Affinity, Ki (nM) | Mouse liver microsomes, MLM t½ (min) | In vitro toxicity, hERG IC50 (nM) | neuronal phenotype |
|---|---|---|---|---|---|---|---|---|
| 1 | 4.68 | 32.7 | 1->20 | 31 | 25 | 11 | 430 | Antagonist/inactive |
| 2 | 4.96 | 32.7 | 6.7-7.7 |  | NA | 28 | 710 | Antagonist |
| 3 | 5.29 | 32.7 | 3.8 | 23 | 240 | 21 | NA | Neuroactive |
| 4 | 6.63 | 3.24 | >20.0 | 33 | 2.2 | 40 | NA | Inactive |
| 5 | 6.96 | 3.24 | >20.0 | 56 | 2.7 | 53 | NA | Inactive |
| 6 | 3.7 | 51.16 | 0.3 |  | NA | 20 | 980 | Antagonist |
| 7 | 3.76 | 51.16 | NA | 42 | 68 | 155 | NA | NA |
| 8 | 4.22 | 32.7 | <0.25-0.4 | 41 | 79 | 16 | 7000 | Antagonist |
| 9 | 5.89 | 3.24 | 0.22 | 17 | 3.6 | 12 | 6700 | Antagonist |
| 10 | 5.37 | 21.7 | 0.5 | 1.4 | 5 | 8 | 41000 | Antagonist |
| 11 | 5.43 | 21.7 | 0.7 | 14 | 0.44 | 61 | 290 | Antagonist |
| 12 | 5.89 | 3.24 | 0.4 |  | NA | 13 | NA | Antagonist |
| 13 | 6.26 | 3.24 | 0.3 |  | NA | 3 | 250 | Antagonist |
| 14 | 4.22 | 32.7 | 0.6 |  | NA | 20 | 2400 | Antagonist |
| 15 | 5.59 | 12.47 | 0.5 |  | NA | 15 | NA | Inactive |
| 16 | 6.35 | 3.24 | >20.0 |  | NA | 12 | NA | Inactive |
| 17 | 5.07 | 32.7 | 0.3 |  | NA | 10 | NA | Antagonist |
| 18 | 6.74 | 3.24 | NA | 42 | 1.5 | 213 | NA | NA |
| 19 | 6.74 | 3.24 | 0.27 | 69 | 1.8 | 25 | 98000 | Weak Antagonist |

TABLE 2-continued

Sigma-2 Receptor Ligands: lipophilicity, ability to inhibit amyloid oligomer effects on membrane trafficking, binding to Sigma-2 Receptors, microsomal Stability, and in vitro toxicity.

| Ex. Cpd. | log P | psa (Å$^2$) | Membrane Trafficking EC50 (uM) | Sigma-1 Receptor Affinity, Ki (nM) | Sigma-2 Receptor Affinity, Ki (nM) | Mouse liver microsomes, MLM t½ (min) | In vitro toxicity, hERG IC50 (nM) | neuronal phenotype |
|---|---|---|---|---|---|---|---|---|
| 20 | 5.43 | 21.7 | 0.067-0.6 | 0.57 | 0.67 | 43 | 660 | antagonist/Agonist |
| 21 | 4.83 | 3.24 | >20.0 | 330 | 12 | 7 | 15000 | Inactive |
| 22 | 4.83 | 3.24 | <0.25 | 44 | 23 | 7 | 350 | Antagonist |
| 23 | 4.31 | 21.7 | <0.25 | 16 | 13 | 5 | 370 | Antagonist |
| 24 | 5.29 | 51.16 | 0.5 | 4.9 | 52 | 5 | 860 | Antagonist |
| 25 | 4.48 | 51.16 | >20.0 | 5.7 | 110 | 4 | 3200 | Inactive/IAACon |
| 26 | 5 | 32.7 | >20.0 | 7.9 | 41 | 4 | 3700 | Inactive |
| 27 | 5.28 | 32.7 | >20.0 | 46 | 71 | 4 | 3200 | Inactive/IAACon |
| 28 | 5.28 | 32.7 | 0.07-0.08 | 120 | 11 | 4 | 9600 | Antagonist |
| 29 | 4.76 | 51.16 | >20.0 | 47 | 13 | 6 | 540 | Inactive/IAACon |
| 30 | 3.68 | 41.93 | 0.3 | 220 | 910 | 126 | 4700 | Antagonist |
| 31 | 5.81 | 32.7 | <0.25 | 3.7 | 58 | 6 | 1900 | Antagonist |
| 33 | 5.11 | 3.24 | 3.3 | 32 | 3.2 | 9 | 910 | Antagonist |
| 34 | 4.65 | 21.7 | 13 | 7.5 | 0.53 | 46 | 15 | Antagonist |
| 35 | 5.11 | 3.24 | 2.2 | 2.1 | 3.6 | 9 | 130 | Antagonist |
| 36 | 4.59 | 21.7 | 0.86 | 4.1 | 5.2 | 47 | 19 | Antagonist |
| 37 | 5 | 32.7 | NA | 9.1 | 140 | 5 | 480 | NA |
| 38 | 5.91 | 21.7 | 0.5 | 18 | 21 | 5 | 2100 | Neuroactive |
| 39 | 5.91 | 21.7 | NA | 62 | 21 | 4 | 3200 | NA |
| 40 | 5.39 | 40.16 | NA | 7.8 | 8.9 | 6 | 350 | NA |
| 41 | 5.84 | 42.01 | >20.0 | 520 | 38 | 9 | 2800 | Inactive/IAACon |
| 42 | 6.19 | 21.7 | >20.0 | 100 | 6.2 | 14 | 800 | Agonist |
| 43 | 5.84 | 42.01 | NA | 380 | 140 | 5 | 670 | NA |
| 44 | 3.96 | 41.93 | NA | 1300 | 140 | 29 | 99 | Antagonist |
| 45 | 3.96 | 41.93 | >20.0 | 2800 | 190 | 96 | 220 | Inactive |
| 46 | 5.49 | 12.47 | NA | 94 | 160 | 5 | 1600 | Inactive |
| 47 | 3.44 | 60.39 | NA | 1000 | 140 | 91 | 130 | Inactive |
| 48 | 3.5 | 60.39 | >20.0 | 3600 | 22 | 582 | 1700 | Inactive |
| 49 | 4.53 | 42.01 | 9.4 | 470 | 25 | 18 | 6100 | Antagonist |
| 50 | 4.53 | 42.01 | NA | 750 | 37 | 33 | 4400 | weak antagonist |
| 51 | 3.68 | 41.93 | NA | 77 | 800 | 66 | 1200 | Neuroactive |
| 52 | 3.16 | 60.39 | 0.3 | 130 | 540 | 97 | 3200 | Antagonist |
| 53 | 4.5 | 32.7 | >20.0 | 110 | 17 | 21 | 2800 | Inactive |
| 54 | 6 | 32.7 | 6.5 | 74 | 18 | 12 | 2500 | Antagonist |
| 55 | 6.23 | 32.7 | NA | 360 | 310 | 34 | 100000 | NA |
| 56 | 2.88 | 70 | 0.3 | 10000 | 10000 | 617 | 49000 | Weak Antagonist |
| 57 | 5.14 | 53.01 | >20.0 | 700 | 95 | 26 | 5000 | Inactive IAACON |
| 58 | 5.56 | 32.7 | 5.6 | 240 | 32 | 16 | 12000 | Antagonist |
| 59 | 4.71 | 53.01 | NA | 10000 | 57 | 8 | 18000 | Inactive |
| 60A | 5.42 | 32.7 | >20.0 | 410 | 1600 | 5 | 100000 | Antagonist |
| 60B | 5.28 | 32.7 | 1.6 | 37 | 76 | 8 | 25000 | Antagonist |
| 61 | 4.79 | 66.84 | <0.02 | 33 | 6.9 | 114 | 790 | Antagonist |
| 62 | 4.25 | 66.84 | 0.06 | 63 | 8.5 | 45 | 26000 | Antagonist |
| 63 | 3.97 | 66.84 | NA | 17 | 380 | 31 | 11000 | Inactive |
| 64 | 3.2 | 66.84 | NA | 180 | 8.6 | 52 | 20000 | Inactive |
| 65 | 2.92 | 66.84 | NA | 1300 | 190 | 41 | 26000 | Neuroactive |
| 66 | 4.25 | 66.84 | NA | 130 | 2.6 | 10 | 19000 | Inactive |
| 67 | 4.79 | 66.84 | NA | 55 | 8.1 | 39 | 44000 | Antagonist |
| 68 | 2.92 | 66.84 | NA | 100 | 400 | 152 | 43000 | Inactive |
| 69 | 3.69 | 66.84 | NA | 27 | 76 | 75 | 9500 | Inactive |
| 70 | 3.97 | 66.84 | NA | 50 | 9 | 79 | 3100 | Inactive |
| 73 | 5.27 | 41.93 | NA | 22 | 140 | NA | 770 | NA |
| 74 | 5.7 | 32.7 | 0.3 | 2300 | 550 | 21 | 100000 | Antagonist |
| 75 | 2.34 | 70 | >20.0 | 10000 | >10000 | 508 | 100000 | Inactive |
| 76 | 2.88 | 65 | 0.87 | 10000 | 2.6 | 115 | 76000 | Antagonist |
| 77 | 3.2 | | 0.1 | | NA | 142 | NA | Antagonist |
| 78 | 3.25 | | 8.8 | 10000 | 10000 | 450 | 110000 | Neuroactive |
| 79 | 2.74 | | 100 | 10000 | 460 | 144 | 11000 | Inactive |
| 80 | 3.44 | | 100 | 10000 | 1400 | 45 | 7400 | Inactive |
| 81 | 3.48 | | 100 | 10000 | 10000 | 88 | 10000 | Inactive |
| 82 | 3.5 | | 100 | 10000 | 10000 | 27 | 52000 | Inactive |
| 83 | 2.73 | | 100 | 10000 | 10000 | 336 | 10000 | Inactive IAACON |
| 84 | 3.39 | | 100 | 10000 | 10000 | 163 | 6600 | NA |

TABLE 2-continued

Sigma-2 Receptor Ligands: lipophilicity, ability to inhibit amyloid oligomer effects on membrane trafficking, binding to Sigma-2 Receptors, microsomal Stability, and in vitro toxicity.

| Ex. Cpd. | log P | psa (Å$^2$) | Membrane Trafficking EC50 (uM) | Sigma-1 Receptor Affinity, Ki (nM) | Sigma-2 Receptor Affinity, Ki (nM) | Mouse liver microsomes, MLM t½ (min) | In vitro toxicity, hERG IC50 (nM) | neuronal phenotype |
|---|---|---|---|---|---|---|---|---|
| 85 | 2.97 | | | 10000 | 360 | 194 | 33000 | NA |
| 86 | 3.61 | | | 10000 | 10000 | 19 | 5100 | NA |
| 87 | 4.44 | | | 69 | 1.1 | 86 | 570 | NA |
| 88 | 5.75 | | 0.36 | 96 | 1.3 | 28 | 2800 | Neuroactive |
| 89 | 4.9 | | | | NA | 17 | NA | NA |
| 90 | 4.68 | | | | NA | 9 | NA | NA |
| 91 | 4.75 | | | | NA | 6 | NA | NA |
| 92 | 3.98 | | | | NA | 7 | NA | NA |
| 93 | 4.98 | | | | NA | 5 | NA | NA |
| 94 | 4.92 | | | | NA | 14 | NA | NA |
| 95 | 4.85 | | 1.7 | | 100 | | NA | Antagonist |
| 96 | 4.16 | | 100 | | 6.6 | <1.75 | NA | Inactive |
| 97 | 4.4 | | | | NA | | NA | NA |
| 98 | 3.43 | | 0.35 | | 10000 | 29.35 | NA | Antagonist/Neuroactive |
| 99 | 3.43 | | 0.2 | | 1200 | 93.3 | NA | Antagonist/Neuroactive |
| 100 | 3.27 | | 1.1 | | 10000 | 156.24 | NA | Antagonist |
| 101 | 3.35 | | 100 | | 11 | 84.21 | NA | Inactive |
| 102 | 3.5 | | 100 | | 1.8 | 20.35 | NA | Inactive |
| 103 | 3.5 | | 100 | | 1.4 | 15.2 | NA | Inactive |
| 104 | 4.1 | | 100 | | 760 | | NA | Inactive |
| 105 | 4.19 | | 2.6 | | 180 | 106.23 | NA | Neuroactive |
| 106 | 4.79 | | 3.4 | | 240 | 160.43 | NA | Agonist |
| 107 | 3.7 | | 100 | | 10000 | 25.21 | NA | Inactive |
| 108 | 5.6 | | 100 | | 15 | 1236.31 | NA | Inactive |
| 109 | 5.6 | | 100 | | 31 | 253.79 | NA | Agonist |
| 110 | 2.72 | | 100 | | 10000 | 15.66 | NA | Inactive |
| 111 | 3.69 | | 100 | | 740 | 27.01 | NA | Inactive |
| 112 | 5.41 | | 0.26 | | NA | NA | NA | Antagonist |
| 113 | 4.11 | | 5.3 | | NA | NA | NA | Antagonist |
| 114 | 2.65 | | 0.25 | | NA | NA | NA | Neuroactive |
| 115 | 2.91 | | 100 | | NA | NA | NA | Inactive |
| 116 | 3.96 | | 100 | | NA | NA | NA | Inactive |
| 117 | 4.81 | | 1.2 | | NA | NA | NA | Antagonist |
| 118 | 4.03 | | 100 | | NA | NA | NA | Inactive |

NA = data not yet available

Certain compounds in Table 2 were shown to block the Abeta oligomer-induced acceleration of exocytosis with the indicated $EC_5$. Accordingly, the compounds in Table 2 significantly blocked Abeta oligomer-mediated changes in membrane trafficking. These results indicate that compounds block/abate the activity/effect of Abeta oligomer on neuron cells and that sigma-2 ligands can be used to block the Abeta oligomer induced membrane trafficking abnormalities.

Selected compounds in Table 2 were dosed in the membrane trafficking assay and were shown to block the Abeta oligomer-induced membrane trafficking abnormalities with the indicated $EC_{50}$. Accordingly, the compounds in Table 2 significantly blocked Abeta oligomer-mediated changes in membrane trafficking. These results indicate that compounds block/abate the activity/effect of Abeta oligomer on neuron cells and that sigma-2receptor ligands can be used as candidate compounds to block the Abeta oligomer induced membrane trafficking abnormalities.

In some embodiments, isoindoline compounds according to formula I and/or formula II, as provided herein, or pharmaceutically acceptable salts thereof, inhibit Abeta oligomer-induced membrane trafficking deficits, with an $EC_{50}$ of not more than 20 uM, not more than 15 uM, not more than 10 uM, not more than 5 uM, not more than 1 uM, not more than 0.5 uM, when tested according to the membrane trafficking assay protocol provided herein.

As the compounds embraced by the above formulae are expected to also be sigma-2 ligands, and will therefore also be useful in blocking the Abeta oligomer induced acceleration of exocytosis.

Example 7. Pharmacokinetic and Metabolic Stability Studies

A first pharmacokinetic study was performed in microsomes of mice mouse liver microsomes, MLM) by a commercial contract research organization. The studies were performed according to Obach, R. S et al. (1997) J. Pharmacol. Exp. Ther., 283: 46-58, which is incorporated herein by reference. The half-life ($t_{1/2}$) of the compounds in MLM assay is shown in Table 2, and ranged from 3-617 minutes.

In some embodiments, isoindoline compounds according to formula I and/or formula II, as provided herein, or pharmaceutically acceptable salts thereof, exhibit a half-life (t½) in a mouse liver microsome (MLM) assay, as provided herein, of at least 5 minutes, at least 10 minutes, at least 25 minutes, at least 50 minutes, at least 100 minutes, or at least 200 minutes.

The results indicate that several of the compounds tested had a substantially longer half-life in mouse liver microsomes. This result portends greater bioavalability after oral administration for these compounds. The same compounds have been tested by the membrane trafficking assay described above and their activity as referred to herein.

If the rate of intrinsic clearance of Test Compound was rapid, it is suggestive of substantial first pass metabolism. In order to improve pharmacokinetic properties, compounds were designed to enhance metabolic stability and improve drug-like properties. Microsomal stability experiments and plasma stability experiments were performed to determine metabolic and hepatic stability of candidate compounds. In some embodiments, in vitro microsomal stability was normalized to standard compound CT010914.

A second PK study can be conducted in vivo and involves measuring plasma levels and brain levels for test compounds administered by various routes and in an acute or chronic manner, as follows:

HPLC-MS Optimization

A solution of each test compound is prepared and infused into the TSQ Quantum spectrometer (Fisher Thermo Scientific) source via syringe pump at a constant rate. Full scan MS (mass spectroscopy) analysis is conducted and total ion current chromatograms and corresponding mass spectra are generated for each test compound in both positive and negative ionization modes. The precursor ions for MS/MS are selected from either the positive or the negative mass spectrum, as a function of the respective ion abundance. In addition, product ion MS/MS analysis is performed in order to determine the appropriate selected fragmentation reaction for use in quantitative analysis. The final reaction monitoring parameters are chosen to maximize the ability to quantify the test compound when present within a complex mixture of components. Following identification of the specific SRM transition to be used for each test compound, the detection parameters are optimized using the automated protocol in the TSQ Quantum Compound Optimization workspace. Finally, the chromatographic conditions to be used for LC-MS analysis are identified by injection and separation of the analyte on a suitable LC column and adjustment of the gradient conditions is performed as necessary.

Formulation for IV Dosing:

The solubility of the test compound in phosphate-buffered saline, pH 7.4 (PBS) is first evaluated by visual inspection. PBS is used as the vehicle if the compound is soluble at the target concentration. (Other vehicles that are compatible with IV dosing may be evaluated if the compound is not completely soluble in PBS. Such vehicles include DMSO, polyethylene glycol (PEG 400), Solutol HS 15, and Cremophor EL among others.) In the experiments reported here a single bolus, 10 mg/kg, of Test Compound is administered IV.

Formulation for PO dosing: The solubility of the test compound in PBS is first evaluated. PBS is used as the vehicle if the compound is soluble at the target concentration. (DMSO/Solutol HS 15/PBS (5/5/90, v/v/v), or DMSO/1% methylcellulose (5/95, v/v) may be used if the test compound is not completely soluble in PBS at the respective concentration.)

Linearity in Plasma

Aliquots of plasma are spiked with the test compounds at the specified concentrations. The spiked samples are processed using acetonitrile precipitation and analyzed by HPLC-MS or HPLC-MS/MS. A calibration curve of peak area versus concentration is constructed. The reportable linear range of the assay is determined, along with the lower limit of quantitation (LLQ).

Quantitative Bioanalysis of Plasma Samples

The plasma samples are processed using acetonitrile precipitation and analyzed by HPLC-MS or HPLC-MS/MS. A plasma calibration curve was generated. Aliquots of drug-free plasma are spiked with the test compound at the specified concentration levels. The spiked plasma samples are processed together with the unknown plasma samples using the same procedure. The processed plasma samples (dried extracts) are typically stored frozen (−20° C.) until the HPLC-MS or HPLC-MS/MS analysis. The dried extracts are reconstituted into a suitable solvent and after centrifugation were analyzed by HPLC-MS or HPLC-MS/MS. Peak areas are recorded, and the concentrations of the test compound in the unknown plasma samples are determined using the respective calibration curve. The reportable linear range of the assay is determined, along with the lower limit of quantitation (LLQ).

Animals used in the study are typically male C57BL/6 mice weighing 20-30 g each or male Sprague-Dawley rats weighing 180-250 g. Three animals are treated for each administration condition and each time point, so that each animal is subjected to only one blood draw. Subcutaneous compound administration was accomplished by intraperitoneal injection. Per oral administration is accomplished by gastric gavage. Intravenous administration is accomplished via jugular catheter.

Following compound administration at various concentrations, plasma samples are collected at, e.g., 10, 30, 60, 120, 240, 360, 480 and 1440 min.

Plasma Sample Collection from Mice and Rats

Animals are sedated under general inhalant anesthesia (3% isoflurane) for blood collection by cardiac puncture (mice) or jugular catheter (rats). Blood aliquots (300-400 µL) are collected in tubes coated with lithium heparin, mixed gently, and are kept on ice and centrifuged at 2,500×g for 15 minutes at 4° C., within 1 hour of collection. The plasma is then harvested and kept frozen at −20° C. until further processing.

Animal Dosing Design—In Vivo PK—Non Cannulated, Nonfasted Animals

Group 1: SC, n=3 animals per time point (24 animals total) or

IV, n=3 animals per time point (24 animals total)

Group 2: PO, n=3 animals per time point (24 animals total)

Group 3: Control animals (for drug-free blood), n=5 mice

Each animal is subject to one blood draw and one brain collection.

Brain Sample Collection from Animals

Immediately after blood sampling, animals are decapitated and the whole brains are quickly removed, rinsed with cold saline (0.9% NaCl, g/mL), surface vasculature ruptured, blotted dry with gauze, weighted, kept on ice until further processing within one hour of collection. Each brain is homogenized in 1.5 mL cold phosphate buffered saline, pH 7.4 (mice=1.5 mL, rats=), for 10 seconds on ice using the Power Gen 125. The brain homogenate from each brain is then stored at −20° C. until further processing.

Linearity in Brain Samples

Aliquots of brain homogenate are spiked with the test compound at the specified concentrations. To each brain aliquot an equal volume of chilled 26% (g/mL) neutral Dextran (average molecular Weight 65,000-85,000 from Sigma, catalog number D-1390) solution is added to obtain a final Dextran concentration of 13%. The homogenate is centrifuged at 54000×g for 15 minutes at 4° C. The supernatants are subsequently processed using acetonitrile precipitation and analyzed by HPLC-MS/MS. A calibration curve of peak versus concentration i constructed. The reportable linear range of the assay is determined, along with the lower limit of quantitation (LLQ).

Quantitative Analysis of Brain Samples

To each brain homogenate aliquot an equal volume of chilled 26% (g/mL) neutral Dextran (average molecular Weight 65,000-85,000 from Sigma, catalog number D-1390) solution is added to obtain a final Dextran concentration of 13%. The homogenate is centrifuged at 54000×g for 15 minutes at 4° C. The supernatants are subsequently processed using acetonitrile precipitation and analyzed by HPLC-MS/MS. A brain calibration curve is generated. Aliquots of drug-free brain homogenate are spiked with the test compound at specified concentration levels. The spiked brain homogenate samples are processed together with the unknown brain homogenate samples using the same procedure. The processed brain samples are stored at −20° C. until the LC-MS/MS analysis, at which time peak areas were recorded, and the concentrations of test compound in the unknown brain samples were determined using the respective calibration curve. The reportable linear range of the assay was determined along with the lower limit of quantitation (LLQ).

Brain Penetratrability

The concentrations of test compound in brain (ng/g tissue) and in plasma (ng/mL) as well as the ratio of the brain concentration and the plasma concentration at each time point are determined by LC-MS/MS and reported as described above.

Pharmacokinetics

Plots of plasma concentration of compound versus time are constructed. The fundamental pharmacokinetic parameters of compound after oral and SC dosing ($AUC_{last}$, $AUC_{INF}$, $T\frac{1}{2}$, Tmax, and Cmax) are obtained from the non-compartmental analysis (NCA) of the plasma data using WinNonlin (Pharsight). Noncompartmental analysis does not require the assumption of a specific compartmental model for either drug or metabolite. NCA allows the application of the trapezoidal rule for measurements of the area under a plasma concentration-time curve (Gabrielsson, J. and Weiner, D. Pharmacokinetic and Pharmacodynamic Data Analysis: Concepts and Applications. Swedish Pharmaceutical Press. 1997).

Definitions of Terms Reported

Area Under the Curve (AUC)—Measure of the total amount of unchanged drug that reaches the systemic circulation. The area under the curve is a geometric measurement that was calculated by plotting concentration versus time and summing the incremental areas of each trapezoid.

WinNonlin has two computational methods for calculation of the area: the linear trapezoidal method and the linear-log trapezoidal method. Because the linear trapezoidal method may give biased results on the descending part of the concentration-time curve and overestimate the AUC, WinNonlin provides the linear-log option for calculation of AUC. By default, the log-linear trapezoidal method is used to measure the post-Tmax area for the remainder of the plasma concentration-time curve.

$AUC_{last}$: area under the curve from the time of dosing to the time of last observation that was greater than the limit of quantitation.

$AUC_{INF}$: Area under the curve from the time of dosing extrapolated to infinity.

$C_{max}$—Maximum plasma drug concentration obtained after oral or non-IV administration of a drug between the time of doing and the final observed time point.

$T_{max}$—Time at maximum observed plasma concentration (Cmax) noted in minutes after administration of drug.

$T_{1/2}$—Terminal elimination half-life from both IV and non-IV dosing.

where lambda Z (z) is the first order rate constant associated with the terminal (log-linear) portion of the plasma concentration-time curve. z is estimated by linear regression of time versus log concentration.

The results are expected to show that certain Test Compounds exhibit good bioavailability and good brain penetrability when administered at doses ranging from 0.1 to 0.5 mg/kg acutely or chronically (daily over 5 days). Selected test compounds are evaluated for oral bioavailability in this manner.

Example 8: Abeta 1-42 Oligomer Binding and Synapse Loss Assay

In this assay, Abeta oligomers are brought in contact with mature primary neurons in culture and their binding was determined by immunohistochemistry (anti-Abeta antibody) and quantified by image processing. The amount of Abeta in neuronal dendrites is assessed by counting the number of labeled puncta on the neuritis. Abeta oligomers are known to bind, saturably (Kd approximately 400 nM; Lauren 2009) and with high affinity to a subset of postsynaptic neurons present on a significant percentage (30 to 50%) of hippocampal neurons in primary cultures (Lacor et al, 2004; Lambert et al, 2007) and this correlates well with observations of Abeta binding in brains from Alzheimer's patients (Lambert et al, 2007). This labeling is associated with synapses, co-localizing with the post-synaptic scaffold protein PSD-95 (Lacor et al., '04). Abeta oligomers are also known to mediate synapse loss, reported as 18% in human hippocampal neurons in brain slices (Schef et al, 2007) and to inhibit long term potentiation (LTP). The number of synapses can also be quantified in this assay by immunofluorochemistry. Similar procedures for binding assays can be found in the literature. See e.g., Look G C, et. al. Discovery of ADDL—targeting small molecule drugs for Alzheimer's disease. Curr Alzheimer Res. 2007 December; 4(5):562-7. Review.

Measurement of the amount of Abeta bound to the surface of neurons can be used as a secondary screen to identify compounds acting via one or more of the following mechanisms: blocking Abeta effects by interference with Abeta oligomer binding to neuronal surface or by effecting alterations to the oligomers themselves (inverse agonism or oligomer dissociation) or alteration of the surface receptors that the oligomers bind to (allosteric modulation or classical receptor antagonism) It can also distinguish these compounds from compounds acting on downstream signaling events. Accordingly, this assay is relevant to disease states characterized by Abeta oligomer nonlethal effects on neurons and forms part of a screening cascade employed by the present inventors to identify clinically relevant compounds. Selected test compounds that are active in membrane trafficking assay and in this binding/synapse loss assay can be tested for activity in two different transgenic models for Alzheimer's disease and in an induced model as well. Accordingly, this as well as the membrane trafficking assay is useful in identifying clinically relevant compounds and appears to have predictive value for in vivo results. The predictive validity of this assay is being confirmed by demonstrating its ability to predict compound properties using compounds outside of the scope of the disclosure.

Primary hippocampal neuronal culture is established as in the membrane trafficking assay above. Test compound (at concentrations of $10^{-8}$ to 30 micromolar) is added to the plate followed by an addition of Abeta 1-42 oligomer containing preparation at a concentration to reach saturation binding. Pretreatment with test compounds for 1 hr and addition of Abeta oligomers or no oligomer (vehicle alone) is followed by incubation for an additional 23 hrs.

The plates are fixed with 3.7% paraformaldehyde in phosphate buffered saline for 15 min. The plates are then washed 3× with PBS for 5 min each. The plates are blocked at RT for 1 hr in 5% goat serum and 0.5% Triton X-100 in PBS. Primary antibodies (anti-MAP 2 polyclonal, Millipore #AB5622 and anti-Beta Amyloid 6E10 monoclonal, Covance #SIG-39300, at 1 microgram/ml, and rabbit polyclonal anti-synaptophysin, Anaspec, at 0.2 microgram/ml) were diluted 1:1000 in 5% goat serum with PBS. Primary antibodies are incubated overnight at 4° C. The plates are then washed 3× with PBS for 5 min each. Secondary antibodies (Alex Flor 488 polyclonal, Invitrogen #A11008 and Alexa Flor 647 monoclonal, Invitrogen #A21235) are diluted 1:1000 in 5% goat serum with PBS. Secondary antibodies are incubated at RT for 1 hr. The plates are washed once with PBS. DAPI (4',6-diamidino-2-phenylindole, Invitrogen) is then applied at 0.03 ug/ul and incubated at RT for 5 min, then washed with PBS.

The results are expected to show that Abeta oligomer, prepared as detailed below and dosed at 3 or 1 μM depending on the preparation used, bound to neurons at synapses, is revealed by a red dye. In humans with early Alzheimer's disease, the number of synapses in the hippocampus has been shown to be reduced by 18% compared to age-matched cognitively normal individuals (Scheff et al., '07) and this result can also be visualized on this assay by 20% regression of fluorescent puncta and therefore of the number of synapses. In the co-presence of selected test compound, the Abeta binding is expected to be reduced to essentially control levels, and the green fluorescence is unaffected indicating an undiminished synapse number. Abeta 42 oligomers bind to postsynaptic spines; and are labeled with synaptophysin in primary neurons Post-synaptic spines and synapses are expected to be shown essentially at control levels when an effective amount of preferred test compound is added to the culture. Abeta 42 oligomers added alone cause a 20% decrease in the density of synaptophysin puncta after 24 hrs when compared to vehicle alone. This loss is reversed by an effective amount of a preferred test compound. In the absence of Abeta oligomer, preferred test compound does not affect synaptic number and it remains at levels comparable to control (vehicle alone). It is expected that Abeta binding intensity as calculated by the Abeta puncta will be reduced by about 18% in the presence of an effective amount of a test compound, yet this decrease is sufficient to permit synapse count to reach control levels in the presence of this compound.

Additionally, punctate synaptic Abeta oligomer binding is expected to be reduced by about 38% in the presence of certain test compounds in a concentration-dependent manner. A histogram of puncta intensity reveals that the normal bimodal binding population (neurons with bright puncta and a population with less bright puncta) is left-shifted in the presence of drug (data not shown). Partial inhibition of Abeta oligomer binding has been reported to restore 100% of LTP function (Strittmatter S M et al., Cellular Prion Protein Mediates Impairment of Synaptic Plasticity by Amyloid-Beta Oligomers *Nature* (2009) 457 (7233:1128-32)).

Abeta oligomer cause a 20% decrease in the density of synaptophysin puncta after 24 hrs compared to vehicle-treated (first bar), which is reversed by an effective amount of test compound. See, e.g., WO2013/029060, which is incorporated herein by reference.

It is desirable that in the absence of Abeta, the test compound does not affect synaptic number. Abeta oligomers cause an 18.2% decrease in synapse number; 100% of this loss is eliminated by an effective amount of a preferred test compound.

Nuclei, visualized with DAPI, exhibit a normal morphology, indicating an absence of neurodegeneration. The procedure is performed with selected test compounds selected from among those encompassed by Formula I and/or II.

Abeta Oligomer Preparations:

Human amyloid peptide 1-42 is obtained from California Peptide, with lot-choice contingent upon quality control analysis. Abeta 1-42 oligomers are made according to published methods as described above. [See e.g. Dahlgren et al., "Oligomeric and fibrillar species of amyloid-beta peptides differentially affect neuronal viability" J Biol Chem. 2002 Aug. 30; 277(35):32046-53. Epub 2002 Jun. 10; LeVine H 3rd. "Alzheimer's beta-peptide oligomer formation at physiologic concentrations" Anal Biochem. 2004 Dec. 1; 335(1): 81-90; Shrestha et. al, "Amyloid beta peptide adversely affects spine number and motility in hippocampal neurons" Mol Cell Neurosci. 2006 November; 33(3):274-82. Epub 2006 Sep. 8; Puzzo et al., "Amyloid-beta peptide inhibits activation of the nitric oxide/cGMP/cAMP-responsive element-binding protein pathway during hippocampal synaptic plasticity" J Neurosci. 2005 Jul. 20; 25(29):6887-97; Barghorn et al., "Globular amyloid beta-peptide oligomer—a homogenous and stable neuropathological protein in Alzheimer's disease" J Neurochem. 2005 November; 95(3): 834-47. Epub 2005 Aug. 31; Johansson et al., Physiochemical characterization of the Alzheimer's disease-related peptides A beta 1-42 Arctic and A beta 1-42 wt. FEBS J. 2006 June; 2 73(12):2618-30] as well as brain-derived Abeta oligomers (See e.g. Walsh et al., Naturally secreted oligomers of amyloid beta protein potently inhibit hippocampal long-term potentiation in vivo. Nature (2002). 416, 535-539; Lesne et al., A specific amyloid-beta protein assembly in the brain impairs memory. Nature. 2006 Mar. 16; 440(7082): 352-7; Shankar et al, Amyloid-beta protein dimers isolated directly from Alzheimer's brains impair synaptic plasticity and memory. Nat Med. 2008 August; 14(8):837-42. Epub 2008 Jun. 22). Quality controls of oligomer preparations consist of Westerns to determine oligomer size ranges and relative concentrations, and the MTT assay to confirm exocytosis acceleration without toxicity. Toxicity is monitored in each image-based assay via quantification of nuclear morphology visualized with the DNA binding dye DAPI (Invitrogen). Nuclei that are fragmented are considered to be in late stage apoptosis and the test rejected (Majno and Joris Apoptosis, oncosis, and necrosis. An overview of cell death. Am J Pathol 1995; 146:3-16). Peptide lots producing unusual peptide size ranges or significant toxicity at standard concentrations on neurons would be rejected.

Controls

Pre-adsorption of anti-Abeta antibody 6E10 with oligomer preparation inhibits synapse binding in a dose dependent manner (at $7.84\times10^{-6}$) and is used as a positive control. The antibody is used at 1:1000 (1 microgram/ml). For the synapse loss assay, the NMDA antagonist dizocilpine (MK-801) is used as the positive control at 80 uM.

Image Processing

Images are captured and analyzed with the Cellomics VTI automated microscope platform, using the Neuronal Profiling algorithm. For statistical analysis, a Tukey-Kramer pairwise comparison with unequal variance is used.

Western Blots

Samples containing Abeta 1-42 are diluted (1:5) in non-reducing lane marker sample buffer (Pierce #1859594). A 30 microliter (μL) sample is loaded onto an eighteen well precast 4-15% Tris-HCl gel (BIORAD #345-0028). Electrophoresis is performed in a BIO-RAD Criterian precast gel system using Tris-Glycine buffer at 125 volt (V) for 90 minutes. The gels ae blotted onto 0.2 μM nitrocellulose membranes in Tris-Glycine/10% methanol buffer at 30V for 120 minutes. The membranes are boiled for 5 minutes in a PBS solution and blocked over night with TBS/5% milk solution at 4° C. The membrane is probed with 6E10-HRP (Covance #SIG-39345) diluted to 10 g/mL in TBS/1% milk solution for one hour at room temperature. Membrane is washed three times for 40 minutes each with a solution of TBS/0.05% tween-20 and developed with ECL reagent (BIO-RAD #162-0112) for 5 minutes. Image acquisition is performed on an Alpha Innotech FluorChem Q quantitative imaging system and analyzed with AlphaView Q software.

Activity

Preferred test compounds are expected to be shown to partially block binding of the Abeta oligomer ligand to neurons by about 25% according to the binding assay (using imaging processing algorithm).

Example 9: Fear Conditioning Assay

Selected test compounds are tested in an animal model of a memory-dependent behavioral task known as fear conditioning. The study protocol was designed based on published protocols (See e.g. Puzzo D, Privitera L, Leznik E, Fà M, Staniszewski A, Palmeri A, Arancio O. Picomolar amyloid-beta positively modulates synaptic plasticity and memory in hippocampus. J Neurosci. 2008 Dec. 31; 28(53):14537-45). The formation of contextual memories is dependent upon the integrity of medial temporal lobe structures such as the hippocampus. In this assay mice are trained to remember that a particular salient context (conditioned stimulus; CS) is associated with an aversive event, in this case a mild foot shock (the unconditioned stimulus, US). Animals that show good learning will express an increase in freezing behavior when placed back into the same context. This freezing is absent in a novel context. Increased freezing in the context indicates strong hippocampal-dependent memory formation in animals. Memory tested in Fear Conditioning is sensitive to elevations of soluble Aβ. Compound II was effective at stopping Abeta oligomer mediated effects on membrane trafficking. When administered to animals prior to Abeta oligomer administration, a preferred test compound is expected to block oligomer effects on memory in a dose-dependent manner.

Certain preferred test compounds are those capable of eliminating Abeta oligomer-induced deficits in memory, but will not affect memory when dosed alone. This behavioral efficacy demonstrates that the membrane trafficking assay is able to predict which compounds will be efficacious in treating the behavioral memory loss caused by oligomers. The fear condition model for memory was performed as described herein. It is desirable that no adverse behavioral changes are observed at any dose. Accordingly, there is a correlation between the performance of this compound in the membrane trafficking assay and its performance in the fear conditioning assay, the latter being an indicator of memory loss. It is anticipated that the isoindoline compounds provided herein will be active in the fear conditioning assay and therefore will be shown to be efficacious in treating memory loss. The correlation between the performance of a compound in the fear condition model and its usefulness in treating memory loss has been established in the literature. (Delgado M R, Olsson A, Phelps E A. "Extending animal models of fear conditioning to humans" Biol. Psychol. 2006 July; 73(1):39-48).

Example 10. Autoradiography Studies with Rat, Rhesus Monkey and Human Postmortem Brain Samples Autoradiography imaging studies for the neurological and pharmacological profiling of the sigma-2 and sigma-1 receptor ligands are conducted by a modification of the protocol previously reported by Xu et al., 2010. Xu, J., Hassanzadeh B, Chu W, Tu Z, Vangveravong S, Tones L A, Leudtke R R, Perlmutter J S, Mintun M A, Mach R H. [$^3H$]4-(Dimethylamino)-N-[4-(4-(2-methoxyphenyl)piperazin-1-yl)butyl] benzamide, a selective radioligand for dopamine D(3) receptors. II. Quantitative analysis of dopamine D3 and D2 receptor density ratio in the caudate-putamen. Synapse 64: 449-459(2010), which is incorporated herein by reference. Labeled RHM-1 was obtained by the method of Xu J, Tu Z, Jones L A, Wheeler K T, Mach R H. [3H]N-[4-(3,4-dihydro-6,7-dimethoxyisoquinolin-2(1H)-yl)butyl]-2-methoxy-5-methylbenzamide: a Novel Sigma-2 Receptor Probe. Eur. J. Pharmacol. 525: 8-17 (2005), which is incorporated herein by reference.

Brain sections in 20 μM thickness from rats, rhesus monkeys and postmortem human brains are cut using with a Microm cryotome and mounted on superfrost plus glass slides (Fisher Scientific, Pittsburgh, Pa.), and serial sections through the brain regions of cerebral cortex and hippocampus are used in this study. Brain section are incubated with 5 nM [$^3H$](+)-Pentazocine for sigma-1 receptor profiling, 4 nM [$^3H$]RHM-1 only for sigma-2 receptor characterization, 10 nM [$^3H$]DTG and [$^3H$]Haloperidol in the presence of sigma-1 receptor block (+)-Pentazocine to image the sigma-2 receptor distribution; after incubation with the radioligands for 30 minutes, the brain sections containing glass slides are rinsed 5 times at one minute each time with ice-cold buffer.

Slides are dried and made conductive by coating with a copper foil tape on the free side and then placed in the gas chamber [mixture of argon and triethylamine (Sigma-Aldrich, USA)] of a gaseous detector, the Beta Imager 2000Z Digital Beta Imaging System (Biospace, France). After the gas is well mixed and a homogenous state is reached, further exposure for 24 hours to 48 hours until high quality images are observed. [$^3H$]Microscale (American Radiolabeled Chemicals, Inc., St. Louis, Mo.) is counted at the same time as a reference for total radioactivity quantitative analysis, i.e., to convert the cpm/mm2 to nCi/mg tissue. Quantitative analysis is performed with the program Beta-Image Plus (BioSpace, France) for the anatomical regions of interest (ROI), i.e., to obtain the quantitative radioactivity uptake (cpm/nlln2) in the regions of cortex and hippocampus. The binding density is normalized to fmol/mg tissue based on the specific activities of the corresponding radioligands and calibration curve from the standard [$^3H$]Microscale. A series of dilutions of test compounds (10 nM, 100 nM, 1,000 nM and 10,000 nM) are tested for competing the binding sites using the quantitative autoradiography, for those four radioligands, [³H](+)-Pentazocine, [³H]RHM-1, [³H]DTG and [³H]Haloperidol, then the specific binding (% control) is analyzed to derive the binding affinity in the regions of the cortex and the hippocampus (dentate gyrus, hippocampal CA I and CA3).

Autoradiography at sigma-1 and sigma-2 receptors with [³H]-(+)-Pentazocine (a sigma-1 receptor ligand) and/or [¹²⁵I]-RHM-4, or [3H]-RHM-1, (sigma-2 receptor ligands) in, e.g., human frontal cortex slices from normal patients, Lewy Body Dementia (DLB) patients, or Alzheimer's Disease (AD) patients specific binding is performed and compared to control. Sigma-1 receptors are statistically down-regulated in Alzheimer's disease and possibly DLB compared to normal control, e.g., Mishina et al. reported low density of sigma-1 receptors in early Alzheimer's disease. Mishina et al., 2008, *Low density of sigma1 receptors in early Alzheimer's disease*. Ann. Nucl Med 22: 151-156. However; sigma-2 receptors are not statistically downregulated in AD. Autoradiogaphy is employed to show displacement of, e.g., 18.4 nM [³H]-RHM-1 in monkey frontal cortex, monkey hippocampus or human temporal cortex by test compound sigma-2 ligands. Siramesine, a known sigma-2 receptor ligand, and test compounds are expected to partially displace [³H]-RHM-1 in the target tissues.

Example 11. MTS Assay: Determination of Agonist or Antagonist Activity of Various Sigma-2 Ligands The cytotoxicity of test compounds is determined using the CellTiter96 Aqueous One Solution Assay (Promega, Madison, Wis.). Briefly, MDA-MB-435 or MDA-MB231 or SKOV-3 cells were seeded in a 96-well plate at a density of 2000 cells/well on the day prior to treatment with sigma-2 receptor selective ligands. After a 24 hour treatment, the CellTiter 96 AQueous One Solution Reagent is added to each well, and the plate incubated for 2 hours at 37° C. The plate is read at 490 nm in a Victor3 plate reader (PerkinElmer Life and Analytical Sciences, Shelton, Conn.). The $EC^{50}$ value, defined as the concentration of the sigma ligand required to inhibit cell viability by 50% relative to untreated cells, is determined from the dose response curve for each cell line. Siramesine is accepted as an agonist. The agonists and antagonists of the sigma-2 ligands are defined as the following: If the EC50s of a sigma-2 ligand test compound is less than 2 fold of EC50 of siramesine, this sigma-2 ligand test compound is considered as an agonist. If the EC50 of a sigma-2 ligand is between 2 and 10 fold of EC50 of siramesine, this sigma-2 ligand is considered as a partial agonist. If the EC50 of a sigma-2 ligand is larger than 10 fold of EC50 of siramesine, this sigma-2 ligand is considered as an antagonist. The sigma-2 ligand standard compounds used for the studies are: agonists (siramesine and SV 119), partial agonist (WC26), and antagonist (RHM-1). Results for standards are shown in Table 3.

TABLE 3

$IC_{50}$ values for TumorCell Viability assay.

| Compound | $IC_{50}$, 48 hrs. (uM) | Action |
|---|---|---|
| RHM-1 | 203 ± 13 | Antagonist |
| Siramesine | 11.8 ± 2.7 | Full agonist |
| SV-119 | 21.7 ± 2.9 | Full agonist |
| WC-26 | 65.6 ± 6.3 | Partial agonist |

Neuronal cultures are treated with various concentrations of sigma compounds for 24 hours and nuclear intensity compared to vehicle is measured. Sigma-2 agonists (siramesine, SV-119, WC-26) cause significant abnormal nuclear morphology in neurons; in contrast to sigma-2 antagonists (RHM-1), which do not decrease nuclear intensity at the test concentrations. See, e.g. WO2013/029060, FIG. 9B, incorporated herein by reference, wherein sigma-2 receptor agonists were shown to be cytotoxic to the neuronal and cancer cells; however sigma-2 receptor antagonists were not toxic and further blocked the cytotoxicity caused by sigma-2 receptor agonists. Isoindoline test compounds of the present disclosure are analyzed in this assay to help determine neuronal phenotype, results are shown in Table 2.

Example 12. Caspase-3 Assays. Determination of Agonist or Antagonist Activity of Sigma-2 Ligands As described herein, Xu et al. identified PGRMC1 protein complex as the putative sigma-2 receptor binding site. Xu et al., 2011. Nature Commun. 2, article number 380, incorporated herein by reference. Sigma-2 receptor agonists can induce Caspase-3-dependent cell death. Xu et al 2011 disclose functional assays to examine the ability of the PGRMC1 to regulate caspase-3 activation by sigma-2 receptor agonist WC-26.

Abeta oligomers cause low levels of caspase-3 activation and lead to LTD. High levels of Abeta oligomers and caspase-3 activation lead to cell death. Li et al., 2010; Olsen and Sheng 2012. It was demonstrated in WO2013/029060, incorporated herein by reference, that sigma-2 receptor agonists (SV-119, siramesine) activate caspase-3 in tumor cells and neurons; see, for example, FIGS. 10A and 10B. Sigma-2 receptor antagonist RHM-1 inhibits the activation in tumor cells (FIG. 10A), but was not able to block activation by agonist SV-119 in neurons in this experiment (FIG. 10B). Test compounds which are sigma 2 receptor antagonists are able to inhibit caspase-3 activation in tumor cells and block sigma-2 receptor agonist SV-119 activation of caspase-3 in neurons. Therefore, certain test compounds are tested for sigma-2 receptor antagonist behavior in caspase-3 assays in tumor cells and neurons, as demonstrated in this example.

The activation of endogenous caspase-3 by sigma-2 receptor ligands is measured using the Caspase-3 Colorimetric Activity Assay Kit (Milipore, Billerica, Mass.) according to the manufacture's protocol. Briefly, MDA-MB 435 or MDA-MB23I cells were plated at $0.5 \times 10^6$ cells 100 mm dish. 24 hours after plating, sigma-2 ligands are added to the culture dishes to induce caspase 3 activation. The final concentration of the sigma-2 ligand is its EC50. 24 hours after treatment, cells are harvested, lysed in 300 uL of Cell Lysis Buffer, and centrifuged for 5 minutes at 10,000×g. Supernatant was collected and incubated with caspase-3 substrate, DEVD-pNA, for 2 hours at 37° C. The protein concentration is determined using Dc protein assay kit (Bio-Rad, Hercules, Calif. The resulting free pNA is measured using a Victor³ microplate reader (PerkinEliner Life and Analytical Sciences, Shelton, Conn.) at 405 nm. The ligands tested include standard sigma-2 agonists (siramesine, SV119, WC26), and sigma-2 antagonist, RHMWU-I-102 (RHM-1), and test compounds The ligands which activate caspase 3 are considered as agonists, whereas the ligands which do not activate caspase 3 are considered antagonists. As shown in—WO2013/029060, FIG. 10A, the sigma-2 agonist siramesine induces caspase-3 activity, whereas sigma-2 antagonists, e.g., RHM-1, and test compounds that are sigma-2 antagonists do not induce caspase-3 activity in both cancer cells and neurons.

Example 13. Therapeutic Phenotype

The therapeutic phenotype for a Test Compound is determined by an in vitro assay platform and is predictive of behavioral efficacy. A compound that (1) selectively binds with high affinity to a sigma-2 receptor; and (2) acts as a functional antagonist in a neuron, is predicted to have behavioral efficacy if: it blocks Aβ-induced membrane trafficking deficits; blocks Aβ-induced synapse loss and does not affect trafficking or synapse number in the absence of Abeta oligomer. This pattern of activity in the in vitro assays is termed the "therapeutic phenotype". The ability of a sigma-2 receptor antagonist to block Abeta oligomer effects in mature neurons without affecting normal function in the absence of Abeta oligomers is one criteria for the therapeutic phenotype. Compounds that affect trafficking or synapse number in the absence of oligomers are not behaviorally efficacious. Only those compounds that selectively block oligomers without affecting normal trafficking or altering synapse number are behaviorally efficacious in preventing and treating Abeta oligomer-induced memory loss. In one embodiment, the in vitro assay platform can predict behavioral efficacy. This pattern of activity in the platform assays is therefore a therapeutic phenotype.

In summary; sigma-2 antagonists with high affinity (preferably Ki less than about 600 nM, 500 nM, 400 nM, 300 nM, 200 nM, 150 nM, 100 nM, or 70 nM) at sigma-2 receptors that have greater than about 20-fold, 30-fold, 50-fold, 70-fold, or preferably greater than 100-fold selectivity for sigma receptors compared to other non-sigma CNS or target receptors, have good drug-like properties including brain penetrability and good metabolic and/or plasma stability, and that possess the therapeutic phenotype, are predicted to have behavioral efficacy and can be used to treat Abeta oligomer-induced synaptic dysfunction in a patient in need thereof.

Functional neuronal phenotype for several isoindoline compounds according to formula I and/or formula II, predicted to have oral bioavailability, with in vitro assay characterization, are shown in Table 2.

Therapeutic Phenotype

Several sigma-2 ligands fall into three functional neuronal phenotypes: antagonists (block Abeta signaling); agonists (block Abeta signaling with U-shaped dose-response curve and toxicity at high doses; and inactive (no effect in neuronal cultures). The known prior art sigma-1 receptor ligands fall into two categories: antagonists (block Abeta signaling) and inactive (no effect in neuronal cultures). Most of the prior art compounds suffer from low selectivity in that they have significant affinity to other, non-sigma, receptors. Several prior art compounds may not be able to penetrate the blood brain barrier (BBB) and are likely substrates for oxidative metabolism, and thus would not fit the therapeutic profile.

Although several clinical compounds have the desired functional phenotype, they do not meet the desired therapeutic profile. Known prior art compounds with the desired antagonist functional neuronal phenotype, but that fail the criteria for therapeutic profile, either by being non-selective, or by failing to cross the BBB, or by being predicted to be an oxidative substrate and having metabolic instability, are shown in WO2013/029060, Tables 11C and 11D, which is incorporated herein by reference.

Example 14: In Vitro Toxicity

Representative sigma-2 antagonists test compounds do not induce neuronal or glial toxicity with acute or chronic dosing in vitro. The sigma-2 receptor antagonists eliminate or reduce Abeta oligomer-induced changes in membrane trafficking. No significant effect of compounds on membrane trafficking occurs when dosed without oligomers. There is no toxicity relative to neuron number, glial number, nuclear size, nuclear morphology, neurite length, cytoskeletal morphology when tested up to 10 times the EC50 concentration for three days. See, e.g., WO2013/029060, Table 12, which is incorporated herein by reference.

In vitro toxicity for Test Compounds is tested in a number of standard assays. Preferably, testing in vitro tox studies reveals there is no genotoxicity at 10 μM (AMES, micronucleus, bacterial cytotox); HepG2 toxicity at 100-fold above affinity at sigma-2 receptor, in HepG2 tumor cell line; inhibition of CYP 450 enzymes 2D6, 3A4, and 2C19 at 10 uM; and hERG inhibition. Results for test compounds for hERG inhibition (IC50, nM) is shown in Table 2.

In some embodiments, isoindoline compounds according to formula I or formula II, as provided herein, or pharmaceutically acceptable salts thereof, exhibit minimal hERG inhibition, with an IC50 of greater than 300 nM, greater than 500 nM, greater than 1,000 nM, greater than 3,000 nM, greater than 5,000 nM, greater than 10,000, or greater than 20,000 nM. In particular embodiments, isoindoline compounds according to formula I or formula II, as provided herein, or pharmaceutically acceptable salts thereof, exhibit minimal hERG inhibition, and exhibit an IC50 of greater than 5,000 nM, greater than 10,000, or greater than 20,000 nM.

Example 15: Separation and Activities of Enantiomers of Compound II in the Membrane Trafficking Assay In some embodiments, the synthesis is performed asymmetrically in order to produce a substantially pure or pure enantiomer of one of an analogue. In some cases, chiral compounds are resolved from a racemic mixture by any technique known in the art.

In some cases, chiral compounds are separated into (+) and (−) enantiomers by chiral chromatography. The racemic mixture can be applied to a chiral column CHIRALPAK AD-H (amylose tris (3,5-dimethylphenylcarbamate) coated on silica-gel; 4.6×250 mm) by known techniques; e.g., WO2013/029060, Example 15, which is incorporated herein by reference. Following elution from the column, specific rotation for each of the (+) enantiomer and (−) enantiomer is determined. The resolved enantiomers are tested individually, e.g., in the membrane trafficking assay Example 16. Behavioral Efficacy of Orally Available Compounds-Improvement of Memory Deficits in Transgenic Alzheimer's Mouse Model Male hAPP Swe/Ldn transgenic (Tg) mice are utilized as a TG model of AD. Transgenic mice that are treated with vehicle, or 10 or 30 mg/kg/day of test compound p.o., for a specific period of time, as well as non-transgenic vehicle-treated littermates are subjected to a standard fear conditioning paradigm. Vehicle-treated 9 month old male hAPP Swe/Ldn transgenic (Tg) mice that are treated p.o. for the same period of time with vehicle exhibited significant memory deficits vs. vehicle-treated non-transgenic littermates in contextual fear conditioning.

When the animals are tested for associative memory 24 hours after training, two-way (genotype and time) ANOVA with repeated measures is used to detect any significant difference in total freezing time between transgenic and nontransgenic vehicle-treated mice. Brain/trough plasma and brain/peak plasma ratios for orally available compounds are determined. Subsequent studies can be used to determine the minimum effective dose of a preferred test compound.

SYNTHETIC EXAMPLES

The compounds provided herein can be synthesized via any synthetic route; for example, see WO2013/029060, and WO2013/029067, each of which is incorporated herein by reference.

Example 17: Synthesis of Gem-Dimethyl Amine Intermediates

Example 17A illustrates preparation of an exemplary gem-dimethyl amine intermediate as shown in Scheme 1.

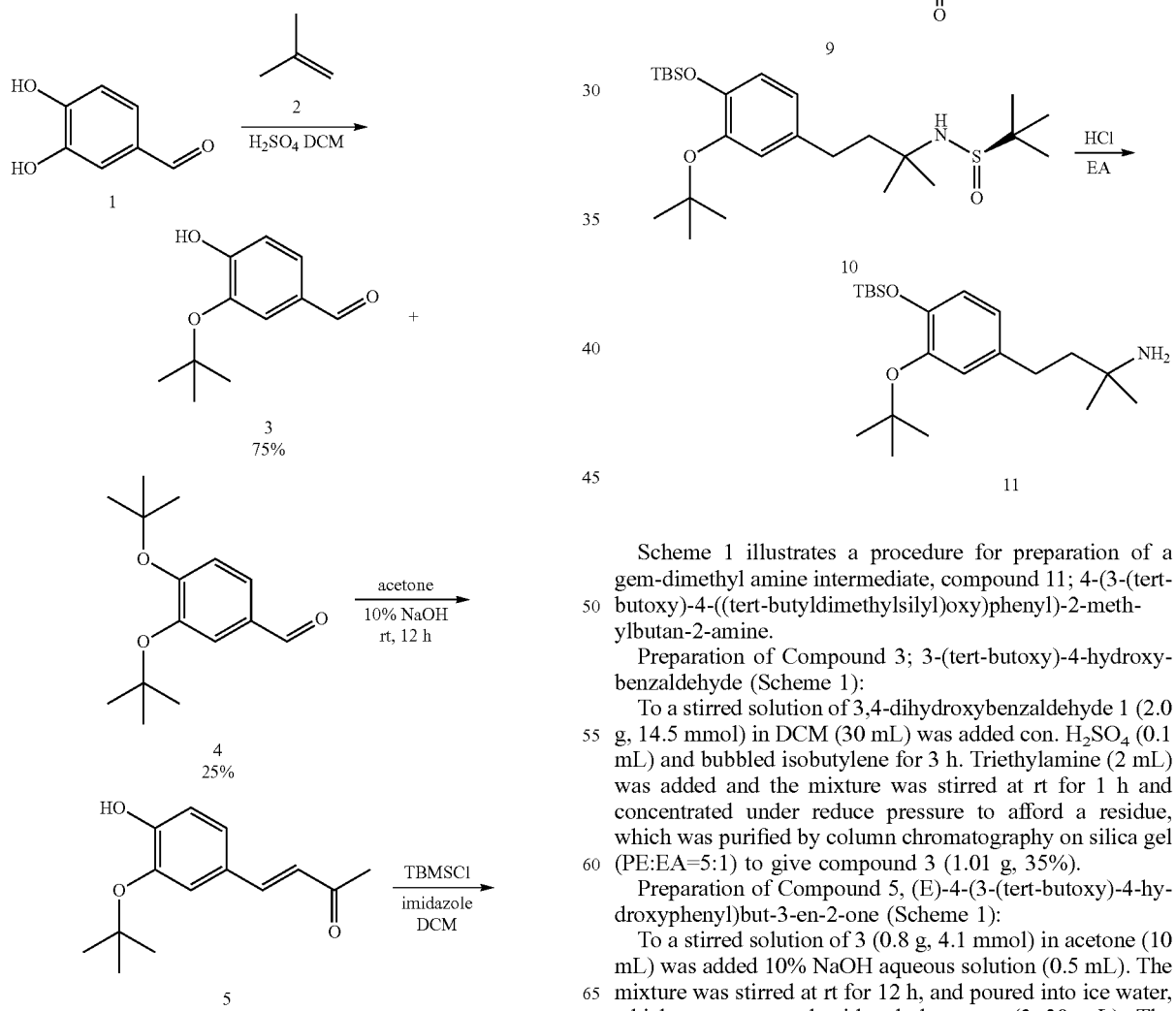

Scheme 1 illustrates a procedure for preparation of a gem-dimethyl amine intermediate, compound 11; 4-(3-(tert-butoxy)-4-((tert-butyldimethylsilyl)oxy)phenyl)-2-methylbutan-2-amine.

Preparation of Compound 3; 3-(tert-butoxy)-4-hydroxybenzaldehyde (Scheme 1):

To a stirred solution of 3,4-dihydroxybenzaldehyde 1 (2.0 g, 14.5 mmol) in DCM (30 mL) was added con. $H_2SO_4$ (0.1 mL) and bubbled isobutylene for 3 h. Triethylamine (2 mL) was added and the mixture was stirred at rt for 1 h and concentrated under reduce pressure to afford a residue, which was purified by column chromatography on silica gel (PE:EA=5:1) to give compound 3 (1.01 g, 35%).

Preparation of Compound 5, (E)-4-(3-(tert-butoxy)-4-hydroxyphenyl)but-3-en-2-one (Scheme 1):

To a stirred solution of 3 (0.8 g, 4.1 mmol) in acetone (10 mL) was added 10% NaOH aqueous solution (0.5 mL). The mixture was stirred at rt for 12 h, and poured into ice water, which was extracted with ethyl acetate (3×20 mL). The aqueous phase was acidified with 1N HCl until pH 6 was achieved. The reaction was extracted with EtOAc (3×30 mL), and organic layers were washed with brine, and water, dried over sodium sulfate, filtered. The filtrate was concentrated under reduced pressure to afford a residue, which was purified by column chromatography on silica gel (PE:EA=3:1) to give title compound 5 (0.5 g, 50%).

Preparation of Compound 7, (E)-4-(3-(tert-butoxy)-4-((tert-butyldimethylsilyl)oxy)phenyl)but-3-en-2-one (Scheme 1):

To a stirred solution of 5 (0.22 g, 0.9 mmol) in DCM (40 mL) was added TBSCl (0.28 g, 1.8 mmol) and imidazole (0.14 g, 2 mmol). The mixture was stirred at rt for 8 h, concentrated under reduced pressure to afford a residue, which was purified by column chromatography on silica gel (PE:EA=10:1) to give the title compound 7 (0.22 g, 67%).

Preparation of Compound 8, 4-(3-(tert-butoxy)-4-((tert-butyldimethylsilyl)oxy)phenyl)butan-2-one (Scheme 1):

To a stirred solution of 7 (0.22 g, 0.6 mmol) in EA (10 mL) was added 10% Pd/C (0.02 g). The mixture was stirred at rt for 12 h, and filtered. The filtrate was concentrated under reduced pressure to afford a residue, which was purified by column chromatography on silica gel (PE:EA=10:1) to give the title compound 8 (0.6 g, 0.4 mmol, 68%).

Preparation of Compound 9, (R,E)-N-(4-(3-(tert-butoxy)-4-((tert-butyldimethylsilyl)oxy)phenyl)butan-2-ylidene)-2-methylpropane-2-sulfinamide (Scheme 1):

To a stirred solution of 8 (2.6 g, 7.4 mmol, 1 eq) in THF (30 mL) was added (R)-(+)-t-butylsulfinamide (1.0 g, 8.14 mmol, 1.1 eq) and Ti(OEt)$_4$ (3.2 g, 14.8 mmol, 2.0 eq). The mixture was stirred at 70° C. overnight. The reaction was quenched with ice water and filtered. The filtrate was extracted with ethyl acetate. The organic layer was dried over Na$_2$SO$_4$, concentrated to get crude product 9 (2.7 g, 80%), which was directly used in next step.

Preparation of Compound 10, (R)—N-(4-(3-(tert-butoxy)-4-((tert-butyldimethylsilyl)oxy)phenyl)-2-methylbutan-2-yl)-2-methylpropane-2-sulfinamide (Scheme 1):

To a stirred solution of 9 (2.7 g, 5.9 mmol, 1 eq) in ether (30 mL) at 0° C. was added methylmagnesium bromide (10 mL, 30 mmol, 5 eq). The mixture was stirred at rt for 4 h. The reaction was quenched with ice water, extracted with ethyl acetate. The organic layer was dried over Na$_2$SO$_4$, concentrated under reduced pressure to afford a residue, which was purified by column chromatography on silica gel (PE:EA=10:1) to give compound 10 (1.6 g, 57%).

Preparation of Compound 11; 4-(3-(tert-butoxy)-4-((tert-butyldimethylsilyl)oxy)phenyl)-2-methylbutan-2-amine (Scheme 1):

To a stirred solution of 10 (1.2 g, 2.55 mmol, 1 eq) in EA (30 mL) was added EA (HCl) (10 mL) at 0° C. The mixture was stirred at rt for 2 h, and concentrated under reduced pressure to afford 11 (1.3 g, 100%) as a yellow oil. Analogous synthetic routes can be employed to prepare gem-dimethyl amine intermediates for use in synthesis of isoindolines of Formula I and/or II The t-butyldimethylsilyl oxy substituent, and/or tert-butoxy substituent can be replaced with alternative substituents, or additional R1 groups can also be used to generate other analogues.

Example 17B illustrates general preparation of gem-dimethyl amine intermediate as shown in Scheme 3.

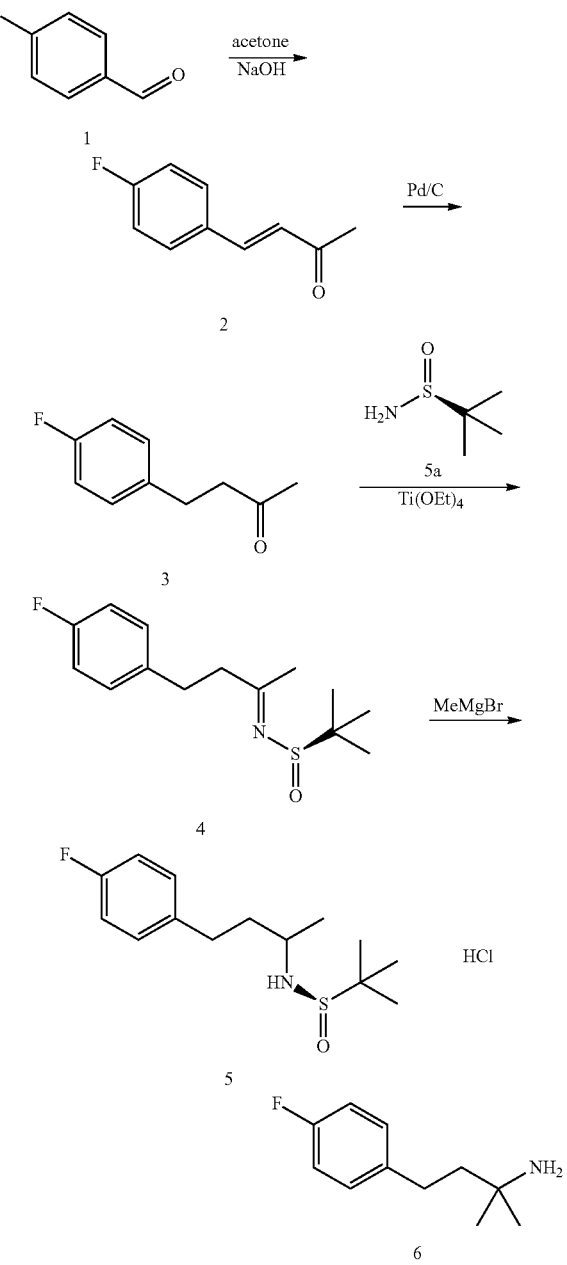

Preparation of Compound 2; (E)-4-(4-fluorophenyl)but-3-en-2-one, (Scheme 3):

To a stirred solution of 1, 4-fluorobenzaldehyde, (100 g, 805.7 mmol, 1 eq) in acetone (1000 mL) was added 10% NaOH aqueous solution (100 mL). The mixture was stirred at rt for 12 h and then poured into ice water, which was extracted with EtOAc (3×300 mL). The organic layer was washed by brine, water, dried over sodium sulfate, filtered and the filtrate was concentrated under reduced pressure to afford a residue, which was purified by column chromatography on silica gel (PE:EA=10:1) to give the title compound 2; (E)-4-(4-fluorophenyl)but-3-en-2-one (110 g, 85%).

Preparation of Compound 3; 4-(4-fluorophenyl)butan-2-one (Scheme 3):

To a stirred solution of 2 (50 g, 304.5 mmol) in MeOH (40 mL) was added Pd/C (10%, 5 g). The mixture was stirred at rt for 4 h, and then filtered. The filtrate was concentrated under reduced pressure to afford compound 3; 4-(4-fluorophenyl)butan-2-one (50 g, 300.9 mmol, 99%), which was directly used in next step.

Preparation of Compound 4; (R,E)-N-(4-(4-fluorophenyl)butan-2-ylidene)-2-methylpropane-2-sulfinamide (Scheme 3):

To a stirred solution of 3 (50 g, 300.9 mmol, 1 eq) in THF (30 mL) was added (R)-(+)-t-butylsulfinamide (40.4 g, 331 mmol, 1.1 eq) and Ti(OEt)$_4$ (136.8 g, 600.2 mmol, 2 eq). The mixture was stirred at 70° C. over night and quenched by ice water, filtered, and washed by EA. The organic layer was dried over Na$_2$SO$_4$, concentrated to get crude product 4 (65 g, 80%), which was directly used in next step.

Preparation of Compound 5; (R)—N-(4-(4-fluorophenyl)-2-methylbutan-2-yl)-2-methylpropane-2-sulfinamide (Scheme 3):

To a stirred solution of 4 (30 g, 111.4 mmol, 1.0 eq) in ether (30 mL) was added MeMgBr (111 mL, 333 mmol, 3.0 eq) at 0° C. The mixture was stirred at rt for 4 h. The reaction was quenched by ice water, extracted by EA. The organic layer was dried over Na$_2$SO$_4$, concentrated under reduced pressure to afford a residue, which was purified by column chromatography on silica gel (PE:EA=10:1) to give the title compound 5 (28.6 g, 90%).

Preparation of Compound 6; 4-(4-fluorophenyl)-2-methylbutan-2-amine (Scheme 3):

To a stirred solution of 5 (28.6 g, 100 mmol, 1 eq) in EA (150 mL) was added EA (HCl) (200 mL) at 0° C. The mixture was stirred at rt for 2 h, concentrated under reduced pressure to afford 6 (18 g, 100%) as a yellow oil.

Example 17C illustrates general preparation of gem-dimethyl amine intermediate 4-(3-amino-3-methylbutyl)-2-(trifluoromethoxy)phenol hydrochloride as shown in Scheme 7.

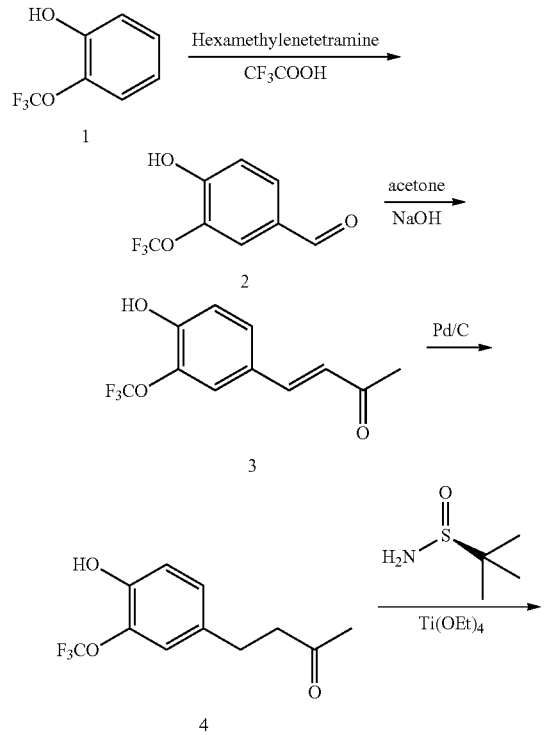

Scheme 7: Preparation of gem-dimethyl amine intermediate 4-(3-amino-3-methylbutyl)-2-(trifluoromethoxy)phenol hydrochloride.

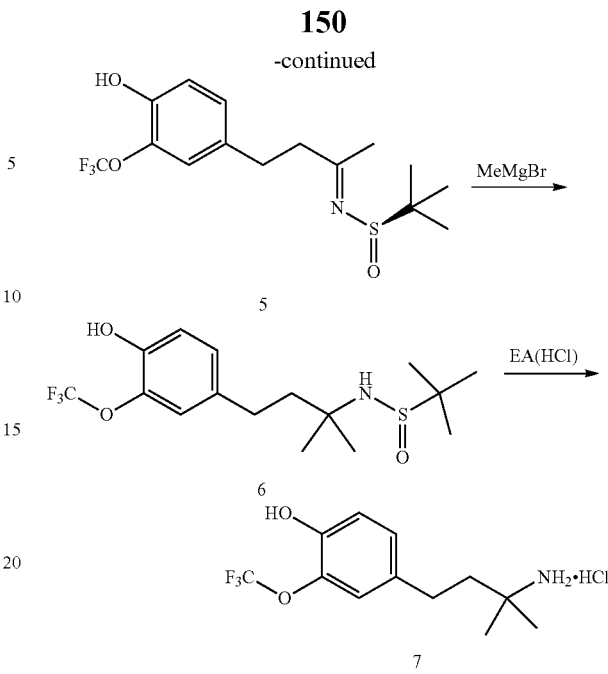

Preparation of Compound 2 (Scheme 7):

To a stirred solution of 2-trifluoromethoxyphenol 1 (40.0 g, 0.224 mol, 1 eq) in trifluoroacetic acid (400 mL) was added hexamethylenetetramine (188.7 g, 1.35 mol, 6 eq). The mixture was stirred at 70° C. for 12 h. After being concentrated by vacuum, the reaction mixture was diluted with 2N HCl, extracted with EA (3×400 mL). The combined organic layers were washed with brine, dried over Na$_2$SO$_4$ and concentrated under vacuum to furnish an orange oil. The crude product was subjected to column chromatography (PE:EA=5:1) to give the title compound 2 (30.0 g, 65%).

Preparation of Compound 3 (Scheme 7):

To a stirred solution of 4-Hydroxy-3-trifluoromethoxybenzaldehyde (30.0 g, 145.5 mmol, 1.0 eq) in acetone (300 mL) was added 10% NaOH aqueous solution (150 mL). The mixture was stirred at rt for 12 h and poured into ice water. The reaction was extracted with EtOAc (3×20 mL). The aqueous phase was acidified with 1N HCl until pH 6 was achieved. The reaction was extracted with EtOAc (3×100 mL). The organic layer was washed with brine, and water, and dried over sodium sulfate, filtered. The filtrate was concentrated under reduced pressure to afford a residue, which was purified by column chromatography on silica gel (PE:EA=3:1) to give the title compound 3 (30.1 g, 84%).

Preparation of Compound 4 (Scheme 7):

To a solution of 4-(4-hydroxy-3-trifluoromethoxy-phenyl)-but-3-en-2-one (12 g, 47.5 mmol) in methanol (100 mL) was added 10% Pd/C (1 g). The resulting solution was stirred under H$_2$ atmosphere for 8 h. The solution was filtered through a pad of Celite, concentrated to afford crude 4-(4-hydroxy-3-trifluoromethoxy-phenyl)-butan-2-one (11 g, 94%).

Preparation of Compound 5 (Scheme 7):

To a solution of 4-(4-hydroxy-3-trifluoromethoxy-phenyl)-butan-2-one (11 g, 44.3 mmol) in THF (100 mL) was added (R)-(+)-t-butylsulfinamide (7.0 g, 58 mmol) and Ti(OEt)$_4$ (22.0 g, 96.7 mmol). The resulting solution was stirred overnight. The reaction was quenched with ice water, filtered. The filtrate was extracted with ethyl acetate. The organic layer was dried over Na$_2$SO$_4$, concentrated to get crude product 5 (11.2 g, 78%), which was used for next step.

Preparation of Compound 6 (Scheme 7):

To a stirred solution of 5 (23 g, 49.4 mmol, 1 eq) in ether (120 mL) was added MeMgBr (82 mL, 247 mmol, 5 eq) at 0° C. The mixture was stirred at rt for 4 h. The reaction was quenched with ice water, extracted with EA. The organic layer was dried over Na₂SO₄, concentrated under reduced pressure to afford a residue, which was purified by column chromatography on silica gel (PE:EA=10:1) to give the title compound 6 (16.7 g, 70%).

Preparation of Compound 7 (Scheme 7):

To a stirred solution of 6 (1.0 g, 2.08 mmol, 1 eq) in ethyl acetate (5 mL) was added saturated HCl in acetate (5 mL) at 0° C. The mixture was stirred at rt for 2 h, and concentrated under reduced pressure to afford compound 7 (0.85 g, 100%) as a yellow oil.

Example 17D illustrates general preparation of gem-dimethyl amine intermediate 4-(4-((tert-butyldimethylsilyl)oxy)-3-(trifluoromethoxy)phenyl)-2-methylbutan-2-amine as shown in Scheme 8.

Scheme 8: Preparation of gem-dimethylamine 4-(4-((tert-butyldimethylsilyl)oxy)-3-(trifluoromethoxy)phenyl)-2-methylbutan-2-amine.

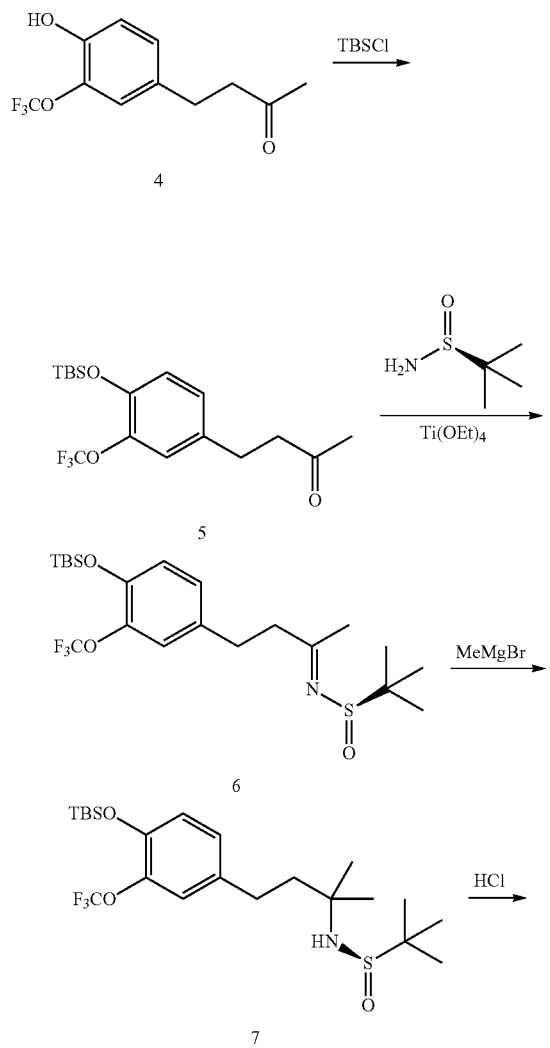

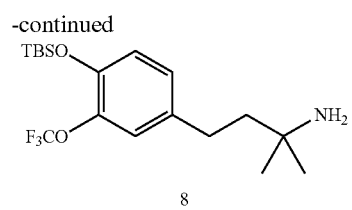

Preparation of Compound 5 (Scheme 8):

To a stirred solution of 4 (18 g, 72.5 mmol, 1 eq) in DCM (200 mL) was added TBSCl (16.4 g, 108.8 mmol, 1.5 eq) and imidazole (9.9 g, 145 mmol, 2.0 eq). The mixture was stirred at rt for 8 hr, concentrated under reduced pressure to afford a residue, which was purified by column chromatography on silica gel (PE:EA=10:1) to give the title compound 5 (19 g, 73%).

Preparation of Compound 6 (Scheme 8):

To a stirred solution of 5 (1.2 g, 3.3 mmol, 1 eq) in THF (20 mL) was added (R)-(+)-t-butylsulfinamide (0.4 g, 3.6 mmol, 1.1 eq) and Ti(OEt)₄ (1.5 g, 6.6 mmol, 2 eq). The mixture was stirred at 70° C. overnight. The reacted quenched with ice water, filtered, and extracted with ethyl acetate. The organic layer was dried over Na₂SO₄, concentrated to get crude product 6 (1.6 g, 97%), which was directly used for next step.

Preparation of Compound 7 (Scheme 8):

To a stirred solution of 6 (1.6 g, 3.4 mmol, 1.0 eq) in ether (30 mL) at 0° C. was added MeMgBr (5 mL, 17 mmol, 5.0 eq). The mixture was stirred at rt for 4 h. The reaction was quenched with ice water, extracted with ethyl acetate. The organic layer was dried over Na₂SO₄, concentrated under reduced pressure to afford a residue, which was purified by column chromatography on silica gel (PE:EA=10:1) to give the title compound 7 (0.6 g, 1.2 mmol, 37%).

Preparation of Compound 8 (Scheme 8):

To a stirred solution of 7 (3.0 g, 6.2 mmol, 1 eq) in ethyl acetate (30 mL) was added saturated HCl in acetate (10 mL) at 0° C. The mixture was stirred at rt for 2 h, and concentrated under reduced pressure to afford compound 8 4-(4-((tert-butyldimethylsilyl)oxy)-3-(trifluoromethoxy)phenyl)-2-methylbutan-2-amine (2.6 g, 100%) as a yellow oil.

Example 17E illustrates general preparation of gem-dimethyl amine intermediate 4-(3-amino-3-methylbutyl)-2-(trifluoromethoxy)phenyl dimethylcarbamate hydrochloride, as shown in Scheme 11.

Scheme 11: Preparation of gem-dimethylamine 4-(3-amino-3-methylbutyl)-2-(trifluoromethoxy)phenyl dimethylcarbamate hydrochloride.

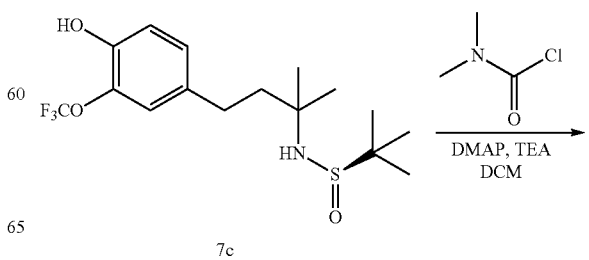

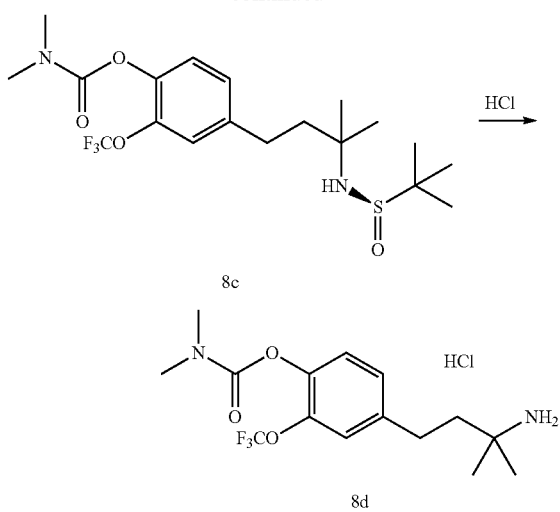

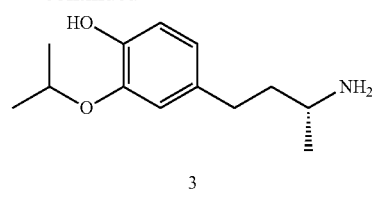

Preparation of Compound 8c (Scheme 11):

To a solution of 7c (5.0 g, 13.6 mmol, 1.0 eq) and dimethylcarbamyl chloride (3.0 g, 27.8 mmol, 2.2 eq) in DCM (100 mL) were added DMAP (0.25 g, 5 mol %), TEA (2.9 g, 22.6 mmol, 2.0 eq). The mixture was stirred at rt for 12 h, After being concentrated by vacuum, the crude product was subjected to column chromatography (20%-30% EtOAc/hexanes) to provide product 8c (4.8 g, 48%).

Preparation of Compound 8d; 4-(3-amino-3-methylbutyl)-2-(trifluoromethoxy)phenyl dimethylcarbamate hydrochloride (Scheme 11):

To a stirred solution of 8c (4.8 g, 11.0 mmol, 1 eq) in EA (30 mL) at 0° C. was added EA (HCl) (30 mL). The mixture was stirred at rt for 2 h, concentrated under reduced pressure to afford 8d (4.1 g, 100%) as a yellow oil.

Example 18: General Preparation of Chiral Amine Intermediates

Example 18A illustrates one exemplary preparation of a chiral amine intermediate (R)-4-(3-aminobutyl)-2-isopropoxyphenol as shown in Scheme 2.

Scheme 2: A general preparation of chiral amine intermediate (R)-4-(3-aminobutyl)-2-isopropoxyphenol.

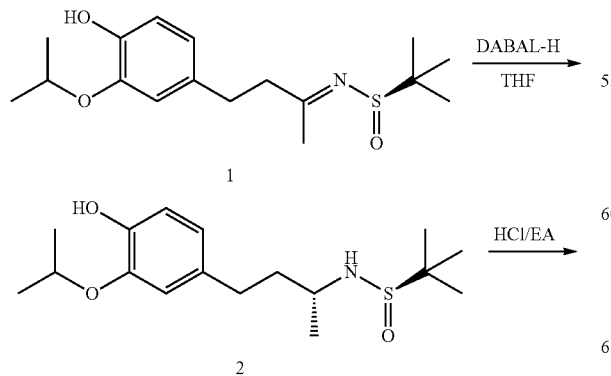

Preparation of Compound 2; (R)—N—((R)-4-(4-hydroxy-3-isopropoxyphenyl)butan-2-yl)-2-methylpropane-2-sulfinamide (Scheme 2):

To a stirred solution of 1; (R,E)-N-(4-(4-hydroxy-3-isopropoxyphenyl)butan-2-ylidene)-2-methylpropane-2-sulfinamide (20 g, 61.4 mmol, 1 eq) in THF (200 mL) was added DABAL-H (180 mL, 180 mmol, 3 eq) at −78° C. The mixture was stirred at −78° C. for 4 h, then quenched with ice water (20 mL), filtered and the filtrate was concentrated under reduced pressure to afford a residue, which was purified by column chromatography on silica gel (PE:EA=5:1) to give the title compound 2 (17.1 g, 52.2 mmol, 85%).

Preparation of Compound 3; (R)-4-(3-aminobutyl)-2-isopropoxyphenol (Scheme 2):

To a stirred solution of 2 (17.1 g, 52.2 mmol, 1 eq) in EA (50 mL) was added EA (HCl) (50 mL, 100 mmol, 2 eq, 2N) at 0° C. The mixture was stirred at rt for 2 h and concentrated under reduced pressure to afford compound 3 (11.6 g, 100%) as a yellow oil.

Example 18B illustrates preparation of chiral amine intermediate (R)-4-(3,4-diisopropoxyphenyl)butan-2-amine from 3,4-benzaldehyde starting material as shown in Scheme 4.

Scheme 4: General preparation of chiral amine (R)-4-(3,4-diisopropoxyphenyl)butan-2-amine.

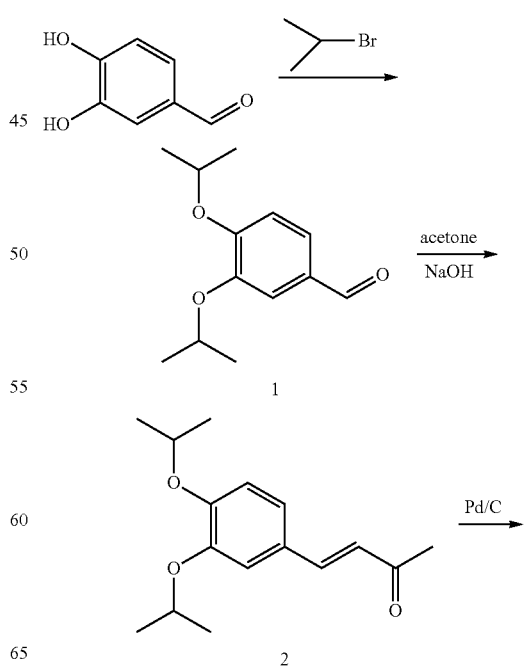

-continued

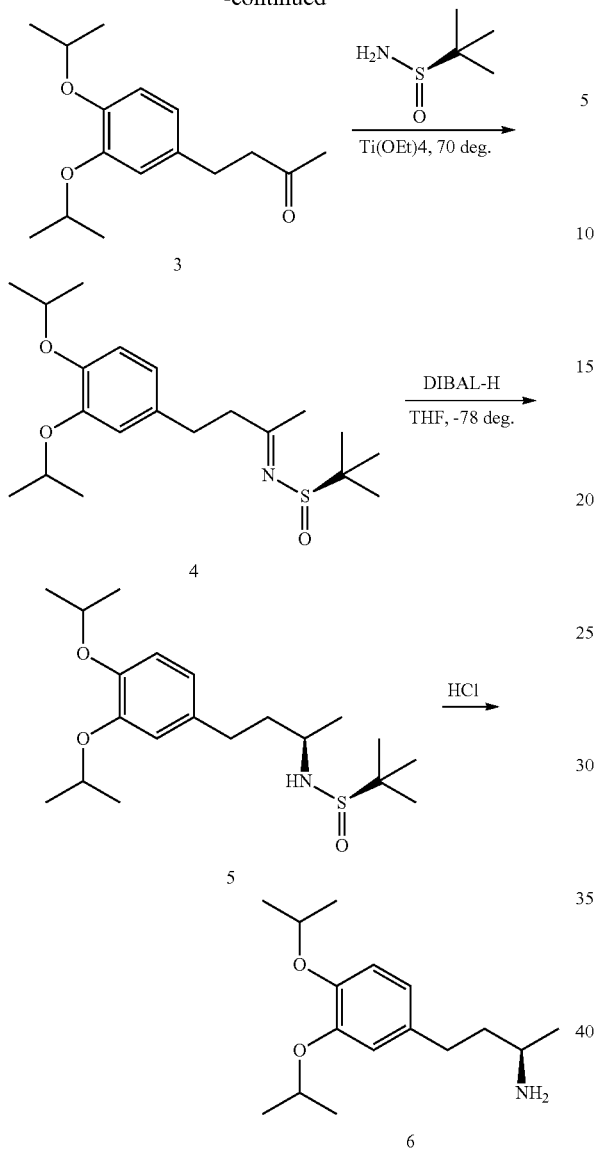

Preparation of Compound 1 (Scheme 4):

A mixture of 3,4-dihydroxy-benzaldehyde 1a (30.0 g, 65.7 mmol, 1 eq) and 2-bromo propane (18.4 g, 131.4 mmol, 2 eq) and NaH (5.4 g, 60% in oil, 130 mmol) in DMF (300 mL) was stirred at 70° C. for 12 h. After being concentrated by vacuum, the mixture diluted with 2N HCl, extracted with ethyl acetate (3×100 mL). The combined organic layers were washed with brine, dried over Na$_2$SO$_4$ and concentrated under vacuum to furnish an orange oil. The crude product was subjected to column chromatography (20%-30% EtOAc/hexanes) to provide product 1; 3,4-diisopropoxybenzaldehyde (10.1 g, 30%).

Preparation of Compound 2 (Scheme 4):

Compound 1 (20 g, 90 mmol) was dissolved in acetone (80 mL). To the vessel was then added ethanol (8 mL), 10% NaOH (80 mL) and water (200 mL). The resulting solution was stirred for 8 h. extracted with EA (3×100 mL). The combined organic layers were washed with brine, dried over Na$_2$SO$_4$ and concentrated under vacuum to furnish orange oil. The crude product was subjected to column chromatography to get compound 2; (E)-4-(3,4-diisopropoxyphenyl)but-3-en-2-one (12 g, 98%).

Preparation of Compound 3 (Scheme 4):

To a stirred solution of compound 2 (30.0 g, 114 mmol, 1 eq) in MeOH (300 mL) was added 10% Pd/C (3 g). The mixture was stirred at rt for 12 hrs, and filtered through a pad of Celite. The filtrate was concentrated under reduced pressure to afford a residue, which was purified by column chromatography on silica gel (PE:EA=5:1) to give the title compound 3; 4-(3,4-diisopropoxyphenyl)butan-2-one (11.4 g, 38%).

Preparation of Compound 4 (Scheme 4):

To a stirred solution of compound 3 (11.4 g, 43.1 mmol, 1.0 eq) in THF (100 mL) was added (R)-(+)-t-butylsulfinamide (5.7 g, 47.4 mmol, 1.1 eq) and Ti(OEt)$_4$ (19.7 g, 86.2 mmol, 2.0 eq). The mixture was stirred at 70° C. overnight. The reaction was quenched with ice water, filtered, and extracted with ethyl acetate. The organic layer was dried over Na$_2$SO$_4$, concentrated to get crude product 4 (15 g, 95%), which was directly used in next step.

Preparation of Compound 5 (Scheme 4):

To a stirred solution of 4 (6.3 g, 17.1 mmol, 1 eq) in THF (50 mL) at −78° C. was added DABAL-H (34 mL, 34 mmol, 2.0 eq). The mixture was stirred at −78° C. for 4 hrs, and quenched with ice water (20 mL), filtered. The filtrate was concentrated under reduced pressure to afford a residue, which was purified by column chromatography on silica gel (PE:EA=5:1) to give the title compound 5; (R)—N—((R)-4-(3,4-diisopropoxyphenyl)butan-2-yl)-2-methylpropane-2-sulfinamide (2.5 g, 40%).

Preparation of Compound 6 (Scheme 4):

To a stirred solution of 5 (2.5 g, 6.8 mmol, 1.0 eq) in EA (30 mL) was added saturated HCl in ethyl acetate (10 mL) at 0° C. The mixture was stirred at rt for 2 h, and concentrated under reduced pressure to afford compound 6; (R)-4-(3,4-diisopropoxyphenyl)butan-2-amine (2.1 g, 100%) as a yellow oil.

Example 18C illustrates preparation of a chiral amine intermediate (R)-2-(4-(3-aminobutyl)-2-methoxyphenoxy)ethan-1-ol as shown in Scheme 5.

General Preparation of Chiral Amines

Scheme 5: Preparation of chiral amine intermediate (R)-2-(4-(3-aminobutyl)-2-methoxyphenoxy)ethan-1-ol.

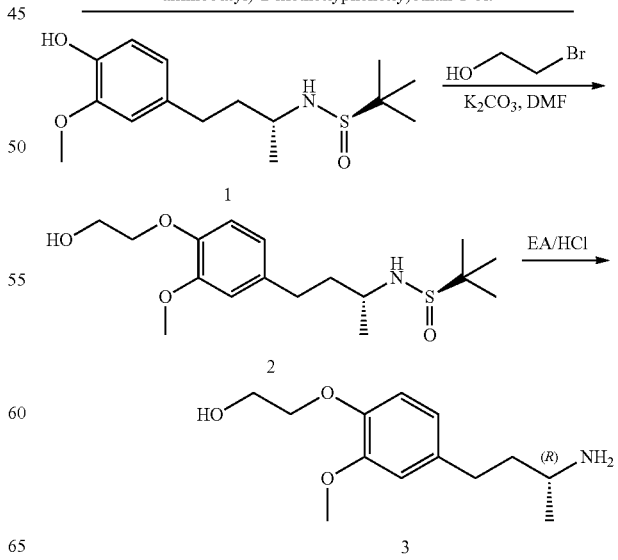

Preparation of Compound 2; (R)—N—((R)-4-(4-(2-hydroxyethoxy)-3-methoxyphenyl)butan-2-yl)-2-methylpropane-2-sulfinamide (Scheme 5):

To a stirred solution of compound 1; (R)—N—((R)-4-(4-hydroxy-3-methoxyphenyl)butan-2-yl)-2-methylpropane-2-sulfinamide (4.3 g, 14.4 mmol, 1.0 eq) in DMF (50 mL) was added $K_2CO_3$ (4.0 g, 28.8 mmol, 2.0 eq) and 2-bromoethanol (1.5 g, 13.6 mmol, 1.2 eq). The mixture was stirred at 80° C. for 8 hrs, and quenched with ice water (100 mL), extracted with EA (3×50 mL). The combined organic layer was washed with brine, dried over $Na_2SO_4$ and concentrated under vacuum to furnish orange oil. The crude product was purified by column chromatography on silica gel (PE:EA=5:1) to give the title compound 2 (3.1 g, 63%).

Preparation of Compound 3; (R)-2-(4-(3-aminobutyl)-2-methoxyphenoxy)ethan-1-ol (Scheme 5):

To a stirred solution of 2 (3.1 g, 9.0 mmol, 1.0 eq) in EA (30 mL) was added HCl-EA (10 mL) at 0° C. The mixture was stirred at rt for 2 h and concentrated under reduced pressure to afford 3 (2.1 g, 100%) as a yellow oil.

Example 18D illustrates preparation of a chiral amine intermediate

Scheme 6: Preparation of chiral amine intermediate, (S)-4-(3,4-dichlorophenyl)-1-methoxybutan-2-amine.

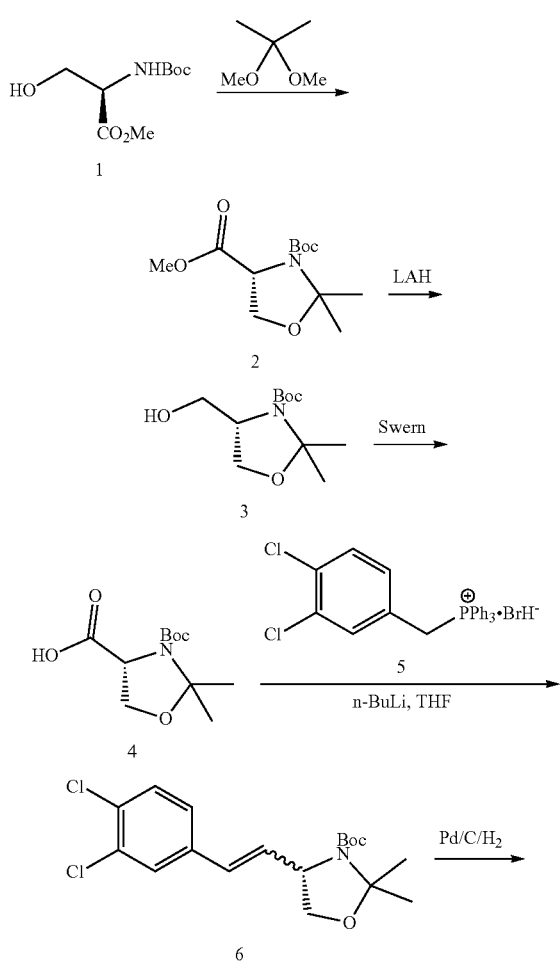

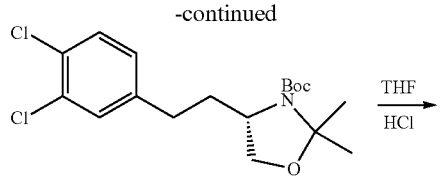

7

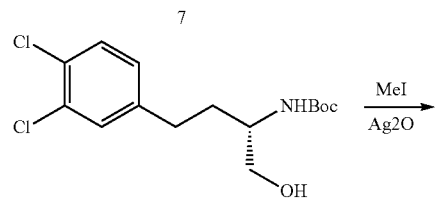

8

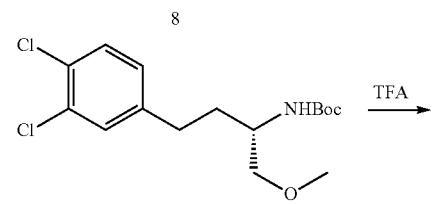

9

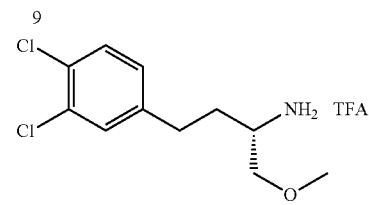

10

Preparation of Compound 2; 3-(tert-butyl) 4-methyl (R)-2,2-dimethyloxazolidine-3,4-dicarboxylate (Scheme 6):

To a solution of compound 1; methyl N-(tert-butoxycarbonyl)-D-serine (13 g, 59.2 mmol) in DCM (150 mL) at rt was added toluene-4-sulfonic acid monohydrate (2.0 g, 10.3 mmol) and 2,2-dimethoxypropane (18.5 g, 177.6 mmol). The mixture was stirred at rt for 48 h, and concentrated to get a residue, which was purified by flash column chromatography (PE:EA=4:1) to give compound 2 (13 g, 84%) as a yellow oil.

Preparation of Compound 3 (Scheme 6):

A mixture of $LiAlH_4$ (2.85 g, 75 mmol) in THF (200 mL) at 0° C. under $N_2$ was stirred for 20 min. To the mixture at 0° C. was added compound 2 (13.0 g, 50.1 mmol) dropwise. The mixture was stirred for 30 min, and quenched with $Na_2SO_4 \cdot 10H_2O$, and filtered. The filtrate was concentrated to get a residue, which was purified by FCC (PE:EA=4:1) to get compound 3 (10.3 g, 89%) as a yellow oil.

Preparation of Compound 4 (Scheme 6):

To a pre-cooled solution of oxalyl chloride (7.6 g, 60.1 mmol) in methylene chloride (200 ml) at −78° C. was added DMSO (9.3 g, 120.21 mmol) in methylene chloride (20 mL). The mixture was stirred for 30 min. To the mixture at −78° C. was added compound 3 (10.3 g, 44.5 mmol) in methylene chloride (30 mL). The reaction mixture was stirred at −78° C. for 2 h, at which time triethylamine (18.0 g, 178.13) was added. The resulting solution was warmed to 0° C., quenched with brine (30 mL), and extracted with diethyl ether (2×300 mL). The organic layer was dried over $Na_2SO_4$, filtered, and concentrated to get compound 4 (9.0 g, 85%) as an oil.

Preparation of Compound 6 (Scheme 6):

To a solution of compound 5 (285 mg, 0.56 mmol) in THF (15 ml) under $N_2$ at −78° C. was added n-BuLi (0.3 mL, 2.5

M). After 10 min, the reaction mixture was warmed to −40° C. until the precipitate disappeared. The reaction mixture was cooled to −78° C., compound 4 (130 mg, 0.56 mmol) in THF (5 mL) was added dropwise at −78° C. The resulting solution was warmed to rt, and stirred overnight before quenching with methanol (2 mL). After being stirred for 30 min, the mixture was concentrated to get a residue, which was purified by flash column chromatography (PE:EA=4:1) to give compound 6 (200 mg, 90%) as a yellow oil.

Preparation of Compound 7 (Scheme 6):

To a solution of compound 6 (2.6 g, 6.98 mmol) in methanol (50 mL) was added Pd/C (2.0 g) at rt under $H_2$ balloon. The mixture was stirred for 12 h, filtered, concentrated to get a residue, which was purified by FCC (PE) to get compound 7 (2.0 g, 77%) as a yellow oil.

Preparation of Compound 8 (Scheme 6):

To a solution of compound 7 (500 mg, 1.34 mmol) in THF (20 mL) was added 0.5 M HCl (1 mL) at rt. The reaction was stirred for 12 h, dried over $Mg_2SO_4$, and filtered. The filtrate was concentrated to get a residue, which was purified by FCC (PE) to get 7 (400 mg, 90%) as a yellow oil.

Preparation of Compound 9 (Scheme 6):

To a solution of compound 8 (140 mg, 0.42 mmol) in acetonitrile (10 mL) was added $Ag_2O$ (200 mg, 0.87 mmol), followed with methyl iodide (0.15 mL, 2.4 mmol). The mixture was stirred for 24 h, and filtered through a pad of Celite. The filtrate was concentrated to get a residue, which was purified by Prep-HPLC to get compound 9 (70 mg, 48%) as a yellow oil.

Preparation of Compound 10 (Scheme 6):

To a solution of compound 9 (70 mg, 0.20 mmol) in DCM (2 mL) was added TFA (1 mL). The mixture was stirred for 24 h, and concentrated to get compound 10; (S)-4-(3,4-dichlorophenyl)-1-methoxybutan-2-amine (50 mg, 100%) as an oil.

Example 18E illustrates preparation of a chiral amine intermediate (R)-4-(3-aminobutyl)-2-(trifluoromethoxy) phenol as shown in Scheme 9.

Scheme 9: Preparation of chiral amine (R)-4-(3-aminobutyl)-2-(trifluoromethoxy)phenol.

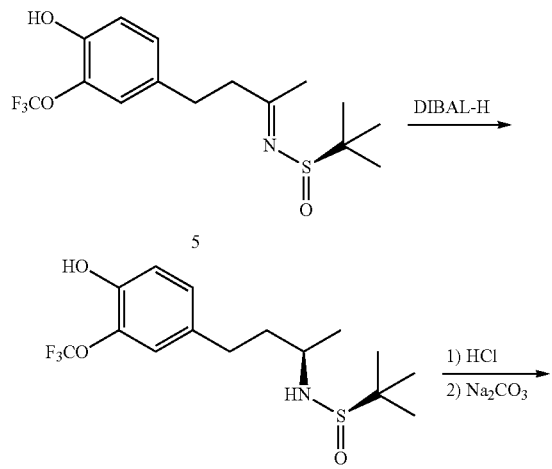

Preparation of Compound 6 (Scheme 9):

Compound 5 (11 g, 31.3 mmol) was dissolved in THF (100 mL) and cooled to −78° C. To the vessel was then added DIBAL-H (60 mL, 1.5 M in THF, 90 mmol), and the resulting solution was stirred for 3 h. Analysis of the reaction mixture by TLC showed complete consumption of the starting imine to give sulfinamide compound 5. The solution was then quenched by water and extracted by EA (3×500 mL). The combined organic layers were washed with brine, dried by $Na_2SO_4$ and concentrated under vacuum to furnish orange oil. The crude product was subjected to column chromatography (50%-75% EtOAc/hexanes) to get product 6 (6 g, 55%).

Preparation of Compound 7; (R)-4-(3-aminobutyl)-2-(trifluoromethoxy)phenol (Scheme 9):

Compound 6 (7 g, 15 mmol) was dissolved in EA (20 mL). To the vessel was then added EA-HCl (20 mL, 1.5 M, 30 mmol), and the resulting solution was stirred for 2 h at RT. The solution was extracted by $H_2O$ (50 mL for 3 times). The combined aqueous layer, adjusted pH to 10 by saturated $Na_2CO_3$, extracted by EA (50 mL for 3 times), dried by $Na_2SO_4$ and concentrated under vacuum to get product 7 (5 g, 95%).

Example 18F illustrates preparation of a chiral amine intermediate (R)-4-(3-aminobutyl)-2-(trifluoromethoxy) phenyl dimethylcarbamate as shown in Scheme 10.

Scheme 10: Preparation of chiral amine (R)-4-(3-aminobutyl)-2-(trifluoromethoxy)phenyl dimethylcarbamate.

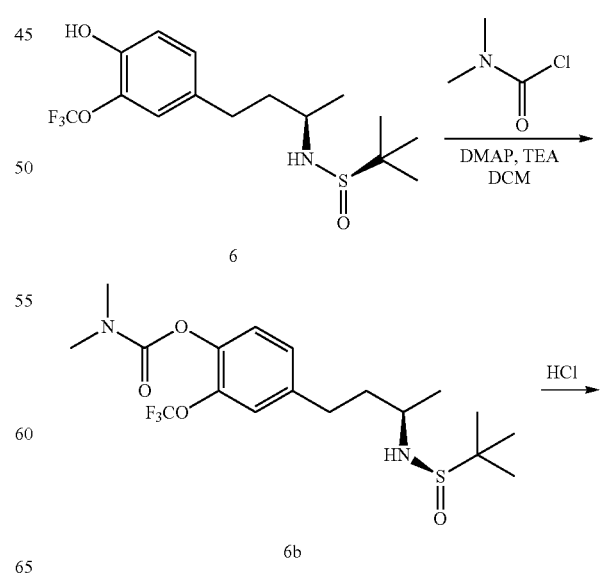

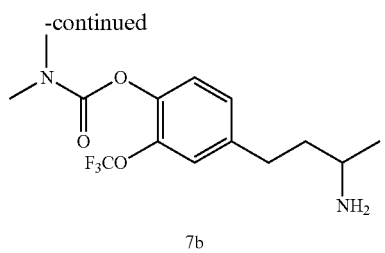

7b

Preparation of Compound 6b (Scheme 10):

To a stirred solution of 6 (4 g, 11.3 mmol, 1.0 eq) in DCM (50 mL) was added DMAP (0.2 g, 5 mol %), TEA (2.3 g, 22.6 mmol, 2.0 eq) and dimethylcarbamyl chloride 5 (1.5 g, 13.6 mmol, 1.2 eq). The mixture was stirred at 40° C. for 4 hrs, and quenched with ice water (20 mL). The mixture was extracted with DCM (3×50 mL). The combined organic layers were washed with brine, dried over $Na_2SO_4$ and concentrated under vacuum to furnish orange oil. The crude product was purified by column chromatography on silica gel (PE:EA=5:1) to give the title compound 6b (2.8 g, 58%).

Preparation of Compound 7b (Scheme 10):

To a stirred solution of 6b (3 g, 7.1 mmol, 1 eq) in EA (30 mL) at 0° C. was added EA (HCl) (10 mL). The mixture was stirred at rt for 2 h, concentrated under reduced pressure to afford 7b (1.8 g, 100%) as a yellow oil.

Example 18G illustrates preparation of a chiral amine intermediate (R)-2-(4-(3-aminobutyl)-2-(trifluoromethoxy)phenoxy)ethan-1-ol, as shown in Scheme 12.

Scheme 12: Preparation of chiral amine (R)-2-(4-(3-aminobutyl)-2-(trifluoromethoxy)phenoxy)ethan-1-ol.

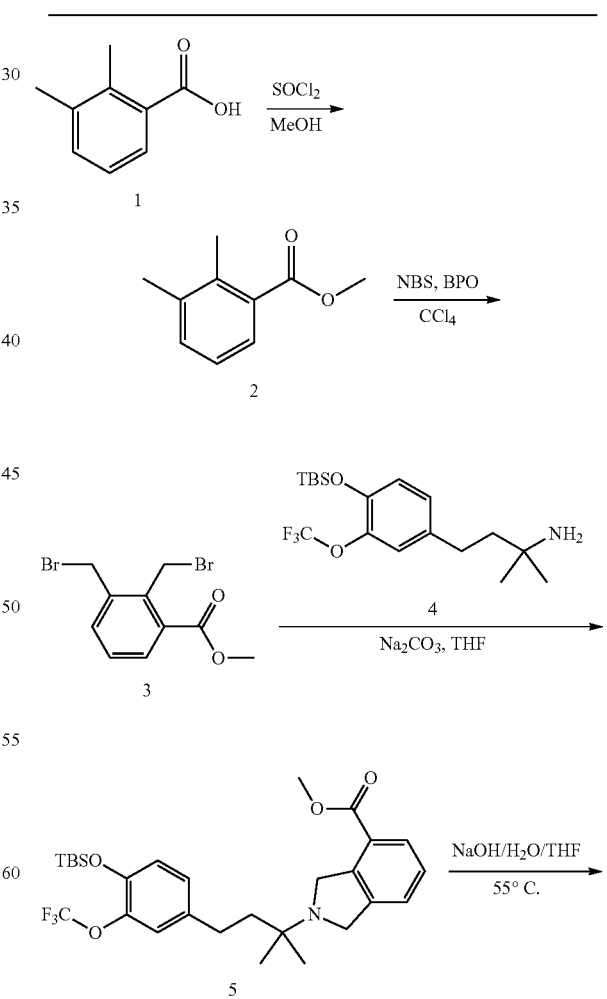

Preparation of Compound 2 (Scheme 12):

To a stirred solution of 1 (0.7 g, 2 mmol, 1.0 eq) in DMF (10 mL) was added $K_2CO_3$ (0.55 g, 4 mmol, 2.0 eq) and 2-bromoethanol (0.3 g, 2.4 mmol, 1.2 eq). The mixture was stirred at 80° C. for 8 hrs, then quenched with ice water (30 mL), extracted by EA (20 mL for 3 times). The combined organic layer was washed with brine, dried by $Na_2SO_4$ and concentrated under vacuum to furnish orange oil. The crude product was purified by column chromatography on silica gel (PE:EA=5:1) to give the title compound 2 (0.66 g, 83%).

Preparation of Compound 3 (Scheme 12):

To a stirred solution of 2 (0.9 g, 2.3 mmol, 1 eq) in EA (30 mL) was added EA (HCl) (10 ml) at 0° C. The mixture was stirred at rt for 2 h, concentrated under reduced pressure to afford 3 (0.75 g, 100%) as a yellow oil.

Example 19: General Preparation of Isoindolines from Chiral Amine Intermediates or Gem-Dimethyl Amine Intermediates Example 19A illustrates preparation of isoindoline compound 56, 2-(4-(4-hydroxy-3-(trifluoromethoxy)phenyl)-2-methylbutan-2-yl)isoindoline-4-carboxylic acid, from gem-dimethyl amine intermediate as shown in Scheme 13.

Scheme 13: Preparation of isoindoline 2-(4-(4-hydroxy-3-(trifluoromethoxy)phenyl)-2-methylbutan-2-yl)isoindoline-4-carboxylic acid (EXAMPLE 56).

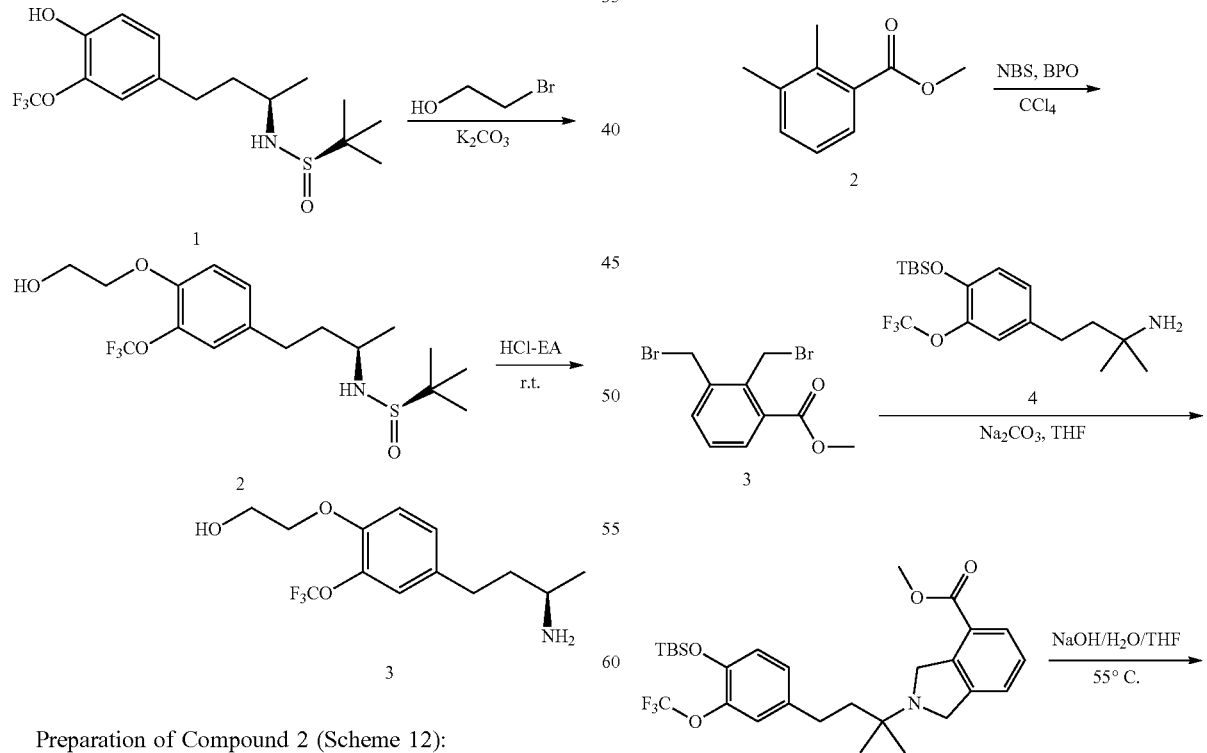

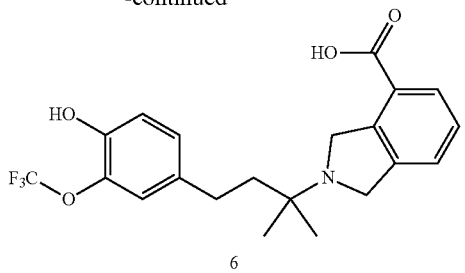

Preparation of Compound 2 (Scheme 13):

To a solution of 1; 2,3-dimethylbenzoic acid (2.0 g, 13.3 mmol, 1.0 eq) in MeOH (30 mL) was added thionyl chloride (1.5 mL) and stirred at reflux for 3 h. The mixture was concentrated, extracted with EA (30 mL). The organic layers were washed with water (2×30 mL), dried over $Na_2SO_4$, concentrated to give the desired product 2 without further purification (2.1 g, 98%).

Preparation of Compound 3 (Scheme 13):

To a solution of 2 (2.1 g, 13.3 mmol, 1.0 eq) in $CCl_4$ (30 mL) was added NBS (4.7 g, 26.6 mmol, 2.0 eq) and BPO (0.2 g). The mixture was heated to reflux for 4 h. The reaction was diluted with DCM (30 mL), washed by water (2×30 mL), dried over $Na_2SO_4$, concentrated to give a crude product, which was purified by column chromatography to give compound 3; methyl 2,3-bis(bromomethyl)benzoate (4.0 g, 94%).

Preparation of Compound 5 (Scheme 13):

To a solution of 3 (0.3 g, 0.93 mmol, 1.0 eq) in THF (10 mL) was added $Na_2CO_3$ (0.2 g, 1.9 mmol, 2.0 eq). The mixture was stirred at reflux for 4 h. The result mixture was diluted with EA, washed with brine, concentrated to get the crude product 5 without further purification (300 mg, 82%).

Preparation of Compound 6 (Scheme 13):

To a solution of 5 (0.3 g, 0.56 mmol, 1.0 eq) in THF (5 mL) was added 10 N NaOH (5 mL). The mixture was stirred at 55° C. for 4 h. The result mixture was concentrated and adjusted to pH 5 with 6N HCl. The mixture was extracted with EA. The organic layer was dried over sodium sulfate, and concentrated to give a residue, which was purified by pre-HPLC to give the desired product, 2-(4-(4-hydroxy-3-(trifluoromethoxy)phenyl)-2-methylbutan-2-yl)isoindoline-4-carboxylic acid (Example compound 56) as white solid (86 mg, 37%). $^1$H NMR (400 MHz, $CD_3OD$): δ 8.04 (d, J=7.6 Hz, 1H), 7.63 (d, J=7.2 Hz, 1H), 7.54 (t, J=8.0 Hz, 1H), 7.14 (s, 1H), 7.10 (d, J=8.8 Hz, 1H), 6.90 (d, J=8.0 Hz, 1H), 5.10-4.70 (m, 4H), 2.73-2.69 (m, 2H), 2.10-2.06 (m, 2H), 1.56 (s, 6H); m/z (ESI+) (M+H)+=410.15. LC-MS: 410.1 (M+1)$^+$.

Example 19B illustrates representative preparation of sulfone-substituted isoindoline compound, 2-methoxy-4-(3-methyl-3-(4-(methylsulfonyl)isoindolin-2-yl)butyl)phenol hydrochloride, from gem-dimethyl amine intermediate as shown in Scheme 14.

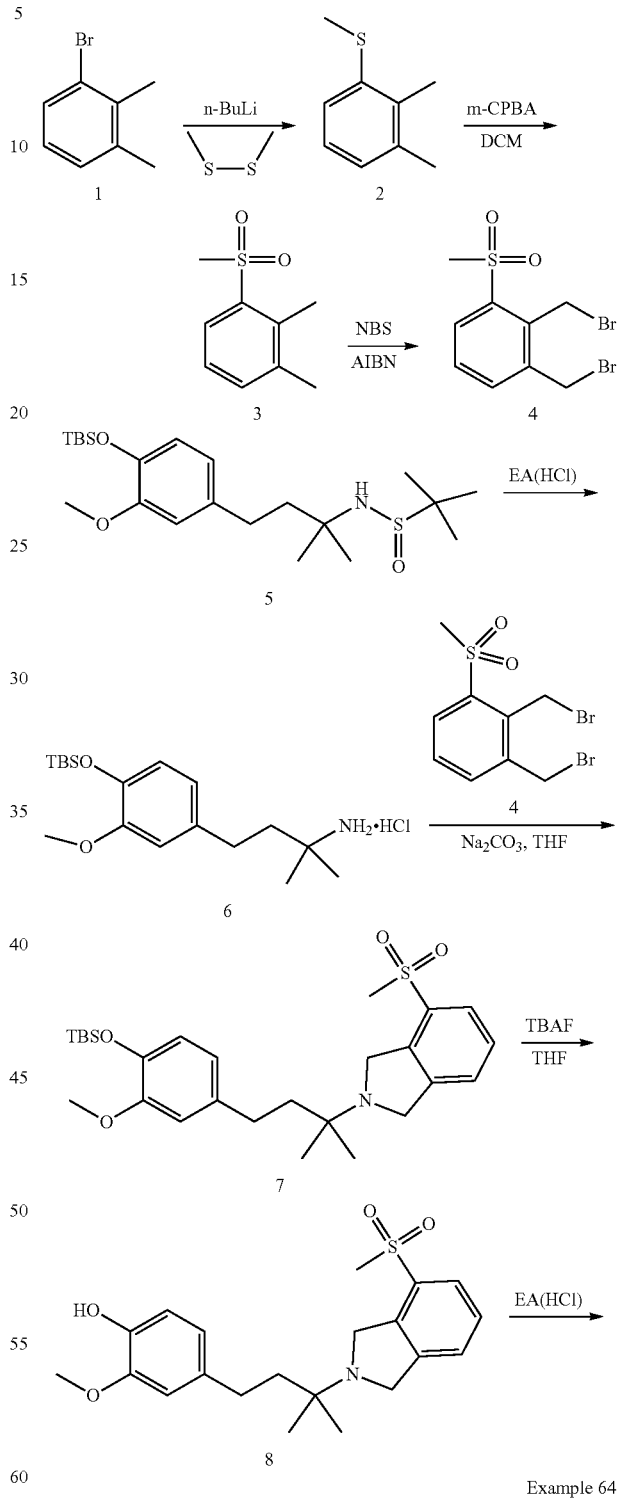

Scheme 14: General procedure for preparation of sulfone-substituted isoindoline 2-methoxy-4-(3-methyl-3-(4-(methylsulfonyl)isoindolin-2-yl)butyl)phenol hydrochloride (Example Compound 64).

Example 64

Preparation of Compound 2 (Scheme 14):

To a stirred solution of 1 (12.0 g, 64.8 mmol, 1 eq) in THF (150 mL) was added n-BuLi (30 mL, 2.5M) at −75° C. The mixture was stirred at −75° C. for 1 h, and then added dimethyl disulfide (7.2 g, 76.4 mmol) dropwisel. The mixture was stirred at −75° C. for 4 h, and quenched with saturated NH$_4$Cl solution, extracted with ethyl acetate, dried over Na$_2$SO$_4$, concentrated under reduced pressure to afford crude product 2 (12 g, 100%). 1-Bromo-2,3-dimethylbenzene was purchased from Shanghai RuiDing Chemical Co. Ltd.

Preparation of Compound 3 (Scheme 14):

To a stirred solution of 2 (12.0 g, 78.8 mmol, 1 eq) in DCM (200 mL) was added m-CPBA (30 g, 173.8 mmol) at 0° C. The mixture was stirred at 10° C. for 2 h and quenched with 10% Na$_2$SO$_3$. The aqueous solution was adjusted to pH 10 with 10% NaOH, extracted with DCM, dried over Na$_2$SO$_4$, concentrated under reduced pressure to afford crude product, which was purified with column chromatography (PE:EA=5:1) to afford the title compound 3 (9.0 g, 62%). 3-Chloroperbenzoic acid was purchased from Shanghai DeMo Chemical Co. Ltd.

Preparation of Compound 4 (Scheme 14):

To a stirred solution of 3 (1.0 g, 5.42 mmol) in CCl$_4$ (15 mL) was added NBS (2.22 g, 12.4 mmol, 1.2 eq) and AIBN (400 mg, 2.43 mmol). The mixture was stirred at 70° C. for 6 h, cooled, concentrated in vacuo, purified by column chromatography (PE:EA=3:1) to afford the title compound 4 (1.4 g, 75%). N-Bromosuccinimide was purchased from Shanghai JingChun Chemical Co. Ltd. Azobisisobutyronitrile was purchased from Shanghai GuoYao Chemical Co. Ltd.

Preparation of Compound 6 (Scheme 14):

To a solution of 6 (4.0 g, 1.2 mol) in EA (100 mL), HCl/EA (1.2 g, 2M, 200 mol) was added. The resulting solution was stirred at rt for 1 h. The reaction was concentrated to get the crude product 7 (2.8 g, 99%), which was used for next step without further purification.

Preparation of Compound 7 (Scheme 14):

To a solution of 6 (280 mg, 1.20 mmol) in THF (10 mL), 4 (410 mg, 1.2 mmol) and K$_2$CO$_3$ (330 mg, 2.4 mmol) was added. The resulting solution was stirred at 70° C. for 12 h. The reaction mixture was filtered through a pad of Celite, washed with EA, and the filtrate was concentrated to obtain the crude product 7 (500 mg, 100%), which was used for next step without further purification.

Preparation of Compound 8 (Scheme 14):

To a solution of 7 (500 mg, crude) in THF (10 mL), TBAF (1.2 mL, 1M) was added. The resulting solution was stirred at rt for 1 h. The reaction mixture was concentrated to get the residue which was purified by Prep-HPLC to get 8 (120 mg, 20% over two steps).

Preparation of Compound 9; 2-methoxy-4-(3-methyl-3-(4-(methylsulfonyl)isoindolin-2-yl)butyl)phenol hydrochloride (Example Compound 64) (Scheme 14):

To a solution of 8 (120 mg, 0.30 mol) in EA (10 mL), HCl/EA (1.2 g, 2M, 2 mmol) was added. The resulting solution was stirred at rt for 1 h. The reaction was concentrated to get the product 9 (90 mg, 75%). 1H NMR (400 MHz, CD3OD): δ 7.97 (d, J=7.2 Hz, 1H), 7.78-7.68 (m, 2H), 6.88 (s, 1H), 6.72 (s, 2H), 5.09 (s, 2H), 4.85 (s, 2H), 3.85 (s, 3H), 3.20 (s, 3H), 2.73-2.70 (m, 2H), 2.13-2.10 (m, 2H), 1.58 (s, 6H); m/z (ESI+) (M+H)+=390.15.

Example 19C illustrates representative preparation of sulfone-substituted isoindoline compound, 2-methoxy-4-(3-methyl-3-(5-(methylsulfonyl)isoindolin-2-yl)butyl)phenol hydrochloride, from gem-dimethyl amine intermediate as shown in Scheme 15.

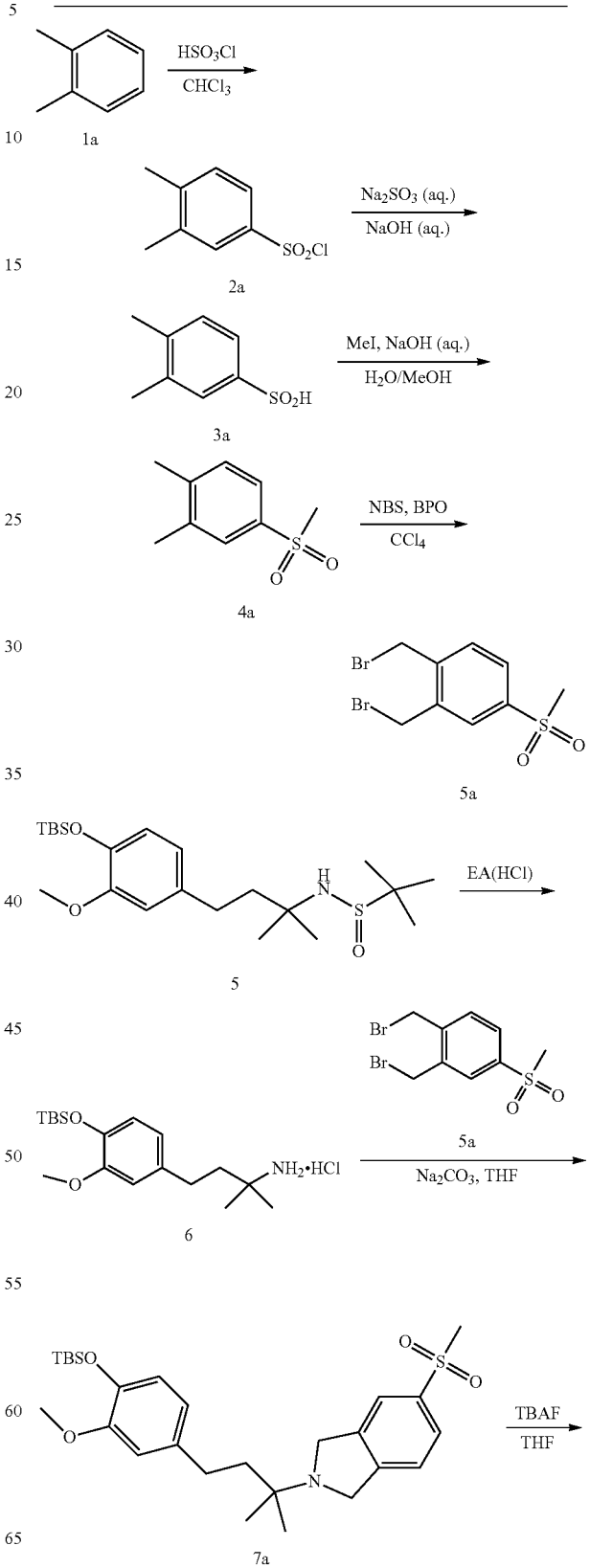

Scheme 15: General procedure for preparation of sulfone-substituted indoline 20-methoxy-4-(3-methyl-3-(5-(methylsulfonyl)isoindolin-2-yl)butyl)phenol hydrochloride.

-continued

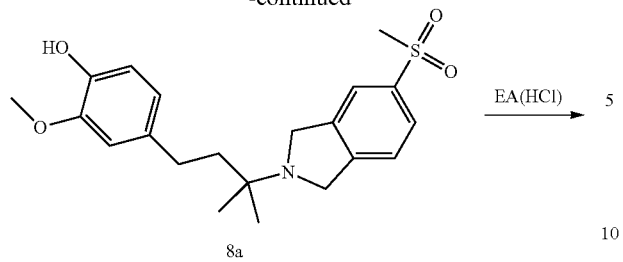

8a

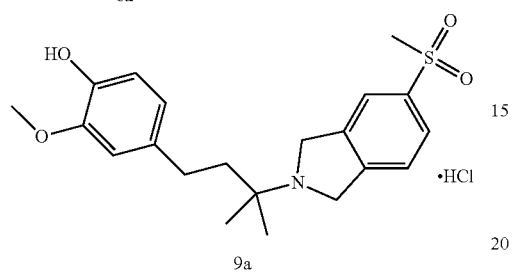

9a

Preparation of Compound 2a (Scheme 15):

To the solution of 1 (50 g, 0.47 mol, 1.00 eq) in CHCl$_3$ (500 mL) was added HSO$_3$Cl (75.5 mL, 0.95 mol, 2.00 eq) dropwisely under ice-cooling bath. After the addition was completed, warmed the mixture to rt, and stirred for 1 h. The resulting mixture was poured into ice-water and then extracted with DCM (500 mL) for 3 times. Combined organic layer was washed with water, brine, dried over Na$_2$SO$_4$, concentrate in vacuo to afford the white solid product 2a (76.5 g, 79.3%). 1,2-Dimethylbenzene was purchased from Shanghai GuoYao Chemical Co. Ltd. Chlorosulfonic acid was purchased from Shanghai AoYue Chemical Co. Ltd.

Preparation of Compound 3a (Scheme 15):

To a suspension of 2 (77 g, 0.38 mol, 1.00 eq) in sat. Na$_2$SO$_3$ (118 g, 0.94 mol, 2.50 eq), 32% NaOH (30 g, 0.75 mol, 2.00 eq) solution was added. After stirring 3 h at rt, the reaction was acidified to pH=1 with 25% HCl solution under ice-cooling bath. The precipitate is the crude product 3a (59.75 g, 93.8%), which was used without further purification.

Preparation of Compound 4a (Scheme 15):

In a sealed glass tube, to a suspension of 3 (20 g, 0.12 mol, 1.00 eq) in a mixture of H$_2$O (50 mL) and MeOH (67.5 mL) solution, methyl iodine (20 g, 0.14 mol, 1.15 eq) and 32% NaOH (47 g, 1.2 mol, 10.00 eq) solution were added. The reaction was heated to 90° C. and stirred overnight. After the reaction was completed, the methanol was removed under reduced pressure, and extracted with EA, concentrate to afford the product 4a (8.33 g, 38.5%). Methyl iodide was purchased from Shanghai AoYue Chemical Co. Ltd.

Preparation of Compound 5a (Scheme 15):

To a solution of compound 4 (9.5 g, 51.6 mmol, 1.00 eq) in CCl4, NBS (18.3 g, 103 mmol, 2.00 eq) and BPO (1.0 g, 5.2 mmol, 0.10 eq) were added. The reaction was heated to reflux for 6 h. After the reaction was completed, the solvent was removed under reduced pressure. The obtained residue was diluted with PE and H$_2$O. The organic layer was dried over Na$_2$SO$_4$ and concentrated to afford the crude product, which was purified by FCC (PE:EA=10:1~3:1) to obtain sulfone intermediate 5a; 1,2-bis(bromomethyl)-4-(methylsulfonyl)benzene.

Preparation of compound 9a, 2-methoxy-4-(3-methyl-3-(5-(methylsulfonyl)isoindolin-2-yl)butyl)phenol hydrochloride, was performed from intermediate 5a, by the techniques described in Example 19B.

Example 20: Preparation of 4-(3-(4-Fluoroisoindolin-2-yl)-3-methylbutyl)-2-isopropoxyphenol hydrochloride, Example Compound 28

Example 20 illustrates representative preparation of 4-(3-(4-Fluoroisoindolin-2-yl)-3-methylbutyl)-2-isopropoxyphenol hydrochloride, Example Compound 28, as shown in Scheme 16.

Scheme 16: Procedure for preparation of 4-(3-(4-Fluoroisoindolin-2-yl)-3-methylbutyl)-2-isopropoxyphenol hydrochloride, Example Compound 28.

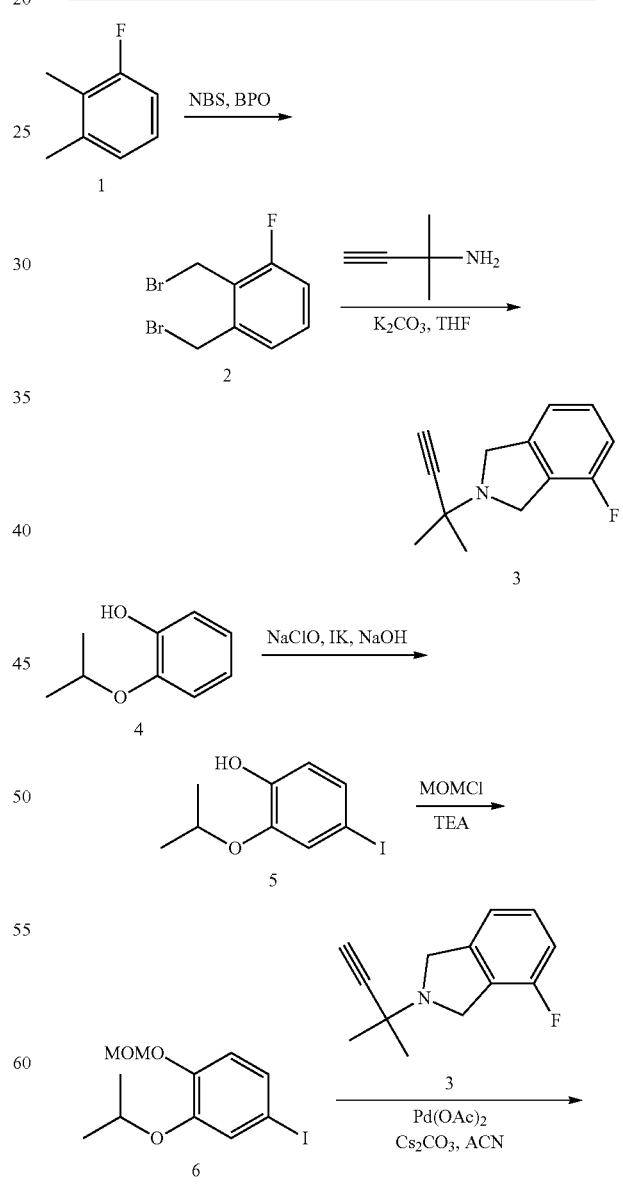

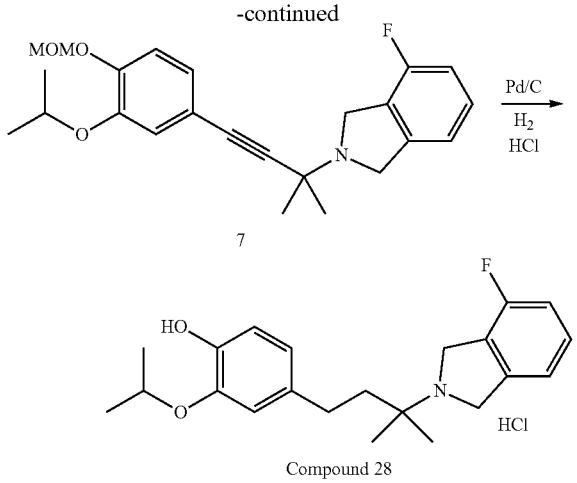

Compound 28

Preparation of Compound 2 (Scheme 16):

To a suspension of 1-fluoro-2,3-dimethylbenzene (100 g, 0.81 mmol) in carbon tetrachloride (1.5 L) were added N-bromosuccinimide (288 g, 1.62 mmol), benzoyl peroxide (10 g). The mixture was heated to 70° C. After stirring for 15 h, the mixture was cooled to rt, poured into water (1 L) and extracted with DCM (3×1 L). The combined organic layers were purified by flash column chromatography with petroleum ether to give the product 2 (161 g, 70%) as white solid.

TLC: PE/EA=10/1; $R_f$ (Compound 1)=1; $R_f$ (Compound 2)=0.8

Preparation of Compound 3 (Scheme 16):

To a mixture of 1,1-dimethylpropargylamine (20 g, 240 mmol, 1.0 eq) in THF (900 mL) was added compound 2 (70.7 g, 253 mmol, 1.05 eq) and triethylamine (73 g, 720 mmol, 3 eq). The reaction was stirred at 60° C. for 12 h. The mixture was filtered through a pad of Celite, and the pad was washed with ethyl acetate. The filtrate was concentrated in vacuo to give an orange oil. The residue was purified by flash column chromatography (PE/EA, 10/1) to afford compound 3 (30 g, 61%) as yellow solid. TLC: PE/EA=10/1; $R_f$ (Compound 2)=0.8; $R_f$ (Compound 3)=0.5.

Preparation of Compound 5 (Scheme 16):

To a solution of 2-isopropoxy-phenol (100 g, 0.66 mol, 1.0 eq) in methanol (700 mL) was added sodium hydroxide (39.4 g, 1.0 mol, 1.5 eq) and potassium iodide (114.5 g, 0.69 mol, 1.05 eq). The reaction was stirred at rt. To the reaction mixture was added sodium hypochlorite (978 g, 1.31 mol, 2.0 eq) dropwise. When LCMS indicated the starting material was gone, concentrate HCl was added until pH 1. Sodium sulfite (56 g, 445 mmol, 1.0 eq) was added. The mixture was extracted with ethyl acetate (3×500 mL), and the combined organic layers were washed with brine, dried over sodium sulfate, filtered and concentrated in vacuo to afford compound 5 (175 g, 96%) as white solid. TLC: PE/EA=10/1; $R_f$ (Compound 4)=0.4; $R_f$ (Compound 5)=0.4

Preparation of Compound 6 (Scheme 16):

To a solution of compound 5 (350 g, 1.26 mol, 1.0 eq) in DMF (2 L) was added sodium hydride (65.4 g, 1.64 mol, 1.3 eq) at 0° C. under nitrogen. After stirring for 0.5 h, chloromethyl methyl ether (131.7 g, 1.64 mmol, 1.3 eq) was slowly added. The reaction was stirred at rt for 2 h. The reaction was quenched with water (4 L) and extracted with ethyl acetate (3×1 L). The combined organic layers were washed with brine, dried over sodium sulfate, filtered and concentrated in vacuo to afford crude product. The residue was purified by flash column chromatography (PE/EA, 10/1) to afford compound 6 (300 g, 74%) as white solid. TLC: PE/EA=10/1; $R_f$ (Compound 5)=0.4; $R_f$ (Compound 6)=0.6

Preparation of Compound 7 (Scheme 16):

To a solution of compound 6 (56.2 g, 174 mmol, 1.0 eq) in acetonitrile (600 mL) was added compound 3 (39 g, 192 mmol, 1.1 eq) and X-Phos (4.16 g, 9.0 mmol, 0.05 eq) followed by cesium carbonate (56.9 g, 174 mmol, 1.0 eq) and palladium diacetate (1.2 g, 5.23 mmol, 0.03 eq). The reaction was stirred at 60° C. for 12 h. The reaction quenched with ice water (1 L) followed by extracting with ethyl acetate (3×500 mL). The combined organic layers were washed with brine, dried over sodium sulfate, filtered and concentrated in vacuo to afford crude product. The residue was purified by flash column chromatography (PE/EA, 10/1) to afford compound 6 (48.5 g, 70%) as brown solid. TLC: PE/EA=10/1; $R_f$ (Compound 6)=0.6; $R_f$ (Compound 7)=0.3.

Preparation of Compound 28 (Scheme 16):

To a solution of compound 7 (72 g, 181 mmol, 1.0 eq) in methanol (1.4 L) was added concentrate HCl (36 mL, 360 mmol, 2.0 eq) and 10% palladium on activated carbon (14 g). The reaction was stirred at rt for 4 h under hydrogen balloon. The mixture was filtered through a Celite pad, and the pad was washed with methanol. The filtrate was concentrated in vacuo to afford a pale orange oil. The residue was diluted with ether, stirred at room temperature and a solid was formed. The solid was filtered and washed with ethanol to afford Example Compound 28 (60 g, 93%) as a white solid. TLC: PE/EA=3/1; $R_f$ (Compound 7)=0.6; $R_f$ (Product example compound 28)=0.3. LC-MS: 358.2 (M+1)+. $^1$H NMR (400 MHz, DMSO-d6) δ 12.17 (s, 1H), δ 8.59 (s, 1H), δ 7.43 (m, 1H), δ 7.21 (m, 2H), δ 6.80 (s, 1H), 6.71-6.63 (m, 2H), 4.88-4.79 (m, 2H), δ 4.66 (m, 2H), δ 4.47 (m, 2H), δ 2.53 (m, 2H), δ 1.97 (m, 2H), δ 1.43 (s, 6H), δ 1.22 (s, 6H).

Example 21: Preparation of 2-(Tert-butoxy)-4-(3-methyl-3-(5-(methylsulfonyl)isoindolin-2-yl)butyl) phenol, Example Compound 62

Example 21 illustrates representative preparation of 2-(Tert-butoxy)-4-(3-methyl-3-(5-(methylsulfonyl)isoindolin-2-yl)butyl)phenol, Example Compound 62, as shown in Scheme 17.

Scheme 17: Procedure for preparation of 2-(Tert-butoxy)-4-(3-methyl-3-(5-(methylsulfonyl)isoindolin-2-yl)butyl)phenol, Example Compound 62.

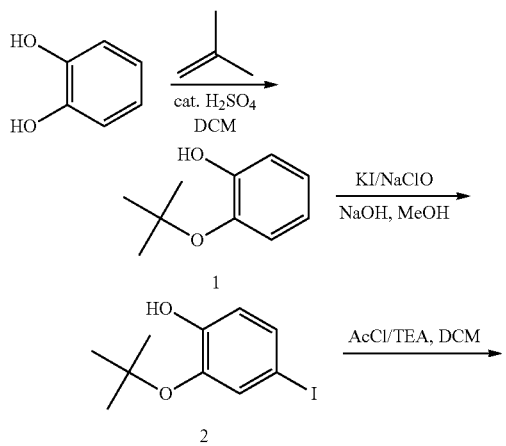

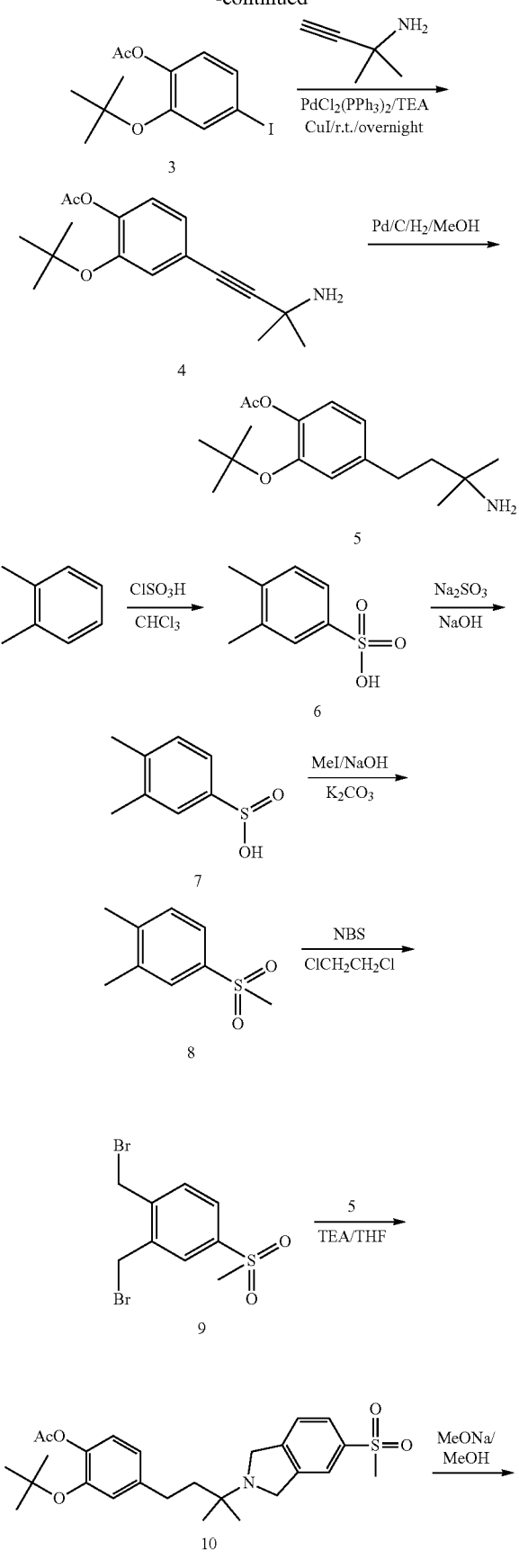

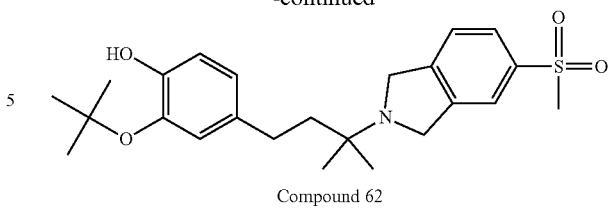

Compound 62

Preparation of Compound 1 (Scheme 17):

To a glass pressure-bottle at −30° C. containing a mixture of catechol (50.0 g, 454 mmol, 1.0 eq), concentrated sulfuric acid (0.3 mL) in dichloromethane (200 mL), isobutene (152.6 g, 2.72 mol, 6.0 eq) was condensed. After sealing the pressure-bottle with a threaded Teflon cap tipped with a Teflon-protected rubber O-ring, the mixture was heated at 35° C. for 3 h until a clear solution was obtained. After cooling (−30° C.), triethylamine (1.5 mL, 10.8 mmol) was added and the mixture was concentrated. The residue was suspended in 0.5 M NaOH (1 L) and stirred for 10 min. The dark-green colored solution was washed with petroleum ether (2×100 mL) and the washing layers were reextracted with 0.5 M NaOH (3×100 mL). The combined aqueous layers were brought to pH 7-8 with 2 N HCl (400 mL), and extracted with ethyl acetate (2×1 L), dried over sodium sulfate and concentrated to afford product 1 (67.7 g, 90%) as a colorless oil, which was used directly for the next step reaction without further purification. TLC: PE/EA=50/1; $R_f$ (Catechol)=0.1; $R_f$ (Compound 1)=0.6.

Preparation of Compound 2 (Scheme 17):

To a stirred solution of compound 1 (112.2 g, 676 mmol, 1.2 eq) and potassium iodide (112.2 g, 676 mmol, 1.0 eq) in methanol (2 L) at 0° C. was slowly added sodium hydroxide (27.0 g, 676 mmol, 1.0 eq), followed with aqueous sodium chlorite (7% aq., 718.8 mL, 710 mmol, 1.05 eq) dropwise over 3 h while keeping the reaction below 0° C. The mixture was stirred at 0° C. for another 30 min and neutralized by adding 2 N HCl at 0° C. till pH 7, extracted with DCM (2×1 L). The organic layers were dried over sodium sulfate and concentrated to afford product 2 (179.8 g, 91%). TLC: PE/EA=50/1; $R_f$ (Compound 1)=0.6; $R_f$ (Compound 2)=0.6.

Preparation of Compound 3 (Scheme 17):

To a stirred solution of compound 2 (179.8 g, 616 mmol, 1.0 eq) and triethylamine (186.6 g, 1.85 mol, 3.0 eq) in dichloromethane (2 L) at 0° C. was slowly added acetyl chloride (53.2 g, 677 mmol, 1.1 eq). The mixture was stirred at 0° C. for another 30 min, and warmed up to rt, and stirred at rt for 3 h, water (1 L) was added into the reaction mixture and the organic layer was washed with brine, dried over sodium sulfate and concentrated to afford product 3 (206 g, 100%), which was used directly to the next step without further purification. TLC: PE/EA=50/1; $R_f$ (Compound 2)=0.6; $R_f$ (Compound 3)=0.5.

Preparation of Compound 4 (Scheme 17):

To a stirred solution of compound 3 (206 g, 616 mmol, 1.0 eq) in triethylamine (4.0 L) was added 2-methylbut-3-yn-2-amine (102.5 g, 1.23 mol, 2.0 eq), Pd(PPh$_3$)$_2$Cl$_2$ (15.1 g, 18.5 mmol, 0.03 eq) and copper(I) iodide (5.9 g, 31 mmol, 0.05 eq) and resulting mixture was stirred at rt for 17 h. The solvent was removed under reduced pressure and the crude product was purified by silica gel chromatography to afford the title compound 4 (132.7 g, 74%). TLC: PE/EA=1/1; $R_f$ (Compound 3)=0.9; $R_f$ (Compound 4)=0.3.

Preparation of Compound 5 (Scheme 17):

To a stirred solution of compound 4 (104.5 g, 0.36 mol) in ethanol (1.5 L) was added Pd/C (10% wt, 10.5 g). The mixture was stirred under hydrogen (balloon) overnight, and filtered. The filtrate was evaporated to dryness to afford compound 5 (106.3 g, 100%), which was used directly to the next step without further purification. TLC: PE/EA=1/1; $R_f$(Compound 4)=0.3; $R_f$(Compound 5)=0.3.

Preparation of Compound 6 (Scheme 17):

To a solution of o-xylene (115.7 g, 1.09 mol, 1.0 eq) in chloroform (1.0 L) at 0° C. was added $ClSO_3H$ (254 g, 2.18 mol, 2.0 eq) dropwise. After the addition, the reaction mixture was stirred at room temperature for 2 days, and poured into ice. The crude mixture was extracted with dichloromethane (3×1.0 L). The organic layers were combined, dried over anhydrous sodium sulfate, concentrated to afford the crude compound 6 (161.5 g, 80%) as a white solid, which was used directly to the next step without further purification. TLC: PE/EA=5/1; $R_f$(Compound 6)=0.7.

General Procedure for the Preparation of Compound 7 (Scheme 17):

To a stirred solution of compound 6 (161.5 g, 0.87 mol, 1.0 eq) in saturated sodium sulfite solution (273 g, 2.17 mol, 2.5 eq, in 2.0 L of water) was added dropwise 32% NaOH (69.4 g, 1.73 mol, 2.0 eq) till the solution reached pH 9. After stirring at rt overnight, the reaction mixture was acidified with conc. HCl in ice-cooling bath till pH 1. The precipitate was filtered, and washed with ice-water (2×), dried in vacuo to afford the crude product 7 (131 g, 88%), which was used directly for next step without further purification. TLC: PE/EA=5/1; $R_f$(Compound 6)=0.7; $R_f$(Compound 7)=0.6.

Preparation of Compound 8 (Scheme 17):

To a stirred solution of compound 7 (130 g, 0.76 mol, 1.0 eq) and potassium carbonate (211 g, 1.53 mol, 2.0 eq) in DMF (300 mL) was added iodomethane (96 mL, 1.53 mol, 2.0 eq). The reaction was stirred at 40° C. overnight. The reaction mixture was evaporated to dryness, extracted with ethyl acetate. The organic layers were washed with water and brine, dried over sodium sulfate and concentrated, purified by flash column chromatography (PE: EA, 10:1 5:1) to afford compound 8 (85.2 g, 61%). TLC: PE/EA=5/1; $R_f$(Compound 7)=0.6; $R_f$(Compound 8)=0.3.

Preparation of Compound 9 (Scheme 17):

To a stirred solution of compound 8 (78.2 g, 424 mmol, 1.0 eq) in 1,2-dichloroethane (1.2 L), were added N-bromosuccinimide (166 g, 934 mmol, 2.2 eq) and AIBN (6.9 g, 42.4 mmol, 0.1 eq). The reaction was stirred at reflux overnight. The reaction was diluted with water and dichloromethane. The organic layer was collected, and dried over sodium sulfate and concentrated, purified by flash column chromatography to afford compound 9, which was further recrystallized from hot methanol to afford the pure product 8 (75 g, 52%). TLC: PE/EA=5/1; $R_f$(Compound 8)=0.3; $R_f$(Compound 9)=0.2.

Preparation of Compound 10 (Scheme 17):

To a stirred solution of compound 5 (46 g, 157 mmol, 1.0 eq) and compound 9 (53.5 g, 157 mmol, 1.0 eq) in THF (460 mL) was added triethylamine (47.7 g, 472 mmol, 3.0 eq). The reaction was stirred at 40° C. overnight, filtered and the filtrate was evaporated to dryness and purified by flash column chromatography to afford compound 10 (45 g, 63%). TLC: PE/EA=1/1; $R_f$(Compound 5)=0.3; $R_f$(Compound 9)=1.0; $R_f$(Compound 10)=0.4.

Preparation of Compound 62 (Scheme 17):

To a stirred solution of compound 10 (45 g, 98.4 mmol) in methanol (300 mL) was added sodium methoxide (844 mg, 15.6 mmol, 0.16 eq) in one portion. The solution was stirred at rt overnight. Water (250 mL) was added dropwise into the reaction mixture over 1 h, the mixture was stirred at rt for 2 h, and filtered. The white solid was collected and dried on vacuum overnight to afford pure example Compound 62 base (38 g, 89%). TLC: PE/EA=1/1; $R_f$ (Compound 10)=0.4; $R_f$ (Compound 62)=0.4; ESI-MS: 432 (M+1)+; $^1$H NMR (400 MHz, $CDCl_3$) δ 7.80-7.78 (m, 2H). 7.40-7.38 (m, 1H), 6.87-6.79 (m, 3H), 5.58 (s, 1H), 4.11 (s, 4H), 3.05 (s, 3H), 2.61-2.57 (m, 2H), 1.76-1.72 (m, 2H), 1.48 (s, 9H), 1.18 (s, 6H).

Example 22: Preparation of (2-(4-(4-Hydroxy-3-methoxyphenyl)-2-methylbutan-2-yl)isoindolin-4-yl)(piperazin-1-yl)methanone, Example Compound 76

Example 22 illustrates representative preparation of (2-(4-(4-hydroxy-3-methoxyphenyl)-2-methylbutan-2-yl)isoindolin-4-yl)(piperazin-1-yl)methanone, Example Compound 76, as shown in Scheme 18.

Scheme 18: Procedure for preparation of (2-(4-(4-Hydroxy-3-methoxyphenyl)-2-methylbutan-2-yl)isoindolin-4-yl)(piperazin-1-yl)methanone, Example Compound 76.

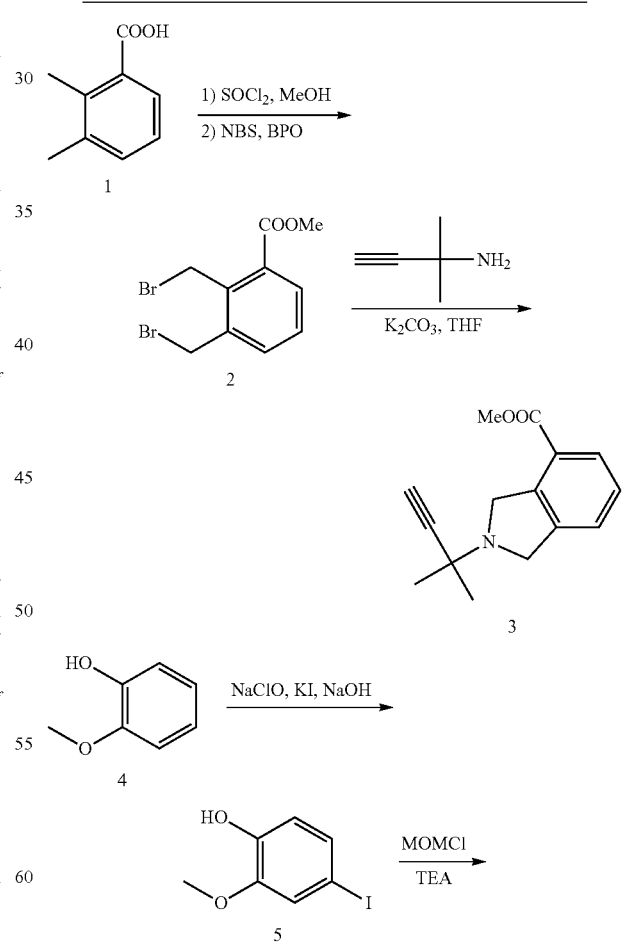

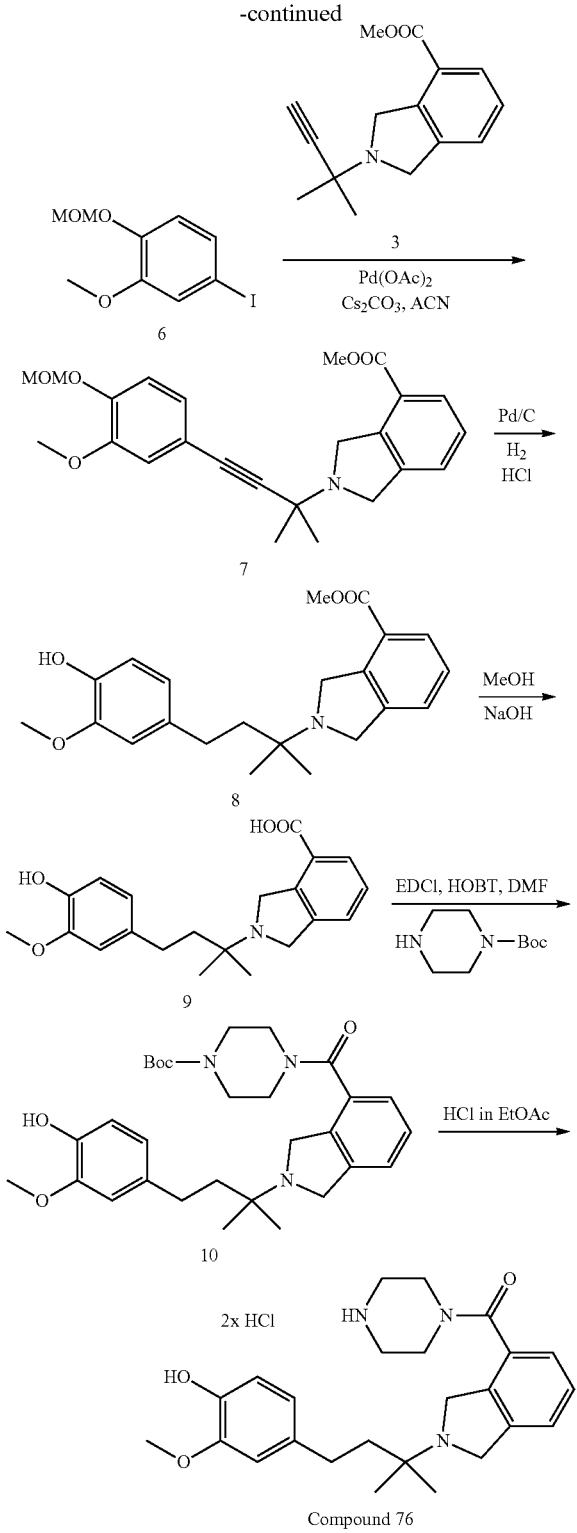

Preparation of Compound 2 (Scheme 18):

To a solution of 2,3-dimethylbenzoic acid (60 g, 0.399 mol) in methanol at 0° C. was added thionyl chloride (20 mL). The reaction was heated to 60° C. After stirring overnight, the reaction was cooled and concentrated to afford crude methyl ester (65 g, 0.396 mol). To a suspension of the crude methyl ester (65 g, 0.396 mol) in carbon tetrachloride (500 mL) were added N-bromosuccinimide (142.2 g, 0.798 mmol), benzoyl peroxide (6 g, 24.8 mmol). The mixture was heated to 70° C. After stirring for 15 h, the mixture was cooled to rt, poured into water (250 mL) and extracted with dichloromethane (3×250 mL). The combined organic layers were purified by flash column chromatography with petroleum ether to give the product 2 (120 g, 94%) as white solid. TLC: PE/EA=10/1; $R_f$ (methyl ester of compound 1)=0.8; $R_f$(Compound 2)=0.7.

Preparation of Compound 3 (Scheme 18):

To a mixture of 1,1-dimethylpropargylamine (11.4 g, 0.14 mol, 1.0 eq) in THF (500 mL) was added methyl 2,3-bis (bromomethyl)benzoate (40.0 g, 0.125 mol, 1.1 eq) and triethylamine (50.5 g, 0.50 mol, 4.0 eq). The reaction was stirred at 60° C. for 12 h. The mixture was filtered through a pad of Celite, and the pad was washed with ethyl acetate. The filtrate was concentrated in vacuo to give an orange oil. The residue was purified by flash column chromatography (PE/EA: 10/1) to afford compound 3 (19 g, 62%) as yellow solid. TLC: PE/EA=10/1; $R_f$(Compound 2)=0.8; $R_f$(Compound 3)=0.5.

Preparation of Compound 5 (Scheme 18):

To a solution of 2-methoxyphenol (100 g, 0.81 mol, 1.0 eq) in methanol (1 L) was added sodium hydroxide (48.3 g, 1.21 mol, 1.5 eq) and potassium iodide (140.4 g, 0.84 mol, 1.05 eq). The reaction was stirred at rt. To the reaction mixture was added sodium hypochlorite (1199 g, 1.61 mol, 2.0 eq) dropwise. When LCMS indicated the starting material was gone. Concentrate HCl was added until pH 1. Sodium sulfite (56 g, 0.44 mol, 0.54 eq) was added. The mixture was extracted with ethyl acetate (3×500 mL), and the combined organic layers were washed with brine, dried over sodium sulfate, filtered and concentrated in vacuo to afford compound 5 (160 g, 79%) as yellow oil. TLC: PE/EA=10/1; $R_f$(Compound 4)=0.4; $R_f$(Compound 5)=0.4.

Preparation of Compound 6 (Scheme 18):

To a solution of compound 5 (31.4 g, 125.8 mmol, 1.0 eq) in DMF (200 mL) was added sodium hydride (6.54 g, 163.6 mmol, 1.3 eq) at 0° C. under nitrogen. After 0.5 h, chloromethyl methyl ether (13.2 g, 163.6 mmol, 1.3 eq) was slowly added. The reaction was stirred at rt for 2 h. The reaction quenched by water (400 mL) and extracted with ethyl acetate (3×200 mL). The combined organic layers were washed with brine, dried over sodium sulfate, filtered and concentrated in vacuo to afford crude product. The residue was purified by flash column chromatography (PE/EA, 10/1) to afford compound 6 (30 g, 74%) as yellow oil. TLC: PE/EA=10/1; $R_f$ (Compound 5)=0.4; $R_f$ (Compound 6)=0.6.

Preparation of Compound 7 (Scheme 18):

To a solution of compound 6 (10.2 g, 34.5 mmol, 1.2 eq) in acetonitrile (120 mL) was added compound 3 (7.00 g, 28.7 mmol, 1.0 eq) and X-Phos (624 mg, 1.30 mmol, 0.05 eq) followed by cesium carbonate (9.38 g, 28.7 mmol, 1.0 eq) and palladium diacetate (168 mg, 0.74 mmol, 0.03 eq). The reaction was stirred at 60° C. for 12 h. The reaction quenched with ice water (100 mL) and extracted with ethyl acetate (3×300 mL). The combined organic layers were washed with brine, dried over sodium sulfate, filtered and concentrated in vacuo to afford crude product. The residue was purified by flash column chromatography (PE/EA, 10/1) to afford compound 6 (9.4 g, 79%) as brown solid. TLC: PE/EA=10/1; $R_f$(Compound 6)=0.6; $R_f$(Compound 7)=0.3.

Preparation of Compound 8 (Scheme 18):

To a solution of compound 7 (3.81 g, 9.31 mmol, 1.0 eq) in methanol (220 mL) was added concentrate HCl (2 mL) and palladium on activated carbon (1.8 g, 10%). The reaction was stirred at rt for 4 h under hydrogen atmosphere. The mixture was filtered through a Celite pad, and the pad was washed with methanol. The filtrate was concentrated in vacuo to afford a pale orange oil. The residue was diluted with ether, stirred at rt, and a solid was formed. The solid was filtered and washed with ethanol to afford 8 (4.8 g, 100%) as a yellow solid. TLC: PE/EA=3/1; $R_f$(Compound 7)=0.6; $R_f$ (Product 8)=0.3.

Preparation of Compound 9 (Scheme 18):

To a solution of compound 8 (4.80 g, 13.0 mmol, 1.0 eq) in methanol (100 mL) was added sodium hydroxide (2.0 g, 50 mmol) and water (15 mL). The reaction was stirred at 40° C. for 6 h. After cooled to rt, the reaction was adjusted to pH 7 with 6 N HCl, extracted with (DCM/MeOH, 10/1; 3×100 mL). The organic phase was dried over sodium sulfate, filtered and concentrated in vacuo to afford a crude product, which was triturated with ethyl acetate to afford 9 (2.8 g, 60%) as a blue solid. TLC: PE/EA=2/1; $R_f$ (Compound 8)=0.6; $R_f$ (Product 9)=0.05.

Preparation of Compound 76 (Scheme 18):

To a mixture of 9 (2.8 g, 7.87 mmol, 1.0 eq) in DMF (50 mL) was added 1-(tert-butoxycarbonyl)piperazine (1.54 g, 8.26 mmol, 1.04 eq), EDCI (1.81 g, 9.44 mmol, 1.2 eq), HOBT (615 mg, 4.55 mmol, 0.57 eq) and triethylamine (1.74 g, 17.2 mmol, 2.18 eq) subsequently. The reaction was stirred at 25° C. for 36 h. The mixture was filtered through a pad of Celite, and the pad was washed with ethyl acetate. The filtrate was concentrated in vacuo to give an oil. The residue was purified by Prep-HPLC to afford compound 10 (2.0 g) as white solid. The compound 10 (2.0 g) was treated with HCl in ethyl acetate (3.5 M, 15 mL). After stirring at 25° C. for 1 h, petroleum ether (100 mL) was added. The resulting white solid was filtered, washed with ether and air-dried to give Example Compound 76 (1.6 g, 41%, two steps) as a white solid. TLC: DCM/MeOH=10/1; $R_f$ (Compound 9)=0.3; $R_f$ (Product 10)=0.35; LC-MS: 424.70 (M+1)+; $^1$H NMR (400 MHz, CD$_3$OD) δ 7.55-7.48 (m, 3H), 6.87 (s, 1H), 6.72-6.70 (m, 2H), 4.95-4.79 (m, 4H) 3.90-3.80 (m, 7H), 3.35-3.30 (m, 4H), 2.72-2.69 (m, 2H), 2.12-2.08 (m, 2H), 1.56 (s, 6H).

Example 23: Analytical Data for Isoindoline Compound Species

Example 23 provides analytical data for compounds prepared in an analogous fashion to those described above.

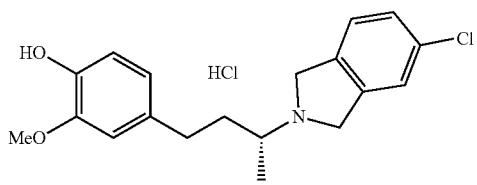 [SMILES: COc1cc(CC[C@@H](C)N2Cc3ccc(Cl)cc3C2)ccc1O ; Cl]

Example Compound 1

$^1$H NMR (400 MHz, DMSO-d6): δ 11.45 (br. s, 1H), 8.76 (br. s, 1H), 7.48-7.41 (m, 3H), 6.82 (s, 1H), 6.69 (d, J=8.0 Hz, 1H), 6.53 (d, J=8.0 Hz, 1H), 4.80-4.50 (m, 4H), 3.75 (s, 3H), 3.53-3.50 (m, 1H), 2.70-2.65 (m, 1H), 2.12-2.10 (m, 1H), 1.83-1.80 (m, 1H), 1.36 (d, J=6.0 Hz, 3H); m/z (ESI+) (M+H)+=332.05.

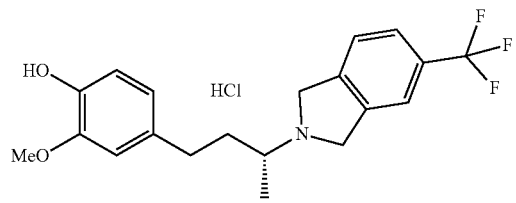 [SMILES: COc1cc(CC[C@@H](C)N2Cc3ccc(C(F)(F)F)cc3C2)ccc1O ; Cl]

Example Compound 2

$^1$H NMR (400 MHz, CDCl$_3$): δ 7.75-7.45 (m, 4H), 6.85-6.60 (m, 5H), 5.71 (br. s, 2H), 4.14-3.75 (m, 7H), 2.90-2.50 (m, 5H), 1.78-1.20 (m, 8H0, 1.26-1.23 (m, 3H); m/z (ESI+) (M+H)+=366.10.

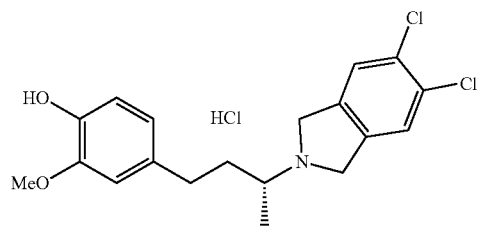 [SMILES: COc1cc(CC[C@@H](C)N2Cc3cc(Cl)c(Cl)cc3C2)ccc1O ; Cl]

Example Compound 3

$^1$H NMR (400 MHz, DMSO-d6): δ 12.57 (br. s, 1H), 8.80 (br. s, 1H), 7.66 (d, J=5.2 Hz, 2H), 6.79 (s, 1H), 6.68 (d, J=7.2 Hz, 1H), 6.60 (d, J=7.2 Hz, 1H) 3.74 (s, 3H), 3.53-3.50 (m, 1H), 2.70-2.60 (m, 1H), 2.12-2.10 (m, 1H), 1.83-1.80 (m, 1H), 1.36 (d, J=6.0 Hz, 3H); m/z (ESI+) (M+H)+=366.20.

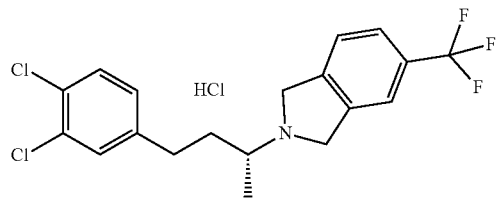 [SMILES: C[C@H](CCc1ccc(Cl)c(Cl)c1)N1Cc2ccc(C(F)(F)F)cc2C1 ; Cl]

Example Compound 4

$^1$H NMR (400 MHz, CD$_3$OD): δ 7.75-7.72 (m, 2H), 7.61 (d, J=7.6 Hz, 1H), 7.51-7.45 (m, 2H), 7.24 (dd, J1=8.0 Hz, J2=2.0 Hz, 1H), 5.05-4.90 (m, 2H), 4.75-4.65 (m, 2H), 3.69-3.64 (m, 1H), 2.89-2.82 (m, 1H), 2.73-2.67 (m, 1H), 2.27-2.22 (m, 1H), 1.98-193 (m, 1H), 1.52 (d, J=6.4 Hz, 3H); m/z (ESI+) (M+H)+=388.10.

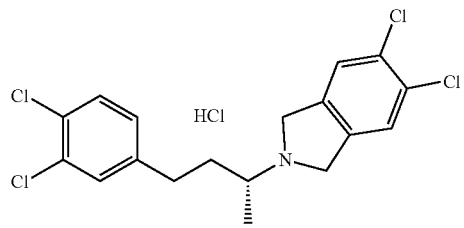 [SMILES: C[C@H](CCc1ccc(Cl)c(Cl)c1)N1Cc2cc(Cl)c(Cl)cc2C1 ; Cl]

Example Compound 5

¹H NMR (400 MHz, CD₃OD): δ 7.61 (br, s. 2H), 7.49-7.45 (m, 2H), 7.22 (dd, J1=8.4 Hz, J2=2.0 Hz, 1H), 4.80-4.20 (m, 4H), 3.66-3.62 (m, 1H), 2.89-2.80 (m, 1H), 2.75-2.65 (m, 1H), 2.25-2.20 (m, 1H), 1.98-1.90 (m, 1H), 1.52 (d, J=6.4 Hz, 3H); m/z (ESI+) (M+H)+=390.00.

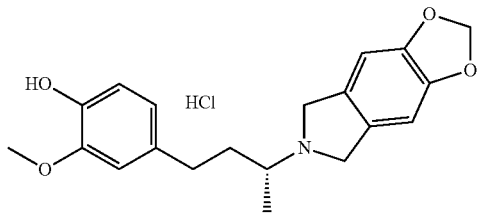 [SMILES: COc1cc(CC[C@@H](C)N2Cc3cc4c(cc3C2)OCO4)ccc1O ; Cl]

Example Compound 6

¹H NMR (400 MHz, CD₃OD): δ 6.84 (s, 2H), 6.74-6.68 (m, 2H), 5.99 (s, 2H), 4.74-4.65 (m, 2H), 4.47-4.41 (m, 2H), 3.85 (s, 3H), 3.60-3.55 (m, 1H), 2.80-2.70 (m, 1H), 2.65-2.55 (m, 1H), 2.25-2.15 (m, 1H), 1.98-1.90 (m, 1H), 1.46 (d, J=6.4 Hz, 3H); m/z (ESI+) (M+H)+=342.05.

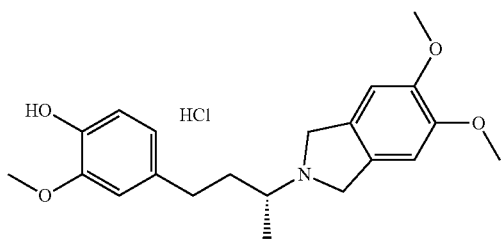

Example Compound 7

¹H NMR (400 MHz, DMSO-d6): δ 8.61 (s, 1H), 6.83 (s, 2H), 6.74 (s, 1H), 6.65 (d, J=8.0 Hz, 1H), 6.57 (d, J=8.0 Hz, 1H), 3.80 (s, 4H), 3.69 (s, 6H), 3.60-3.55 (m, 1H), 2.85-2.80 (m, 1H), 2.75-2.70 (m, 1H), 1.82-1.75 (m, 1H), 1.60-1.55 (m, 1H), 1.06 (d, J=6.4 Hz, 3H); m/z (ESI+) (M+H)+=358.25.

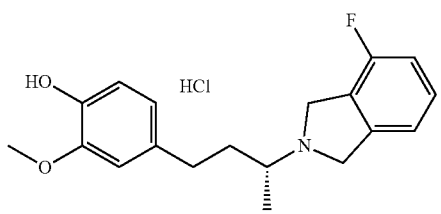 [SMILES: COc1cc(CC[C@@H](C)N2Cc3cccc(F)c3C2)ccc1O ; Cl]

Example Compound 8

¹H NMR (400 MHz, DMSO-d6): δ 12.20 (s, 1H), 8.79 (s, 1H), 7.44-7.40 (m, 1H), 7.24-7.19 (m, 2H), 6.84 (s, 1H), 6.70 (d, J=8.0 Hz, 1H), 6.65 (d, J=8.0 Hz, 1H), 4.85-4.57 (m, 4H), 3.52-3.48 (m, 1H), 2.71-2.64 (m, 1H), 2.20-2.17 (m, 1H), 1.97-1.84 (m, 1H), 1.40-1.38 (m, 3H); m/z (ESI+) (M+H)+=316.10.

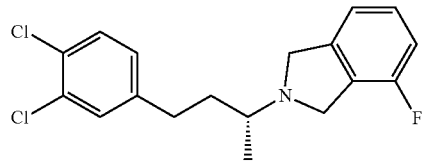 [SMILES: C[C@H](CCc1ccc(Cl)c(Cl)c1)N1Cc2cccc(F)c2C1]

Example Compound 9

¹H NMR (400 MHz, CD₃OD): δ 7.60 (d, J=2.0 Hz, 1H), 7.48-7.43 (m, 2H), 7.24 (dd, J1=8.8 Hz, J2=2.0 Hz, 2H), 7.15 (t, J=8.4 Hz, 1H), 4.90-4.70 (m, 4H), 3.70-3.60 (m, 1H), 2.90-2.80 (m, 1H), 2.30-2.20 (m, 1H), 2.00-1.80 (m, 1H), 1.51 (d, J=6.8 Hz, 3H); m/z (ESI+) (M+H)+=338.10.

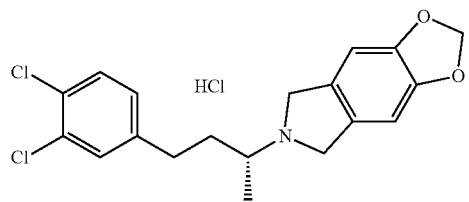 [SMILES: C[C@H](CCc1ccc(Cl)c(Cl)c1)N1Cc2cc3c(cc2C1)OCO3 ; Cl]

Example Compound 10

¹H NMR (400 MHz, DMSO-d6): δ 11.90 (s, 1H), 7.58 (d, J=2.0 Hz, 1H), 7.54 (d, J=8.4 Hz, 1H), 7.28 (dd, J1=8.0 Hz, J2=2.0 Hz, 1H), 6.90 (d, J=5.2 Hz, 2H), 4.65-4.50 (m, 2H), 4.48-4.35 (m, 2H), 3.55-3.45 (m, 1H), 2.82-2.78 (m, 1H), 2.65-2.55 (m, 1H), 2.15-2.05 (m, 1H), 1.90-1.80 (m, 1H), 1.35 (d, J=6.4 Hz, 3H); m/z (ESI+) (M+H)+=364.10.

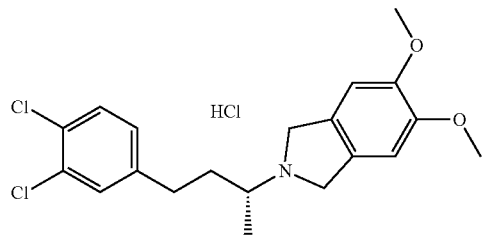 [SMILES: COc1cc2c(cc1OC)CN([C@H](C)CCc1ccc(Cl)c(Cl)c1)C2 ; Cl]

Example Compound 11

¹H NMR (400 MHz, DMSO-d6): δ 11.96 (s, 1H), 7.59 (s, 1H), 7.55 (d, J=8.4 Hz, 1H), 7.29 (dd, J1=8.0 Hz, J2=2.0 Hz, 1H), 6.94 (d, J=5.2 Hz, 2H), 4.66-4.55 (m, 2H), 4.48-4.35 (m, 2H), 3.74 (s, 6H), 3.55-3.45 (m, 1H), 2.82-2.78 (m, 1H), 2.65-2.55 (m, 1H), 2.20-2.10 (m, 1H), 1.95-1.80 (m, 1H), 1.37 (d, J=6.4 Hz, 3H); m/z (ESI+) (M+H)+=380.15.

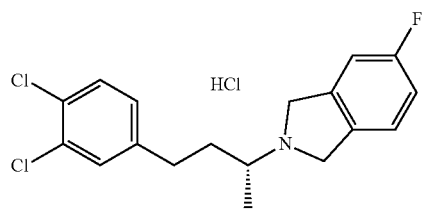 [SMILES: C[C@H](CCc1ccc(Cl)c(Cl)c1)N1Cc2ccc(F)cc2C1 ; Cl]

Example Compound 12

¹H NMR (400 MHz, DMSO-d6): δ 7.58 d, J=2.0 Hz, 1H), 7.55 (d, J=8.4 Hz, 1H), 7.41-7.38 (m, 1H), 7.28 (dd, J1=8.0 Hz, J2=2.0 Hz, 1H), 7.24-7.16 (m, 3H), 4.73-4.62 (m, 2H), 4.58-4.45 (m, 2H), 3.55-3.45 (m, 1H), 2.82-2.78 (m, 1H), 2.65-2.55 (m, 1H), 2.20-2.10 (m, 1H), 1.95-1.80 (m, 1H), 1.37 (d, J=6.4 Hz, 3H); m/z (ESI+) (M+H)+=338.10.

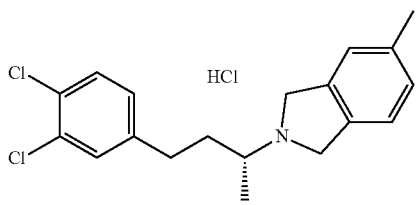 [SMILES: Cc1ccc2c(c1)CN([C@H](C)CCc1ccc(Cl)c(Cl)c1)C2 ; Cl]

Example Compound 13

¹H NMR (400 MHz, DMSO-d6): δ 7.58 (d, J=2.0 Hz, 1H), 7.55 (d, J=8.4 Hz, 1H), 7.28 (dd, J1=8.0 Hz, J2=2.0 Hz, 1H), 7.22 (dd, J1=8.0 Hz, J2=3.2 Hz, 1H), 7.14 (d, J=6.4 Hz, 2H), 4.73-4.61 (m, 2H), 4.54-4.45 (m, 2H), 3.52-3.49 (m, 1H), 2.80-2.75 (m, 1H), 2.65-2.59 (m, 1H), 2.30 (s, 3H), 2.16-2.14 (m, 1H), 1.90-1.85 (m, 1H), 1.35 (d, J=6.4 Hz, 3H); m/z (ESI+) (M+H)+=334.15.

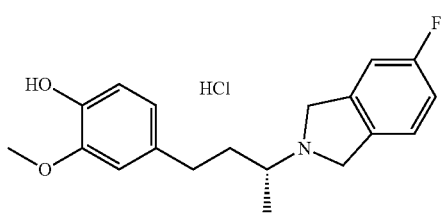 [SMILES: COc1cc(CC[C@@H](C)N2Cc3ccc(F)cc3C2)ccc1O ; Cl]

Example Compound 14

¹H NMR (400 MHz, DMSO-d6): δ 7.41-7.38 9m, 1H), 7.25-7.15 (m, 2H), 6.80 (d, J=6.0 Hz, 1H), 6.68 (d, 8.0 Hz, 1H), 6.62 (dd, J1=8.0 Hz, J2=2.0 Hz, 1H), 4.77-4.63 (m, 2H), 4.59-4.44 (m, 2H), 3.75 (s, 3H), 3.51-3.48 (m, 1H), 2.70-2.62 (m, 1H), 2.52-2.44 (m, 1H), 2.14-2.11 (m, 1H), 1.90-1.85 (m, 1H), 1.35 (d, J=6.4 Hz, 3H); m/z (ESI+) (M+H)+=316.60.

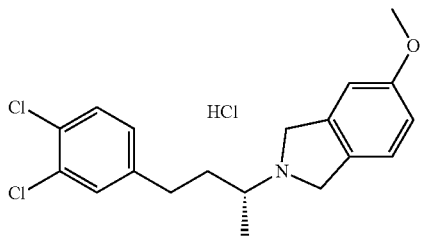 [SMILES: COc1ccc2c(c1)CN([C@H](C)CCc1ccc(Cl)c(Cl)c1)C2 ; Cl]

Example Compound 15

¹H NMR (400 MHz, DMSO-d6): δ 11.60 (s, 1H), 7.59 (s, 1H), 7.55 (d, J=8.4 Hz, 1H), 7.29-7.24 (m, 2H), 6.93-6.90 (m, 2H), 4.75-4.58 (m, 2H), 4.58-4.44 (m, 2H), 3.74 (s, 3H), 3.52-3.50 (m, 1H), 2.81-2.74 (m, 1H), 2.65-2.57 (m, 1H), 2.20-2.10 (m, 1H), 1.90-1.80 (m, 1H), 1.36 (d, J=6.0 Hz, 3H); m/z (ESI+) (M+H)+=350.15.

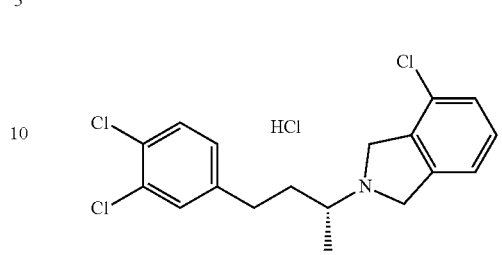

Example Compound 16

¹H NMR (400 MHz, DMSO-d6): δ 12.32 (s, 1H), 7.60 (s, 1H), 7.56-7.54 (m, 1H), 7.44-7.28 (m, 4H), 4.86-4.40 (m, 4H), 3.60-3.50 (m, 1H), 2.83-2.75 (m, 1H), 2.65-2.59 (m, 1H), 2.30-2.15 (m, 1H), 1.95-1.82 (m, 1H), 1.17-1.13 (m, 3H); m/z (ESI+) (M+H)+=356.15.

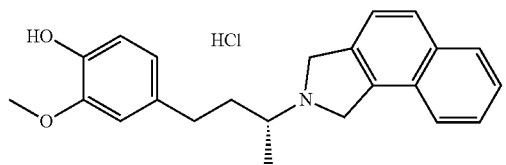 [SMILES: COc1cc(CC[C@@H](C)N2Cc3ccc4ccccc4c3C2)ccc1O ; Cl]

Example Compound 17

¹H NMR (400 MHz, CD₃OD): δ 7.93 (dd, J1=11.6 Hz, J2=8.4 Hz, 2H), 7.82 (d, J=8.4 Hz, 1H), 7.63-7.54 (m, 2H), 7.48 (d, J=11.6 Hz, 1H), 6.92-6.86 (m, 1H), 6.78-6.70 (m, 2H), 5.22-4.76 (m, 4H), 3.85 (s, 3H), 3.75-3.65 (m, 1H), 2.83-2.77 (m, 1H), 2.68-2.60 (m, 1H), 2.40-2.30 (m, 1H), 2.10-1.95 (m, 1H), 1.58-1.50 (m, 3H); m/z (ESI+) (M+H)+=348.65.

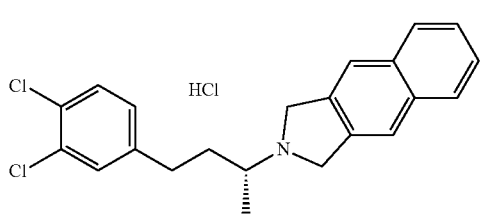 [SMILES: C[C@H](CCc1ccc(Cl)c(Cl)c1)N1Cc2cc3ccccc3cc2C1 ; Cl]

Example Compound 18

¹H NMR (400 MHz, DMSO-d6): δ 12.06 (s, 1H), 7.95-7.87 (m, 4H), 7.62-7.50 (m, 4H), 7.31 (d, J=8.0 Hz, 1H), 4.98-4.85 (m, 2H), 4.73-4.63 (m, 2H), 3.59-3.55 (m, 1H), 2.86-2.78 (m, 1H), 2.68-2.60 (m, 1H), 2.25-2.20 (m, 1H), 2.00-1.90 (m, 1H), 1.43 (d, J=6.4 Hz, 3H); m/z (ESI+) (M+H)+=370.20.

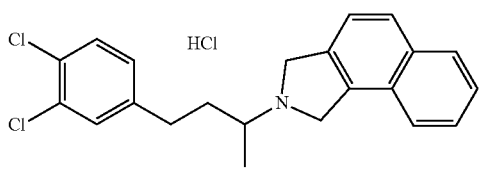 [SMILES: CC(CCc1ccc(Cl)c(Cl)c1)N1Cc2ccc3ccccc3c2C1 ; Cl]

Example Compound 19

¹H NMR (400 MHz, CD₃OD): δ 7.94 (t, J=8.8 Hz, 2H), 7.83 (d, J=8.0 Hz, 1H), 7.64-7.43 (m, 5H), 7.40-7.30 (m, 1H), 5.34-4.80 (m, 4H), 3.80-3.70 (m, 1H), 2.90-2.80 (m, 1H), 2.80-2.70 (m, 1H), 2.40-2.30 (m, 1H), 2.10-2.00 (m, 1H), 1.60-1.55 (m, 3H); m/z (ESI+) (M+H)+=370.10.

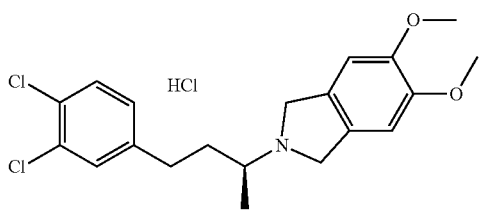 [SMILES: COc1cc2c(cc1OC)CN([C@@H](C)CCc1ccc(Cl)c(Cl)c1)C2 ; Cl]

Example Compound 20

¹H NMR (400 MHz, DMSO-d6): δ 11.62 (s, 1H), 7.59 (s, 1H), 7.56 (d, J=8.0 Hz, 1H), 7.29 (d, J=8.4 Hz, 1H), 6.94 (s, 2H), 4.68-5.55 (m, 2H), 4.49-4.40 (m, 2H), 3.73 (s, 6H), 3.55-3.48 (m, 1H), 2.82-2.78 (m, 1H), 2.65-2.57 (m, 1H), 2.20-2.08 (m, 1H), 1.90-1.80 (m, 1H), 1.36 (d, J=6.4 Hz, 3H); m/z (ESI+) (M+H)+=380.10.

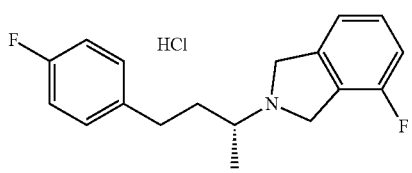 [SMILES: C[C@H](CCc1ccc(F)cc1)N1Cc2cccc(F)c2C1 ; Cl]

Example Compound 21

¹H NMR (400 MHz, DMSO-d6): δ 12.20 (s, 1H), 7.42 (dd, J1=12.8 Hz, J2=8.0 Hz, 1H), 7.33-7.30 (m, 2H), 7.23-7.18 (m, 2H), 7.15-7.05 (m, 2H), 4.88-4.72 (m, 2H), 4.70-4.55 (m, 2H), 3.60-3.50 (m, 1H), 2.80-2.70 (m, 1H), 2.65-2.52 (m, 1H), 2.22-2.10 (m, 1H), 1.90-1.82 (m, 1H), 1.42-1.35 (m, 3H); m/z (ESI+) (M+H)+=288.15.

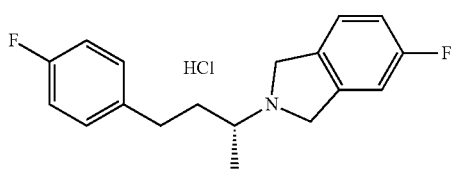

Example Compound 22

¹H NMR (400 MHz, DMSO-d6): δ 12.05 (s, 1H), 7.40-7.09 (m, 7H), 4.76-4.65 (m, 2H), 4.60-4.45 (m, 2H), 3.55-3.48 (m, 1H), 2.80-2.70 (m, 1H), 2.62-2.52 (m, 1H), 2.20-2.08 (m, 1H), 1.90-1.82 (m, 1H), 1.37 (d, J=6.0 Hz, 3H); m/z (ESI+) (M+H)+=288.15.

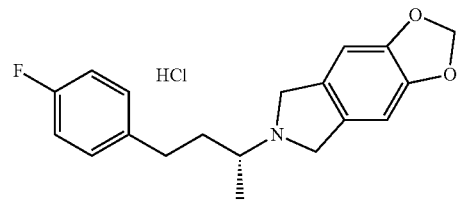 [SMILES: C[C@H](CCc1ccc(F)cc1)N1Cc2cc3c(cc2C1)OCO3 ; Cl]

Example Compound 23

¹H NMR (400 MHz, CD₃OD): δ 7.29 (dd, J1=8.0 Hz, J2-6.4 Hz, 2H), 7.03 (t, J=8.8 Hz, 2H), 6.85 (s, 2H), 6.00 (d, J=2.4 Hz, 2H), 4.75-4.67 (m, 2H), 4.51-4.44 (m, 2H), 3.60-3.55 (m, 1H), 2.83-2.79 (m, 1H), 2.72-2.67 (m, 1H), 2.22-2.18 (m, 1H), 1.93-1.89 (m, 1H), 1.47 (d, J=6.4 Hz, 3H); m/z (ESI+) (M+H)+=314.20.

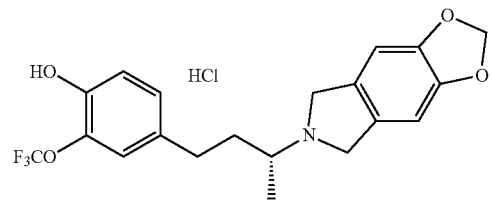 [SMILES: C[C@H](CCc1ccc(O)c(OC(F)(F)F)c1)N1Cc2cc3c(cc2C1)OCO3 ; Cl]

Example Compound 24

¹H NMR (400 MHz, CD₃OD): δ 7.12 (s, 1H), 7.08 (dd, J1=8.4 Hz, J2=2.0 Hz, 1H), 6.90 (d, 8.4 Hz, 1H), 6.84 (s, 2H), 6.00 (s, 2H), 4.75-4.50 (m, 4H), 3.58-3.53 (m, 1H), 2.81-2.73 (m, 1H), 2.65-2.58 (m, 1H), 2.22-2.18 (m, 1H), 1.93-1.82 (m, 1H), 1.45 (d, J=6.4 Hz, 3H); m/z (ESI+) (M+H)+=396.15.

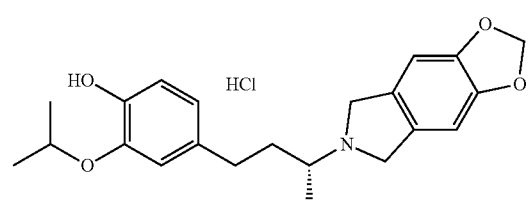

Example Compound 25

¹H NMR (400 MHz, CD₃OD): δ 6.91 (br. s, 3H), 6.81 (d, J=8.0 Hz, 1H), 6.76 (d, J=8.0 Hz, 1H), 6.06 (d, J=2.8 Hz, 2H), 4.82-4.72 (m, 2H), 4.68-4.61 (m, 1H), 4.55-4.48 (m, 2H), 3.62-3.57 (1H), 2.86-2.78 (m, 1H), 2.68-2.60 (m, 1H), 2.26-2.22 (m, 1H), 1.97-1.91 (m, 1H), 1.52 (d, J=6.8 Hz, 3H), 1.38 (d, J=6.0 Hz, 6H); m/z (ESI+) (M+H)+=370.20.

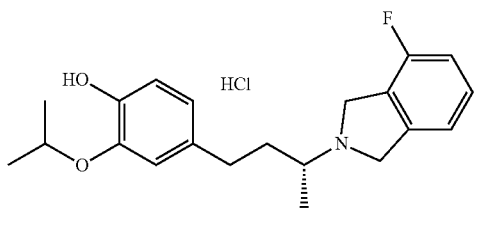 [SMILES: CC(C)Oc1cc(CC[C@@H](C)N2Cc3cccc(F)c3C2)ccc1O ; Cl]

Example Compound 26

¹H NMR (400 MHz, CD₃OD): δ 7.45-7.41 (m, 1H), 7.21 (d, J=7.6 Hz, 1H), 7.17-7.11 (m, 1H), 6.84 (s, 1H), 6.74 (d, J=8.0 Hz, 1H), 6.69 (d, J=8.0 Hz, 1H), 4.82-4.50 (m, 5H), 3.61-3.56 (, 1H), 2.80-2.70 (m, 1H), 2.62-2.55 (m, 1H), 2.25-2.18 (m, 1H), 1.95-1.85 (m, 1H), 1.48 (d, J=6.8 Hz, 3H), 1.30 (d, J=6.0 Hz, 6H); m/z (ESI+) (M+H)+=370.20.

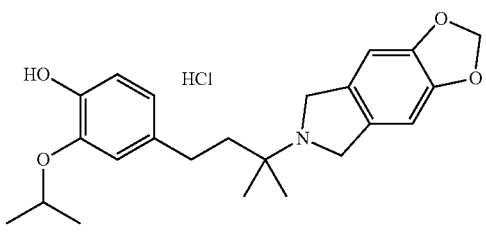

Example Compound 29

¹H NMR (400 MHz, CD₃OD): δ 6.84 (d, J=8.0 Hz, 1H), 6.83 (s, 2H), 6.73 (d, J=8.0 Hz, 1H), 6.70 (d, J=8.0 Hz, 1H), 5.98 (d, J=2.4 Hz, 2H), 4.68-4.54 (m, 5H), 2.66-2.62 (m, 2H), 2.04-2.00 (m, 2H), 1.50 (s, 6H), 1.30 (d, J=6.0 Hz, 6H); m/z (ESI+) (M+H)+=384.25.

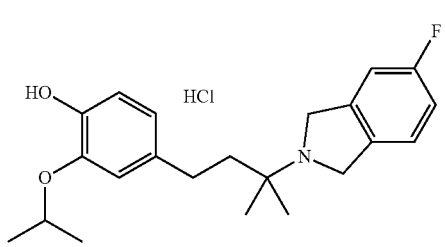 [SMILES: CC(C)Oc1cc(CCC(C)(C)N2Cc3ccc(F)cc3C2)ccc1O ; Cl]

Example Compound 27

¹H NMR (400 MHz, CD₃OD): δ 7.41 (dd, J1=8.0 Hz, J2=4.8 Hz, 1H), 7.17 (d, J=8.0 Hz, 1H), 6.16-7.14 (m, 1H), 6.84 (d, J=1.6 Hz, 1H), 6.74 (d, J=8.4 Hz, 1H), 6.71 (dd, J1=8.0 Hz, J2=1.6 Hz, 1H), 4.82-4.62 (m, 4H), 4.58-4.55 (m, 1H), 2.67-2.63 (m, 2H), 2.05-2.00 (m, 2H), 1.52 (s, 6H), 1.30 (d, J=6.0 Hz, 6H); m/z (ESI+) (M+H)+=358.15.

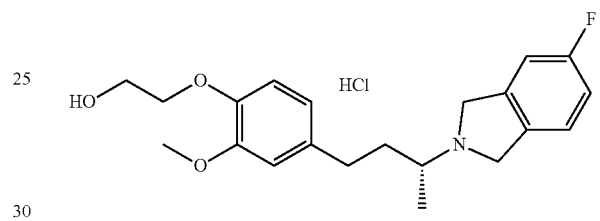

Example Compound 30

¹H NMR (400 MHz, CD₃OD): δ 7.40 (dd, J1=8.0 Hz, J2=4.8 Hz, 1H), 7.16 (d, J=8.4 Hz, 1H), 7.15-7.12 (m, 1H), 6.92-6.90 (m, 2H), 6.80 (dd, J1=8.0 Hz, J2=2.0 Hz, 1H), 4.85-4.52 (m, 4H), 4.02-4.00 (m, 1H), 3.85 (s, 3H), 3.85-3.82 (m, 2H), 3.61-3.55 (m, 1H), 2.84-2.77 (m, 1H), 2.67-2.59 (m, 1H), 2.24-2.18 (m, 1H), 1.94-1.88 (m, 1H), 1.48 (d, J=6.4 Hz, 3H); m/z (ESI+) (M+H)+=360.20.

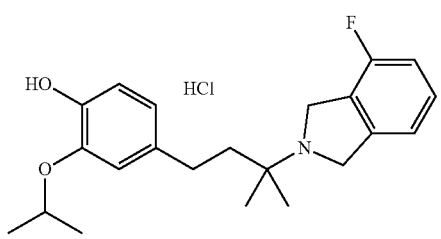 [SMILES: CC(C)Oc1cc(CCC(C)(C)N2Cc3cccc(F)c3C2)ccc1O ; Cl]

Example Compound 28

¹H NMR (400 MHz, CD₃OD): δ 7.49-7.43 (m, 1H), 7.24 (d, J=7.6 Hz, 1H), 7.16 (t, J=8.4 Hz, 1H), 6.85 (s, 1H), 6.74 (d, J=8.0 Hz, 1H), 6.71 (dd, J1=8.0 Hz, J2=1.6 Hz, 1H), 4.87-4.79 (m, 4H), 4.58-4.56 (m, 1H), 2.67-2.63 (m, 2H), 2.07-2.03 (m, 2H), 1.54 (s, 6H), 1.30 (d, J=6.0 Hz, 6H); m/z (ESI+) (M+H)+=358.25.

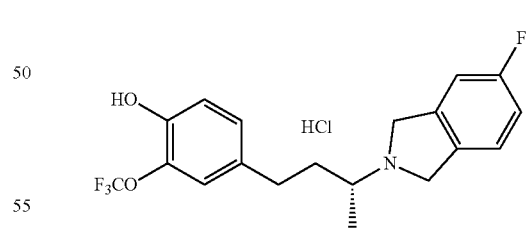

Example Compound 31

¹H NMR (400 MHz, CD₃OD): δ 7.38-7.34 (m, 1H), 7.14-7.08 (m, 3H), 7.04 (dd, J1=8.0 Hz, J2=2.0 Hz, 1H), 6.86 (d, J=8.8 Hz, 1H), 4.86-4.73 (m, 2H), 4.60-4.48 (m, 2H), 3.60-3.53 (m, 1H), 2.76-2.69 (m, 1H), 2.61-2.53 (m, 1H), 2.16-2.12 (m, 1H), 1.86-1.82 (m, 1H), 1.42 (d, J=6.8 Hz, 3H); m/z (ESI+) (M+H)+=370.10.

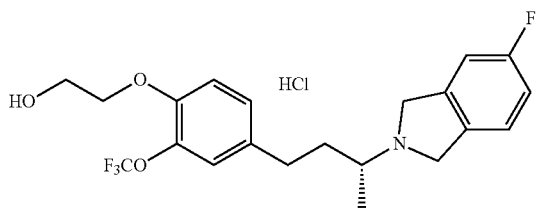 [SMILES: C[C@H](CCc1ccc(OCCO)c(OC(F)(F)F)c1)N1Cc2ccc(F)cc2C1 ; Cl]

Example Compound 32

¹H NMR (400 MHz, CD₃OD): δ 7.42-7.38 (m, 1H), 7.24-7.11 (m, 5H), 4.92-4.80 (m, 2H), 4.68-4.55 (m, 2H), 4.10-4.07 (m, 2H), 3.88-3.86 (m, 2H), 6.64-3.60 (m, 1H), 2.85-2.75 (m, 1H), 2.72-2.60 (m, 1H), 2.24-2.18 (m, 1H), 1.98-1.88 (m, 1H), 1.49 (d, J=6.0 Hz, 3H); m/z (ESI+) (M+H)+=414.20.

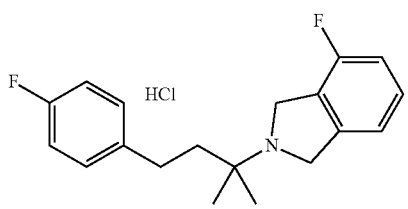 [SMILES: CC(C)(CCc1ccc(F)cc1)N1Cc2cccc(F)c2C1 ; Cl]

Example Compound 33

¹H NMR (400 MHz, CD₃OD): δ 7.46-7.41 (m, 1H), 7.32-7.29 (m, 2H), 7.23 (d, J=7.6 Hz, 1H), 7.13 (t, J=8.4 Hz, 1H), 7.01 (t, 8.8 Hz, 2H), 4.86-4.80 (m, 4H), 2.78-2.73 (m, 2H), 2.12-2.08 (m, 2H), 1.56 (s, 6H); m/z (ESI+) (M+H)+=302.10.

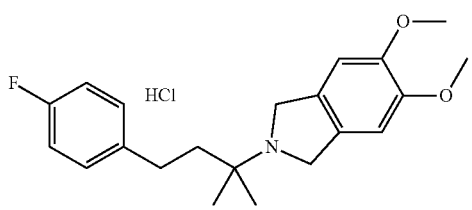 [SMILES: COc1cc2c(cc1OC)CN(C(C)(C)CCc1ccc(F)cc1)C2 ; Cl]

Example Compound 34

¹H NMR (400 MHz, CD₃OD): δ 7.31-7.27 (m, 2H), 7.03 (t, J=8.8 Hz, 2H), 6.98 (s, 2H), 4.72 (d, J=13.6 Hz, 2H), 4.61 (d, J=13.6 Hz, 2H), 3.83 (6H), 2.81-2.72 (m, 2H), 2.07-1.98 (m, 2H), 1.56 (s, 6H); m/z (ESI+) (M+H)+=344.20.

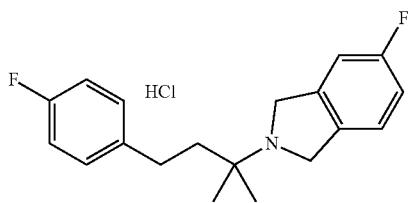 [SMILES: CC(C)(CCc1ccc(F)cc1)N1Cc2ccc(F)cc2C1 ; Cl]

Example Compound 35

¹H NMR (400 MHz, CD₃OD): δ 7.43-7.40 (m, 2H), 7.32-7.27 (m, 2H), 7.20-7.14 (m, 2H), 7.03 (t, J=8.8 Hz, 2H), 4.85-4.70 (m, 4H), 2.77-2.72 (m, 2H), 2.08-2.03 (m, 2H), 1.54 (s, 6H); m/z (ESI+) (M+H)+=302.20.

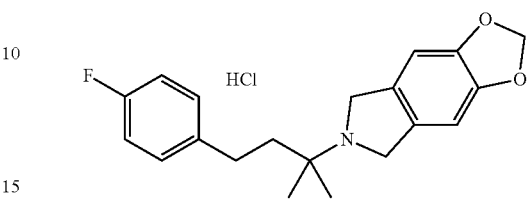

Example Compound 36

¹H NMR (400 MHz, CD₃OD): δ 7.29 (dd, J1=8.4 Hz, J2=5.6 Hz, 2H), 7.01 (t, J=8.4 Hz, 2H), 6.83 (s, 2H), 4.67 (d, J=14.0 Hz, 2H), 4.58 (d, J=14.0 Hz, 2H), 2.78-2.71 (m, 2H), 2.07-2.03 (m, 2H), 1.53 (s, 6H); m/z (ESI+) (M+H)+=328.10.

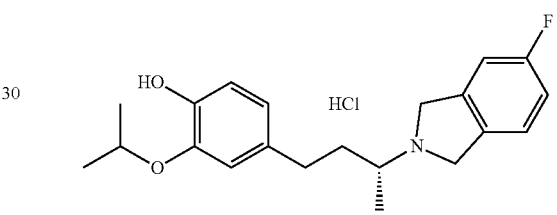

Example Compound 37

¹H NMR (400 MHz, CD₃OD): δ 7.38 (dd, J1=8.0 Hz, J2=4.4 Hz, 1H), 7.16-7.10 (m, 2H), 6.86 (s, 1H), 6.75 (d, J=8.0 HZ, 1H), 6.70 (d, J=8.8 Hz, 1H), 4.93-4.76 (m, 2H), 4.62-4.50 (m, 3H), 3.60-3.52 (m, 1H), 2.78-2.70 (m, 1H), 2.62-2.55 (m, 1H), 2.25-2.15 (m, 1H), 1.95-1.85 (m, 1H), 1.47 (d, J=6.4 Hz, 3H), 1.30 (d, J=6.4 Hz, 6H); m/z (ESI+) (M+H)+=344.15.

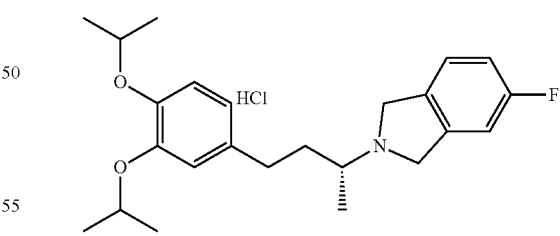

Example Compound 38

¹H NMR (400 MHz, CD₃OD): δ 7.39 (dd, J1=8.4 Hz, J2=4.8 Hz, 1H), 7.17-7.10 (m, 2H), 6.89 (s, 1H), 6.88 (d, J=8.4 HZ, 1H), 6.81 (d, J=8.0 Hz, 1H), 4.92-4.83 (m, 2H), 4.58-4.42 (m, 4H), 3.60-3.55 (m, 1H), 2.80-2.70 (m, 1H), 2.65-2.55 (m, 1H), 2.25-2.15 (m, 1H), 1.95-1.85 (m, 1H), 1.47 (d, J=6.4 Hz, 3H), 1.30-1.25 (m, 12H); m/z (ESI+) (M+H)+=386.25.

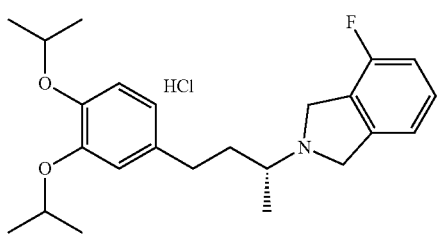 [SMILES: CC(C)Oc1ccc(CC[C@@H](C)N2Cc3cccc(F)c3C2)cc1OC(C)C ; Cl]

Example Compound 39

¹H NMR (400 MHz, CD₃OD): δ 7.46-7.40 (m, 1H), 7.22 (d, J=7.6 Hz, 1H), 7.12 (t, J=8.8 Hz, 1H), 6.90 (s, 1H), 6.89 (d, J=8.4 HZ, 1H), 6.82 (dd, J1=8.0 Hz, J2=2.0 Hz, 1H), 4.95-4.85 (m, 2H), 4.70-4.62 (m, 2H), 4.60-4.52 (m, 1H), 4.50-4.42 (m, 1H), 3.60-3.52 (m, 1H), 2.82-2.72 (m, 1H), 2.65-2.55 (m, 1H), 2.28-2.18 (m, 1H), 1.95-1.88 (m, 1H), 1.49 (d, J=6.4 Hz, 3H), 1.30-1.25 (m, 12H); m/z (ESI+) (M+H)+=386.70.

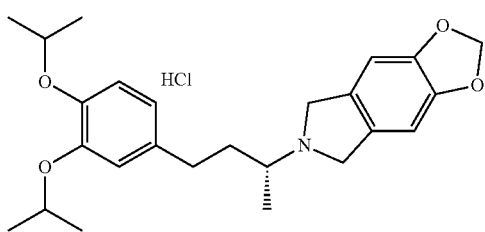 [SMILES: CC(C)Oc1ccc(CC[C@@H](C)N2Cc3cc4c(cc3C2)OCO4)cc1OC(C)C ; Cl]

Example Compound 40

¹H NMR (400 MHz, CD3OD): δ 7.26 (s, 1H), 6.84 (d, J=8.8 Hz, 1H), 6.72-6.65 (m, 4H), 6.00 (d, J=5.2 Hz, 2H), 4.96-4.87 (m, 2H), 4.50-4.41 (m, 2H), 4.18-4.10 (m, 2H), 3.42-3.36 (m, 1H), 2.77-2.74 (m, 1H), 2.58-2.50 (m, 1H), 2.18-2.10 (m, 1H), 1.92-1.86 (m, 1H), 1.42 (d, J=5.6 Hz, 3H), 1.30-1.25 (m, 12H); m/z (ESI+) (M+H)+=412.30.

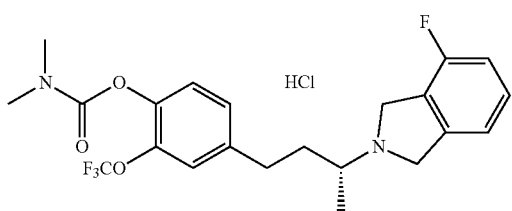 [SMILES: C[C@H](CCc1ccc(OC(=O)N(C)C)c(OC(F)(F)F)c1)N1Cc2cccc(F)c2C1 ; Cl]

Example Compound 41

¹H NMR (400 MHz, CD3OD): δ 7.47-7.42 (m, 1H), 7.35-7.30 (m, 2H), 7.25-7.22 (m, 2H), 7.13 (t, J=8.8 Hz, 1H), 5.01-4.91 (m, 2H), 4.72-4.65 (m, 2H), 3.72-3.65 (m, 1H), 3.12 (s, 3H), 2.98 (s, 3H), 2.92-2.85 (m, 1H), 2.80-2.70 (m, 1H), 2.30-2.20 (m, 1H), 2.02-1.95 (m, 1H), 1.52 (d, J=4.0 Hz, 3H); m/z (ESI+) (M+H)+=441.20.

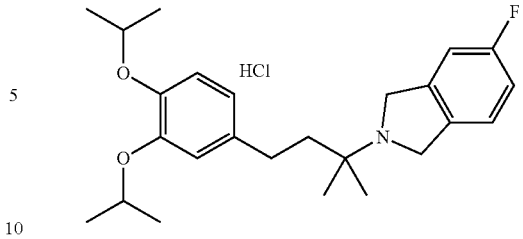

Example Compound 42

¹H NMR (400 MHz, CD3OD): δ 7.43-7.40 (m, 1H), 7.19-7.16 (m, 2H), 6.89-6.87 (m, 2H), 6.82 (dd, J1=8.8 Hz, J2=2.0 Hz, 1H), 4.84-4.67 (m, 4H), 4.55-4.45 (m, 2H), 2.71-2.66 (m, 2H), 2.08-2.03 (m, 2H), 1.53 (s, 6H), 1.30-1.26 (m, 12H); m/z (ESI+) (M+H)+=400.25.

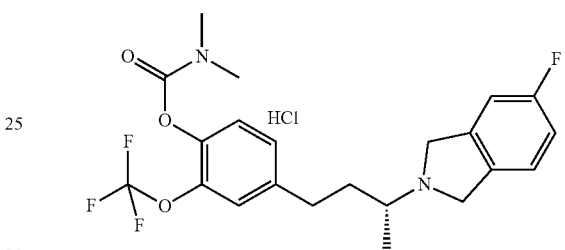

Example Compound 43

¹H NMR (400 MHz, CD3OD): δ 7.46-7.38 (m, 1H), 7.36-7.32 (m, 2H), 7.26-7.22 (m, 1H), 7.20-7.12 (m, 2H), 4.90-4.80 (m, 2H), 4.70-4.55 (m, 2H), 3.70-3.60 (m, 1H), 3.12 (s, 3H), 2.99 (s, 3H), 2.95-2.85 (m, 1H), 2.80-2.70 (m, 1H), 2.30-2.20 (m, 1H), 2.00-1.90 (m, 1H), 1.50 (d, J=6.0 Hz, 3H); m/z (ESI+) (M+H)+=441.15.

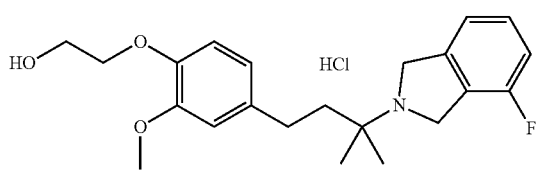 [SMILES: COc1cc(CCC(C)(C)N2Cc3cccc(F)c3C2)ccc1OCCO ; Cl]

Example Compound 44

¹H NMR (400 MHz, DMSO-d6): δ 12.15 (s, 1H), 7.44-7.42 (m, 1H), 7.24-7.21 (m, 2H), 6.88-6.86 (m, 2H), 6.77-6.75 (m, 1H), 4.88-4.79 (m, 2H), 4.71-4.66 (m, 2H), 3.93-3.90 (m, 2H), 3.76 (s, 3H), 3.69-3.66 (m, 2H), 2.63-2.58 (m, 2H), 2.05-2.00 (m, 2H), 1.45 (s, 3H); m/z (ESI+) (M+H)+=347.15.

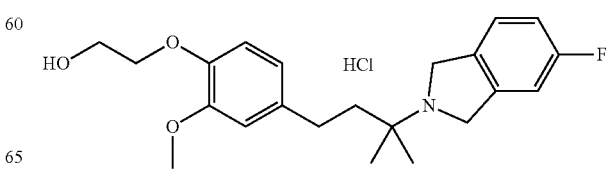

Example Compound 45

$^1$H NMR (400 MHz, CD3OD): δ 7.43-7.39 (m, 1H), 7.18-7.12 (m, 2H), 6.92-6.88 (m, 2H), 6.82-6.80 (m, 1H), 4.85-4.70 (m, 4H), 4.02-3.99 (m, 2H), 3.85-3.82 (m, 5H), 2.73-2.69 (m, 2H), 2.10-2.05 (m, 2H), 1.54 (s, 3H); m/z (ESI+) (M+H)+=374.15.

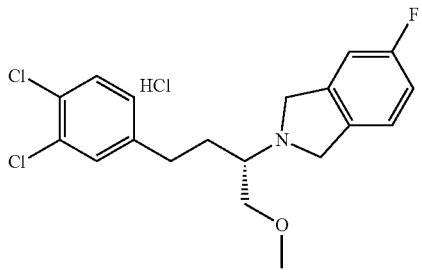 [SMILES: COC[C@H](CCc1ccc(Cl)c(Cl)c1)N1Cc2ccc(F)cc2C1 ; Cl]

Example Compound 46

$^1$H NMR (400 MHz, CD3OD): δ 7.48 (d, J=1.6 Hz, 1H), 7.46 (d, J=8.4 Hz, 1H), 7.44-7.38 (m, 1H), 7.23 (dd, J1=8.0 Hz, J2=2.0 hz, 1H), 7.20-7.12 (m, 2H), 4.85-4.55 (m, 4H), 3.86-3.75 (m, 2H), 3.72-3.65 (m, 1H), 3.46 (s, 3H), 2.85-2.70 (m, 2H), 2.18-2.12 (m, 2H); m/z (ESI+) (M+H)+=368.05.

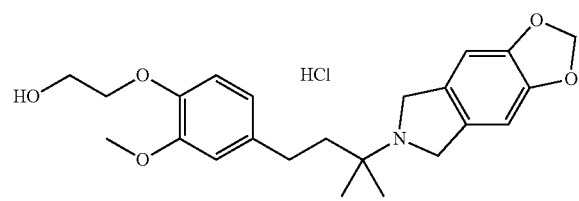 [SMILES: COc1cc(CCC(C)(C)N2Cc3cc4c(cc3C2)OCO4)ccc1OCCO ; Cl]

Example Compound 47

$^1$H NMR (400 MHz, DMSO-d6): δ 6.90-6.86 (m, 4H), 6.74 (d, J=8.0 Hz, 1H), 6.04 (d, J=8.8 Hz, 2H), 4.63 (dd, J1=14.0 Hz, J2=6.4 Hz, 2H), 4.46 (dd, J1=14.0 Hz, J2=6.4 Hz, 2H), 3.75 (s, 3H), 3.69-3.67 (m, 2H), 2.62-2.57 (m, 2H), 1.99-1.96 (m, 2H), 1.42 (s, 6H); m/z (ESI+) (M+H)+=400.15.

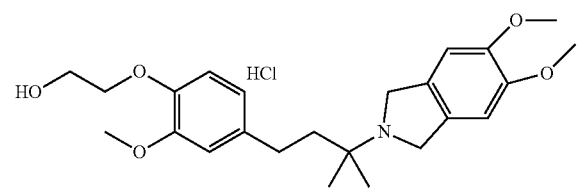 [SMILES: COc1cc2c(cc1OC)CN(C(C)(C)CCc1ccc(OCCO)c(OC)c1)C2 ; Cl]

Example Compound 48

$^1$H NMR (400 MHz, CD3OD): δ 6.99 (br. s, 2H), 6.92-6.89 (m, 2H), 6.81 (d, J=8.0 Hz, 1H), 4.72 (d, J=11.6 Hz, 2H), 4.62 (d, J=11.6 Hz, 2H), 4.02-4.00 (m, 2H), 3.86-3.82 (m, 11H), 2.73-2.68 (m, 2H), 2.09-2.05 (m, 2H), 1.53 (s, 6H); m/z (ESI+) (M+H)+=416.20.

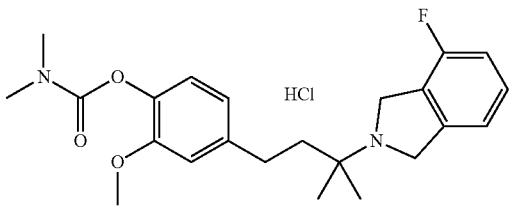 [SMILES: COc1cc(CCC(C)(C)N2Cc3cccc(F)c3C2)ccc1OC(=O)N(C)C ; Cl]

Example Compound 49

$^1$H NMR (400 MHz, DMSO-d6): δ 12.22 (br. s, 1H), 7.46-7.41 (m, 1H), 7.24-7.20 (m, 2H), 7.01 (s, 1H), 6.96 (d, J=8.0 HZ, 1H), 6.82 (d, J=7.2 Hz, 1H), 4.92-4.80 (m, 2H), 4.72-4.69 (m, 2H), 3.02 (s, 3H), 2.88 (s, 3H), 2.70-2.66 (m, 2H), 2.09-2.05 (m, 2H), 1.47 (s, 6H); m/z (ESI+) (M+H)+=401.20.

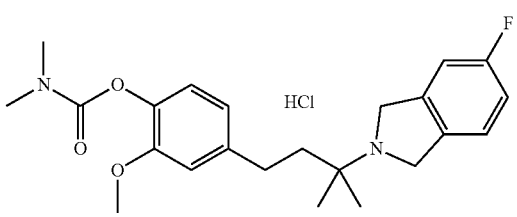 [SMILES: COc1cc(CCC(C)(C)N2Cc3ccc(F)cc3C2)ccc1OC(=O)N(C)C ; Cl]

Example Compound 50

$^1$H NMR (400 MHz, DMSO-d6): δ 12.07 (br. s, 1H), 7.42-7.39 (m, 1H), 7.24-7.18 (m, 2H), 7.01-6.95 (m, 2H), 6.82 (d, J=8.0 Hz, 1H), 4.82-4.60 (m, 4H), 3.02 (s, 3H), 2.88 (s, 3H), 2.70-2.65 (m, 2H), 2.07-2.04 (m, 2H), 1.44 (s, 6H); m/z (ESI+) (M+H)+=401.15.

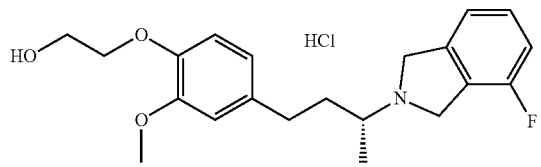 [SMILES: COc1cc(CC[C@@H](C)N2Cc3cccc(F)c3C2)ccc1OCCO ; Cl]

Example Compound 51

$^1$H NMR (400 MHz, CD3OD): δ 7.48-7.42 (m, 1H), 7.23 (d, J=7.2 Hz, 1H), 7.14 (t, J=8.4 Hz, 1H), 6.92 (s, 1H), 6.90 (d, J=8.4 Hz, 1H), 6.80 (d, J=8.0 Hz, 1H), 5.01-4.89 (m, 2H), 4.69-4.63 (m, 2H), 4.03-4.00 (m, 2H), 3.86-3.83 (m, 5H), 3.64-3.60 (m, 1H), 2.86-2.78 (m, 1H), 2.67-2.60 (m, 1H), 2.30-2.20 (m, 1H), 1.98-1.90 (m, 1H), 1.50 (d, J=6.0 Hz, 3H); m/z (ESI+) (M+H)+=360.15.

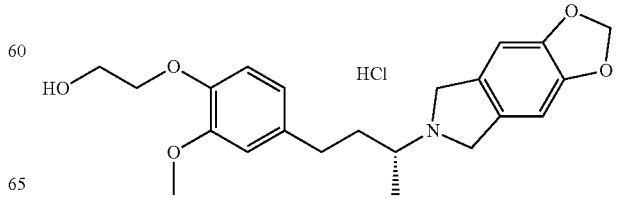

Example Compound 52

¹H NMR (400 MHz, CD3OD): δ 6.91 (s, 1H), 6.90 (d, J=8.4 Hz, 1H), 6.83 (s, 2H), 6.79 (d, J=8.8 Hz, 1H), 5.98 (d, J=2.4 Hz, 2H), 4.75-4.66 (m, 2H), 4.49-4.42 (m, 2H), 4.02-3.99 (m, 2H), 3.86-3.79 (m, 5H), 3.50-3.44 (m, 1H), 2.82-2.75 (m, 1H), 2.66-2.58 (m, 1H), 2.25-2.18 (m, 1H), 1.95-1.86 (m, 1H), 1.46 (d, J=6.4 Hz, 3H); m/z (ESI+) (M+H)+=386.20.

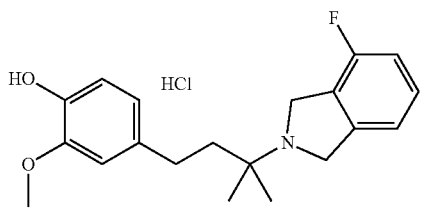 [SMILES: COc1cc(CCC(C)(C)N2Cc3cccc(F)c3C2)ccc1O ; Cl]

Example Compound 53

¹H NMR (400 MHz, CD3OD): δ 7.40-7.36 (m, 1H), 7.18 (d, J=7.6 Hz, 1H), 7.08 (t, J=8.8 Hz, 1H), 6.86 (s, 1H), 6.73 (d, J=7.6 Hz, 1H), 6.68 (d, J=8.0 Hz, 1H), 3.58 (br. s, 4H), 4.81-4.75 (m, 3H), 3.82 (s, 3H), 2.67-2.63 (m, 2H), 2.10-2.06 (m, 2H), 1.52 (s, 6H); m/z (ESI+) (M+H)+=330.10.

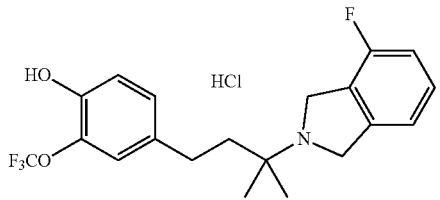 [SMILES: CC(C)(CCc1ccc(O)c(OC(F)(F)F)c1)N1Cc2cccc(F)c2C1 ; Cl]

Example Compound 54

¹H NMR (400 MHz, DMSO-d6): δ 10.04 (s, 1H), 7.46-7.40 (m, 1H), 7.23-7.18 (m, 3H), 7.10 (d, J=8.4 Hz, 1H), 6.97 (d, J=8.0 Hz, 1H), 4.85-4.78 (m, 2H), 4.69-4.66 (m, 2H), 2.63-2.59 (m, 2H), 2.03-1.98 (m, 2H), 1.46 (s, 6H); m/z (ESI+) (M+H)+=384.15.

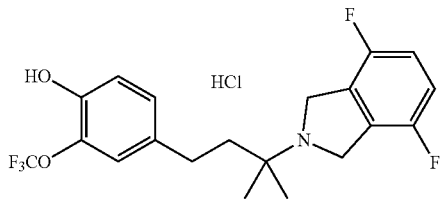 [SMILES: CC(C)(CCc1ccc(O)c(OC(F)(F)F)c1)N1Cc2c(F)ccc(F)c2C1 ; Cl]

Example Compound 55

¹H NMR (400 MHz, CD3OD): δ 7.20 (t, J=6.0 Hz, 2H), 7.15 (s, 1H), 7.11 (d, J=8.0 Hz, 1H), 6.90 (d, J=8.4 Hz, 1H), 4.90-4.86 (m, 4H), 2.73-2.68 (m, 2H), 2.10-2.06 (m, 2H), 1.54 (s, 6H); m/z (ESI+) (M+H)+=402.15.

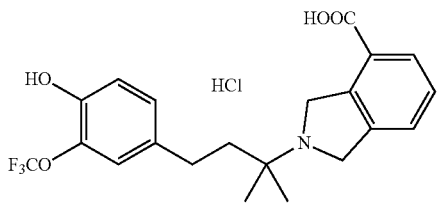 [SMILES: CC(C)(CCc1ccc(O)c(OC(F)(F)F)c1)N1Cc2cccc(C(=O)O)c2C1 ; Cl]

Example Compound 56

¹H NMR (400 MHz, CD3OD): δ 8.04 (d, J=7.6 Hz, 1H), 7.63 (d, J=7.2 Hz, 1H), 7.54 (t, J=8.0 Hz, 1H), 7.14 (s, 1H), 7.10 (d, J=8.8 Hz, 1H), 6.90 (d, J=8.0 Hz, 1H), 5.10-4.70 (m, 4H), 2.73-2.69 (m, 2H), 2.10-2.06 (m, 2H), 1.56 (s, 6H); m/z (ESI+) (M+H)+=410.15.

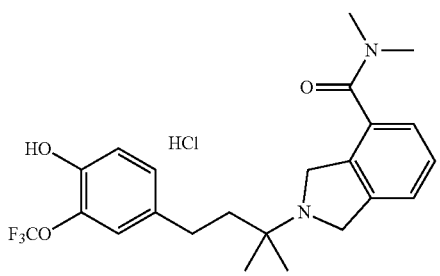 [SMILES: CN(C)C(=O)c1cccc2c1CN(C(C)(C)CCc1ccc(O)c(OC(F)(F)F)c1)C2 ; Cl]

Example Compound 57

¹H NMR (400 MHz, CD3OD): δ 7.48-7.38 (m, 3H), 7.12 (s, 1H), 7.10 (d, J=8.4 Hz, 1H), 6.90 (d, J=8.0 Hz, 1H), 4.81-4.71 (m, 4H), 3.09 9s, 3H), 209 (s, 3H), 2.71-2.66 (m, 2H), 2.07-2.03 (m, 2H), 1.62 (s, 6H); m/z (ESI+) (M+H)+=437.25.

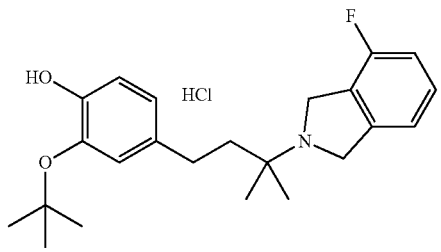 [SMILES: CC(C)(C)Oc1cc(CCC(C)(C)N2Cc3cccc(F)c3C2)ccc1O ; Cl]

Example Compound 58

¹H NMR (400 MHz, CD3OD): δ 8.07-8.05 (m, 1H), 7.66-7.54 (m, 2H), 6.90-6.78 (m, 3H), 5.20-4.80 (m, 4H), 2.67-2.60 (m, 2H), 2.07-2.00 (m, 2H), 1.55 (s, 6H), 1.35 (s, 9H); m/z (ESI+) (M+H)+=398.25.

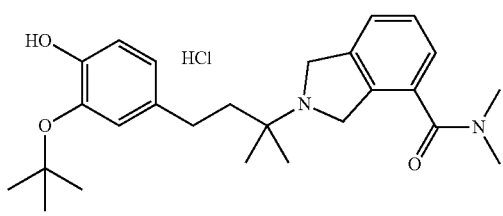 [SMILES: CN(C)C(=O)c1cccc2c1CN(C(C)(C)CCc1ccc(O)c(OC(C)(C)C)c1)C2 ; Cl]

Example Compound 59

¹H NMR (400 MHz, DMSO-d6): δ 11.32 (s, 1H), 7.44-7.37 (m, 3H), 6.83-6.74 (m, 3H), 4.81-4.56 (m, 4H), 3.00 (s, 3H), 2.91 (s, 3H), 2.60-2.50 (m, 2H), 2.00-1.90 (m, 2H), 1.43 (s, 6H), 1.28 (s, 9H); m/z (ESI+) (M+H)+=425.35.

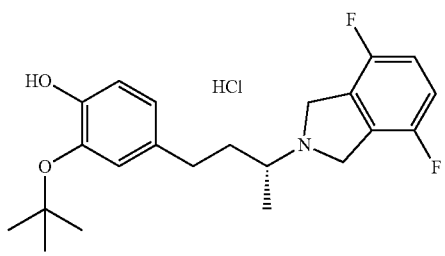 [SMILES: C[C@H](CCc1ccc(O)c(OC(C)(C)C)c1)N1Cc2c(F)ccc(F)c2C1 ; Cl]

Example Compound 60A

¹H NMR (400 MHz, CD3OD): δ 7.19 (t, J=6.0 Hz, 2H), 6.90 (s, 1H), 6.85 (d, J=7.6 Hz, 1H), 6.79 (d, J=8.0 Hz, 1H), 4.86-4.80 (m, 4H), 3.65-3.60 (m, 1H), 2.80-2.70 (m, 1H), 2.62-2.52 (m, 1H), 2.25-2.15 (m, 2H), 1.95-1.85 (m, 1H), 1.48 (d, J=6.0 Hz, 3H), 1.36 (s, 9H); m/z (ESI+) (M+H)+=376.25.

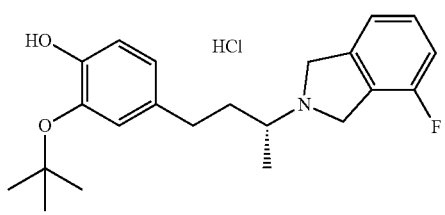 [SMILES: C[C@H](CCc1ccc(O)c(OC(C)(C)C)c1)N1Cc2cccc(F)c2C1 ; Cl]

Example Compound 60B

¹H NMR (400 MHz, CDCl3): δ 7.18-7.15 (m, 1H), 6.98 (d, J=7.2 Hz, 1H), 6.88-6.80 (m, 4H), 4.04-4.00 (m, 4H), 2.80-2.72 (m, 1H), 2.70-2.62 (m, 1H), 2.60-2.50 (m, 1H), 1.95-1.88 (m, 1H), 1.76-1.70 (m, 1H), 1.42 (s, 9H), 1.20 (d, J=6.4 Hz, 3H); m/z (ESI+) (M+H)+=358.25.

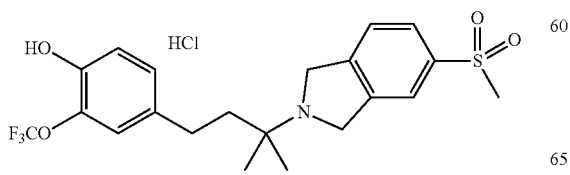

Example Compound 61

¹H NMR (400 MHz, DMSO-d6): δ 11.95 (br. s, 1H), 10.00 (br. s, 1H), 7.93 (s, 2H), 7.65-7.64 (m, 1), 7.22-7.09 (m, 2H), 6.92-6.90 (m, 1H), 4.85-4.75 (m, 4H), 3.23 (s, 3H), 2.65-2.60 (m, 2H), 2.02-1.95 (m, 2H), 1.45 (s, 6H); m/z (ESI+) (M+H)+=444.20.

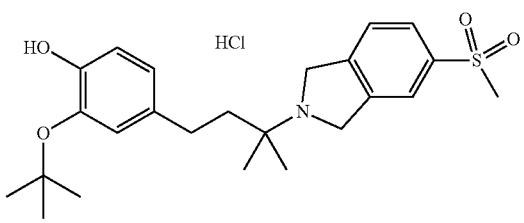 [SMILES: CC(C)(C)Oc1cc(CCC(C)(C)N2Cc3ccc(S(C)(=O)=O)cc3C2)ccc1O ; Cl]

Example Compound 62

¹H NMR (400 MHz, CDCl3): δ 7.80-7.78 (m, 2H), 7.40-7.38 (m, 1H), 6.87-6.78 (m, 3H), 4.18-4.10 (m, 4H), 3.02 (s, 3H), 2.62-2.56 (m, 2H), 1.80-1.60 (m, 2H), 1.45 (s, 9H), 1.20 (s, 6H); m/z (ESI+) (M+H)+=432.25.

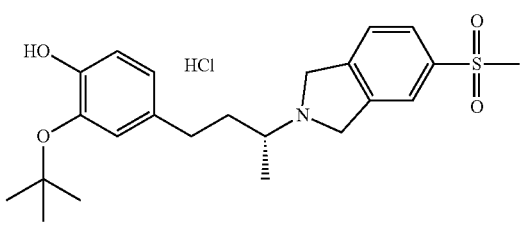 [SMILES: C[C@H](CCc1ccc(O)c(OC(C)(C)C)c1)N1Cc2ccc(S(C)(=O)=O)cc2C1 ; Cl]

Example Compound 63

¹H NMR (400 MHz, CD3OD): δ 7.98-7.95 (m, 1H), 7.63 (d, J=7.6 Hz, 1H), 6.90 (s, 1H), 6.85 (d, J=8.0 Hz, 1H), 6.79 (d, J=8.0 Hz, 1H), 4.90-4.80 (m, 4H), 3.66-3.60 (m, 1H), 3.12 (s, 3H), 2.80-2.72 (m, 1H), 2.65-2.55 (m, 1H), 2.25-2.15 (m, 1H), 1.95-1.85 (m, 1H), 1.47 (d, J=6.4 Hz, 3H), 1.36 (s, 9H); m/z (ESI+) (M+H)+=418.20.

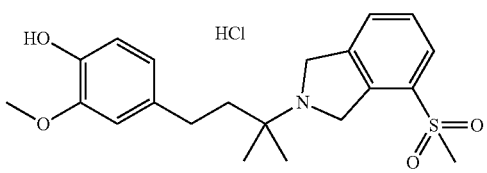 [SMILES: COc1cc(CCC(C)(C)N2Cc3cccc(S(C)(=O)=O)c3C2)ccc1O ; Cl]

Example Compound 64

¹H NMR (400 MHz, CD3OD): δ 7.97 (d, J=7.2 Hz, 1H), 7.78-7.68 (m, 2H), 6.88 (s, 1H), 6.72 (s, 2H), 5.09 (s, 2H), 4.85 (s, 2H), 3.85 (s, 3H), 3.20 (s, 3H), 2.73-2.70 (m, 2H), 2.13-2.10 (m, 2H), 1.58 (s, 6H); m/z (ESI+) (M+H)+=390.15.

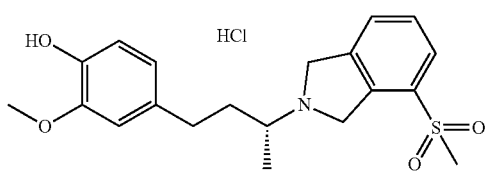 [SMILES: COc1cc(CC[C@@H](C)N2Cc3cccc(S(C)(=O)=O)c3C2)ccc1O ; Cl]

Example Compound 65

¹H NMR (400 MHz, CD3OD): δ 8.75 (s, 1H), 7.85 (d, J=7.2 Hz, 1H), 7.74 (d, J=6.8 Hz, 1H), 7.68 (d, J=6.8 Hz, 1H), 6.83 (s, 1H), 6.70 (d, J=7.6 Hz, 1H), 6.64 (d, J=8.0 Hz, 1H), 5.05-4.60 (m, 4H), 3.76 (s, 3H), 3.60-3.50 (m, 1H), 3.40-3.30 (m, 2H), 2.72-2.65 (m, 1H), 2.20-2.10 (m, 1H), 1.90-1.80 (m, 1H), 1.45-1.40 (m, 3H); m/z (ESI+) (M+H)+=376.10.

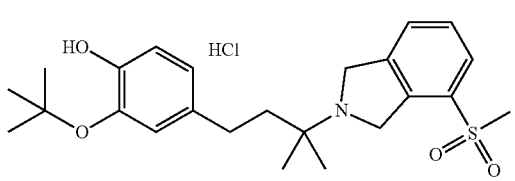 [SMILES: CC(C)(C)Oc1cc(CCC(C)(C)N2Cc3cccc(S(C)(=O)=O)c3C2)ccc1O ; Cl]

Example Compound 66

¹H NMR (400 MHz, CD3OD): δ 8.55 (br. s, 1H), 7.86 (d, J=6.4 Hz, 1H), 7.74-7.67 (m, 2H), 6.83-6.77 (m, 3H), 4.93 (s, 2H), 4.81-4.73 (m, 2H), 3.28 (s, 3H), 2.60-2.55 (m, 2H), 2.02-1.98 (m, 2H), 1.48-1.46 (m, 6H), 1.28 (s, 9H); m/z (ESI+) (M+H)+=432.30.

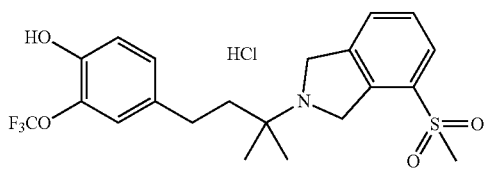 [SMILES: CC(C)(CCc1ccc(O)c(OC(F)(F)F)c1)N1Cc2cccc(S(C)(=O)=O)c2C1 ; Cl]

Example Compound 67

¹H NMR (400 MHz, CD3OD): δ 7.93 (d, J=7.2 Hz, 1H), 7.76-7.66 (m, 2H), 7.15 (s, 1H), 7.11 (d, J=8.0 Hz, 1H), 6.91 (d, J=7.2 Hz, 1H), 5.05 (s, 2H), 4.82 (s, 2H), 3.20 (s, 3H), 2.75-2.70 (m, 2H), 2.30-2.00 (m, 2H), 1.57-1.56 (m, 6H); m/z (ESI+) (M+H)+=444.15.

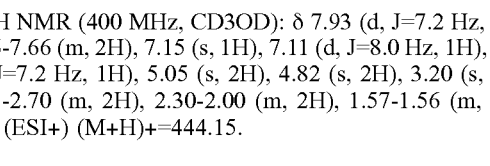

Example Compound 68

¹H NMR (400 MHz, CD3OD): δ 7.98 (s, 2H), 7.66-7.63 (m, 1H), 6.84 (s, 1H), 6.75-6.69 (m, 2H), 4.83 (s, 4H), 3.85 (s, 3H), 3.63-3.59 (m, 1H), 3.13 (s, 3H), 2.82-2.76 (m, 1H), 2.66-2.58 (m, 1H), 2.24-2.21 (m, 1H), 1.96-1.91 (m, 1H), 1.49 (d, J=6.4 Hz, 3H); m/z (ESI+) (M+H)+=376.15.

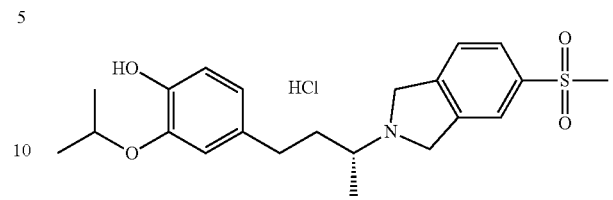

Example Compound 69

1H NMR (400 MHz, CD3OD): δ 7.99 (s, 2H), 7.64 (d, J=8.4 Hz, 1H), 6.85 (s, 1H), 6.75 (d, J=8.0 Hz, 1H), 6.71 (d, J=7.6 Hz, 1H), 4.84 (s, 4H), 4.60-4.55 (m, 1H), 3.60-3.56 (m, 1H), 3.13 (s, 3H), 2.78-2.73 (m, 1H), 2.62-2.58 (m, 1H), 2.22-2.18 (m, 1H), 1.93-1.89 (m, 1H), 1.48 (d, J=6.4 Hz, 3H), 1.31 (d, J=6.0 Hz, 6H); m/z (ESI+) (M+H)+=404.20.

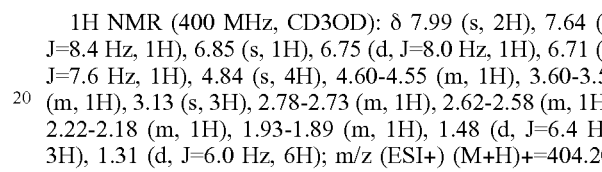

Example Compound 70

1H NMR (400 MHz, CD3OD): δ 8.01 (s, 2H), 7.67 (d, J=8.4 Hz, 1H), 6.85 (s, 1H), 6.78-6.70 (m, 2H), 4.84 (s, 4H), 4.60-4.56 (m, 1H), 3.13 (s, 3H), 2.70-2.66 (m, 2H), 2.08-2.04 (m, 2H), 1.55 (s, 6H), 1.31 (d, J=6.0 Hz, 6H); m/z (ESI+) (M+H)+=418.25.

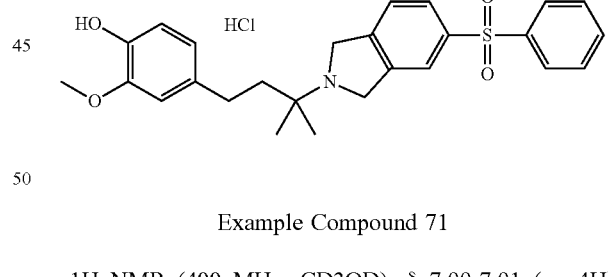

Example Compound 71

1H NMR (400 MHz, CD3OD): δ 7.99-7.91 (m, 4H), 7.62-7.54 (m, 4H), 6.83 (s, 1H), 6.72-6.68 (m, 2H), 4.82 (s, 4H), 3.81 (s, 3H), 2.70-2.65 (m, 2H), 2.08-2.02 (m, 2H), 1.51 (s, 6H); m/z (ESI+) (M+H)+=452.00.

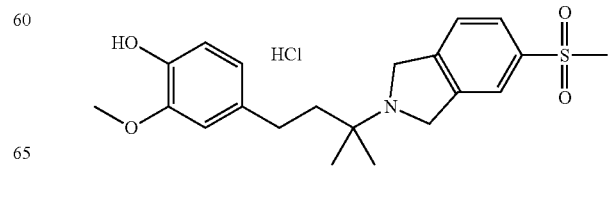

Example Compound 72

1H NMR (400 MHz, CD3OD): δ 8.00 (s, 1H), 7.86 (d, J=8.0 Hz, 1H), 6.85 (s, 1H), 6.74-6.70 (m, 2H), 4.85 (s, 4H), 3.85 (s, 3H), 3.13 (s, 3H), 2.72-2.68 (m, 2H), 2.10-2.06 (m, 2H), 1.56 (s, 6H); m/z (ESI+) (M+H)+=390.15.

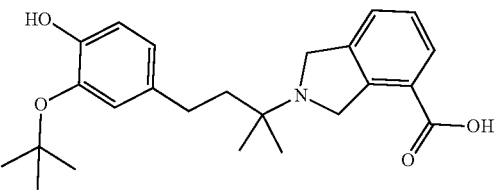

Example Compound 73

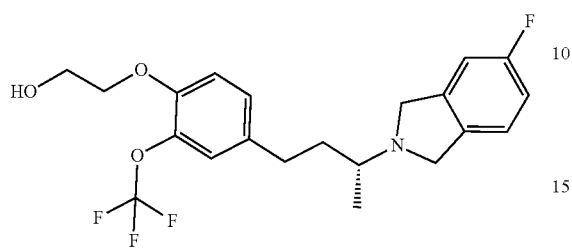

Example Compound 75

¹H NMR (400 MHz, CD3OD): δ 8.07-8.05 (m, 1H), 7.66-7.54 (m, 2H), 6.90-6.78 (m, 3H), 5.20-4.80 (m, 4H), 2.67-2.60 (m, 2H), 2.07-2.00 (m, 2H), 1.55 (s, 6H), 1.35 (s, 9H); m/z (ESI+) (M+H)+=398.25.

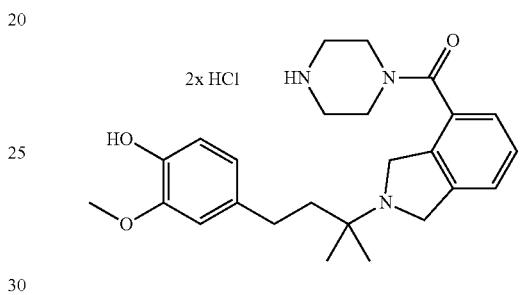

Example Compound 74

1H NMR (400 MHz, CD3OD): 1H NMR (400 MHz, CDCl3): δ 7.03-6.99 (m, 2H), 6.88-6.83 (m, 2H), 6.78-6.75 (m, 1H), 4.80-4.65 (m, 4H), 2.65-2.60 (m, 2H), 2.03-1.99 (m, 2H), 1.52 (s, 6H), 1.40 (s, 9H); m/z (ESI+) (M+H)+=390.20.

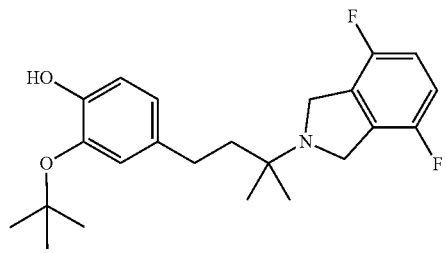 [SMILES: CC(C)(C)Oc1cc(CCC(C)(C)N2Cc3c(F)ccc(F)c3C2)ccc1O]

Example Compound 76

¹H NMR (400 MHz, CD₃OD) δ 7.55-7.48 (m, 3H), 6.87 (s, 1H), 6.72-6.70 (m, 2H), 4.95-4.79 (m, 4H) 3.90-3.80 (m, 7H), 3.35-3.30 (m, 4H), 2.72-2.69 (m, 2H), 2.12-2.08 (m, 2H), 1.56 (s, 6H). LC-MS: 424.70 (M+1)⁺.

Additional compounds were prepared in an analogous fashion to those provided above and structure for each was confirmed by ¹H-NMR and MS, as shown in Table 4.

TABLE 4

Additional Isoindoline Compounds.

| Structure | Ex. Cpd. No. |
|---|---|
| 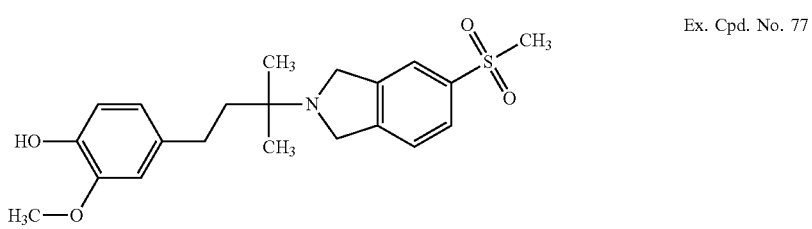 | 77 |

TABLE 4-continued
Additional Isoindoline Compounds.
Structure
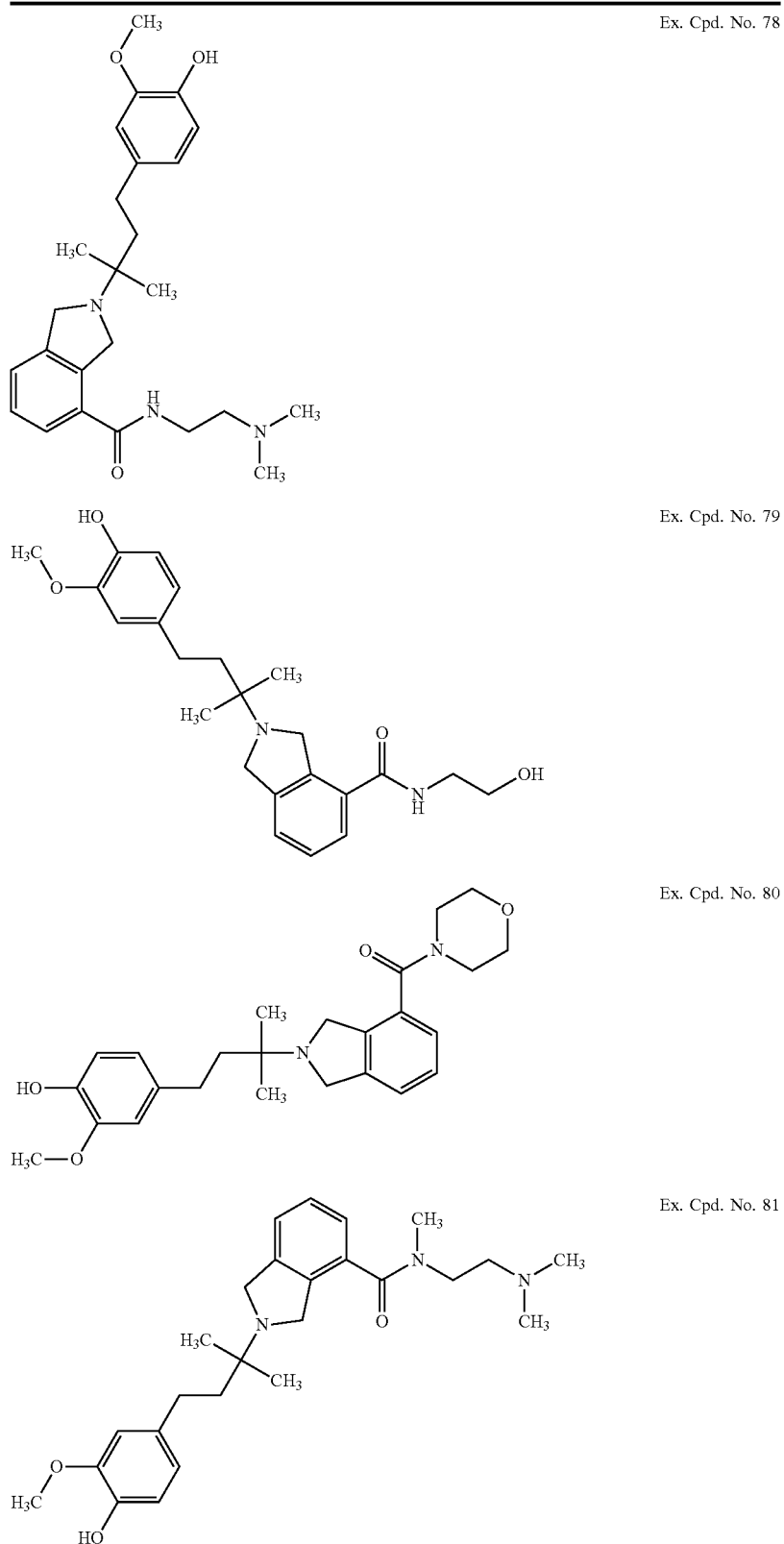
Ex. Cpd. No. 78
Ex. Cpd. No. 79
Ex. Cpd. No. 80
Ex. Cpd. No. 81

TABLE 4-continued
Additional Isoindoline Compounds.
Structure
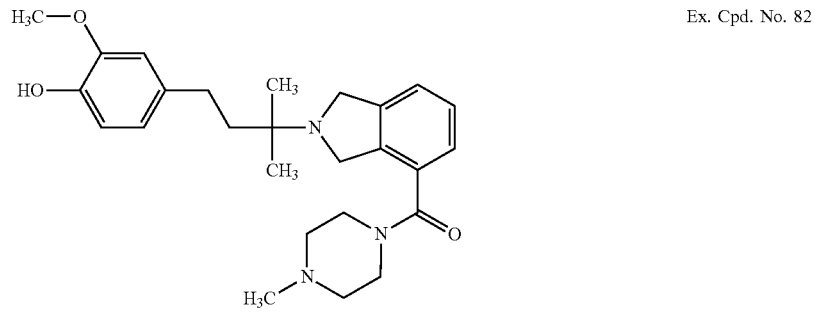
Ex. Cpd. No. 82
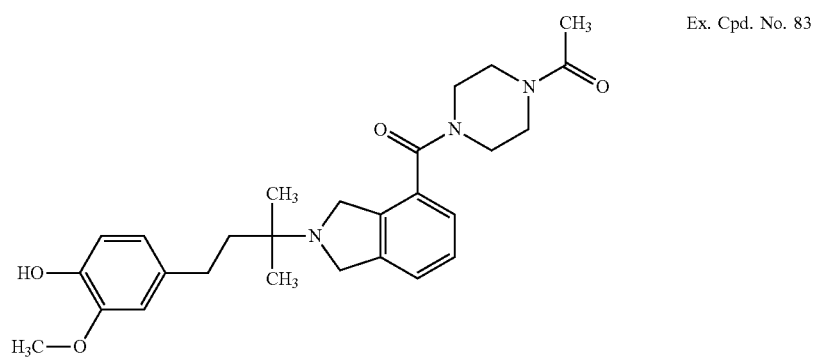
Ex. Cpd. No. 83
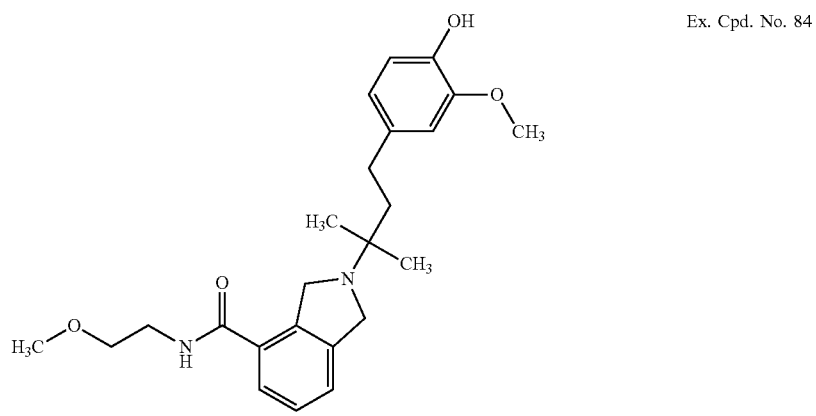
Ex. Cpd. No. 84
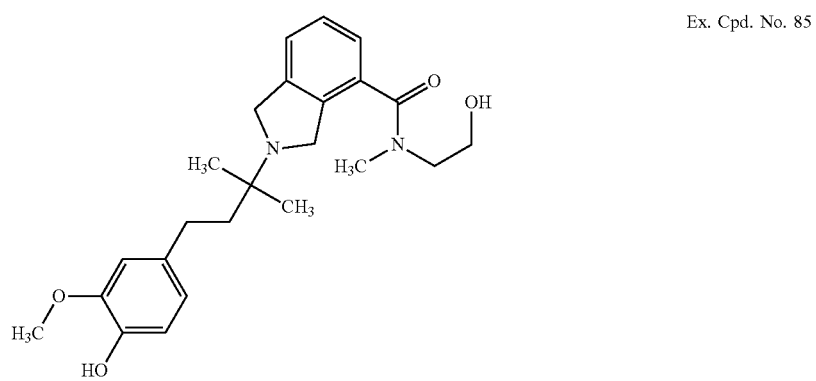
Ex. Cpd. No. 85

TABLE 4-continued
Additional Isoindoline Compounds.
Structure
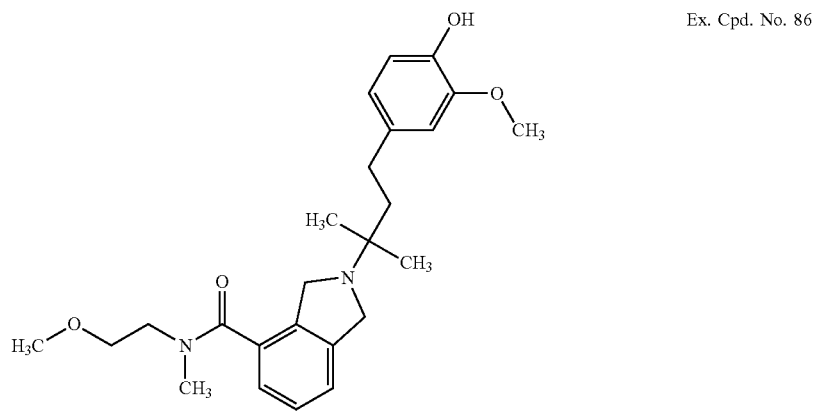
Ex. Cpd. No. 86
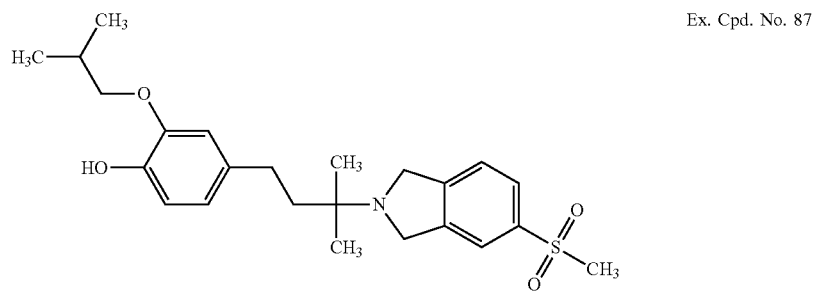
Ex. Cpd. No. 87
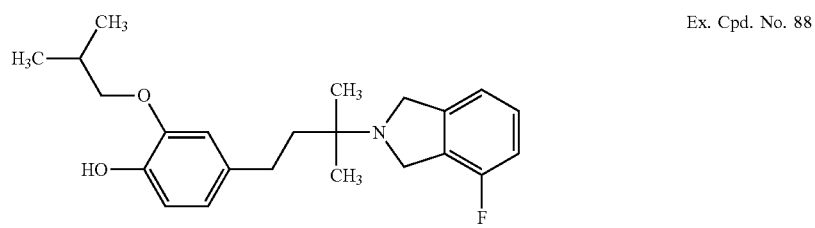
Ex. Cpd. No. 88
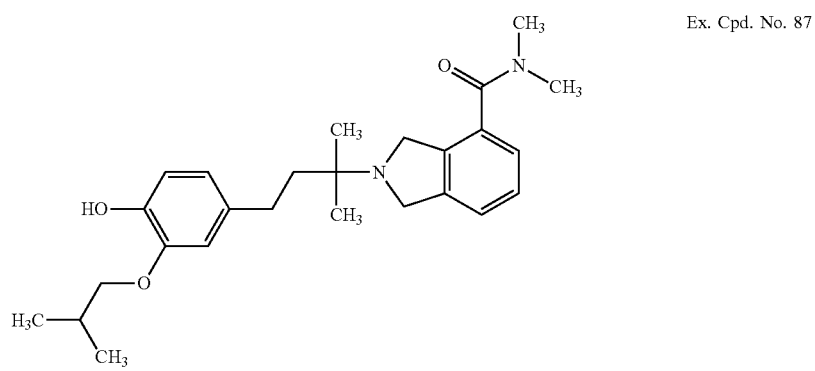
Ex. Cpd. No. 87

TABLE 4-continued
Additional Isoindoline Compounds.
Structure
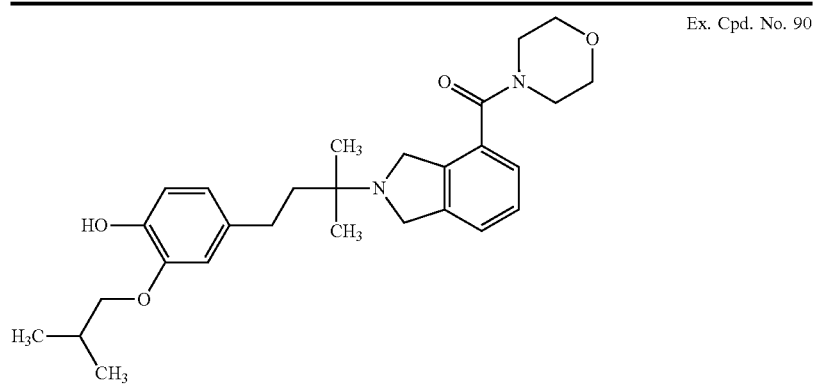
Ex. Cpd. No. 90
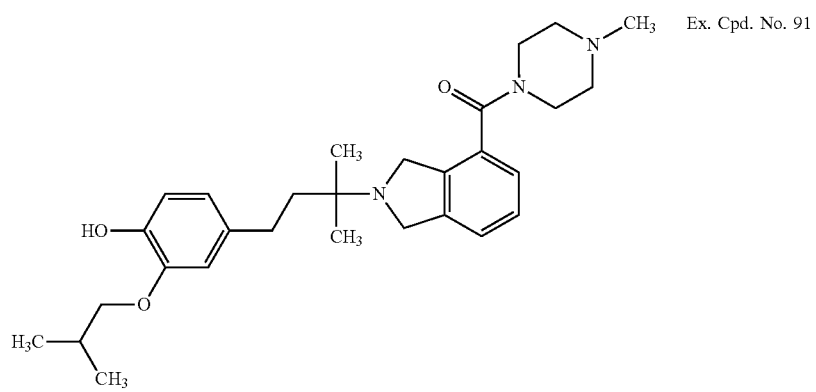
Ex. Cpd. No. 91
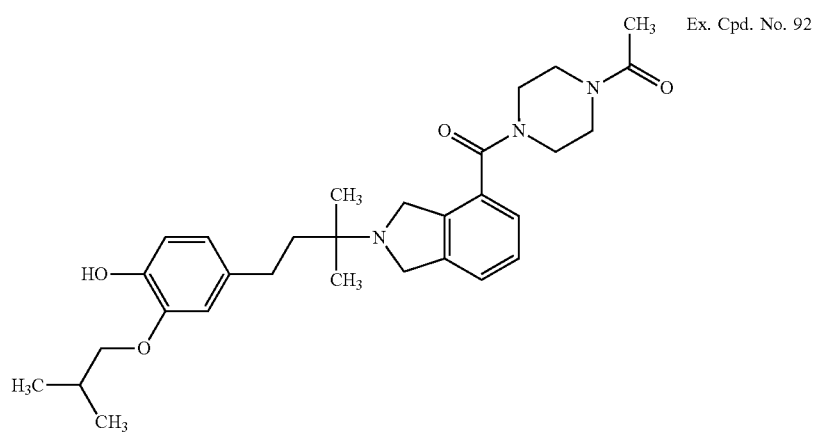
Ex. Cpd. No. 92
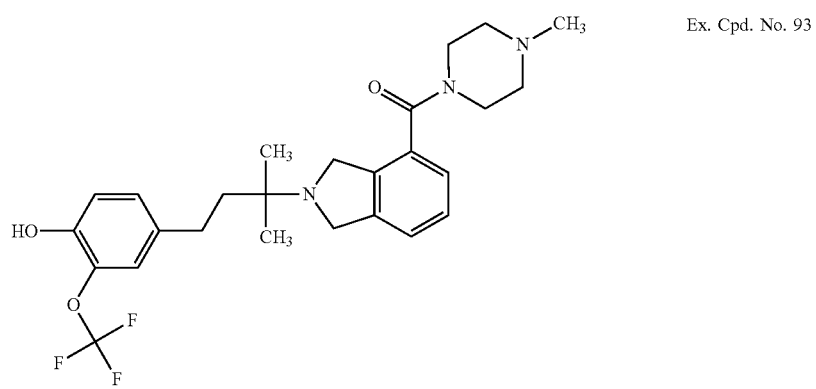
Ex. Cpd. No. 93

TABLE 4-continued
Additional Isoindoline Compounds.
Structure
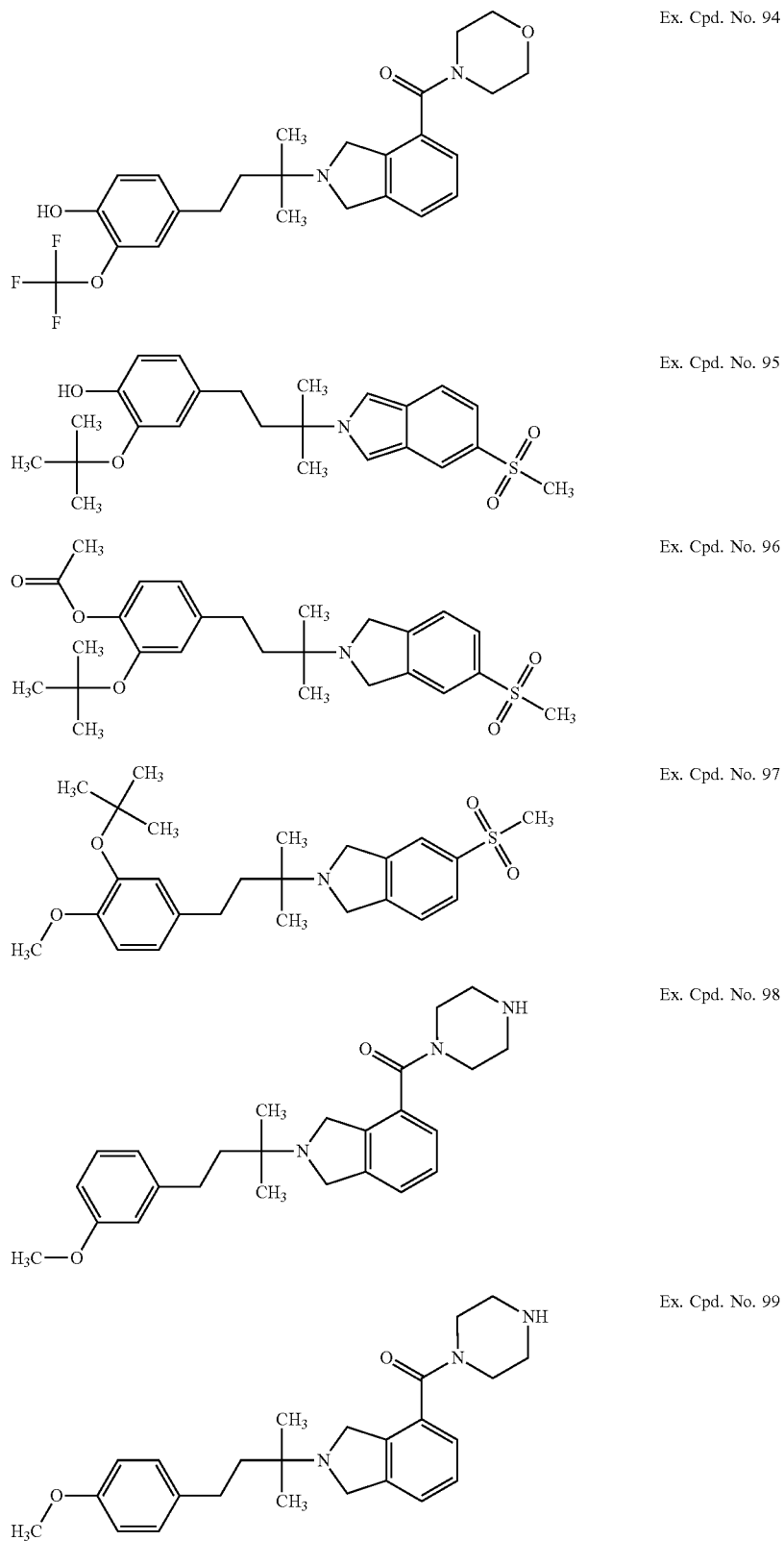
Ex. Cpd. No. 94
Ex. Cpd. No. 95
Ex. Cpd. No. 96
Ex. Cpd. No. 97
Ex. Cpd. No. 98
Ex. Cpd. No. 99

TABLE 4-continued
Additional Isoindoline Compounds.
Structure
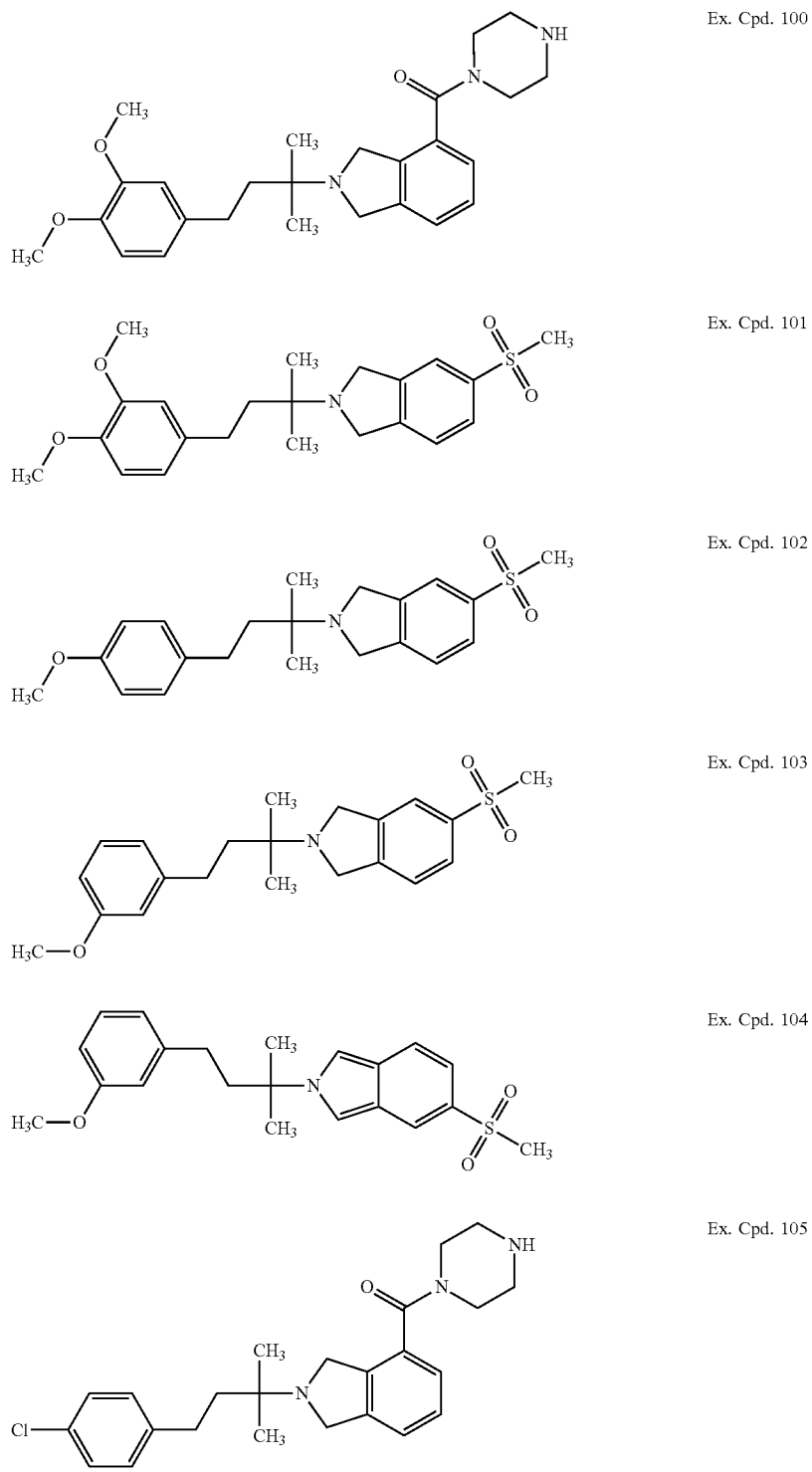
Ex. Cpd. 100
Ex. Cpd. 101
Ex. Cpd. 102
Ex. Cpd. 103
Ex. Cpd. 104
Ex. Cpd. 105

TABLE 4-continued
Additional Isoindoline Compounds.
Structure
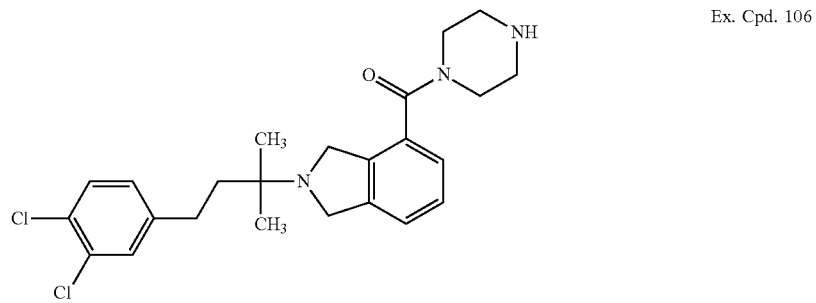
Ex. Cpd. 106
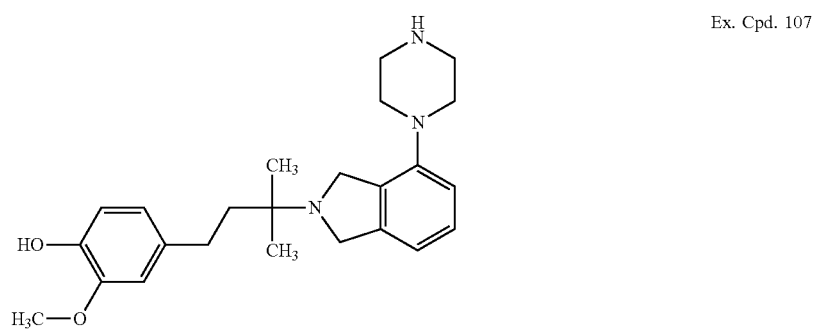
Ex. Cpd. 107
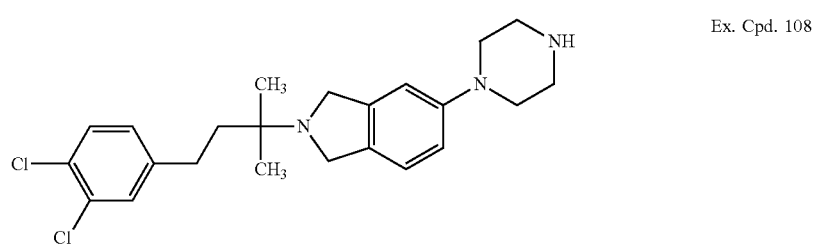
Ex. Cpd. 108
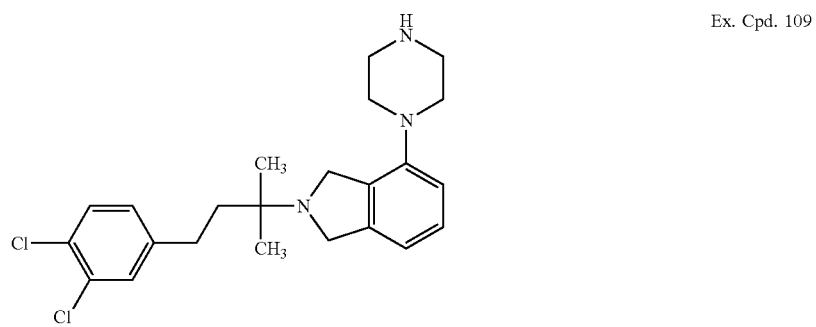
Ex. Cpd. 109
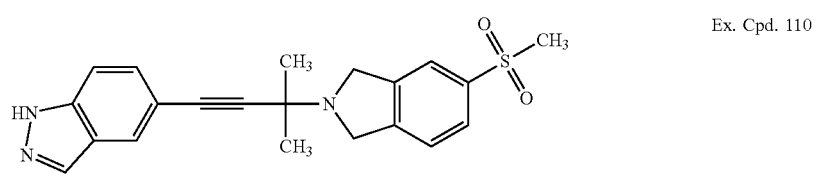
Ex. Cpd. 110

TABLE 4-continued
Additional Isoindoline Compounds.
Structure
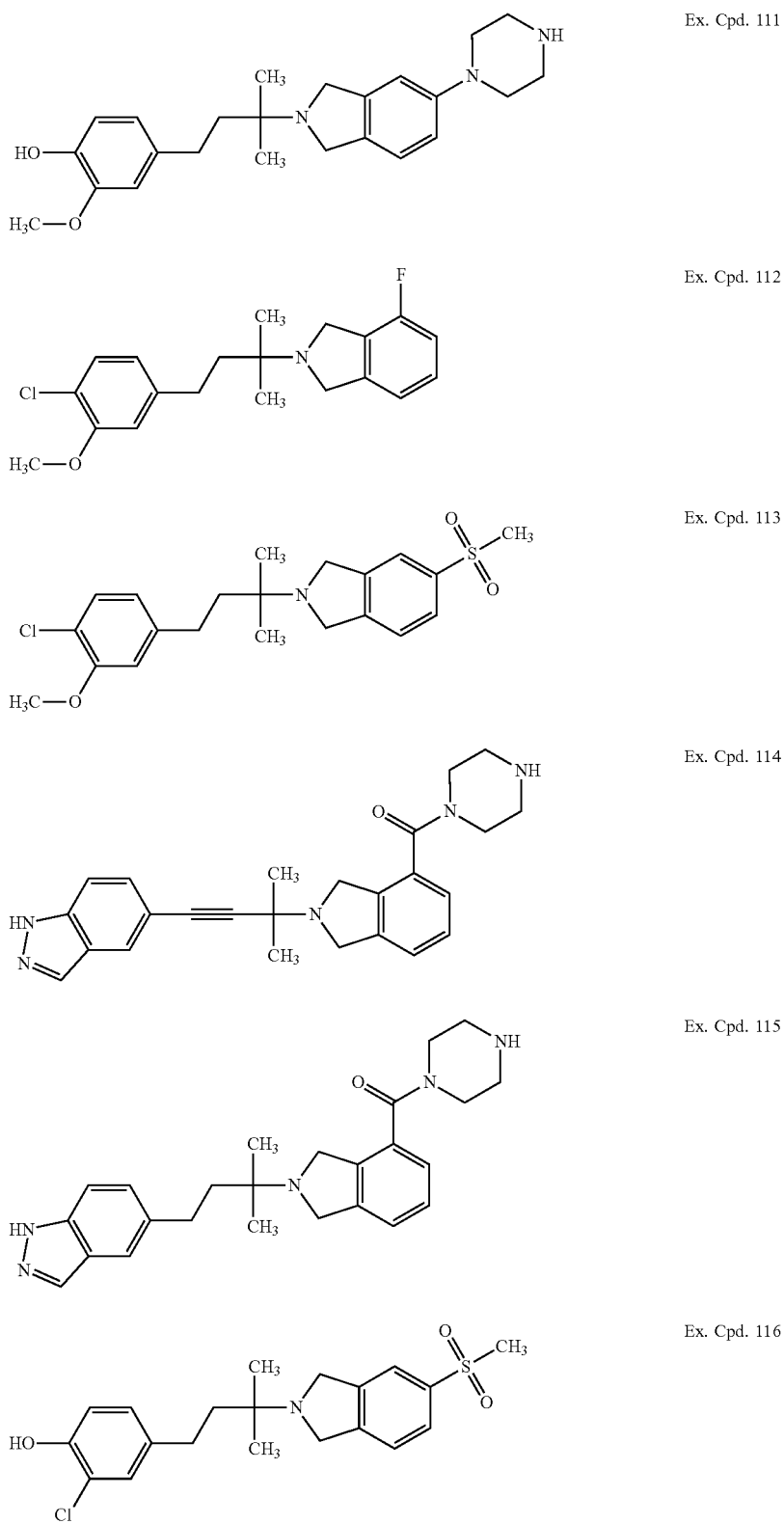
Ex. Cpd. 111
Ex. Cpd. 112
Ex. Cpd. 113
Ex. Cpd. 114
Ex. Cpd. 115
Ex. Cpd. 116

TABLE 4-continued

Additional Isoindoline Compounds.

Structure

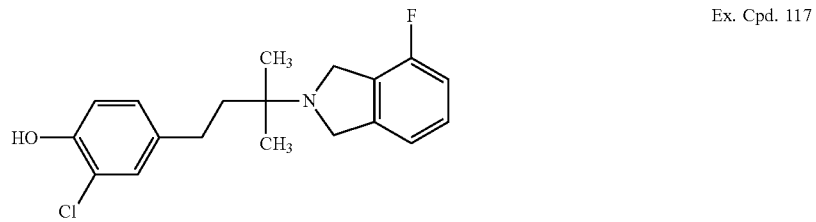

Ex. Cpd. 117

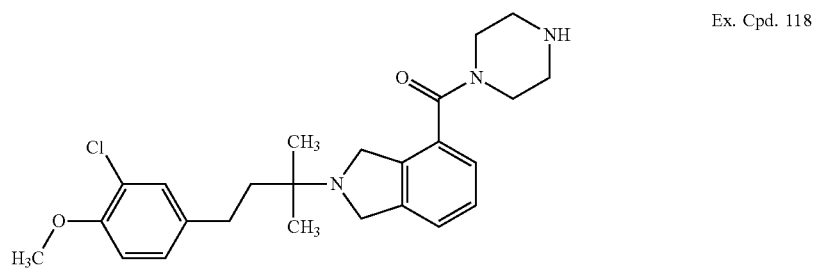

Ex. Cpd. 118

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the disclosure, in addition to those described herein, will be apparent to those skilled in the art from the foregoing description. Such modifications are also intended to fall within the scope of the appended claims.

All publications mentioned herein are incorporated by reference in their entirety. Nothing herein is to be construed as an admission that the disclosure is not entitled to antedate such disclosure by virtue of prior disclosure.

We claim:

1. A method of treating Alzheimer's disease comprising administering to a subject having said disease a dose of about 0.01 mg/kg/day to about 25 mg/kg/day, of a compound of the Formula:

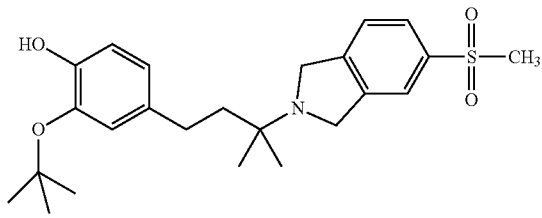 [SMILES: CC(C)(C)Oc1cc(CCC(C)(C)N2Cc3ccc(S(C)(=O)=O)cc3C2)ccc1O]

or a pharmaceutically acceptable salt thereof.

2. The method of claim 1 wherein the compound pharmaceutically acceptable salt is

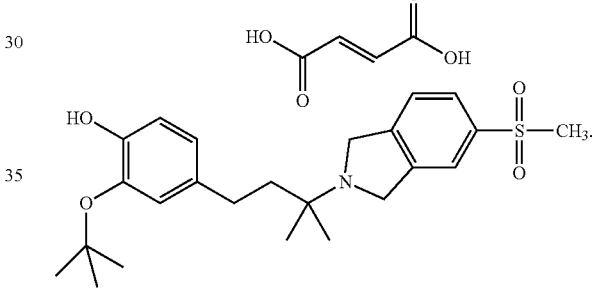

3. The method of claim 1 wherein the dose is about 0.1 mg/kg/day to about 10 mg/kg/day.

4. The method of claim 1 wherein the dose is about 0.2 mg/kg/day to about 5 mg/kg/day.

5. The method of claim 1 wherein the total daily dose is administered in a single dose.

6. The method of claim 1 wherein the total daily dose is administered in multiple doses per day.

7. The method of claim 1 wherein the compound or pharmaceutically acceptable salt thereof is formulated in a capsule or tablet.

8. The method of claim 7 wherein the capsule or tablet comprises 0.1 mg/kg/day to about 10 mg/kg/day of the compound or a pharmaceutically acceptable salt thereof.

9. The method of claim 7 wherein the capsule or tablet comprises 0.2 mg/kg/day to about 5 mg/kg/day of the compound or a pharmaceutically acceptable salt thereof.

10. The method of claim 1 wherein the compound or pharmaceutically acceptable salt thereof is administered orally.

11. A method of treating Alzheimer's disease comprising administering to a subject having said disease a pharmaceutical composition comprising a compound of the Formula:

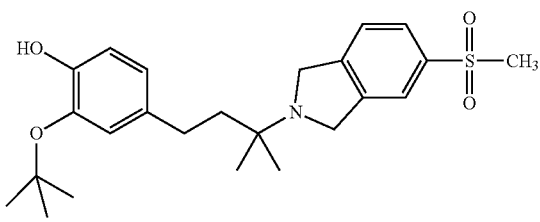 [SMILES: CC(C)(C)Oc1cc(CCC(C)(C)N2Cc3ccc(S(C)(=O)=O)cc3C2)ccc1O]

or a pharmaceutically acceptable salt thereof, and a pharmaceutically acceptable carrier or excipient, wherein a dose of the compound or pharmaceutically acceptable salt thereof is administered is 0.01 mg/kg/day to about 25 mg/kg/day.

12. The method of claim 11 wherein the pharmaceutically acceptable salt is

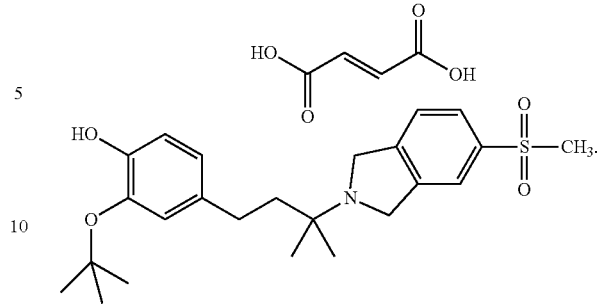

13. The method of claim 11 wherein the total daily dose of the compound administered is about 0.1 mg/kg/day to about 10 mg/kg/day.

14. The method of claim 11 wherein the total daily dose of the compound administered is about 0.2 mg/kg/day to about 5 mg/kg/day.

15. The method of claim 11 wherein the dose is administered in a single dose.

16. The method of claim 11 wherein the dose is administered in multiple doses per day.

17. The method of claim 11 wherein the pharmaceutical composition is a capsule or tablet.

18. The method of claim 17 wherein the capsule or tablet comprises about 0.1 mg/kg/day to about 10 mg/kg/day of the compound or a pharmaceutically acceptable salt thereof.

19. The method of claim 17 wherein the total daily dose is about 0.2 mg/kg/day to about 5 mg/kg/day.

20. The method of claim 17 wherein the pharmaceutical composition is administered orally.

* * * * *